(12) United States Patent
Bruno

(10) Patent No.: US 8,648,181 B2
(45) Date of Patent: Feb. 11, 2014

(54) METHODS AND COMPOSITIONS OF DNA LIGANDS FOR ARTHROPOD-BORNE PATHOGEN DETECTION AND PROPHYLAXIS OR THERAPY

(75) Inventor: John G. Bruno, San Antonio, TX (US)

(73) Assignee: OTC Biotechnologies, LLC, San Antonio, TX (US)

( * ) Notice: Subject to any disclaimer, the term of this patent is extended or adjusted under 35 U.S.C. 154(b) by 0 days.

(21) Appl. No.: 13/199,082

(22) Filed: Aug. 18, 2011

(65) Prior Publication Data

US 2012/0149889 A1    Jun. 14, 2012

Related U.S. Application Data

(60) Provisional application No. 61/401,731, filed on Aug. 18, 2010.

(51) Int. Cl.
*C07H 21/04* (2006.01)

(52) U.S. Cl.
USPC ........................................................ 536/23.1

(58) Field of Classification Search
None
See application file for complete search history.

*Primary Examiner* — Tracy Vivlemore
(74) *Attorney, Agent, or Firm* — Rosenthal Pauerstein Sandoloski Agather LLP; William H. Quirk; Daniel A. Rogers

(57) ABSTRACT

Specific DNA ligand sequences for binding various arthropod-borne pathogens including arboviruses, rickettsia and parasites are described. Each of these sequences or their linear, two-and three-dimesional linked sequences can function in varying assay and sensor formats with varying degrees of success. Linkage of the whole or partial DNA sequences (putative binding sites) can be used to enhance specificity and affinity towards complex targets, thereby improving assay selectivity and sensitivity in many instances. In addition, the DNA sequences may bind and neutralize or prevent infection from arthropod-borne viruses, rickettsia and *Leishmania* or other parasites.

2 Claims, 14 Drawing Sheets

Fig. 2

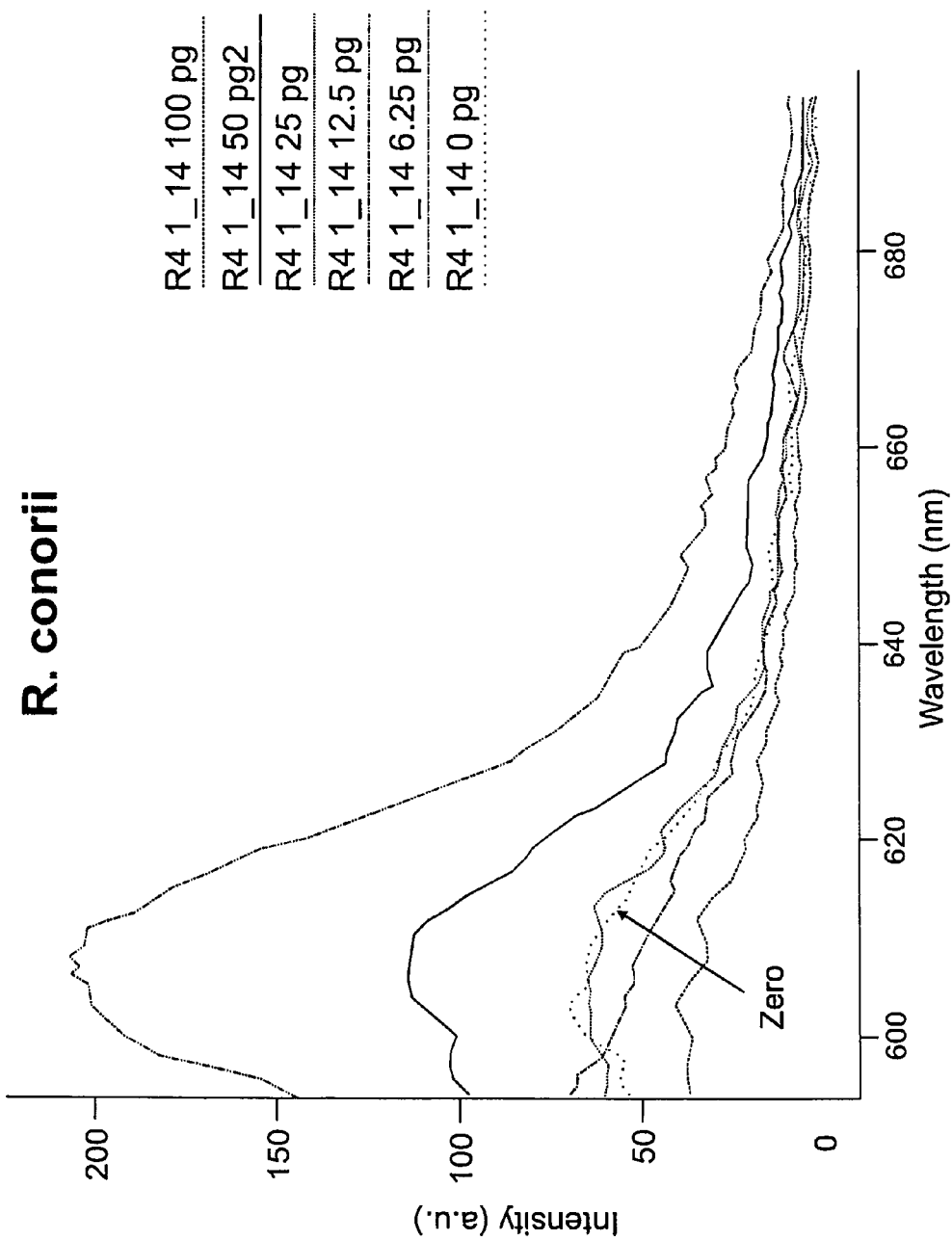

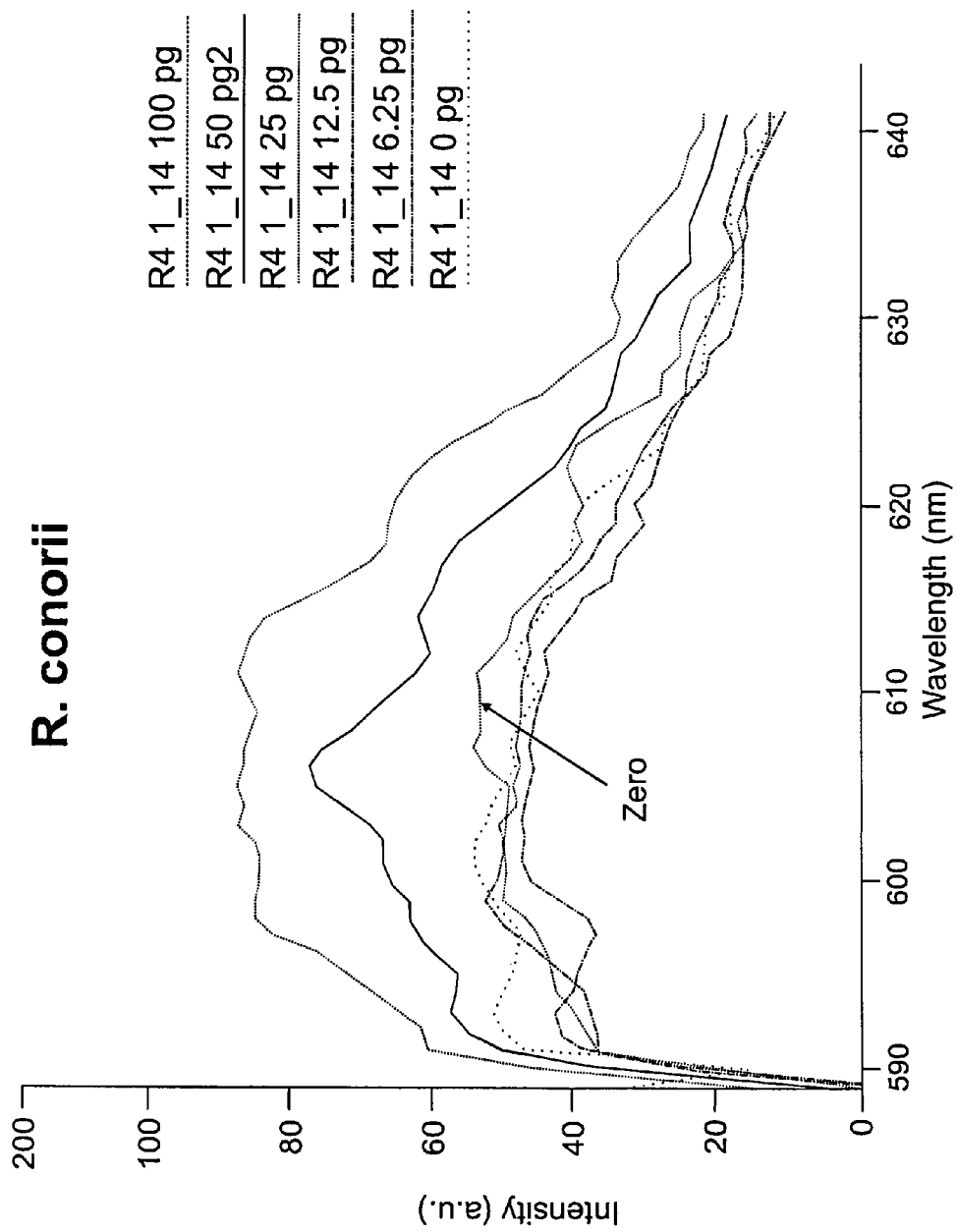

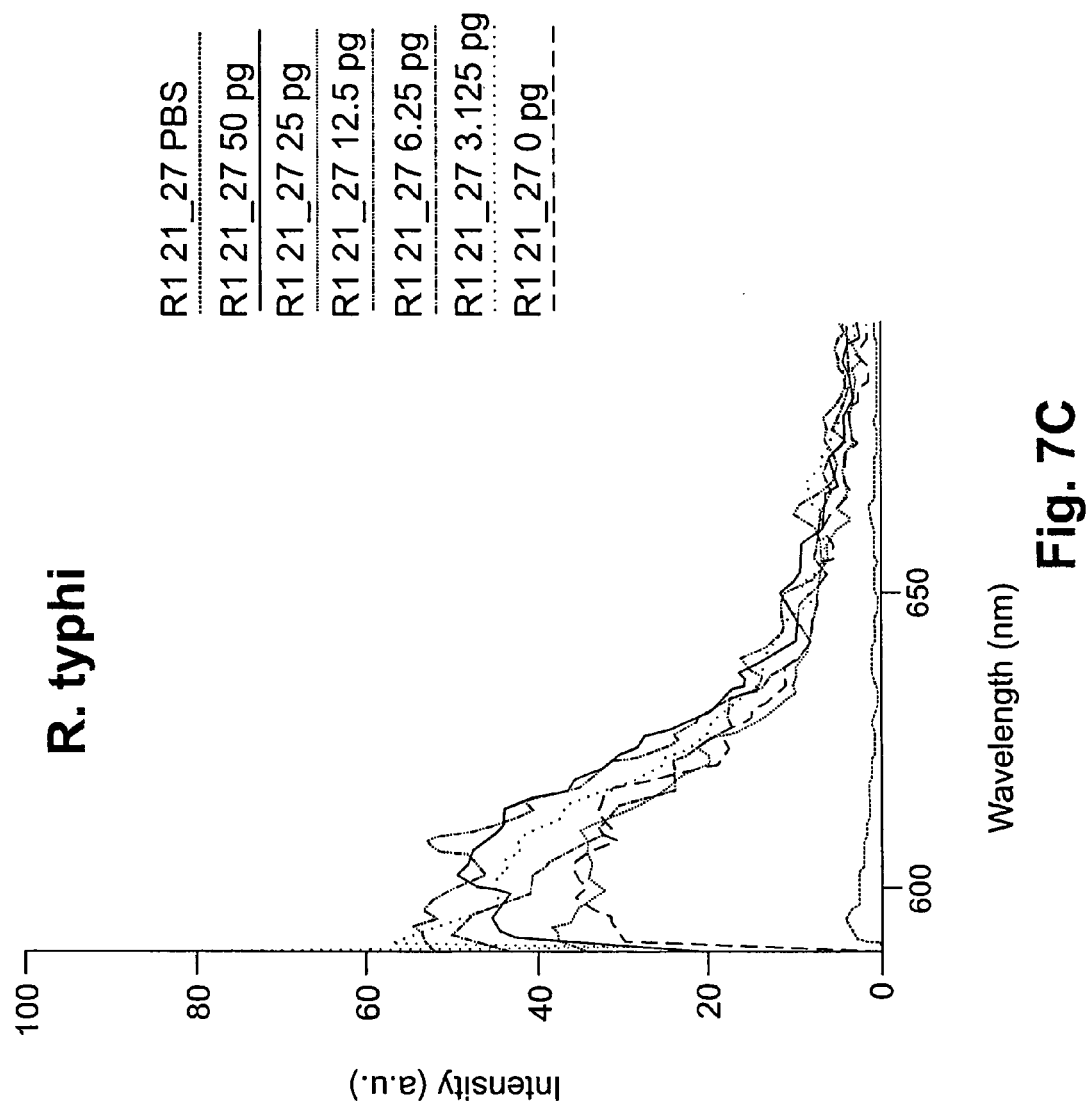

General DNA Ligand or Aptamer Lateral Flow Test Strip Format

GNP; Gold Nanoparticle
NC; Nitrocellulose

Chikungunya Envelope

← ChE 20R
← ChE 17R

Fig. 9A

Crimean-Congo Hemmorhagic Fever Strain

IbAr10200
C3-6R ↑ ↑ C1-9F

Drosdoff
C3-6R ↑ ↑ C1-9F

Fig. 9B

West Nile Virus Aptamer

SEQUENCE LISTING

<160> NUMBER OF SEQ ID NOS: 774

<210> SEQ ID NO 1
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 1
atacgggagc caacaccaat aaagagcgga acttttagaa ctggatagac tcatagagca      60
ggtgtgacgg at                                                         72

<210> SEQ ID NO 2
<211> LENGTH: 72
<212> TYPE: DNA
<213> ORGANISM: Artificial Sequence
<220> FEATURE:
<223> OTHER INFORMATION: chemically synthesized

<400> SEQUENCE: 2
atccgtcaca cctgctctat gagtctatcc agttctaaaa gttccgctct ttattggtgt      60
tggctcccgt at                                                         72

<210> SEQ ID NO 3
<211> LENGTH: 69
<212> TYPE: DNA
<213> ORGANISM: Artificial Sequence
<220> FEATURE:
<223> OTHER INFORMATION: chemically synthesized

<400> SEQUENCE: 3
atacgggagc caacaccata gtgttgggcc aatacggtaa cgtgtccttg gagagcaggt      60
gtgacggat                                                             69

<210> SEQ ID NO 4
<211> LENGTH: 69
<212> TYPE: DNA
<213> ORGANISM: Artificial Sequence
<220> FEATURE:
<223> OTHER INFORMATION: chemically synthesized

<400> SEQUENCE: 4
atccgtcaca cctgctctcc aaggacacgt taccgtattg gcccaacact atggtgttgg      60
ctcccgtat                                                             69

<210> SEQ ID NO 5
<211> LENGTH: 59
<212> TYPE: DNA
<213> ORGANISM: Artificial Sequence
<220> FEATURE:
<223> OTHER INFORMATION: chemically synthesized

<400> SEQUENCE: 5
atacgggagc caacaccact aacttgttgc tgatcttatc cagagcaggt gtgacggat       59

<210> SEQ ID NO 6
<211> LENGTH: 59
<212> TYPE: DNA
<213> ORGANISM: Artificial Sequence
<220> FEATURE:
<223> OTHER INFORMATION: chemically synthesized

<400> SEQUENCE: 6
atccgtcaca cctgctctgg ataagatcag caacaagtta gtggtgttgg ctcccgtat       59

<210> SEQ ID NO 7
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 7
atacgggagc caacaccaat gagagcaaag atcccaggat acactaatcc ctgtagagca    60
ggtgtgacgg at                                                       72

<210> SEQ ID NO 8
<211> LENGTH: 72
<212> TYPE: DNA
<213> ORGANISM: Artificial Sequence
<220> FEATURE:
<223> OTHER INFORMATION: chemically synthesized

<400> SEQUENCE: 8
atccgtcaca cctgctctac agggattagt gtatcctggg atctttgctc tcattggtgt    60
tggctcccgt at                                                       72

<210> SEQ ID NO 9
<211> LENGTH: 72
<212> TYPE: DNA
<213> ORGANISM: Artificial Sequence
<220> FEATURE:
<223> OTHER INFORMATION: chemically synthesized

<400> SEQUENCE: 9
atacgggagc caacaccacc tagtgttgaa tctgaccaca agctaagtct tcggagagca    60
ggtgtgacgg at                                                       72

<210> SEQ ID NO 10
<211> LENGTH: 72
<212> TYPE: DNA
<213> ORGANISM: Artificial Sequence
<220> FEATURE:
<223> OTHER INFORMATION: chemically synthesized

<400> SEQUENCE: 10
atccgtcaca cctgctctcc gaagacttag cttgtggtca gattcaacac taggtggtgt    60
tggctcccgt at                                                       72

<210> SEQ ID NO 11
<211> LENGTH: 72
<212> TYPE: DNA
<213> ORGANISM: Artificial Sequence
<220> FEATURE:
<223> OTHER INFORMATION: chemically synthesized

<400> SEQUENCE: 11
atacgggagc caacaccaag cacggaaaga gggtcgcctg atagcccgcc aatcagagca    60
ggtgtgacgg at                                                       72

<210> SEQ ID NO 12
<211> LENGTH: 72
<212> TYPE: DNA
<213> ORGANISM: Artificial Sequence
<220> FEATURE:
<223> OTHER INFORMATION: chemically synthesized

<400> SEQUENCE: 12
atccgtcaca cctgctctga ttggcgggct atcaggcgac cctctttccg tgcttggtgt    60
tggctcccgt at                                                       72
```

```
<210> SEQ ID NO 13
<211> LENGTH: 72
<212> TYPE: DNA
<213> ORGANISM: Artificial Sequence
<220> FEATURE:
<223> OTHER INFORMATION: chemically synthesized

<400> SEQUENCE: 13
atacgggagc caacaccaag aaatgccaac acaacgacac cggtagtgct gcccagagca      60
ggtgtgacgg at                                                         72

<210> SEQ ID NO 14
<211> LENGTH: 72
<212> TYPE: DNA
<213> ORGANISM: Artificial Sequence
<220> FEATURE:
<223> OTHER INFORMATION: chemically synthesized

<400> SEQUENCE: 14
atccgtcaca cctgctctgg gcagcactac cggtgtcgtt gtgttggcat ttcttggtgt      60
tggctcccgt at                                                         72

<210> SEQ ID NO 15
<211> LENGTH: 72
<212> TYPE: DNA
<213> ORGANISM: Artificial Sequence
<220> FEATURE:
<223> OTHER INFORMATION: chemically synthesized

<400> SEQUENCE: 15
atacgggagc caacaccatg gtgacggacc ttgagagcaa gaccgctacg attcagagca      60
ggtgtgacgg at                                                         72

<210> SEQ ID NO 16
<211> LENGTH: 72
<212> TYPE: DNA
<213> ORGANISM: Artificial Sequence
<220> FEATURE:
<223> OTHER INFORMATION: chemically synthesized

<400> SEQUENCE: 16
atccgtcaca cctgctctga atcgtagcgg tcttgctctc aaggtccgtc accatggtgt      60
tggctcccgt at                                                         72

<210> SEQ ID NO 17
<211> LENGTH: 72
<212> TYPE: DNA
<213> ORGANISM: Artificial Sequence
<220> FEATURE:
<223> OTHER INFORMATION: chemically synthesized

<400> SEQUENCE: 17
atacgggagc caacaccaga agaacactgc ctagaataag tggtgcaggg ccgtagagca      60
ggtgtgacgg at                                                         72

<210> SEQ ID NO 18
<211> LENGTH: 72
<212> TYPE: DNA
<213> ORGANISM: Artificial Sequence
<220> FEATURE:
<223> OTHER INFORMATION: chemically synthesized

<400> SEQUENCE: 18
atccgtcaca cctgctctac ggccctgcac cacttattct aggcagtgtt cttctggtgt      60
```

```
tggctcccgt at                                                          72

<210> SEQ ID NO 19
<211> LENGTH: 71
<212> TYPE: DNA
<213> ORGANISM: Artificial Sequence
<220> FEATURE:
<223> OTHER INFORMATION: chemically synthesized

<400> SEQUENCE: 19
atacgggagc caacaccatt aggtggtaga ctgtaggtta cagatagccg gggagagcag      60
gtgtgacgga t                                                           71

<210> SEQ ID NO 20
<211> LENGTH: 71
<212> TYPE: DNA
<213> ORGANISM: Artificial Sequence
<220> FEATURE:
<223> OTHER INFORMATION: chemically synthesized

<400> SEQUENCE: 20
atccgtcaca cctgctctcc ccggctatct gtaacctaca gtctaccacc taatggtgtt      60
ggctcccgta t                                                           71

<210> SEQ ID NO 21
<211> LENGTH: 72
<212> TYPE: DNA
<213> ORGANISM: Artificial Sequence
<220> FEATURE:
<223> OTHER INFORMATION: chemically synthesized

<400> SEQUENCE: 21
atacgggagc caacaccatc tggcgccgac cctgtggatt gcagtcgcgg ttacagagca      60
ggtgtgacgg at                                                          72

<210> SEQ ID NO 22
<211> LENGTH: 72
<212> TYPE: DNA
<213> ORGANISM: Artificial Sequence
<220> FEATURE:
<223> OTHER INFORMATION: chemically synthesized

<400> SEQUENCE: 22
atccgtcaca cctgctctgt aaccgcgact gcaatccaca gggtcggcgc cagatggtgt      60
tggctcccgt at                                                          72

<210> SEQ ID NO 23
<211> LENGTH: 69
<212> TYPE: DNA
<213> ORGANISM: Artificial Sequence
<220> FEATURE:
<223> OTHER INFORMATION: chemically synthesized

<400> SEQUENCE: 23
atacgggagc caacaccata gtgttgggcc aatacggtaa cgtgtccttg gagagcaggt      60
gtgacggat                                                              69

<210> SEQ ID NO 24
<211> LENGTH: 69
<212> TYPE: DNA
<213> ORGANISM: Artificial Sequence
<220> FEATURE:
<223> OTHER INFORMATION: chemically synthesized
```

<400> SEQUENCE: 24
atccgtcaca cctgctctcc aaggacacgt taccgtattg gcccaacact atggtgttgg    60
ctcccgtat                                                            69

<210> SEQ ID NO 25
<211> LENGTH: 72
<212> TYPE: DNA
<213> ORGANISM: Artificial Sequence
<220> FEATURE:
<223> OTHER INFORMATION: chemically synthesized

<400> SEQUENCE: 25
atacgggagc caacaccaca gacaccgaat gagcaacaca acaacgggac ccgtagagca    60
ggtgtgacgg at                                                        72

<210> SEQ ID NO 26
<211> LENGTH: 72
<212> TYPE: DNA
<213> ORGANISM: Artificial Sequence
<220> FEATURE:
<223> OTHER INFORMATION: chemically synthesized

<400> SEQUENCE: 26
atccgtcaca cctgctctac gggtcccgtt gttgtgttgc tcattcggtg tctgtggtgt    60
tggctcccgt at                                                        72

<210> SEQ ID NO 27
<211> LENGTH: 72
<212> TYPE: DNA
<213> ORGANISM: Artificial Sequence
<220> FEATURE:
<223> OTHER INFORMATION: chemically synthesized

<400> SEQUENCE: 27
atacgggagc caacaccagg tatccgaccg gacacggcac tacgacctct ttgcagagca    60
ggtgtgacgg at                                                        72

<210> SEQ ID NO 28
<211> LENGTH: 72
<212> TYPE: DNA
<213> ORGANISM: Artificial Sequence
<220> FEATURE:
<223> OTHER INFORMATION: chemically synthesized

<400> SEQUENCE: 28
atccgtcaca cctgctctgc aaagaggtcg tagtgccgtg tccggtcgga tacctggtgt    60
tggctcccgt at                                                        72

<210> SEQ ID NO 29
<211> LENGTH: 72
<212> TYPE: DNA
<213> ORGANISM: Artificial Sequence
<220> FEATURE:
<223> OTHER INFORMATION: chemically synthesized

<400> SEQUENCE: 29
atacgggagc caacaccagg gttggtgtaa agtggccagc cctttacgct aagtagagca    60
ggtgtgacgg at                                                        72

<210> SEQ ID NO 30
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 30
atccgtcaca cctgctctac ttagcgtaaa gggctggcca ctttacacca accctggtgt      60
tggctcccgt at                                                          72

<210> SEQ ID NO 31
<211> LENGTH: 72
<212> TYPE: DNA
<213> ORGANISM: Artificial Sequence
<220> FEATURE:
<223> OTHER INFORMATION: chemically synthesized

<400> SEQUENCE: 31
atacgggagc caacaccaca gctgacaata gaaggatatc ctgggtaccg atgcagagca      60
ggtgtgacgg at                                                          72

<210> SEQ ID NO 32
<211> LENGTH: 72
<212> TYPE: DNA
<213> ORGANISM: Artificial Sequence
<220> FEATURE:
<223> OTHER INFORMATION: chemically synthesized

<400> SEQUENCE: 32
atccgtcaca cctgctctgc atcggtaccc aggatatcct tctattgtca gctgtggtgt      60
tggctcccgt at                                                          72

<210> SEQ ID NO 33
<211> LENGTH: 72
<212> TYPE: DNA
<213> ORGANISM: Artificial Sequence
<220> FEATURE:
<223> OTHER INFORMATION: chemically synthesized

<400> SEQUENCE: 33
atacgggagc caacaccact gtgtataacc ctaacgctct atgttcgtta tgcaagagca      60
ggtgtgacgg at                                                          72

<210> SEQ ID NO 34
<211> LENGTH: 72
<212> TYPE: DNA
<213> ORGANISM: Artificial Sequence
<220> FEATURE:
<223> OTHER INFORMATION: chemically synthesized

<400> SEQUENCE: 34
atccgtcaca cctgctcttg cataacgaac atagagcgtt agggttatac acagtggtgt      60
tggctcccgt at                                                          72

<210> SEQ ID NO 35
<211> LENGTH: 72
<212> TYPE: DNA
<213> ORGANISM: Artificial Sequence
<220> FEATURE:
<223> OTHER INFORMATION: chemically synthesized

<400> SEQUENCE: 35
atacgggagc caacaccagc ccccgcctgg ttcccgcagg ccgctcgcgt cccgagagca      60
ggtgtgacgg at                                                          72
```

```
<210> SEQ ID NO 36
<211> LENGTH: 72
<212> TYPE: DNA
<213> ORGANISM: Artificial Sequence
<220> FEATURE:
<223> OTHER INFORMATION: chemically synthesized

<400> SEQUENCE: 36
atccgtcaca cctgctctcg ggacgcgagc ggcctgcggg aaccaggcgg gggctggtgt      60
tggctcccgt at                                                         72

<210> SEQ ID NO 37
<211> LENGTH: 72
<212> TYPE: DNA
<213> ORGANISM: Artificial Sequence
<220> FEATURE:
<223> OTHER INFORMATION: chemically synthesized

<400> SEQUENCE: 37
atacgggagc caacaccacg ggcgtcacta gctcagaccg tcccccgttg gtatagagca      60
ggtgtgacgg at                                                         72

<210> SEQ ID NO 38
<211> LENGTH: 72
<212> TYPE: DNA
<213> ORGANISM: Artificial Sequence
<220> FEATURE:
<223> OTHER INFORMATION: chemically synthesized

<400> SEQUENCE: 38
atccgtcaca cctgctctat accaacgggg gacggtctga gctagtgacg cccgtggtgt      60
tggctcccgt at                                                         72

<210> SEQ ID NO 39
<211> LENGTH: 69
<212> TYPE: DNA
<213> ORGANISM: Artificial Sequence
<220> FEATURE:
<223> OTHER INFORMATION: chemically synthesized

<400> SEQUENCE: 39
atacgggagc caacaccata gtgttgggcc aatacggtga cgtgtccttg gagagcaggt      60
gtgacggat                                                             69

<210> SEQ ID NO 40
<211> LENGTH: 69
<212> TYPE: DNA
<213> ORGANISM: Artificial Sequence
<220> FEATURE:
<223> OTHER INFORMATION: chemically synthesized

<400> SEQUENCE: 40
atccgtcaca cctgctctcc aaggacacgt caccgtattg gcccaacact atggtgttgg      60
ctcccgtat                                                             69

<210> SEQ ID NO 41
<211> LENGTH: 72
<212> TYPE: DNA
<213> ORGANISM: Artificial Sequence
<220> FEATURE:
<223> OTHER INFORMATION: chemically synthesized

<400> SEQUENCE: 41
```

```
atacgggagc caacaccaat gtcctcgtta caagaatatt tcctgttacg caccagagca    60
ggtgtgacgg at                                                        72
```

<210> SEQ ID NO 42
<211> LENGTH: 72
<212> TYPE: DNA
<213> ORGANISM: Artificial Sequence
<220> FEATURE:
<223> OTHER INFORMATION: chemically synthesized

<400> SEQUENCE: 42

```
atccgtcaca cctgctctgg tgcgtaacag gaaatattct tgtaacgagg acattggtgt    60
tggctcccgt at                                                        72
```

<210> SEQ ID NO 43
<211> LENGTH: 69
<212> TYPE: DNA
<213> ORGANISM: Artificial Sequence
<220> FEATURE:
<223> OTHER INFORMATION: chemically synthesized

<400> SEQUENCE: 43

```
atacgggagc caacaccata gtgttgggcc aatacggtaa cgtgtccttg gagagcaggt    60
gtgacggat                                                            69
```

<210> SEQ ID NO 44
<211> LENGTH: 69
<212> TYPE: DNA
<213> ORGANISM: Artificial Sequence
<220> FEATURE:
<223> OTHER INFORMATION: chemically synthesized

<400> SEQUENCE: 44

```
atccgtcaca cctgctctcc aaggacacgt taccgtattg gcccaacact atggtgttgg    60
ctcccgtat                                                            69
```

<210> SEQ ID NO 45
<211> LENGTH: 72
<212> TYPE: DNA
<213> ORGANISM: Artificial Sequence
<220> FEATURE:
<223> OTHER INFORMATION: chemically synthesized

<400> SEQUENCE: 45

```
atacgggagc caacaccaac tgaaaactaa gacttggttc caaatccttt ctctagagca    60
ggtgtgacgg at                                                        72
```

<210> SEQ ID NO 46
<211> LENGTH: 72
<212> TYPE: DNA
<213> ORGANISM: Artificial Sequence
<220> FEATURE:
<223> OTHER INFORMATION: chemically synthesized

<400> SEQUENCE: 46

```
atccgtcaca cctgctctag agaaaggatt tggaaccaag tcttagtttt cagttggtgt    60
tggctcccgt at                                                        72
```

<210> SEQ ID NO 47
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 47
atacgggagc caacaccagg ccggagacta gccgaaccct acttttact gtgtagagca    60 ggtgtgacgg at                                                      72

<210> SEQ ID NO 48
<211> LENGTH: 72
<212> TYPE: DNA
<213> ORGANISM: Artificial Sequence
<220> FEATURE:
<223> OTHER INFORMATION: chemically synthesized

<400> SEQUENCE: 48
atccgtcaca cctgctctac acagtaaaaa gtagggttcg gctagtctcc ggcctggtgt    60
tggctcccgt at                                                      72

<210> SEQ ID NO 49
<211> LENGTH: 72
<212> TYPE: DNA
<213> ORGANISM: Artificial Sequence
<220> FEATURE:
<223> OTHER INFORMATION: chemically synthesized

<400> SEQUENCE: 49
atacgggagc caacaccacg tgctgactat actattcaaa acaacaccc taggagagca    60 ggtgtgacgg at                                                      72

<210> SEQ ID NO 50
<211> LENGTH: 72
<212> TYPE: DNA
<213> ORGANISM: Artificial Sequence
<220> FEATURE:
<223> OTHER INFORMATION: chemically synthesized

<400> SEQUENCE: 50
atccgtcaca cctgctctcc tagggtgttg tttttgaata gtatagtcag cacgtggtgt    60
tggctcccgt at                                                      72

<210> SEQ ID NO 51
<211> LENGTH: 72
<212> TYPE: DNA
<213> ORGANISM: Artificial Sequence
<220> FEATURE:
<223> OTHER INFORMATION: chemically synthesized

<400> SEQUENCE: 51
atacgggagc caacaccacg ccttgtctat tctcttagtt tcctgctact ccacagagca    60
ggtgtgacgg at                                                      72

<210> SEQ ID NO 52
<211> LENGTH: 72
<212> TYPE: DNA
<213> ORGANISM: Artificial Sequence
<220> FEATURE:
<223> OTHER INFORMATION: chemically synthesized

<400> SEQUENCE: 52
atccgtcaca cctgctctgt ggagtagcag gaaactaaga gaatagacaa ggcgtggtgt    60
tggctcccgt at                                                      72
```

```
<210> SEQ ID NO 53
<211> LENGTH: 72
<212> TYPE: DNA
<213> ORGANISM: Artificial Sequence
<220> FEATURE:
<223> OTHER INFORMATION: chemically synthesized

<400> SEQUENCE: 53
atacgggagc caacaccagg atagttacca gtcccttgtt aaaaatttat atgcagagca    60
ggtgtgacgg at                                                       72

<210> SEQ ID NO 54
<211> LENGTH: 72
<212> TYPE: DNA
<213> ORGANISM: Artificial Sequence
<220> FEATURE:
<223> OTHER INFORMATION: chemically synthesized

<400> SEQUENCE: 54
atccgtcaca cctgctctgc atataaattt ttaacaaggg actggtaact atcctggtgt    60
tggctcccgt at                                                       72

<210> SEQ ID NO 55
<211> LENGTH: 71
<212> TYPE: DNA
<213> ORGANISM: Artificial Sequence
<220> FEATURE:
<223> OTHER INFORMATION: chemically synthesized

<400> SEQUENCE: 55
atacgggagc caacaccata gctttaggtt acttttcaga cactatatgt cccagagcag    60
gtgtgacgga t                                                        71

<210> SEQ ID NO 56
<211> LENGTH: 71
<212> TYPE: DNA
<213> ORGANISM: Artificial Sequence
<220> FEATURE:
<223> OTHER INFORMATION: chemically synthesized

<400> SEQUENCE: 56
atccgtcaca cctgctctgg gacatatagt gtctgaaaag taacctaaag ctatggtgtt    60
ggctcccgta t                                                        71

<210> SEQ ID NO 57
<211> LENGTH: 69
<212> TYPE: DNA
<213> ORGANISM: Artificial Sequence
<220> FEATURE:
<223> OTHER INFORMATION: chemically synthesized

<400> SEQUENCE: 57
atacgggagc caacaccaat gcccgcctcg atagagactg accagtatgt gagagcaggt    60
gtgacggat                                                           69

<210> SEQ ID NO 58
<211> LENGTH: 69
<212> TYPE: DNA
<213> ORGANISM: Artificial Sequence
<220> FEATURE:
<223> OTHER INFORMATION: chemically synthesized

<400> SEQUENCE: 58
atccgtcaca cctgctctca catactggtc agtctctatc gaggcgggca ttggtgttgg    60
```

```
ctcccgtat                                                              69

<210> SEQ ID NO 59
<211> LENGTH: 72
<212> TYPE: DNA
<213> ORGANISM: Artificial Sequence
<220> FEATURE:
<223> OTHER INFORMATION: chemically synthesized

<400> SEQUENCE: 59
atacgggagc caacaccacc tcatagttat gtaataacgc ttatcttgtc cggcagagca      60
ggtgtgacgg at                                                          72

<210> SEQ ID NO 60
<211> LENGTH: 72
<212> TYPE: DNA
<213> ORGANISM: Artificial Sequence
<220> FEATURE:
<223> OTHER INFORMATION: chemically synthesized

<400> SEQUENCE: 60
atccgtcaca cctgctctgc cggacaagat aagcgttatt acataactat gaggtggtgt      60
tggctcccgt at                                                          72

<210> SEQ ID NO 61
<211> LENGTH: 72
<212> TYPE: DNA
<213> ORGANISM: Artificial Sequence
<220> FEATURE:
<223> OTHER INFORMATION: chemically synthesized

<400> SEQUENCE: 61
atacgggagc caacaccacc catctcaacc accgtacctc actcggcgac ttacagagca      60
ggtgtgacgg at                                                          72

<210> SEQ ID NO 62
<211> LENGTH: 72
<212> TYPE: DNA
<213> ORGANISM: Artificial Sequence
<220> FEATURE:
<223> OTHER INFORMATION: chemically synthesized

<400> SEQUENCE: 62
atccgtcaca cctgctctgt aagtcgccga gtgaggtacg gtggttgaga tgggtggtgt      60
tggctcccgt at                                                          72

<210> SEQ ID NO 63
<211> LENGTH: 72
<212> TYPE: DNA
<213> ORGANISM: Artificial Sequence
<220> FEATURE:
<223> OTHER INFORMATION: chemically synthesized

<400> SEQUENCE: 63
atacgggagc caacaccacg ctgtccccaa gacattcagt ctttgcaacc cggtagagca      60
ggtgtgacgg at                                                          72

<210> SEQ ID NO 64
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 64
atccgtcaca cctgctctac cgggttgcaa agactgaatg tcttggggac agcgtggtgt    60
tggctcccgt at                                                        72

<210> SEQ ID NO 65
<211> LENGTH: 72
<212> TYPE: DNA
<213> ORGANISM: Artificial Sequence
<220> FEATURE:
<223> OTHER INFORMATION: chemically synthesized

<400> SEQUENCE: 65
atacgggagc caacaccacg ccatcccctt gacactacca ctaaatcggc ggtcagagca    60
ggtgtgacgg at                                                        72

<210> SEQ ID NO 66
<211> LENGTH: 72
<212> TYPE: DNA
<213> ORGANISM: Artificial Sequence
<220> FEATURE:
<223> OTHER INFORMATION: chemically synthesized

<400> SEQUENCE: 66
atccgtcaca cctgctctga ccgccgattt agtggtagtg tcaaggggat ggcgtggtgt    60
tggctcccgt at                                                        72

<210> SEQ ID NO 67
<211> LENGTH: 72
<212> TYPE: DNA
<213> ORGANISM: Artificial Sequence
<220> FEATURE:
<223> OTHER INFORMATION: chemically synthesized

<400> SEQUENCE: 67
atacgggagc caacaccaat agatggataa gggggaaact gccattcggt tagtagagca    60
ggtgtgacgg at                                                        72

<210> SEQ ID NO 68
<211> LENGTH: 72
<212> TYPE: DNA
<213> ORGANISM: Artificial Sequence
<220> FEATURE:
<223> OTHER INFORMATION: chemically synthesized

<400> SEQUENCE: 68
atccgtcaca cctgctctac taaccgaatg gcagtttccc ccttatccat ctattggtgt    60
tggctcccgt at                                                        72

<210> SEQ ID NO 69
<211> LENGTH: 72
<212> TYPE: DNA
<213> ORGANISM: Artificial Sequence
<220> FEATURE:
<223> OTHER INFORMATION: chemically synthesized

<400> SEQUENCE: 69
atacgggagc caacaccatt accaggacta actcgttttg cactggtctc agtcagagca    60
ggtgtgacgg at                                                        72

<210> SEQ ID NO 70
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 70
atccgtcaca cctgctctga ctgagaccag tgcaaaacga gttagtcctg gtaatggtgt      60
tggctcccgt at                                                         72

<210> SEQ ID NO 71
<211> LENGTH: 72
<212> TYPE: DNA
<213> ORGANISM: Artificial Sequence
<220> FEATURE:
<223> OTHER INFORMATION: chemically synthesized

<400> SEQUENCE: 71
atacgggagc caacaccacg gacgcgtaca gagtttattc ctgagatccg tgctagagca      60
ggtgtgacgg at                                                         72

<210> SEQ ID NO 72
<211> LENGTH: 72
<212> TYPE: DNA
<213> ORGANISM: Artificial Sequence
<220> FEATURE:
<223> OTHER INFORMATION: chemically synthesized

<400> SEQUENCE: 72
atccgtcaca cctgctctag cacggatctc aggaataaac tctgtacgcg tccgtggtgt      60
tggctcccgt at                                                         72

<210> SEQ ID NO 73
<211> LENGTH: 72
<212> TYPE: DNA
<213> ORGANISM: Artificial Sequence
<220> FEATURE:
<223> OTHER INFORMATION: chemically synthesized

<400> SEQUENCE: 73
atacgggagc caacaccaga aaaaaacaaa cccaaggaat tacaccacaa aagtagagca      60
ggtgtgacgg at                                                         72

<210> SEQ ID NO 74
<211> LENGTH: 72
<212> TYPE: DNA
<213> ORGANISM: Artificial Sequence
<220> FEATURE:
<223> OTHER INFORMATION: chemically synthesized

<400> SEQUENCE: 74
atccgtcaca cctgctctac ttttgtggtg taattccttg ggtttgtttt tttctggtgt      60
tggctcccgt at                                                         72

<210> SEQ ID NO 75
<211> LENGTH: 72
<212> TYPE: DNA
<213> ORGANISM: Artificial Sequence
<220> FEATURE:
<223> OTHER INFORMATION: chemically synthesized

<400> SEQUENCE: 75
atacgggagc caacaccaca tgtattacac agctcgcatc ttcttacctg gcccagagca      60
ggtgtgacgg at                                                         72
```

<210> SEQ ID NO 76
<211> LENGTH: 72
<212> TYPE: DNA
<213> ORGANISM: Artificial Sequence
<220> FEATURE:
<223> OTHER INFORMATION: chemically synthesized

<400> SEQUENCE: 76

```
atccgtcaca cctgctctgg gccaggtaag aagatgcgag ctgtgtaata catgtggtgt    60
tggctcccgt at                                                       72
```

<210> SEQ ID NO 77
<211> LENGTH: 72
<212> TYPE: DNA
<213> ORGANISM: Artificial Sequence
<220> FEATURE:
<223> OTHER INFORMATION: chemically synthesized

<400> SEQUENCE: 77

```
atacgggagc caacaccagc ctttccacct acactagcta tcttatctcc ttatagagca    60
ggtgtgacgg at                                                       72
```

<210> SEQ ID NO 78
<211> LENGTH: 72
<212> TYPE: DNA
<213> ORGANISM: Artificial Sequence
<220> FEATURE:
<223> OTHER INFORMATION: chemically synthesized

<400> SEQUENCE: 78

```
atccgtcaca cctgctctat aaggagataa gatagctagt gtaggtggaa aggctggtgt    60
tggctcccgt at                                                       72
```

<210> SEQ ID NO 79
<211> LENGTH: 72
<212> TYPE: DNA
<213> ORGANISM: Artificial Sequence
<220> FEATURE:
<223> OTHER INFORMATION: chemically synthesized

<400> SEQUENCE: 79

```
atacgggagc caacaccatt aggttggaat ttacattcat gttctgtggt cataagagca    60
ggtgtgacgg at                                                       72
```

<210> SEQ ID NO 80
<211> LENGTH: 72
<212> TYPE: DNA
<213> ORGANISM: Artificial Sequence
<220> FEATURE:
<223> OTHER INFORMATION: chemically synthesized

<400> SEQUENCE: 80

```
atccgtcaca cctgctctta tgaccacaga acatgaatgt aaattccaac ctaatggtgt    60
tggctcccgt at                                                       72
```

<210> SEQ ID NO 81
<211> LENGTH: 72
<212> TYPE: DNA
<213> ORGANISM: Artificial Sequence
<220> FEATURE:
<223> OTHER INFORMATION: chemically synthesized

<400> SEQUENCE: 81

```
atacgggagc caacaccaga gcacactaat catggcggcc cggcgcatcc cgacagagca    60
ggtgtgacgg at                                                       72

<210> SEQ ID NO 82
<211> LENGTH: 72
<212> TYPE: DNA
<213> ORGANISM: Artificial Sequence
<220> FEATURE:
<223> OTHER INFORMATION: chemically synthesized

<400> SEQUENCE: 82
atccgtcaca cctgctctgt cgggatgcgc cgggccgcca tgattagtgt gctctggtgt    60
tggctcccgt at                                                       72

<210> SEQ ID NO 83
<211> LENGTH: 71
<212> TYPE: DNA
<213> ORGANISM: Artificial Sequence
<220> FEATURE:
<223> OTHER INFORMATION: chemically synthesized

<400> SEQUENCE: 83
atacgggagc caacaccaaa ctagacaacc gcccttatac acactgtacc agtagagcag    60
gtgtgacgga t                                                        71

<210> SEQ ID NO 84
<211> LENGTH: 71
<212> TYPE: DNA
<213> ORGANISM: Artificial Sequence
<220> FEATURE:
<223> OTHER INFORMATION: chemically synthesized

<400> SEQUENCE: 84
atccgtcaca cctgctctac tggtacagtg tgtataaggg cggttgtcta gtttggtgtt    60
ggctcccgta t                                                        71

<210> SEQ ID NO 85
<211> LENGTH: 72
<212> TYPE: DNA
<213> ORGANISM: Artificial Sequence
<220> FEATURE:
<223> OTHER INFORMATION: chemically synthesized

<400> SEQUENCE: 85
atacgggagc caacaccagc atccccgaat aaataatgct gcgctgttaa agatagagca    60
ggtgtgacgg at                                                       72

<210> SEQ ID NO 86
<211> LENGTH: 72
<212> TYPE: DNA
<213> ORGANISM: Artificial Sequence
<220> FEATURE:
<223> OTHER INFORMATION: chemically synthesized

<400> SEQUENCE: 86
atccgtcaca cctgctctat ctttaacagc gcagcattat ttattcgggg atgctggtgt    60
tggctcccgt at                                                       72

<210> SEQ ID NO 87
<211> LENGTH: 70
<212> TYPE: DNA
<213> ORGANISM: Artificial Sequence
```

```
<220> FEATURE:
<223> OTHER INFORMATION: chemically synthesized

<400> SEQUENCE: 87
atacgggagc caacaccaaa ttcctcgttg acccctaact gtactcttag ccagagcagg    60
tgtgacggat                                                          70

<210> SEQ ID NO 88
<211> LENGTH: 70
<212> TYPE: DNA
<213> ORGANISM: Artificial Sequence
<220> FEATURE:
<223> OTHER INFORMATION: chemically synthesized

<400> SEQUENCE: 88
atccgtcaca cctgctctgg ctaagagtac agttaggggt caacgaggaa tttggtgttg    60
gctcccgtat                                                          70

<210> SEQ ID NO 89
<211> LENGTH: 72
<212> TYPE: DNA
<213> ORGANISM: Artificial Sequence
<220> FEATURE:
<223> OTHER INFORMATION: chemically synthesized

<400> SEQUENCE: 89
atacgggagc caacaccacc cattctgaga ccccccgcgc atgtattggt cttgagagca    60
ggtgtgacgg at                                                       72

<210> SEQ ID NO 90
<211> LENGTH: 72
<212> TYPE: DNA
<213> ORGANISM: Artificial Sequence
<220> FEATURE:
<223> OTHER INFORMATION: chemically synthesized

<400> SEQUENCE: 90
atccgtcaca cctgctctca agaccaatac atgcgcgggg ggtctcagaa tgggtggtgt    60
tggctcccgt at                                                       72

<210> SEQ ID NO 91
<211> LENGTH: 72
<212> TYPE: DNA
<213> ORGANISM: Artificial Sequence
<220> FEATURE:
<223> OTHER INFORMATION: chemically synthesized

<400> SEQUENCE: 91
atacgggagc caacaccatg ctagtgcccc cacagacgca cactaaagta ttccagagca    60
ggtgtgacgg at                                                       72

<210> SEQ ID NO 92
<211> LENGTH: 72
<212> TYPE: DNA
<213> ORGANISM: Artificial Sequence
<220> FEATURE:
<223> OTHER INFORMATION: chemically synthesized

<400> SEQUENCE: 92
atccgtcaca cctgctctgg aatactttag tgtgcgtctg tggggcact agcatggtgt    60 tggctcccgt at                                                       72
```

```
<210> SEQ ID NO 93
<211> LENGTH: 71
<212> TYPE: DNA
<213> ORGANISM: Artificial Sequence
<220> FEATURE:
<223> OTHER INFORMATION: chemically synthesized

<400> SEQUENCE: 93
atacgggagc caacaccagg ccgtgcgcgc tcattttgag aaccactgcc cccagagcag    60
gtgtgacgga t                                                         71

<210> SEQ ID NO 94
<211> LENGTH: 71
<212> TYPE: DNA
<213> ORGANISM: Artificial Sequence
<220> FEATURE:
<223> OTHER INFORMATION: chemically synthesized

<400> SEQUENCE: 94
atccgtcaca cctgctctgg gggcagtggt tctcaaaatg agcgcgcacg gcctggtgtt    60
ggctcccgta t                                                         71

<210> SEQ ID NO 95
<211> LENGTH: 72
<212> TYPE: DNA
<213> ORGANISM: Artificial Sequence
<220> FEATURE:
<223> OTHER INFORMATION: chemically synthesized

<400> SEQUENCE: 95
atacgggagc caacaccagt actacccacg ggcttattac cccctcatcc ttgcagagca    60
ggtgtgacgg at                                                        72

<210> SEQ ID NO 96
<211> LENGTH: 72
<212> TYPE: DNA
<213> ORGANISM: Artificial Sequence
<220> FEATURE:
<223> OTHER INFORMATION: chemically synthesized

<400> SEQUENCE: 96
atccgtcaca cctgctctgc aaggatgagg gggtaataag cccgtgggta gtactggtgt    60
tggctcccgt at                                                        72

<210> SEQ ID NO 97
<211> LENGTH: 72
<212> TYPE: DNA
<213> ORGANISM: Artificial Sequence
<220> FEATURE:
<223> OTHER INFORMATION: chemically synthesized

<400> SEQUENCE: 97
atacgggagc caacaccatt atgttaacaa aggcatacgg caagctctaa ctgtagagca    60
ggtgtgacgg at                                                        72

<210> SEQ ID NO 98
<211> LENGTH: 72
<212> TYPE: DNA
<213> ORGANISM: Artificial Sequence
<220> FEATURE:
<223> OTHER INFORMATION: chemically synthesized

<400> SEQUENCE: 98
atccgtcaca cctgctctac agttagagct tgccgtatgc ctttgttaac ataatggtgt    60
```

-continued tggctcccgt at                                                          72

<210> SEQ ID NO 99
<211> LENGTH: 72
<212> TYPE: DNA
<213> ORGANISM: Artificial Sequence
<220> FEATURE:
<223> OTHER INFORMATION: chemically synthesized

<400> SEQUENCE: 99
atacgggagc caacaccacc tcaagatagc cgttcatccg actgtcgcca ttgtagagca      60
ggtgtgacgg at                                                          72

<210> SEQ ID NO 100
<211> LENGTH: 72
<212> TYPE: DNA
<213> ORGANISM: Artificial Sequence
<220> FEATURE:
<223> OTHER INFORMATION: chemically synthesized

<400> SEQUENCE: 100
atccgtcaca cctgctctac aatggcgaca gtcggatgaa cggctatctt gaggtggtgt      60
tggctcccgt at                                                          72

<210> SEQ ID NO 101
<211> LENGTH: 72
<212> TYPE: DNA
<213> ORGANISM: Artificial Sequence
<220> FEATURE:
<223> OTHER INFORMATION: chemically synthesized

<400> SEQUENCE: 101
atacgggagc caacaccaca taatggacaa tcccactggg cacgttctat aaccagagca      60
ggtgtgacgg at                                                          72

<210> SEQ ID NO 102
<211> LENGTH: 72
<212> TYPE: DNA
<213> ORGANISM: Artificial Sequence
<220> FEATURE:
<223> OTHER INFORMATION: chemically synthesized

<400> SEQUENCE: 102
atccgtcaca cctgctctgg ttatagaacg tgcccagtgg gattgtccat tatgtggtgt      60
tggctcccgt at                                                          72

<210> SEQ ID NO 103
<211> LENGTH: 72
<212> TYPE: DNA
<213> ORGANISM: Artificial Sequence
<220> FEATURE:
<223> OTHER INFORMATION: chemically synthesized

<400> SEQUENCE: 103
atacgggagc caacaccaag cccgagcccg ccgttatatc ccatcgagtt ccccagagca      60
ggtgtgacgg at                                                          72

<210> SEQ ID NO 104
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 104
atccgtcaca cctgctctgg ggaactcgat gggatataac ggcgggctcg ggcttggtgt    60
tggctcccgt at                                                        72

<210> SEQ ID NO 105
<211> LENGTH: 71
<212> TYPE: DNA
<213> ORGANISM: Artificial Sequence
<220> FEATURE:
<223> OTHER INFORMATION: chemically synthesized

<400> SEQUENCE: 105
atacgggagc caacaccatc ccaccgaata tccgctttcc tcgtcctcct ttcagagcag    60
gtgtgacgga t                                                         71

<210> SEQ ID NO 106
<211> LENGTH: 71
<212> TYPE: DNA
<213> ORGANISM: Artificial Sequence
<220> FEATURE:
<223> OTHER INFORMATION: chemically synthesized

<400> SEQUENCE: 106
atccgtcaca cctgctctga aggaggacg aggaaagcgg atattcggtg ggatggtgtt     60
ggctcccgta t                                                         71

<210> SEQ ID NO 107
<211> LENGTH: 72
<212> TYPE: DNA
<213> ORGANISM: Artificial Sequence
<220> FEATURE:
<223> OTHER INFORMATION: chemically synthesized

<400> SEQUENCE: 107
atacgggagc caacaccaat agatggataa gggggaaact gccattcggt tagtagagca    60
ggtgtgacgg at                                                        72

<210> SEQ ID NO 108
<211> LENGTH: 72
<212> TYPE: DNA
<213> ORGANISM: Artificial Sequence
<220> FEATURE:
<223> OTHER INFORMATION: chemically synthesized

<400> SEQUENCE: 108
atccgtcaca cctgctctac taaccgaatg gcagtttccc ccttatccat ctattggtgt    60
tggctcccgt at                                                        72

<210> SEQ ID NO 109
<211> LENGTH: 72
<212> TYPE: DNA
<213> ORGANISM: Artificial Sequence
<220> FEATURE:
<223> OTHER INFORMATION: chemically synthesized

<400> SEQUENCE: 109
atacgggagc caacaccaca tctacgccca agcctctatg tacaagtagc aacaagagca    60
ggtgtgacgg at                                                        72

<210> SEQ ID NO 110
<211> LENGTH: 72
```

```
<212> TYPE: DNA
<213> ORGANISM: Artificial Sequence
<220> FEATURE:
<223> OTHER INFORMATION: chemically synthesized

<400> SEQUENCE: 110
atccgtcaca cctgctcttg ttgctacttg tacatagagg cttgggcgta gatgtggtgt    60
tggctcccgt at                                                        72

<210> SEQ ID NO 111
<211> LENGTH: 71
<212> TYPE: DNA
<213> ORGANISM: Artificial Sequence
<220> FEATURE:
<223> OTHER INFORMATION: chemically synthesized

<400> SEQUENCE: 111
atacgggagc caacaccaat ctccactgtg aaccttatcg agtttttgt acgagagcag     60 gtgtgacgga t                                                         71

<210> SEQ ID NO 112
<211> LENGTH: 71
<212> TYPE: DNA
<213> ORGANISM: Artificial Sequence
<220> FEATURE:
<223> OTHER INFORMATION: chemically synthesized

<400> SEQUENCE: 112
atccgtcaca cctgctctcg tacaaaaaac tcgataaggt tcacagtgga gattggtgtt    60
ggctcccgta t                                                         71

<210> SEQ ID NO 113
<211> LENGTH: 72
<212> TYPE: DNA
<213> ORGANISM: Artificial Sequence
<220> FEATURE:
<223> OTHER INFORMATION: chemically synthesized

<400> SEQUENCE: 113
atacgggagc caacaccata ggctataccg cgttagactt tctgagtcgt cctcagagca    60
ggtgtgacgg at                                                        72

<210> SEQ ID NO 114
<211> LENGTH: 72
<212> TYPE: DNA
<213> ORGANISM: Artificial Sequence
<220> FEATURE:
<223> OTHER INFORMATION: chemically synthesized

<400> SEQUENCE: 114
atccgtcaca cctgctctga ggacgactca gaaagtctaa cgcggtatag cctatggtgt    60
tggctcccgt at                                                        72

<210> SEQ ID NO 115
<211> LENGTH: 72
<212> TYPE: DNA
<213> ORGANISM: Artificial Sequence
<220> FEATURE:
<223> OTHER INFORMATION: chemically synthesized

<400> SEQUENCE: 115
atacgggagc caacaccagc acgccctttt agtgtccaac tgaatcttca cctaagagca    60
ggtgtgacgg at                                                        72
```

```
<210> SEQ ID NO 116
<211> LENGTH: 72
<212> TYPE: DNA
<213> ORGANISM: Artificial Sequence
<220> FEATURE:
<223> OTHER INFORMATION: chemically synthesized

<400> SEQUENCE: 116
atccgtcaca cctgctctta ggtgaagatt cagttggaca ctaaaagggc gtgctggtgt    60
tggctcccgt at                                                       72

<210> SEQ ID NO 117
<211> LENGTH: 72
<212> TYPE: DNA
<213> ORGANISM: Artificial Sequence
<220> FEATURE:
<223> OTHER INFORMATION: chemically synthesized

<400> SEQUENCE: 117
atacgggagc caacaccatg cttttggagt atttcgcctc caagctactc ccctagagca    60
ggtgtgacgg at                                                       72

<210> SEQ ID NO 118
<211> LENGTH: 72
<212> TYPE: DNA
<213> ORGANISM: Artificial Sequence
<220> FEATURE:
<223> OTHER INFORMATION: chemically synthesized

<400> SEQUENCE: 118
atccgtcaca cctgctctag gggagtagct tggaggcgaa atactccaaa agcatggtgt    60
tggctcccgt at                                                       72

<210> SEQ ID NO 119
<211> LENGTH: 72
<212> TYPE: DNA
<213> ORGANISM: Artificial Sequence
<220> FEATURE:
<223> OTHER INFORMATION: chemically synthesized

<400> SEQUENCE: 119
atacgggagc caacaccatt gatcctgccg gttcgcccct tgttcccacc ttttagagca    60
ggtgtgacgg at                                                       72

<210> SEQ ID NO 120
<211> LENGTH: 72
<212> TYPE: DNA
<213> ORGANISM: Artificial Sequence
<220> FEATURE:
<223> OTHER INFORMATION: chemically synthesized

<400> SEQUENCE: 120
atccgtcaca cctgctctaa aaggtgggaa caagggcga accggcagga tcaatggtgt    60
tggctcccgt at                                                       72

<210> SEQ ID NO 121
<211> LENGTH: 72
<212> TYPE: DNA
<213> ORGANISM: Artificial Sequence
<220> FEATURE:
<223> OTHER INFORMATION: chemically synthesized

<400> SEQUENCE: 121
```

```
atacgggagc caacaccacc actgtttagg cacaacttgc tttcttagcc ccgcagagca    60
ggtgtgacgg at                                                       72

<210> SEQ ID NO 122
<211> LENGTH: 72
<212> TYPE: DNA
<213> ORGANISM: Artificial Sequence
<220> FEATURE:
<223> OTHER INFORMATION: chemically synthesized

<400> SEQUENCE: 122
atccgtcaca cctgctctgc ggggctaaga aagcaagttg tgcctaaaca gtggtggtgt    60
tggctcccgt at                                                       72

<210> SEQ ID NO 123
<211> LENGTH: 72
<212> TYPE: DNA
<213> ORGANISM: Artificial Sequence
<220> FEATURE:
<223> OTHER INFORMATION: chemically synthesized

<400> SEQUENCE: 123
atacgggagc caacaccacg cgtttattat gttccccatg attgccacgg ctacagagca    60
ggtgtgacgg at                                                       72

<210> SEQ ID NO 124
<211> LENGTH: 72
<212> TYPE: DNA
<213> ORGANISM: Artificial Sequence
<220> FEATURE:
<223> OTHER INFORMATION: chemically synthesized

<400> SEQUENCE: 124
atccgtcaca cctgctctgt agccgtggca atcatgggga acataataaa cgcgtggtgt    60
tggctcccgt at                                                       72

<210> SEQ ID NO 125
<211> LENGTH: 72
<212> TYPE: DNA
<213> ORGANISM: Artificial Sequence
<220> FEATURE:
<223> OTHER INFORMATION: chemically synthesized

<400> SEQUENCE: 125
atacgggagc caacaccata tactgccgca gtttgggccc gcagtccatg ggcaagagca    60
ggtgtgacgg at                                                       72

<210> SEQ ID NO 126
<211> LENGTH: 72
<212> TYPE: DNA
<213> ORGANISM: Artificial Sequence
<220> FEATURE:
<223> OTHER INFORMATION: chemically synthesized

<400> SEQUENCE: 126
atccgtcaca cctgctcttg cccatggact gcgggcccaa actgcggcag tatatggtgt    60
tggctcccgt at                                                       72

<210> SEQ ID NO 127
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 127
atacgggagc caacaccacc taagtaatgc caaaaacaac tcgggtacgc aatgagagca    60
ggtgtgacgg at                                                       72

<210> SEQ ID NO 128
<211> LENGTH: 72
<212> TYPE: DNA
<213> ORGANISM: Artificial Sequence
<220> FEATURE:
<223> OTHER INFORMATION: chemically synthesized

<400> SEQUENCE: 128
atccgtcaca cctgctctca ttgcgtaccc gagttgtttt tggcattact taggtggtgt    60
tggctcccgt at                                                       72

<210> SEQ ID NO 129
<211> LENGTH: 72
<212> TYPE: DNA
<213> ORGANISM: Artificial Sequence
<220> FEATURE:
<223> OTHER INFORMATION: chemically synthesized

<400> SEQUENCE: 129
atacgggagc caacaccact tctctgtgac cagtatacgt cccatttccc tattagagca    60
ggtgtgacgg at                                                       72

<210> SEQ ID NO 130
<211> LENGTH: 72
<212> TYPE: DNA
<213> ORGANISM: Artificial Sequence
<220> FEATURE:
<223> OTHER INFORMATION: chemically synthesized

<400> SEQUENCE: 130
atccgtcaca cctgctctaa tagggaaatg ggacgtatac tggtcacaga gaagtggtgt    60
tggctcccgt at                                                       72

<210> SEQ ID NO 131
<211> LENGTH: 72
<212> TYPE: DNA
<213> ORGANISM: Artificial Sequence
<220> FEATURE:
<223> OTHER INFORMATION: chemically synthesized

<400> SEQUENCE: 131
atacgggagc caacaccagg atacgttccg tgcatggatg tgctgcccca tgttagagca    60
ggtgtgacgg at                                                       72

<210> SEQ ID NO 132
<211> LENGTH: 72
<212> TYPE: DNA
<213> ORGANISM: Artificial Sequence
<220> FEATURE:
<223> OTHER INFORMATION: chemically synthesized

<400> SEQUENCE: 132
atccgtcaca cctgctctaa catggggcag cacatccatg cacggaacgt atcctggtgt    60
tggctcccgt at                                                       72
```

```
<210> SEQ ID NO 133
<211> LENGTH: 72
<212> TYPE: DNA
<213> ORGANISM: Artificial Sequence
<220> FEATURE:
<223> OTHER INFORMATION: chemically synthesized

<400> SEQUENCE: 133
atacgggagc caacaccacc attttcgttt tcttgagta tttcgacctt agtgagagca      60
ggtgtgacgg at                                                         72

<210> SEQ ID NO 134
<211> LENGTH: 72
<212> TYPE: DNA
<213> ORGANISM: Artificial Sequence
<220> FEATURE:
<223> OTHER INFORMATION: chemically synthesized

<400> SEQUENCE: 134
atccgtcaca cctgctctca ctaaggtcga aatactcaag aaaaacgaaa atggtggtgt      60
tggctcccgt at                                                         72

<210> SEQ ID NO 135
<211> LENGTH: 72
<212> TYPE: DNA
<213> ORGANISM: Artificial Sequence
<220> FEATURE:
<223> OTHER INFORMATION: chemically synthesized

<400> SEQUENCE: 135
atacgggagc caacaccatt cgaaacccat aatcttttcc tcactctgcg tattagagca      60
ggtgtgacgg at                                                         72

<210> SEQ ID NO 136
<211> LENGTH: 72
<212> TYPE: DNA
<213> ORGANISM: Artificial Sequence
<220> FEATURE:
<223> OTHER INFORMATION: chemically synthesized

<400> SEQUENCE: 136
atccgtcaca cctgctctaa tacgcagagt gaggaaaaga ttatgggttt cgaatggtgt      60
tggctcccgt at                                                         72

<210> SEQ ID NO 137
<211> LENGTH: 72
<212> TYPE: DNA
<213> ORGANISM: Artificial Sequence
<220> FEATURE:
<223> OTHER INFORMATION: chemically synthesized

<400> SEQUENCE: 137
atacgggagc caacaccacg catggggctc tccctattac gcaatccgtt gtagagagca      60
ggtgtgacgg at                                                         72

<210> SEQ ID NO 138
<211> LENGTH: 72
<212> TYPE: DNA
<213> ORGANISM: Artificial Sequence
<220> FEATURE:
<223> OTHER INFORMATION: chemically synthesized

<400> SEQUENCE: 138
atccgtcaca cctgctctct acaacggatt gcgtaatagg gagagcccca tgcgtggtgt      60
```
tggctcccgt at                                                               72

<210> SEQ ID NO 139
<211> LENGTH: 72
<212> TYPE: DNA
<213> ORGANISM: Artificial Sequence
<220> FEATURE:
<223> OTHER INFORMATION: chemically synthesized

<400> SEQUENCE: 139
atacgggagc caacaccatc ttgtcctcgg tccgtctttg cattctggtc taaaagagca      60
ggtgtgacgg at                                                               72

<210> SEQ ID NO 140
<211> LENGTH: 72
<212> TYPE: DNA
<213> ORGANISM: Artificial Sequence
<220> FEATURE:
<223> OTHER INFORMATION: chemically synthesized

<400> SEQUENCE: 140
atccgtcaca cctgctcttt tagaccagaa tgcaaagacg gaccgaggac aagatggtgt      60
tggctcccgt at                                                               72

<210> SEQ ID NO 141
<211> LENGTH: 72
<212> TYPE: DNA
<213> ORGANISM: Artificial Sequence
<220> FEATURE:
<223> OTHER INFORMATION: chemically synthesized

<400> SEQUENCE: 141
atacgggagc caacaccacc gctgtaagtg cttgggtcga ccgcgcccgc tgccagagca      60
ggtgtgacgg at                                                               72

<210> SEQ ID NO 142
<211> LENGTH: 72
<212> TYPE: DNA
<213> ORGANISM: Artificial Sequence
<220> FEATURE:
<223> OTHER INFORMATION: chemically synthesized

<400> SEQUENCE: 142
atccgtcaca cctgctctgg cagcgggcgc ggtcgaccca agcacttaca gcggtggtgt      60
tggctcccgt at                                                               72

<210> SEQ ID NO 143
<211> LENGTH: 72
<212> TYPE: DNA
<213> ORGANISM: Artificial Sequence
<220> FEATURE:
<223> OTHER INFORMATION: chemically synthesized

<400> SEQUENCE: 143
atacgggagc caacaccagg tgacgcaggt gagtctgcct ccccatgtgc tcccagagca      60
ggtgtgacgg at                                                               72

<210> SEQ ID NO 144
<211> LENGTH: 72
<212> TYPE: DNA
<213> ORGANISM: Artificial Sequence
<220> FEATURE:
<223> OTHER INFORMATION: chemically synthesized

<400> SEQUENCE: 144
atccgtcaca cctgctctgg gagcacatgg ggaggcagac tcacctgcgt cacctggtgt    60
tggctcccgt at                                                        72

<210> SEQ ID NO 145
<211> LENGTH: 72
<212> TYPE: DNA
<213> ORGANISM: Artificial Sequence
<220> FEATURE:
<223> OTHER INFORMATION: chemically synthesized

<400> SEQUENCE: 145
atacgggagc caacaccaat agatggataa gggggaaact gccattcggt tagtagagca    60
ggtgtgacgg at                                                        72

<210> SEQ ID NO 146
<211> LENGTH: 72
<212> TYPE: DNA
<213> ORGANISM: Artificial Sequence
<220> FEATURE:
<223> OTHER INFORMATION: chemically synthesized

<400> SEQUENCE: 146
atccgtcaca cctgctctac taaccgaatg gcagtttccc ccttatccat ctattggtgt    60
tggctcccgt at                                                        72

<210> SEQ ID NO 147
<211> LENGTH: 72
<212> TYPE: DNA
<213> ORGANISM: Artificial Sequence
<220> FEATURE:
<223> OTHER INFORMATION: chemically synthesized

<400> SEQUENCE: 147
atacgggagc caacaccact tccgggctat accggggctc gcgcaattct gaccagagca    60
ggtgtgacgg at                                                        72

<210> SEQ ID NO 148
<211> LENGTH: 72
<212> TYPE: DNA
<213> ORGANISM: Artificial Sequence
<220> FEATURE:
<223> OTHER INFORMATION: chemically synthesized

<400> SEQUENCE: 148
atccgtcaca cctgctctgg tcagaattgc gcgagccccg gtatagcccg gaagtggtgt    60
tggctcccgt at                                                        72

<210> SEQ ID NO 149
<211> LENGTH: 72
<212> TYPE: DNA
<213> ORGANISM: Artificial Sequence
<220> FEATURE:
<223> OTHER INFORMATION: chemically synthesized

<400> SEQUENCE: 149
atacgggagc caacaccaat agatggataa gggggaaact gccattcggt tagtagagca    60
ggtgtgacgg at                                                        72

<210> SEQ ID NO 150
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 150
atccgtcaca cctgctctac taaccgaatg gcagtttccc ccttatccat ctattggtgt    60
tggctcccgt at                                                        72

<210> SEQ ID NO 151
<211> LENGTH: 72
<212> TYPE: DNA
<213> ORGANISM: Artificial Sequence
<220> FEATURE:
<223> OTHER INFORMATION: chemically synthesized

<400> SEQUENCE: 151
atacgggagc caacaccagt cttttattca tcatgatcgc tgacctacac cccaagagca    60
ggtgtgacgg at                                                        72

<210> SEQ ID NO 152
<211> LENGTH: 72
<212> TYPE: DNA
<213> ORGANISM: Artificial Sequence
<220> FEATURE:
<223> OTHER INFORMATION: chemically synthesized

<400> SEQUENCE: 152
atccgtcaca cctgctcttg gggtgtaggt cagcgatcat gatgaataaa agactggtgt    60
tggctcccgt at                                                        72

<210> SEQ ID NO 153
<211> LENGTH: 72
<212> TYPE: DNA
<213> ORGANISM: Artificial Sequence
<220> FEATURE:
<223> OTHER INFORMATION: chemically synthesized

<400> SEQUENCE: 153
atacgggagc caacaccact tcaaaagtca gatacaaaga cagagattgg acttagagca    60
ggtgtgacgg at                                                        72

<210> SEQ ID NO 154
<211> LENGTH: 72
<212> TYPE: DNA
<213> ORGANISM: Artificial Sequence
<220> FEATURE:
<223> OTHER INFORMATION: chemically synthesized

<400> SEQUENCE: 154
atccgtcaca cctgctctaa gtccaatctc tgtctttgta tctgactttt gaagtggtgt    60
tggctcccgt at                                                        72

<210> SEQ ID NO 155
<211> LENGTH: 72
<212> TYPE: DNA
<213> ORGANISM: Artificial Sequence
<220> FEATURE:
<223> OTHER INFORMATION: chemically synthesized

<400> SEQUENCE: 155
atacgggagc caacaccatt atgttaacaa aggcatacgg caagctctaa ctgtagagca    60
ggtgtgacgg at                                                        72
```

<210> SEQ ID NO 156
<211> LENGTH: 72
<212> TYPE: DNA
<213> ORGANISM: Artificial Sequence
<220> FEATURE:
<223> OTHER INFORMATION: chemically synthesized

<400> SEQUENCE: 156
atccgtcaca cctgctctac agttagagct tgccgtatgc ctttgttaac ataatggtgt    60
tggctcccgt at                                                        72

<210> SEQ ID NO 157
<211> LENGTH: 72
<212> TYPE: DNA
<213> ORGANISM: Artificial Sequence
<220> FEATURE:
<223> OTHER INFORMATION: chemically synthesized

<400> SEQUENCE: 157
atacgggagc caacaccata atattacaat gccagaatct acacataatc ctatagagca    60
ggtgtgacgg at                                                        72

<210> SEQ ID NO 158
<211> LENGTH: 72
<212> TYPE: DNA
<213> ORGANISM: Artificial Sequence
<220> FEATURE:
<223> OTHER INFORMATION: chemically synthesized

<400> SEQUENCE: 158
atccgtcaca cctgctctat aggattatgt gtagattctg gcattgtaat attatggtgt    60
tggctcccgt at                                                        72

<210> SEQ ID NO 159
<211> LENGTH: 72
<212> TYPE: DNA
<213> ORGANISM: Artificial Sequence
<220> FEATURE:
<223> OTHER INFORMATION: chemically synthesized

<400> SEQUENCE: 159
atacgggagc caacaccatt atgttaacaa aggcatacgg caagctctaa ctgtagagca    60
ggtgtgacgg at                                                        72

<210> SEQ ID NO 160
<211> LENGTH: 72
<212> TYPE: DNA
<213> ORGANISM: Artificial Sequence
<220> FEATURE:
<223> OTHER INFORMATION: chemically synthesized

<400> SEQUENCE: 160
atccgtcaca cctgctctac agttagagct tgccgtatgc ctttgttaac ataatggtgt    60
tggctcccgt at                                                        72

<210> SEQ ID NO 161
<211> LENGTH: 72
<212> TYPE: DNA
<213> ORGANISM: Artificial Sequence
<220> FEATURE:
<223> OTHER INFORMATION: chemically synthesized

<400> SEQUENCE: 161

```
atacgggagc caacaccact tgacgccgtg gcaacacgct gacgagcttt acccagagca    60
ggtgtgacgg at                                                        72

<210> SEQ ID NO 162
<211> LENGTH: 72
<212> TYPE: DNA
<213> ORGANISM: Artificial Sequence
<220> FEATURE:
<223> OTHER INFORMATION: chemically synthesized

<400> SEQUENCE: 162
atccgtcaca cctgctctgg gtaaagctcg tcagcgtgtt gccacggcgt caagtggtgt    60
tggctcccgt at                                                        72

<210> SEQ ID NO 163
<211> LENGTH: 72
<212> TYPE: DNA
<213> ORGANISM: Artificial Sequence
<220> FEATURE:
<223> OTHER INFORMATION: chemically synthesized

<400> SEQUENCE: 163
atacgggagc caacaccagc caactcacta ttacttagta accctaacga tggcagagca    60
ggtgtgacgg at                                                        72

<210> SEQ ID NO 164
<211> LENGTH: 72
<212> TYPE: DNA
<213> ORGANISM: Artificial Sequence
<220> FEATURE:
<223> OTHER INFORMATION: chemically synthesized

<400> SEQUENCE: 164
atccgtcaca cctgctctgc catcgttagg gttactaagt aatagtgagt tggctggtgt    60
tggctcccgt at                                                        72

<210> SEQ ID NO 165
<211> LENGTH: 72
<212> TYPE: DNA
<213> ORGANISM: Artificial Sequence
<220> FEATURE:
<223> OTHER INFORMATION: chemically synthesized

<400> SEQUENCE: 165
atacgggagc caacaccata cgatccaatg atggaccgt gcggactgat ttacagagca    60
ggtgtgacgg at                                                        72

<210> SEQ ID NO 166
<211> LENGTH: 72
<212> TYPE: DNA
<213> ORGANISM: Artificial Sequence
<220> FEATURE:
<223> OTHER INFORMATION: chemically synthesized

<400> SEQUENCE: 166
atccgtcaca cctgctctgt aaatcagtcc gcacgggtcc atcattggat cgtatggtgt    60
tggctcccgt at                                                        72

<210> SEQ ID NO 167
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 167
atacgggagc caacaccatt ccatctccat gtagctaaag tcgatactcc atccagagca    60
ggtgtgacgg at                                                        72

<210> SEQ ID NO 168
<211> LENGTH: 72
<212> TYPE: DNA
<213> ORGANISM: Artificial Sequence
<220> FEATURE:
<223> OTHER INFORMATION: chemically synthesized

<400> SEQUENCE: 168
atccgtcaca cctgctctgg atggagtatc gactttagct acatggagat ggaatggtgt    60
tggctcccgt at                                                        72

<210> SEQ ID NO 169
<211> LENGTH: 72
<212> TYPE: DNA
<213> ORGANISM: Artificial Sequence
<220> FEATURE:
<223> OTHER INFORMATION: chemically synthesized

<400> SEQUENCE: 169
atacgggagc caacaccaca cagaggacgg ttcgtcagat gccgtttgcc acgaagagca    60
ggtgtgacgg at                                                        72

<210> SEQ ID NO 170
<211> LENGTH: 72
<212> TYPE: DNA
<213> ORGANISM: Artificial Sequence
<220> FEATURE:
<223> OTHER INFORMATION: chemically synthesized

<400> SEQUENCE: 170
atccgtcaca cctgctcttc gtggcaaacg gcatctgacg aaccgtcctc tgtgtggtgt    60
tggctcccgt at                                                        72

<210> SEQ ID NO 171
<211> LENGTH: 72
<212> TYPE: DNA
<213> ORGANISM: Artificial Sequence
<220> FEATURE:
<223> OTHER INFORMATION: chemically synthesized

<400> SEQUENCE: 171
atacgggagc caacaccaaa aaaggtcttc tcccacgatg tgtccaatgc atccagagca    60
ggtgtgacgg at                                                        72

<210> SEQ ID NO 172
<211> LENGTH: 72
<212> TYPE: DNA
<213> ORGANISM: Artificial Sequence
<220> FEATURE:
<223> OTHER INFORMATION: chemically synthesized

<400> SEQUENCE: 172
atccgtcaca cctgctctgg atgcattgga cacatcgtgg gagaagacct tttttggtgt    60
tggctcccgt at                                                        72
```

```
<210> SEQ ID NO 173
<211> LENGTH: 71
<212> TYPE: DNA
<213> ORGANISM: Artificial Sequence
<220> FEATURE:
<223> OTHER INFORMATION: chemically synthesized

<400> SEQUENCE: 173
atacgggagc caacaccacc gcctcgaccg ctcggggccc ttaccctagc ttcagagcag      60
gtgtgacgga t                                                          71

<210> SEQ ID NO 174
<211> LENGTH: 71
<212> TYPE: DNA
<213> ORGANISM: Artificial Sequence
<220> FEATURE:
<223> OTHER INFORMATION: chemically synthesized

<400> SEQUENCE: 174
atccgtcaca cctgctctga agctagggta agggccccga gcggtcgagg cggtggtgtt      60
ggctcccgta t                                                          71

<210> SEQ ID NO 175
<211> LENGTH: 72
<212> TYPE: DNA
<213> ORGANISM: Artificial Sequence
<220> FEATURE:
<223> OTHER INFORMATION: chemically synthesized

<400> SEQUENCE: 175
atacgggagc caacaccacc acaaccgtag ggacccgcct ggtccccaac ctagagagca      60
ggtgtgacgg at                                                         72

<210> SEQ ID NO 176
<211> LENGTH: 72
<212> TYPE: DNA
<213> ORGANISM: Artificial Sequence
<220> FEATURE:
<223> OTHER INFORMATION: chemically synthesized

<400> SEQUENCE: 176
atccgtcaca cctgctctct aggttgggga ccaggcgggt ccctacggtt gtggtggtgt      60
tggctcccgt at                                                         72

<210> SEQ ID NO 177
<211> LENGTH: 72
<212> TYPE: DNA
<213> ORGANISM: Artificial Sequence
<220> FEATURE:
<223> OTHER INFORMATION: chemically synthesized

<400> SEQUENCE: 177
atacgggagc caacaccacc tcggatggtt atgatatagt ttacaatcat gaagagagca      60
ggtgtgacgg at                                                         72

<210> SEQ ID NO 178
<211> LENGTH: 72
<212> TYPE: DNA
<213> ORGANISM: Artificial Sequence
<220> FEATURE:
<223> OTHER INFORMATION: chemically synthesized

<400> SEQUENCE: 178
atccgtcaca cctgctctct tcatgattgt aaactatatc ataaccatcc gaggtggtgt      60
```

-continued tggctcccgt at                                                          72

<210> SEQ ID NO 179
<211> LENGTH: 72
<212> TYPE: DNA
<213> ORGANISM: Artificial Sequence
<220> FEATURE:
<223> OTHER INFORMATION: chemically synthesized

<400> SEQUENCE: 179
atacgggagc caacaccaca tagccaacct cagccacacc gactacgctt ggccagagca      60
ggtgtgacgg at                                                          72

<210> SEQ ID NO 180
<211> LENGTH: 72
<212> TYPE: DNA
<213> ORGANISM: Artificial Sequence
<220> FEATURE:
<223> OTHER INFORMATION: chemically synthesized

<400> SEQUENCE: 180
atccgtcaca cctgctctgg ccaagcgtag tcggtgtggc tgaggttggc tatgtggtgt      60
tggctcccgt at                                                          72

<210> SEQ ID NO 181
<211> LENGTH: 72
<212> TYPE: DNA
<213> ORGANISM: Artificial Sequence
<220> FEATURE:
<223> OTHER INFORMATION: chemically synthesized

<400> SEQUENCE: 181
atacgggagc caacaccatt tatctaatgg caactaggga tagtgaaaac taccagagca      60
ggtgtgacgg at                                                          72

<210> SEQ ID NO 182
<211> LENGTH: 72
<212> TYPE: DNA
<213> ORGANISM: Artificial Sequence
<220> FEATURE:
<223> OTHER INFORMATION: chemically synthesized

<400> SEQUENCE: 182
atccgtcaca cctgctctcc tcctaggaat gtagtcgggc ggataaagtg acaatggtgt      60
tggctcccgt at                                                          72

<210> SEQ ID NO 183
<211> LENGTH: 72
<212> TYPE: DNA
<213> ORGANISM: Artificial Sequence
<220> FEATURE:
<223> OTHER INFORMATION: chemically synthesized

<400> SEQUENCE: 183
atacgggagc caacaccatt gtcactttat ccgcccgact acattcctag gaggagagca      60
ggtgtgacgg at                                                          72

<210> SEQ ID NO 184
<211> LENGTH: 72
<212> TYPE: DNA
<213> ORGANISM: Artificial Sequence
<220> FEATURE:
<223> OTHER INFORMATION: chemically synthesized

<400> SEQUENCE: 184
atccgtcaca cctgctctcc tcctaggaat gtagtcgggc ggataaagtg acaatggtgt    60
tggctcccgt at    72

<210> SEQ ID NO 185
<211> LENGTH: 72
<212> TYPE: DNA
<213> ORGANISM: Artificial Sequence
<220> FEATURE:
<223> OTHER INFORMATION: chemically synthesized

<400> SEQUENCE: 185
atacgggagc caacaccacc ttcgacgcca acgacgaacg gctttgaaag gctaagagca    60
ggtgtgacgg at    72

<210> SEQ ID NO 186
<211> LENGTH: 72
<212> TYPE: DNA
<213> ORGANISM: Artificial Sequence
<220> FEATURE:
<223> OTHER INFORMATION: chemically synthesized

<400> SEQUENCE: 186
atccgtcaca cctgctctta gcctttcaaa gccgttcgtc gttggcgtcg aaggtggtgt    60
tggctcccgt at    72

<210> SEQ ID NO 187
<211> LENGTH: 72
<212> TYPE: DNA
<213> ORGANISM: Artificial Sequence
<220> FEATURE:
<223> OTHER INFORMATION: chemically synthesized

<400> SEQUENCE: 187
atacgggagc caacaccaat ggaagccgta ccttcacacc cgttatttaa aaacagagca    60
ggtgtgacgg at    72

<210> SEQ ID NO 188
<211> LENGTH: 72
<212> TYPE: DNA
<213> ORGANISM: Artificial Sequence
<220> FEATURE:
<223> OTHER INFORMATION: chemically synthesized

<400> SEQUENCE: 188
atccgtcaca cctgctctgt ttttaaataa cgggtgtgaa ggtacggctt ccattggtgt    60
tggctcccgt at    72

<210> SEQ ID NO 189
<211> LENGTH: 72
<212> TYPE: DNA
<213> ORGANISM: Artificial Sequence
<220> FEATURE:
<223> OTHER INFORMATION: chemically synthesized

<400> SEQUENCE: 189
atacgggagc caacaccacg ctggccggga ggcccgtcca agccattacc gtcaagagca    60
ggtgtgacgg at    72

<210> SEQ ID NO 190
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 190
atccgtcaca cctgctcttg acggtaatgg cttggacggg cctcccggcc agcgtggtgt      60
tggctcccgt at                                                          72

<210> SEQ ID NO 191
<211> LENGTH: 72
<212> TYPE: DNA
<213> ORGANISM: Artificial Sequence
<220> FEATURE:
<223> OTHER INFORMATION: chemically synthesized

<400> SEQUENCE: 191
atacgggagc caacaccaca tatcaccgca cgcctattcc atgtgacgaa tctaagagca      60
ggtgtgacgg at                                                          72

<210> SEQ ID NO 192
<211> LENGTH: 72
<212> TYPE: DNA
<213> ORGANISM: Artificial Sequence
<220> FEATURE:
<223> OTHER INFORMATION: chemically synthesized

<400> SEQUENCE: 192
atccgtcaca cctgctctta gattcgtcac atggaatagg cgtgcggtga tatgtggtgt      60
tggctcccgt at                                                          72

<210> SEQ ID NO 193
<211> LENGTH: 72
<212> TYPE: DNA
<213> ORGANISM: Artificial Sequence
<220> FEATURE:
<223> OTHER INFORMATION: chemically synthesized

<400> SEQUENCE: 193
atacgggagc caacaccacg gcgggcgggg catctcgtgg gggacgaagg cgcaagagca      60
ggtgtgacgg at                                                          72

<210> SEQ ID NO 194
<211> LENGTH: 72
<212> TYPE: DNA
<213> ORGANISM: Artificial Sequence
<220> FEATURE:
<223> OTHER INFORMATION: chemically synthesized

<400> SEQUENCE: 194
atccgtcaca cctgctcttg cgccttcgtc ccccacgaga tgccccgccc gccgtggtgt      60
tggctcccgt at                                                          72

<210> SEQ ID NO 195
<211> LENGTH: 72
<212> TYPE: DNA
<213> ORGANISM: Artificial Sequence
<220> FEATURE:
<223> OTHER INFORMATION: chemically synthesized

<400> SEQUENCE: 195
atacgggagc caacaccatc ctcctgcgac gtctggagaa cagcctctac tttaagagca      60
ggtgtgacgg at                                                          72
```

<210> SEQ ID NO 196
<211> LENGTH: 72
<212> TYPE: DNA
<213> ORGANISM: Artificial Sequence
<220> FEATURE:
<223> OTHER INFORMATION: chemically synthesized

<400> SEQUENCE: 196
atccgtcaca cctgctctta aagtagaggc tgttctccag acgtcgcagg aggatggtgt    60
tggctcccgt at    72

<210> SEQ ID NO 197
<211> LENGTH: 72
<212> TYPE: DNA
<213> ORGANISM: Artificial Sequence
<220> FEATURE:
<223> OTHER INFORMATION: chemically synthesized

<400> SEQUENCE: 197
atacgggagc caacaccaaa acccgcacta catctcctct gcccccttct gataagagca    60
ggtgtgacgg at    72

<210> SEQ ID NO 198
<211> LENGTH: 72
<212> TYPE: DNA
<213> ORGANISM: Artificial Sequence
<220> FEATURE:
<223> OTHER INFORMATION: chemically synthesized

<400> SEQUENCE: 198
atccgtcaca cctgctctta tcagaagggg gcagaggaga tgtagtgcgg gttttggtgt    60
tggctcccgt at    72

<210> SEQ ID NO 199
<211> LENGTH: 72
<212> TYPE: DNA
<213> ORGANISM: Artificial Sequence
<220> FEATURE:
<223> OTHER INFORMATION: chemically synthesized

<400> SEQUENCE: 199
atacgggagc caacaccagt ggtcttgttt tggatgttta gtgatgcggg ttctagagca    60
ggtgtgacgg at    72

<210> SEQ ID NO 200
<211> LENGTH: 72
<212> TYPE: DNA
<213> ORGANISM: Artificial Sequence
<220> FEATURE:
<223> OTHER INFORMATION: chemically synthesized

<400> SEQUENCE: 200
atccgtcaca cctgctctag aacccgcatc actaaacatc caaaacaaga ccactggtgt    60
tggctcccgt at    72

<210> SEQ ID NO 201
<211> LENGTH: 72
<212> TYPE: DNA
<213> ORGANISM: Artificial Sequence
<220> FEATURE:
<223> OTHER INFORMATION: chemically synthesized

<400> SEQUENCE: 201

```
atacgggagc caacaccatc tttcgtgata gctattaagg cctattcgta tcgtagagca    60
ggtgtgacgg at                                                       72

<210> SEQ ID NO 202
<211> LENGTH: 72
<212> TYPE: DNA
<213> ORGANISM: Artificial Sequence
<220> FEATURE:
<223> OTHER INFORMATION: chemically synthesized

<400> SEQUENCE: 202
atccgtcaca cctgctctac gatacgaata ggccttaata gctatcacga aagatggtgt    60
tggctcccgt at                                                       72

<210> SEQ ID NO 203
<211> LENGTH: 72
<212> TYPE: DNA
<213> ORGANISM: Artificial Sequence
<220> FEATURE:
<223> OTHER INFORMATION: chemically synthesized

<400> SEQUENCE: 203
atacgggagc caacaccata ctgaagccat acgtctgtcc aaccgtcata acttagagca    60
ggtgtgacgg at                                                       72

<210> SEQ ID NO 204
<211> LENGTH: 72
<212> TYPE: DNA
<213> ORGANISM: Artificial Sequence
<220> FEATURE:
<223> OTHER INFORMATION: chemically synthesized

<400> SEQUENCE: 204
atccgtcaca cctgctctaa gttatgacgg ttggacagac gtatggcttc agtatggtgt    60
tggctcccgt at                                                       72

<210> SEQ ID NO 205
<211> LENGTH: 72
<212> TYPE: DNA
<213> ORGANISM: Artificial Sequence
<220> FEATURE:
<223> OTHER INFORMATION: chemically synthesized

<400> SEQUENCE: 205
atacgggagc caacaccacc ctaaattcca gagtgtacaa gagaacgaac taccagagca    60
ggtgtgacgg at                                                       72

<210> SEQ ID NO 206
<211> LENGTH: 72
<212> TYPE: DNA
<213> ORGANISM: Artificial Sequence
<220> FEATURE:
<223> OTHER INFORMATION: chemically synthesized

<400> SEQUENCE: 206
atccgtcaca cctgctctgg tagttcgttc tcttgtacac tctggaattt agggtggtgt    60
tggctcccgt at                                                       72

<210> SEQ ID NO 207
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 207
atacgggagc caacaccact actcatatac cttatactat aaacaatctg cgcgagagca     60
ggtgtgacgg at                                                        72

<210> SEQ ID NO 208
<211> LENGTH: 72
<212> TYPE: DNA
<213> ORGANISM: Artificial Sequence
<220> FEATURE:
<223> OTHER INFORMATION: chemically synthesized

<400> SEQUENCE: 208
atccgtcaca cctgctctcg cgcagattgt ttatagtata aggtatatga gtagtggtgt     60
tggctcccgt at                                                        72

<210> SEQ ID NO 209
<211> LENGTH: 72
<212> TYPE: DNA
<213> ORGANISM: Artificial Sequence
<220> FEATURE:
<223> OTHER INFORMATION: chemically synthesized

<400> SEQUENCE: 209
atacgggagc caacaccaca ttcgtactag ccccggttgc ccgtcgaccg gacaagagca     60
ggtgtgacgg at                                                        72

<210> SEQ ID NO 210
<211> LENGTH: 72
<212> TYPE: DNA
<213> ORGANISM: Artificial Sequence
<220> FEATURE:
<223> OTHER INFORMATION: chemically synthesized

<400> SEQUENCE: 210
atacgggagc caacaccagg agggcgcgcc tatttcgcca attcgtccgc agcgagagca     60
ggtgtgacgg at                                                        72

<210> SEQ ID NO 211
<211> LENGTH: 72
<212> TYPE: DNA
<213> ORGANISM: Artificial Sequence
<220> FEATURE:
<223> OTHER INFORMATION: chemically synthesized

<400> SEQUENCE: 211
atccgtcaca cctgctcttg tccggtcgac gggcaaccgg ggctagtacg aatgtggtgt     60
tggctcccgt at                                                        72

<210> SEQ ID NO 212
<211> LENGTH: 72
<212> TYPE: DNA
<213> ORGANISM: Artificial Sequence
<220> FEATURE:
<223> OTHER INFORMATION: chemically synthesized

<400> SEQUENCE: 212
atccgtcaca cctgctctcg ctgcggacga attggcgaaa taggcgcgcc ctcctggtgt     60
tggctcccgt at                                                        72
```

```
<210> SEQ ID NO 213
<211> LENGTH: 72
<212> TYPE: DNA
<213> ORGANISM: Artificial Sequence
<220> FEATURE:
<223> OTHER INFORMATION: chemically synthesized

<400> SEQUENCE: 213
atacgggagc caacaccaca cattatcggc aactggcaag gctaaggtac tggtagagca      60
ggtgtgacgg at                                                         72

<210> SEQ ID NO 214
<211> LENGTH: 72
<212> TYPE: DNA
<213> ORGANISM: Artificial Sequence
<220> FEATURE:
<223> OTHER INFORMATION: chemically synthesized

<400> SEQUENCE: 214
atccgtcaca cctgctctac cagtacctta gccttgccag ttgccgataa tgtgtggtgt      60
tggctcccgt at                                                         72

<210> SEQ ID NO 215
<211> LENGTH: 72
<212> TYPE: DNA
<213> ORGANISM: Artificial Sequence
<220> FEATURE:
<223> OTHER INFORMATION: chemically synthesized

<400> SEQUENCE: 215
atacgggagc caacaccact ggcgacccac tcccctggta cgtcaccaca gcctagagca      60
ggtgtgacgg at                                                         72

<210> SEQ ID NO 216
<211> LENGTH: 72
<212> TYPE: DNA
<213> ORGANISM: Artificial Sequence
<220> FEATURE:
<223> OTHER INFORMATION: chemically synthesized

<400> SEQUENCE: 216
atccgtcaca cctgctctag gctgtggtga cgtaccaggg gagtgggtcg ccagtggtgt      60
tggctcccgt at                                                         72

<210> SEQ ID NO 217
<211> LENGTH: 72
<212> TYPE: DNA
<213> ORGANISM: Artificial Sequence
<220> FEATURE:
<223> OTHER INFORMATION: chemically synthesized

<400> SEQUENCE: 217
atacgggagc caacaccaag acaaccgagc taataggcat ttcaacacct gtccagagca      60
ggtgtgacgg at                                                         72

<210> SEQ ID NO 218
<211> LENGTH: 72
<212> TYPE: DNA
<213> ORGANISM: Artificial Sequence
<220> FEATURE:
<223> OTHER INFORMATION: chemically synthesized

<400> SEQUENCE: 218
atccgtcaca cctgctctgg acaggtgttg aaatgcctat tagctcggtt gtcttggtgt      60
```

```
tggctcccgt at                                                         72

<210> SEQ ID NO 219
<211> LENGTH: 72
<212> TYPE: DNA
<213> ORGANISM: Artificial Sequence
<220> FEATURE:
<223> OTHER INFORMATION: chemically synthesized

<400> SEQUENCE: 219
atacgggagc caacaccaga agaccatgtg aagtaaagac ttcaattatc agtcagagca     60
ggtgtgacgg at                                                         72

<210> SEQ ID NO 220
<211> LENGTH: 72
<212> TYPE: DNA
<213> ORGANISM: Artificial Sequence
<220> FEATURE:
<223> OTHER INFORMATION: chemically synthesized

<400> SEQUENCE: 220
atccgtcaca cctgctctga ctgataattg aagtctttac ttcacatggt cttctggtgt     60
tggctcccgt at                                                         72

<210> SEQ ID NO 221
<211> LENGTH: 72
<212> TYPE: DNA
<213> ORGANISM: Artificial Sequence
<220> FEATURE:
<223> OTHER INFORMATION: chemically synthesized

<400> SEQUENCE: 221
atacgggagc caacaccaca ataaatccgt gcgcgtgacg cgtttcatac agtcagagca     60
ggtgtgacgg at                                                         72

<210> SEQ ID NO 222
<211> LENGTH: 72
<212> TYPE: DNA
<213> ORGANISM: Artificial Sequence
<220> FEATURE:
<223> OTHER INFORMATION: chemically synthesized

<400> SEQUENCE: 222
atccgtcaca cctgctctga ctgtatgaaa cgcgtcacgc gcacggattt attgtggtgt     60
tggctcccgt at                                                         72

<210> SEQ ID NO 223
<211> LENGTH: 72
<212> TYPE: DNA
<213> ORGANISM: Artificial Sequence
<220> FEATURE:
<223> OTHER INFORMATION: chemically synthesized

<400> SEQUENCE: 223
atacgggagc caacaccact attggctata cattcgttgt gagaaacgca ccgcagagca     60
ggtgtgacgg at                                                         72

<210> SEQ ID NO 224
<211> LENGTH: 72
<212> TYPE: DNA
<213> ORGANISM: Artificial Sequence
<220> FEATURE:
<223> OTHER INFORMATION: chemically synthesized
```

```
<400> SEQUENCE: 224
atccgtcaca cctgctctgc ggtgcgtttc tcacaacgaa tgtatagcca atagtggtgt    60
tggctcccgt at                                                       72

<210> SEQ ID NO 225
<211> LENGTH: 72
<212> TYPE: DNA
<213> ORGANISM: Artificial Sequence
<220> FEATURE:
<223> OTHER INFORMATION: chemically synthesized

<400> SEQUENCE: 225
atacgggagc caacaccatg gggaccaact gtccggagag agtcctgtcg agggagagca    60
ggtgtgacgg at                                                       72

<210> SEQ ID NO 226
<211> LENGTH: 68
<212> TYPE: DNA
<213> ORGANISM: Artificial Sequence
<220> FEATURE:
<223> OTHER INFORMATION: chemically synthesized

<400> SEQUENCE: 226
atacgggagc caacaccaca tagacacaag atatatcata tattgctcgc agagcaggtg    60
tgacggat                                                            68

<210> SEQ ID NO 227
<211> LENGTH: 72
<212> TYPE: DNA
<213> ORGANISM: Artificial Sequence
<220> FEATURE:
<223> OTHER INFORMATION: chemically synthesized

<400> SEQUENCE: 227
atccgtcaca cctgctctcc ctcgacagga ctctctccgg acagttggtc cccatggtgt    60
tggctcccgt at                                                       72

<210> SEQ ID NO 228
<211> LENGTH: 68
<212> TYPE: DNA
<213> ORGANISM: Artificial Sequence
<220> FEATURE:
<223> OTHER INFORMATION: chemically synthesized

<400> SEQUENCE: 228
atccgtcaca cctgctctgc gagcaatata tgatatatct tgtgtctatg tggtgttggc    60
tcccgtat                                                            68

<210> SEQ ID NO 229
<211> LENGTH: 69
<212> TYPE: DNA
<213> ORGANISM: Artificial Sequence
<220> FEATURE:
<223> OTHER INFORMATION: chemically synthesized

<400> SEQUENCE: 229
atacgggagc caacaccatt gtagctgaca actgttttac atgaacactt cagagcaggt    60
gtgacggat                                                           69

<210> SEQ ID NO 230
<211> LENGTH: 69
```

```
<212> TYPE: DNA
<213> ORGANISM: Artificial Sequence
<220> FEATURE:
<223> OTHER INFORMATION: chemically synthesized

<400> SEQUENCE: 230
atccgtcaca cctgctctga agtgttcatg taaaacagtt gtcagctaca atggtgttgg      60
ctcccgtat                                                              69

<210> SEQ ID NO 231
<211> LENGTH: 72
<212> TYPE: DNA
<213> ORGANISM: Artificial Sequence
<220> FEATURE:
<223> OTHER INFORMATION: chemically synthesized

<400> SEQUENCE: 231
atacgggagc caacaccagg gtgccagcag attataattg aacaaaccag cgatagagca      60
ggtgtgacgg at                                                          72

<210> SEQ ID NO 232
<211> LENGTH: 72
<212> TYPE: DNA
<213> ORGANISM: Artificial Sequence
<220> FEATURE:
<223> OTHER INFORMATION: chemically synthesized

<400> SEQUENCE: 232
atccgtcaca cctgctctat cgctggtttg ttcaattata atctgctggc accctggtgt      60
tggctcccgt at                                                          72

<210> SEQ ID NO 233
<211> LENGTH: 72
<212> TYPE: DNA
<213> ORGANISM: Artificial Sequence
<220> FEATURE:
<223> OTHER INFORMATION: chemically synthesized

<400> SEQUENCE: 233
atacgggagc caacaccagc acatagaaaa aaaatacaac cacatcgatt gaccagagca      60
ggtgtgacgg at                                                          72

<210> SEQ ID NO 234
<211> LENGTH: 72
<212> TYPE: DNA
<213> ORGANISM: Artificial Sequence
<220> FEATURE:
<223> OTHER INFORMATION: chemically synthesized

<400> SEQUENCE: 234
atccgtcaca cctgctctgg tcaatcgatg tggttgtatt tttttctat gtgctggtgt       60 tggctcccgt at                                                          72

<210> SEQ ID NO 235
<211> LENGTH: 72
<212> TYPE: DNA
<213> ORGANISM: Artificial Sequence
<220> FEATURE:
<223> OTHER INFORMATION: chemically synthesized

<400> SEQUENCE: 235
atacgggagc caacaccaac caggtattgt ccaaaatgga acaaatgag gaatagagca       60 ggtgtgacgg at                                                          72
```

```
<210> SEQ ID NO 236
<211> LENGTH: 72
<212> TYPE: DNA
<213> ORGANISM: Artificial Sequence
<220> FEATURE:
<223> OTHER INFORMATION: chemically synthesized

<400> SEQUENCE: 236
atccgtcaca cctgctctat tcctcatttg tttccatttt ggacaatacc tggttggtgt      60
tggctcccgt at                                                         72

<210> SEQ ID NO 237
<211> LENGTH: 72
<212> TYPE: DNA
<213> ORGANISM: Artificial Sequence
<220> FEATURE:
<223> OTHER INFORMATION: chemically synthesized

<400> SEQUENCE: 237
atacgggagc caacaccaca cacaaaagga attgtatact cgcataaggc cgccagagca      60
ggtgtgacgg at                                                         72

<210> SEQ ID NO 238
<211> LENGTH: 72
<212> TYPE: DNA
<213> ORGANISM: Artificial Sequence
<220> FEATURE:
<223> OTHER INFORMATION: chemically synthesized

<400> SEQUENCE: 238
atccgtcaca cctgctctgg cggccttatg cgagtataca attccttttg tgtgtggtgt      60
tggctcccgt at                                                         72

<210> SEQ ID NO 239
<211> LENGTH: 72
<212> TYPE: DNA
<213> ORGANISM: Artificial Sequence
<220> FEATURE:
<223> OTHER INFORMATION: chemically synthesized

<400> SEQUENCE: 239
atacgggagc caacaccaga aacgtggact gtgtaggcaa acctattatt ttctagagca      60
ggtgtgacgg at                                                         72

<210> SEQ ID NO 240
<211> LENGTH: 72
<212> TYPE: DNA
<213> ORGANISM: Artificial Sequence
<220> FEATURE:
<223> OTHER INFORMATION: chemically synthesized

<400> SEQUENCE: 240
atccgtcaca cctgctctag aaaataatag gtttgcctac acagtccacg tttctggtgt      60
tggctcccgt at                                                         72

<210> SEQ ID NO 241
<211> LENGTH: 72
<212> TYPE: DNA
<213> ORGANISM: Artificial Sequence
<220> FEATURE:
<223> OTHER INFORMATION: chemically synthesized

<400> SEQUENCE: 241
```

```
atacgggagc caacaccagc gcaattgatg actaccctaa gaaatctatt ggccagagca    60
ggtgtgacgg at                                                        72

<210> SEQ ID NO 242
<211> LENGTH: 72
<212> TYPE: DNA
<213> ORGANISM: Artificial Sequence
<220> FEATURE:
<223> OTHER INFORMATION: chemically synthesized

<400> SEQUENCE: 242
atccgtcaca cctgctctgg ccaatagatt tcttagggta gtcatcaatt gcgctggtgt    60
tggctcccgt at                                                        72

<210> SEQ ID NO 243
<211> LENGTH: 72
<212> TYPE: DNA
<213> ORGANISM: Artificial Sequence
<220> FEATURE:
<223> OTHER INFORMATION: chemically synthesized

<400> SEQUENCE: 243
atacgggagc caacaccacg gccgaggtcc actaccccta tggctggccc ttccagagca    60
ggtgtgacgg at                                                        72

<210> SEQ ID NO 244
<211> LENGTH: 69
<212> TYPE: DNA
<213> ORGANISM: Artificial Sequence
<220> FEATURE:
<223> OTHER INFORMATION: chemically synthesized

<400> SEQUENCE: 244
atacgggagc caacaccagc ctacgggtgg atgatccgcg gtgttcgagt gttagagcag    60
gtgtgacgg                                                            69

<210> SEQ ID NO 245
<211> LENGTH: 72
<212> TYPE: DNA
<213> ORGANISM: Artificial Sequence
<220> FEATURE:
<223> OTHER INFORMATION: chemically synthesized

<400> SEQUENCE: 245
atccgtcaca cctgctctgg aagggccagc cataggggta gtggacctcg gccgtggtgt    60
tggctcccgt at                                                        72

<210> SEQ ID NO 246
<211> LENGTH: 69
<212> TYPE: DNA
<213> ORGANISM: Artificial Sequence
<220> FEATURE:
<223> OTHER INFORMATION: chemically synthesized

<400> SEQUENCE: 246
ccgtcacacc tgctctaaca ctcgaacacc gcggatcatc cacccgtagg ctggtgttgg    60
ctcccgtat                                                            69

<210> SEQ ID NO 247
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 247
atacgggagc caacaccatg cagtatccac cttctctttt ttctcactcc actgagagca    60
ggtgtgacgg at                                                        72

<210> SEQ ID NO 248
<211> LENGTH: 72
<212> TYPE: DNA
<213> ORGANISM: Artificial Sequence
<220> FEATURE:
<223> OTHER INFORMATION: chemically synthesized

<400> SEQUENCE: 248
atccgtcaca cctgctctca gtggagtgag aaaaaagaga aggtggatac tgcatggtgt    60
tggctcccgt at                                                        72

<210> SEQ ID NO 249
<211> LENGTH: 72
<212> TYPE: DNA
<213> ORGANISM: Artificial Sequence
<220> FEATURE:
<223> OTHER INFORMATION: chemically synthesized

<400> SEQUENCE: 249
atccgtcaca cctgctctcg aatgggacaa cttctcgata tctactatgg ttggtggtgt    60
tggctcccgt at                                                        72

<210> SEQ ID NO 250
<211> LENGTH: 72
<212> TYPE: DNA
<213> ORGANISM: Artificial Sequence
<220> FEATURE:
<223> OTHER INFORMATION: chemically synthesized

<400> SEQUENCE: 250
atacgggagc caacaccacc aaccatagta gatatcgaga agttgtccca ttcgagagca    60
ggtgtgacgg at                                                        72

<210> SEQ ID NO 251
<211> LENGTH: 71
<212> TYPE: DNA
<213> ORGANISM: Artificial Sequence
<220> FEATURE:
<223> OTHER INFORMATION: chemically synthesized

<400> SEQUENCE: 251
atacgggagc caacaccagg gatgggtaaa gaaagtcgcg agacgatgat gccagagcag    60
gtgtgacgga t                                                         71

<210> SEQ ID NO 252
<211> LENGTH: 71
<212> TYPE: DNA
<213> ORGANISM: Artificial Sequence
<220> FEATURE:
<223> OTHER INFORMATION: chemically synthesized

<400> SEQUENCE: 252
atccgtcaca cctgctctgg catcatcgtc tcgcgacttt ctttacccat ccctggtgtt    60
ggctcccgta t                                                         71
```

-continued

```
<210> SEQ ID NO 253
<211> LENGTH: 72
<212> TYPE: DNA
<213> ORGANISM: Artificial Sequence
<220> FEATURE:
<223> OTHER INFORMATION: chemically synthesized

<400> SEQUENCE: 253
atacgggagc caacaccacg acatccgttc tgaacacacg atagtgatga ttgtagagca    60
ggtgtgacgg at                                                       72

<210> SEQ ID NO 254
<211> LENGTH: 72
<212> TYPE: DNA
<213> ORGANISM: Artificial Sequence
<220> FEATURE:
<223> OTHER INFORMATION: chemically synthesized

<400> SEQUENCE: 254
atccgtcaca cctgctctac aatcatcact atcgtgtgtt cagaacggat gtcgtggtgt    60
tggctcccgt at                                                       72

<210> SEQ ID NO 255
<211> LENGTH: 72
<212> TYPE: DNA
<213> ORGANISM: Artificial Sequence
<220> FEATURE:
<223> OTHER INFORMATION: chemically synthesized

<400> SEQUENCE: 255
atacgggagc caacaccacg gtattgtaaa gaaatgaaat cagtaatata ttccagagca    60
ggtgtgacgg at                                                       72

<210> SEQ ID NO 256
<211> LENGTH: 72
<212> TYPE: DNA
<213> ORGANISM: Artificial Sequence
<220> FEATURE:
<223> OTHER INFORMATION: chemically synthesized

<400> SEQUENCE: 256
atccgtcaca cctgctctgg aatatattac tgatttcatt tctttacaat accgtggtgt    60
tggctcccgt at                                                       72

<210> SEQ ID NO 257
<211> LENGTH: 72
<212> TYPE: DNA
<213> ORGANISM: Artificial Sequence
<220> FEATURE:
<223> OTHER INFORMATION: chemically synthesized

<400> SEQUENCE: 257
atacgggagc caacaccata caaaaatccg aagttaagac agctcacgct tatcagagca    60
ggtgtgacgg at                                                       72

<210> SEQ ID NO 258
<211> LENGTH: 72
<212> TYPE: DNA
<213> ORGANISM: Artificial Sequence
<220> FEATURE:
<223> OTHER INFORMATION: chemically synthesized

<400> SEQUENCE: 258
atccgtcaca cctgctctga taagcgtgag ctgtcttaac ttcggatttt tgtatggtgt    60
```
tggctcccgt at                                                             72

<210> SEQ ID NO 259
<211> LENGTH: 72
<212> TYPE: DNA
<213> ORGANISM: Artificial Sequence
<220> FEATURE:
<223> OTHER INFORMATION: chemically synthesized

<400> SEQUENCE: 259
atacgggagc caacaccata catggcagct cctacagatc accactctaa gagtagagca      60
ggtgtgacgg at                                                             72

<210> SEQ ID NO 260
<211> LENGTH: 72
<212> TYPE: DNA
<213> ORGANISM: Artificial Sequence
<220> FEATURE:
<223> OTHER INFORMATION: chemically synthesized

<400> SEQUENCE: 260
atccgtcaca cctgctctac tcttagagtg gtgatctgta ggagctgcca tgtatggtgt      60
tggctcccgt at                                                             72

<210> SEQ ID NO 261
<211> LENGTH: 72
<212> TYPE: DNA
<213> ORGANISM: Artificial Sequence
<220> FEATURE:
<223> OTHER INFORMATION: chemically synthesized

<400> SEQUENCE: 261
atacgggagc caacaccaca actcaccagg acactcggcc gcccggtccc caatagagca      60
ggtgtgacgg at                                                             72

<210> SEQ ID NO 262
<211> LENGTH: 72
<212> TYPE: DNA
<213> ORGANISM: Artificial Sequence
<220> FEATURE:
<223> OTHER INFORMATION: chemically synthesized

<400> SEQUENCE: 262
atccgtcaca cctgctctat tggggaccgg gcggccgagt gtcctggtga gttgtggtgt      60
tggctcccgt at                                                             72

<210> SEQ ID NO 263
<211> LENGTH: 72
<212> TYPE: DNA
<213> ORGANISM: Artificial Sequence
<220> FEATURE:
<223> OTHER INFORMATION: chemically synthesized

<400> SEQUENCE: 263
atacgggagc caacaccagt tgacaacaca tgactctaca cgatatgtca cacaagagca      60
ggtgtgacgg at                                                             72

<210> SEQ ID NO 264
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 264
atccgtcaca cctgctcttg tgtgacatat cgtgtagagt catgtgttgt caactggtgt    60
tggctcccgt at                                                        72

<210> SEQ ID NO 265
<211> LENGTH: 72
<212> TYPE: DNA
<213> ORGANISM: Artificial Sequence
<220> FEATURE:
<223> OTHER INFORMATION: chemically synthesized

<400> SEQUENCE: 265
atacgggagc caacaccagg ctatgaagaa agaaaaatga gtaacacata acgcagagca    60
ggtgtgacgg at                                                        72

<210> SEQ ID NO 266
<211> LENGTH: 72
<212> TYPE: DNA
<213> ORGANISM: Artificial Sequence
<220> FEATURE:
<223> OTHER INFORMATION: chemically synthesized

<400> SEQUENCE: 266
atccgtcaca cctgctctgc gttatgtgtt actcattttt ctttcttcat agcctggtgt    60
tggctcccgt at                                                        72

<210> SEQ ID NO 267
<211> LENGTH: 72
<212> TYPE: DNA
<213> ORGANISM: Artificial Sequence
<220> FEATURE:
<223> OTHER INFORMATION: chemically synthesized

<400> SEQUENCE: 267
atacgggagc caacaccacg cccccctca ctactgtccc gcccccgcc gtggagagca      60 ggtgtgacgg at                                                        72

<210> SEQ ID NO 268
<211> LENGTH: 72
<212> TYPE: DNA
<213> ORGANISM: Artificial Sequence
<220> FEATURE:
<223> OTHER INFORMATION: chemically synthesized

<400> SEQUENCE: 268
atccgtcaca cctgctctcc acggcggggg gcgggacagt agtgaggggg ggcgtggtgt    60
tggctcccgt at                                                        72

<210> SEQ ID NO 269
<211> LENGTH: 72
<212> TYPE: DNA
<213> ORGANISM: Artificial Sequence
<220> FEATURE:
<223> OTHER INFORMATION: chemically synthesized

<400> SEQUENCE: 269
atacgggagc caacaccacc ggccaacgaa agacctcgct cactagacac ccctagagca    60
ggtgtgacgg at                                                        72

<210> SEQ ID NO 270
<211> LENGTH: 71
```

```
<212> TYPE: DNA
<213> ORGANISM: Artificial Sequence
<220> FEATURE:
<223> OTHER INFORMATION: chemically synthesized

<400> SEQUENCE: 270
atacgggagc caacaccacc agaaaatcaa tataacaacg tatgctggct ccgagagcag    60
gtgtgacgga t                                                        71

<210> SEQ ID NO 271
<211> LENGTH: 72
<212> TYPE: DNA
<213> ORGANISM: Artificial Sequence
<220> FEATURE:
<223> OTHER INFORMATION: chemically synthesized

<400> SEQUENCE: 271
atccgtcaca cctgctctag gggtgtctag tgagcgaggt ctttcgttgg ccggtggtgt    60
tggctcccgt at                                                       72

<210> SEQ ID NO 272
<211> LENGTH: 71
<212> TYPE: DNA
<213> ORGANISM: Artificial Sequence
<220> FEATURE:
<223> OTHER INFORMATION: chemically synthesized

<400> SEQUENCE: 272
atccgtcaca cctgctctcg gagccagcat acgttgttat attgattttc tggtggtgtt    60
ggctcccgta t                                                        71

<210> SEQ ID NO 273
<211> LENGTH: 72
<212> TYPE: DNA
<213> ORGANISM: Artificial Sequence
<220> FEATURE:
<223> OTHER INFORMATION: chemically synthesized

<400> SEQUENCE: 273
atacgggagc caacaccaat agatggataa gggggaaact gccattcggt tagtagagca    60
ggtgtgacgg at                                                       72

<210> SEQ ID NO 274
<211> LENGTH: 72
<212> TYPE: DNA
<213> ORGANISM: Artificial Sequence
<220> FEATURE:
<223> OTHER INFORMATION: chemically synthesized

<400> SEQUENCE: 274
atccgtcaca cctgctctac taaccgaatg gcagtttccc ccttatccat ctattggtgt    60
tggctcccgt at                                                       72

<210> SEQ ID NO 275
<211> LENGTH: 72
<212> TYPE: DNA
<213> ORGANISM: Artificial Sequence
<220> FEATURE:
<223> OTHER INFORMATION: chemically synthesized

<400> SEQUENCE: 275
atacgggagc caacaccaga ttgaagctca agcctaaagg tgaccaaagg tagaagagca    60
ggtgtgacgg at                                                       72
```

<210> SEQ ID NO 276
<211> LENGTH: 72
<212> TYPE: DNA
<213> ORGANISM: Artificial Sequence
<220> FEATURE:
<223> OTHER INFORMATION: chemically synthesized

<400> SEQUENCE: 276
atccgtcaca cctgctcttc tacctttggt cacctttagg cttgagcttc aatctggtgt    60
tggctcccgt at                                                       72

<210> SEQ ID NO 277
<211> LENGTH: 72
<212> TYPE: DNA
<213> ORGANISM: Artificial Sequence
<220> FEATURE:
<223> OTHER INFORMATION: chemically synthesized

<400> SEQUENCE: 277
atacgggagc caacaccaca ggagaggcag taaaagggtt ggctgcctgg gtagagagca    60
ggtgtgacgg at                                                       72

<210> SEQ ID NO 278
<211> LENGTH: 72
<212> TYPE: DNA
<213> ORGANISM: Artificial Sequence
<220> FEATURE:
<223> OTHER INFORMATION: chemically synthesized

<400> SEQUENCE: 278
atccgtcaca cctgctctct acccaggcag ccaacccttt tactgcctct cctgtggtgt    60
tggctcccgt at                                                       72

<210> SEQ ID NO 279
<211> LENGTH: 72
<212> TYPE: DNA
<213> ORGANISM: Artificial Sequence
<220> FEATURE:
<223> OTHER INFORMATION: chemically synthesized

<400> SEQUENCE: 279
atacgggagc caacaccatt attactgagc tgtgcgccgc tacctgccta gattagagca    60
ggtgtgacgg at                                                       72

<210> SEQ ID NO 280
<211> LENGTH: 72
<212> TYPE: DNA
<213> ORGANISM: Artificial Sequence
<220> FEATURE:
<223> OTHER INFORMATION: chemically synthesized

<400> SEQUENCE: 280
atccgtcaca cctgctctaa tctaggcagg tagcggcgca cagctcagta ataatggtgt    60
tggctcccgt at                                                       72

<210> SEQ ID NO 281
<211> LENGTH: 71
<212> TYPE: DNA
<213> ORGANISM: Artificial Sequence
<220> FEATURE:
<223> OTHER INFORMATION: chemically synthesized

<400> SEQUENCE: 281

```
atacgggagc caacaccaat gcgggcttcc tactccaacc caggaccttc accagagcag    60
gtgtgacgga t                                                         71

<210> SEQ ID NO 282
<211> LENGTH: 71
<212> TYPE: DNA
<213> ORGANISM: Artificial Sequence
<220> FEATURE:
<223> OTHER INFORMATION: chemically synthesized

<400> SEQUENCE: 282
atccgtcaca cctgctctgg tgaaggtcct gggttggagt aggaagcccg cattggtgtt    60
ggctcccgta t                                                         71

<210> SEQ ID NO 283
<211> LENGTH: 72
<212> TYPE: DNA
<213> ORGANISM: Artificial Sequence
<220> FEATURE:
<223> OTHER INFORMATION: chemically synthesized

<400> SEQUENCE: 283
atacgggagc caacaccacg cggctgtcta tgaccgggct tgttgtttct gctaagagca    60
ggtgtgacgg at                                                        72

<210> SEQ ID NO 284
<211> LENGTH: 72
<212> TYPE: DNA
<213> ORGANISM: Artificial Sequence
<220> FEATURE:
<223> OTHER INFORMATION: chemically synthesized

<400> SEQUENCE: 284
atccgtcaca cctgctctta gcagaaacaa caagcccggt catagacagc cgcgtggtgt    60
tggctcccgt at                                                        72

<210> SEQ ID NO 285
<211> LENGTH: 72
<212> TYPE: DNA
<213> ORGANISM: Artificial Sequence
<220> FEATURE:
<223> OTHER INFORMATION: chemically synthesized

<400> SEQUENCE: 285
atacgggagc caacaccaca ggagaggcag taaaagggtt ggctgcctgg gtagagagca    60
ggtgtgacgg at                                                        72

<210> SEQ ID NO 286
<211> LENGTH: 72
<212> TYPE: DNA
<213> ORGANISM: Artificial Sequence
<220> FEATURE:
<223> OTHER INFORMATION: chemically synthesized

<400> SEQUENCE: 286
atccgtcaca cctgctctct acccaggcag ccaaccctttt tactgcctct cctgtggtgt    60
tggctcccgt at                                                        72

<210> SEQ ID NO 287
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 287
atacgggagc caacaccacg aggattacaa ctttatgcgt gcaaccagac accaagagca      60
ggtgtgacgg at                                                          72

<210> SEQ ID NO 288
<211> LENGTH: 72
<212> TYPE: DNA
<213> ORGANISM: Artificial Sequence
<220> FEATURE:
<223> OTHER INFORMATION: chemically synthesized

<400> SEQUENCE: 288
atccgtcaca cctgctcttg gtgtctggtt gcacgcataa agttgtaatc ctcgtggtgt      60
tggctcccgt at                                                          72

<210> SEQ ID NO 289
<211> LENGTH: 72
<212> TYPE: DNA
<213> ORGANISM: Artificial Sequence
<220> FEATURE:
<223> OTHER INFORMATION: chemically synthesized

<400> SEQUENCE: 289
atacgggagc caacaccacc tacagatccg cgaaccagcc gactactcgt ccacagagca      60
ggtgtgacgg at                                                          72

<210> SEQ ID NO 290
<211> LENGTH: 72
<212> TYPE: DNA
<213> ORGANISM: Artificial Sequence
<220> FEATURE:
<223> OTHER INFORMATION: chemically synthesized

<400> SEQUENCE: 290
atccgtcaca cctgctctgt ggacgagtag tcggctggtt cgcggatctg taggtggtgt      60
tggctcccgt at                                                          72

<210> SEQ ID NO 291
<211> LENGTH: 59
<212> TYPE: DNA
<213> ORGANISM: Artificial Sequence
<220> FEATURE:
<223> OTHER INFORMATION: chemically synthesized

<400> SEQUENCE: 291
atacgggagc caacaccaca gctgatattg gatggtccgg cagagcaggt gtgacggat       59

<210> SEQ ID NO 292
<211> LENGTH: 59
<212> TYPE: DNA
<213> ORGANISM: Artificial Sequence
<220> FEATURE:
<223> OTHER INFORMATION: chemically synthesized

<400> SEQUENCE: 292
atccgtcaca cctgctctgc cggaccatcc aatatcagct gtggtgttgg ctcccgtat       59

<210> SEQ ID NO 293
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 293
atacgggagc caacaccaca ggagaggcag taaaagggtt ggctgcctgg gtagagagca    60
ggtgtgacgg at                                                       72

<210> SEQ ID NO 294
<211> LENGTH: 72
<212> TYPE: DNA
<213> ORGANISM: Artificial Sequence
<220> FEATURE:
<223> OTHER INFORMATION: chemically synthesized

<400> SEQUENCE: 294
atccgtcaca cctgctctct acccaggcag ccaacccttt tactgcctct cctgtggtgt    60
tggctcccgt at                                                       72

<210> SEQ ID NO 295
<211> LENGTH: 72
<212> TYPE: DNA
<213> ORGANISM: Artificial Sequence
<220> FEATURE:
<223> OTHER INFORMATION: chemically synthesized

<400> SEQUENCE: 295
atacgggagc caacaccaag ctctcacgtg acacagtgct ccgccgtcaa aatgagagca    60
ggtgtgacgg at                                                       72

<210> SEQ ID NO 296
<211> LENGTH: 72
<212> TYPE: DNA
<213> ORGANISM: Artificial Sequence
<220> FEATURE:
<223> OTHER INFORMATION: chemically synthesized

<400> SEQUENCE: 296
atccgtcaca cctgctctca ttttgacggc ggagcactgt gtcacgtgag agcttggtgt    60
tggctcccgt at                                                       72

<210> SEQ ID NO 297
<211> LENGTH: 72
<212> TYPE: DNA
<213> ORGANISM: Artificial Sequence
<220> FEATURE:
<223> OTHER INFORMATION: chemically synthesized

<400> SEQUENCE: 297
atacgggagc caacaccatc ccgcgcccac tgcttgtcac ctcttagccc ccgcagagca    60
ggtgtgacgg at                                                       72

<210> SEQ ID NO 298
<211> LENGTH: 72
<212> TYPE: DNA
<213> ORGANISM: Artificial Sequence
<220> FEATURE:
<223> OTHER INFORMATION: chemically synthesized

<400> SEQUENCE: 298
atccgtcaca cctgctctgc gggggctaag aggtgacaag cagtgggcgc gggatggtgt    60
tggctcccgt at                                                       72
```

```
<210> SEQ ID NO 299
<211> LENGTH: 72
<212> TYPE: DNA
<213> ORGANISM: Artificial Sequence
<220> FEATURE:
<223> OTHER INFORMATION: chemically synthesized

<400> SEQUENCE: 299
atacgggagc caacaccaac ccaataaact tattggacct acgctttgat gattagagca    60
ggtgtgacgg at                                                        72

<210> SEQ ID NO 300
<211> LENGTH: 72
<212> TYPE: DNA
<213> ORGANISM: Artificial Sequence
<220> FEATURE:
<223> OTHER INFORMATION: chemically synthesized

<400> SEQUENCE: 300
atccgtcaca cctgctctaa tcatcaaagc gtaggtccaa taagtttatt gggttggtgt    60
tggctcccgt at                                                        72

<210> SEQ ID NO 301
<211> LENGTH: 72
<212> TYPE: DNA
<213> ORGANISM: Artificial Sequence
<220> FEATURE:
<223> OTHER INFORMATION: chemically synthesized

<400> SEQUENCE: 301
atacgggagc caacaccaca ctgcatccct ctaccgtact tacattcctg acatagagca    60
ggtgtgacgg at                                                        72

<210> SEQ ID NO 302
<211> LENGTH: 72
<212> TYPE: DNA
<213> ORGANISM: Artificial Sequence
<220> FEATURE:
<223> OTHER INFORMATION: chemically synthesized

<400> SEQUENCE: 302
atccgtcaca cctgctctat gtcaggaatg taagtacggt agagggatgc agtgtggtgt    60
tggctcccgt at                                                        72

<210> SEQ ID NO 303
<211> LENGTH: 72
<212> TYPE: DNA
<213> ORGANISM: Artificial Sequence
<220> FEATURE:
<223> OTHER INFORMATION: chemically synthesized

<400> SEQUENCE: 303
atacgggagc caacaccatg tcaggacctc catcgcccgg gcccgccgcc gctgagagca    60
ggtgtgacgg at                                                        72

<210> SEQ ID NO 304
<211> LENGTH: 72
<212> TYPE: DNA
<213> ORGANISM: Artificial Sequence
<220> FEATURE:
<223> OTHER INFORMATION: chemically synthesized

<400> SEQUENCE: 304
atccgtcaca cctgctctca gcggcggcgg gcccgggcga tggaggtcct gacatggtgt    60
```

```
tggctcccgt at                                                             72

<210> SEQ ID NO 305
<211> LENGTH: 72
<212> TYPE: DNA
<213> ORGANISM: Artificial Sequence
<220> FEATURE:
<223> OTHER INFORMATION: chemically synthesized

<400> SEQUENCE: 305
atacgggagc caacaccacc ccgtcgccaa gcacttggct gggctctaac ggccagagca         60
ggtgtgacgg at                                                             72

<210> SEQ ID NO 306
<211> LENGTH: 72
<212> TYPE: DNA
<213> ORGANISM: Artificial Sequence
<220> FEATURE:
<223> OTHER INFORMATION: chemically synthesized

<400> SEQUENCE: 306
atccgtcaca cctgctctgg ccgttagagc ccagccaagt gcttggcgac ggggtggtgt         60
tggctcccgt at                                                             72

<210> SEQ ID NO 307
<211> LENGTH: 59
<212> TYPE: DNA
<213> ORGANISM: Artificial Sequence
<220> FEATURE:
<223> OTHER INFORMATION: chemically synthesized

<400> SEQUENCE: 307
atacgggagc caacaccaca gctgatatcg gatggtccgg cagagcaggt gtgacggat          59

<210> SEQ ID NO 308
<211> LENGTH: 59
<212> TYPE: DNA
<213> ORGANISM: Artificial Sequence
<220> FEATURE:
<223> OTHER INFORMATION: chemically synthesized

<400> SEQUENCE: 308
atccgtcaca cctgctctgc cggaccatcc gatatcagct gtggtgttgg ctcccgtat          59

<210> SEQ ID NO 309
<211> LENGTH: 72
<212> TYPE: DNA
<213> ORGANISM: Artificial Sequence
<220> FEATURE:
<223> OTHER INFORMATION: chemically synthesized

<400> SEQUENCE: 309
atacgggagc caacaccacc cgtggccttc acccagccag ggccccgtc tctgagagca         60 ggtgtgacgg at                                                             72

<210> SEQ ID NO 310
<211> LENGTH: 72
<212> TYPE: DNA
<213> ORGANISM: Artificial Sequence
<220> FEATURE:
<223> OTHER INFORMATION: chemically synthesized

<400> SEQUENCE: 310
atccgtcaca cctgctctca gagacggggc cctggctgg gtgaaggcca cgggtggtgt         60
```

```
tggctcccgt at                                                           72

<210> SEQ ID NO 311
<211> LENGTH: 72
<212> TYPE: DNA
<213> ORGANISM: Artificial Sequence
<220> FEATURE:
<223> OTHER INFORMATION: chemically synthesized

<400> SEQUENCE: 311
atacgggagc caacaccatg tctcttagga tacaaagcca aactgagccc gtgcagagca      60
ggtgtgacgg at                                                           72

<210> SEQ ID NO 312
<211> LENGTH: 72
<212> TYPE: DNA
<213> ORGANISM: Artificial Sequence
<220> FEATURE:
<223> OTHER INFORMATION: chemically synthesized

<400> SEQUENCE: 312
atccgtcaca cctgctctgc acgggctcag tttggctttg tatcctaaga gacatggtgt      60
tggctcccgt at                                                           72

<210> SEQ ID NO 313
<211> LENGTH: 72
<212> TYPE: DNA
<213> ORGANISM: Artificial Sequence
<220> FEATURE:
<223> OTHER INFORMATION: chemically synthesized

<400> SEQUENCE: 313
atacgggagc caacaccagt cacagtgtct ggccagaatg ccaagggaat cgttagagca      60
ggtgtgacgg at                                                           72

<210> SEQ ID NO 314
<211> LENGTH: 72
<212> TYPE: DNA
<213> ORGANISM: Artificial Sequence
<220> FEATURE:
<223> OTHER INFORMATION: chemically synthesized

<400> SEQUENCE: 314
atccgtcaca cctgctctaa cgattccctt ggcattctgg ccagacactg tgactggtgt      60
tggctcccgt at                                                           72

<210> SEQ ID NO 315
<211> LENGTH: 71
<212> TYPE: DNA
<213> ORGANISM: Artificial Sequence
<220> FEATURE:
<223> OTHER INFORMATION: chemically synthesized

<400> SEQUENCE: 315
atacgggagc caacaccaac actaatacta atgccattat gcgtgatcta tttagagcag      60
gtgtgacgga t                                                            71

<210> SEQ ID NO 316
<211> LENGTH: 71
<212> TYPE: DNA
<213> ORGANISM: Artificial Sequence
<220> FEATURE:
<223> OTHER INFORMATION: chemically synthesized
```

-continued

<400> SEQUENCE: 316
atccgtcaca cctgctctaa atagatcacg cataatggca ttagtattag tgttggtgtt    60
ggctcccgta t                                                          71

<210> SEQ ID NO 317
<211> LENGTH: 72
<212> TYPE: DNA
<213> ORGANISM: Artificial Sequence
<220> FEATURE:
<223> OTHER INFORMATION: chemically synthesized

<400> SEQUENCE: 317
atacgggagc caacaccata acaaataacc accctcaatg ctagatagtg gcttagagca    60
ggtgtgacgg at                                                         72

<210> SEQ ID NO 318
<211> LENGTH: 72
<212> TYPE: DNA
<213> ORGANISM: Artificial Sequence
<220> FEATURE:
<223> OTHER INFORMATION: chemically synthesized

<400> SEQUENCE: 318
atccgtcaca cctgctctaa gccactatct agcattgagg gtggttatttt gttatggtgt    60 tggctcccgt at                                                         72

<210> SEQ ID NO 319
<211> LENGTH: 72
<212> TYPE: DNA
<213> ORGANISM: Artificial Sequence
<220> FEATURE:
<223> OTHER INFORMATION: chemically synthesized

<400> SEQUENCE: 319
atacgggagc caacaccagc acttacccac ctataaggaa tattctagat cggaagagca    60
ggtgtgacgg at                                                         72

<210> SEQ ID NO 320
<211> LENGTH: 72
<212> TYPE: DNA
<213> ORGANISM: Artificial Sequence
<220> FEATURE:
<223> OTHER INFORMATION: chemically synthesized

<400> SEQUENCE: 320
atccgtcaca cctgctcttc cgatctagaa tattccttat aggtgggtaa gtgctggtgt    60
tggctcccgt at                                                         72

<210> SEQ ID NO 321
<211> LENGTH: 72
<212> TYPE: DNA
<213> ORGANISM: Artificial Sequence
<220> FEATURE:
<223> OTHER INFORMATION: chemically synthesized

<400> SEQUENCE: 321
atacgggagc caacaccatc gggcattaac atggaatatc cttccccagc gtctagagca    60
ggtgtgacgg at                                                         72

<210> SEQ ID NO 322
<211> LENGTH: 72

<212> TYPE: DNA
<213> ORGANISM: Artificial Sequence
<220> FEATURE:
<223> OTHER INFORMATION: chemically synthesized

<400> SEQUENCE: 322
atccgtcaca cctgctctag acgctgggga aggatattcc atgttaatgc ccgatggtgt    60
tggctcccgt at    72

<210> SEQ ID NO 323
<211> LENGTH: 72
<212> TYPE: DNA
<213> ORGANISM: Artificial Sequence
<220> FEATURE:
<223> OTHER INFORMATION: chemically synthesized

<400> SEQUENCE: 323
atacgggagc caacaccagt ccacacttga ccacaaaaca taatcccata ttgtagagca    60
ggtgtgacgg at    72

<210> SEQ ID NO 324
<211> LENGTH: 72
<212> TYPE: DNA
<213> ORGANISM: Artificial Sequence
<220> FEATURE:
<223> OTHER INFORMATION: chemically synthesized

<400> SEQUENCE: 324
atccgtcaca cctgctctac aatatgggat tatgttttgt ggtcaagtgt ggactggtgt    60
tggctcccgt at    72

<210> SEQ ID NO 325
<211> LENGTH: 72
<212> TYPE: DNA
<213> ORGANISM: Artificial Sequence
<220> FEATURE:
<223> OTHER INFORMATION: chemically synthesized

<400> SEQUENCE: 325
atacgggagc caacaccata agatagtaaa gctagagaca tctcagagca ggagagagca    60
ggtgtgacgg at    72

<210> SEQ ID NO 326
<211> LENGTH: 72
<212> TYPE: DNA
<213> ORGANISM: Artificial Sequence
<220> FEATURE:
<223> OTHER INFORMATION: chemically synthesized

<400> SEQUENCE: 326
atccgtcaca cctgctctct cctgctctga gatgtctcta gctttactat cttatggtgt    60
tggctcccgt at    72

<210> SEQ ID NO 327
<211> LENGTH: 72
<212> TYPE: DNA
<213> ORGANISM: Artificial Sequence
<220> FEATURE:
<223> OTHER INFORMATION: chemically synthesized

<400> SEQUENCE: 327
atacgggagc caacaccaaa ggcaacagtc tcttcctact attaaaacga aacgagagca    60
ggtgtgacgg at    72

<210> SEQ ID NO 328
<211> LENGTH: 72
<212> TYPE: DNA
<213> ORGANISM: Artificial Sequence
<220> FEATURE:
<223> OTHER INFORMATION: chemically synthesized

<400> SEQUENCE: 328
atccgtcaca cctgctctcg tttcgtttta atagtaggaa gagactgttg cctttggtgt    60
tggctcccgt at    72

<210> SEQ ID NO 329
<211> LENGTH: 72
<212> TYPE: DNA
<213> ORGANISM: Artificial Sequence
<220> FEATURE:
<223> OTHER INFORMATION: chemically synthesized

<400> SEQUENCE: 329
atacgggagc caacaccagc gtcataatat tcctgttgtg gccctattgg acggagagca    60
ggtgtgacgg at    72

<210> SEQ ID NO 330
<211> LENGTH: 72
<212> TYPE: DNA
<213> ORGANISM: Artificial Sequence
<220> FEATURE:
<223> OTHER INFORMATION: chemically synthesized

<400> SEQUENCE: 330
atccgtcaca cctgctctcc gtccaatagg gccacaacag gaatattatg acgctggtgt    60
tggctcccgt at    72

<210> SEQ ID NO 331
<211> LENGTH: 72
<212> TYPE: DNA
<213> ORGANISM: Artificial Sequence
<220> FEATURE:
<223> OTHER INFORMATION: chemically synthesized

<400> SEQUENCE: 331
atacgggagc caacaccaaa tatctaacca tacatttata caagtggttc atagagagca    60
ggtgtgacgg at    72

<210> SEQ ID NO 332
<211> LENGTH: 72
<212> TYPE: DNA
<213> ORGANISM: Artificial Sequence
<220> FEATURE:
<223> OTHER INFORMATION: chemically synthesized

<400> SEQUENCE: 332
atccgtcaca cctgctctct atgaaccact tgtataaatg tatggttaga tatttggtgt    60
tggctcccgt at    72

<210> SEQ ID NO 333
<211> LENGTH: 72
<212> TYPE: DNA
<213> ORGANISM: Artificial Sequence
<220> FEATURE:
<223> OTHER INFORMATION: chemically synthesized

<400> SEQUENCE: 333

```
atacgggagc caacaccaca agttcaacga gttgataaca caacatgacc gcccagagca    60
ggtgtgacgg at                                                        72

<210> SEQ ID NO 334
<211> LENGTH: 72
<212> TYPE: DNA
<213> ORGANISM: Artificial Sequence
<220> FEATURE:
<223> OTHER INFORMATION: chemically synthesized

<400> SEQUENCE: 334
atccgtcaca cctgctctgg gcggtcatgt tgtgttatca actcgttgaa cttgtggtgt    60
tggctcccgt at                                                        72

<210> SEQ ID NO 335
<211> LENGTH: 71
<212> TYPE: DNA
<213> ORGANISM: Artificial Sequence
<220> FEATURE:
<223> OTHER INFORMATION: chemically synthesized

<400> SEQUENCE: 335
atacgggagc caacaccact aataaaaatg aaaaacaccc ctcaacaccc atgagagcag    60
gtgtgacgga t                                                         71

<210> SEQ ID NO 336
<211> LENGTH: 71
<212> TYPE: DNA
<213> ORGANISM: Artificial Sequence
<220> FEATURE:
<223> OTHER INFORMATION: chemically synthesized

<400> SEQUENCE: 336
atccgtcaca cctgctctca tgggtgttga ggggtgtttt tcatttttat tagtggtgtt    60
ggctcccgta t                                                         71

<210> SEQ ID NO 337
<211> LENGTH: 72
<212> TYPE: DNA
<213> ORGANISM: Artificial Sequence
<220> FEATURE:
<223> OTHER INFORMATION: chemically synthesized

<400> SEQUENCE: 337
atacgggagc caacaccaca ttgagcgtaa gcaccacgcc ttctaggtcg agctagagca    60
ggtgtgacgg at                                                        72

<210> SEQ ID NO 338
<211> LENGTH: 72
<212> TYPE: DNA
<213> ORGANISM: Artificial Sequence
<220> FEATURE:
<223> OTHER INFORMATION: chemically synthesized

<400> SEQUENCE: 338
atccgtcaca cctgctctag ctcgacctag aaggcgtggt gcttacgctc aatgtggtgt    60
tggctcccgt at                                                        72

<210> SEQ ID NO 339
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 339
atacgggagc caacaccata gtcgttctga catgtacttt tgaggaaatg gtgcagagca    60
ggtgtgacgg at                                                        72

<210> SEQ ID NO 340
<211> LENGTH: 73
<212> TYPE: DNA
<213> ORGANISM: Artificial Sequence
<220> FEATURE:
<223> OTHER INFORMATION: chemically synthesized

<400> SEQUENCE: 340
ratccgtcac acctgctctg caccatttcc tcaaaagtac atgtcagaac gactatggtg    60
ttggctcccg tat                                                       73

<210> SEQ ID NO 341
<211> LENGTH: 72
<212> TYPE: DNA
<213> ORGANISM: Artificial Sequence
<220> FEATURE:
<223> OTHER INFORMATION: chemically synthesized

<400> SEQUENCE: 341
atacgggagc caacaccatt actcgctctg tatgcgcctc ccaccctctg atagagagca    60
ggtgtgacgg at                                                        72

<210> SEQ ID NO 342
<211> LENGTH: 72
<212> TYPE: DNA
<213> ORGANISM: Artificial Sequence
<220> FEATURE:
<223> OTHER INFORMATION: chemically synthesized

<400> SEQUENCE: 342
atccgtcaca cctgctctct atcagagggt gggaggcgca tacagagcga gtaatggtgt    60
tggctcccgt at                                                        72

<210> SEQ ID NO 343
<211> LENGTH: 72
<212> TYPE: DNA
<213> ORGANISM: Artificial Sequence
<220> FEATURE:
<223> OTHER INFORMATION: chemically synthesized

<400> SEQUENCE: 343
atacgggagc caacaccaga gtcggctaca gaggtctgat gttaaagcga tggtagagca    60
ggtgtgacgg at                                                        72

<210> SEQ ID NO 344
<211> LENGTH: 72
<212> TYPE: DNA
<213> ORGANISM: Artificial Sequence
<220> FEATURE:
<223> OTHER INFORMATION: chemically synthesized

<400> SEQUENCE: 344
atccgtcaca cctgctctac catcgcttta acatcagacc tctgtagccg actctggtgt    60
tggctcccgt at                                                        72
```

```
<210> SEQ ID NO 345
<211> LENGTH: 72
<212> TYPE: DNA
<213> ORGANISM: Artificial Sequence
<220> FEATURE:
<223> OTHER INFORMATION: chemically synthesized

<400> SEQUENCE: 345
atacgggagc caacaccaca ccattctggc cccctcccct tcaccgatcc tctcagagca      60
ggtgtgacgg at                                                          72

<210> SEQ ID NO 346
<211> LENGTH: 72
<212> TYPE: DNA
<213> ORGANISM: Artificial Sequence
<220> FEATURE:
<223> OTHER INFORMATION: chemically synthesized

<400> SEQUENCE: 346
atccgtcaca cctgctctga gaggatcggt gaaggggagg gggccagaat ggtgtggtgt      60
tggctcccgt at                                                          72

<210> SEQ ID NO 347
<211> LENGTH: 72
<212> TYPE: DNA
<213> ORGANISM: Artificial Sequence
<220> FEATURE:
<223> OTHER INFORMATION: chemically synthesized

<400> SEQUENCE: 347
atacgggagc caacaccagc actgcagtta acatttacga agaggcttta atgcagagca      60
ggtgtgacgg at                                                          72

<210> SEQ ID NO 348
<211> LENGTH: 72
<212> TYPE: DNA
<213> ORGANISM: Artificial Sequence
<220> FEATURE:
<223> OTHER INFORMATION: chemically synthesized

<400> SEQUENCE: 348
atccgtcaca cctgctctgc attaaagcct cttcgtaaat gttaactgca gtgctggtgt      60
tggctcccgt at                                                          72

<210> SEQ ID NO 349
<211> LENGTH: 72
<212> TYPE: DNA
<213> ORGANISM: Artificial Sequence
<220> FEATURE:
<223> OTHER INFORMATION: chemically synthesized

<400> SEQUENCE: 349
atacgggagc caacaccaac ccggcgttat atcacctcat ggagaaaagt gcgtagagca      60
ggtgtgacgg at                                                          72

<210> SEQ ID NO 350
<211> LENGTH: 72
<212> TYPE: DNA
<213> ORGANISM: Artificial Sequence
<220> FEATURE:
<223> OTHER INFORMATION: chemically synthesized

<400> SEQUENCE: 350
atccgtcaca cctgctctac gcactttttct ccatgaggtg atataacgcc gggttggtgt     60
```

```
tggctcccgt at                                                            72

<210> SEQ ID NO 351
<211> LENGTH: 72
<212> TYPE: DNA
<213> ORGANISM: Artificial Sequence
<220> FEATURE:
<223> OTHER INFORMATION: chemically synthesized

<400> SEQUENCE: 351
atacgggagc caacaccagc acaacttaag tgcaagcaaa ttcggattaa ccaaagagca        60
ggtgtgacgg at                                                            72

<210> SEQ ID NO 352
<211> LENGTH: 72
<212> TYPE: DNA
<213> ORGANISM: Artificial Sequence
<220> FEATURE:
<223> OTHER INFORMATION: chemically synthesized

<400> SEQUENCE: 352
atccgtcaca cctgctcttt ggttaatccg aatttgcttg cacttaagtt gtgctggtgt        60
tggctcccgt at                                                            72

<210> SEQ ID NO 353
<211> LENGTH: 72
<212> TYPE: DNA
<213> ORGANISM: Artificial Sequence
<220> FEATURE:
<223> OTHER INFORMATION: chemically synthesized

<400> SEQUENCE: 353
atacgggagc caacaccacg actacattgt gttcaagcgc cgaagacgct atcaagagca        60
ggtgtgacgg at                                                            72

<210> SEQ ID NO 354
<211> LENGTH: 72
<212> TYPE: DNA
<213> ORGANISM: Artificial Sequence
<220> FEATURE:
<223> OTHER INFORMATION: chemically synthesized

<400> SEQUENCE: 354
atccgtcaca cctgctcttg atagcgtctt cggcgcttga acacaatgta gtcgtggtgt        60
tggctcccgt at                                                            72

<210> SEQ ID NO 355
<211> LENGTH: 70
<212> TYPE: DNA
<213> ORGANISM: Artificial Sequence
<220> FEATURE:
<223> OTHER INFORMATION: chemically synthesized

<400> SEQUENCE: 355
atacgggagc caacaccagc ataccagcaa cggaagctgc ccaaagaatt tcagagcagg        60
tgtgacggat                                                               70

<210> SEQ ID NO 356
<211> LENGTH: 70
<212> TYPE: DNA
<213> ORGANISM: Artificial Sequence
<220> FEATURE:
<223> OTHER INFORMATION: chemically synthesized
```

<400> SEQUENCE: 356
atccgtcaca cctgctctga aattctttgg gcagcttccg ttgctggtat gctggtgttg     60
gctcccgtat                                                            70

<210> SEQ ID NO 357
<211> LENGTH: 71
<212> TYPE: DNA
<213> ORGANISM: Artificial Sequence
<220> FEATURE:
<223> OTHER INFORMATION: chemically synthesized

<400> SEQUENCE: 357
atacgggagc caacaccaat gctaaatacc gatgcttttc aatgtgatgg tcaagagcag     60
gtgtgacgga t                                                          71

<210> SEQ ID NO 358
<211> LENGTH: 71
<212> TYPE: DNA
<213> ORGANISM: Artificial Sequence
<220> FEATURE:
<223> OTHER INFORMATION: chemically synthesized

<400> SEQUENCE: 358
atccgtcaca cctgctcttg accatcacat tgaaaagcat cggtatttag cattggtgtt     60
ggctcccgta t                                                          71

<210> SEQ ID NO 359
<211> LENGTH: 70
<212> TYPE: DNA
<213> ORGANISM: Artificial Sequence
<220> FEATURE:
<223> OTHER INFORMATION: chemically synthesized

<400> SEQUENCE: 359
atacgggagc caacaccatc cgggccatgg tagagtgtta taatcgaaca aaagagcagg     60
tgtgacggat                                                            70

<210> SEQ ID NO 360
<211> LENGTH: 70
<212> TYPE: DNA
<213> ORGANISM: Artificial Sequence
<220> FEATURE:
<223> OTHER INFORMATION: chemically synthesized

<400> SEQUENCE: 360
atccgtcaca cctgctcttt tgttcgatta taacactcta ccatggcccg gatggtgttg     60
gctcccgtat                                                            70

<210> SEQ ID NO 361
<211> LENGTH: 72
<212> TYPE: DNA
<213> ORGANISM: Artificial Sequence
<220> FEATURE:
<223> OTHER INFORMATION: chemically synthesized

<400> SEQUENCE: 361
atacgggagc caacaccaag tccaagccaa acaagagcat aacaccaaat ctggagagca     60
ggtgtgacgg at                                                         72

<210> SEQ ID NO 362
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 362
atccgtcaca cctgctctcc agatttggtg ttatgctctt gtttggcttg gacttggtgt    60
tggctcccgt at                                                       72

<210> SEQ ID NO 363
<211> LENGTH: 71
<212> TYPE: DNA
<213> ORGANISM: Artificial Sequence
<220> FEATURE:
<223> OTHER INFORMATION: chemically synthesized

<400> SEQUENCE: 363
atacgggagc caacaccaat gctaaatacc gatgcttttc aatgtgatgg tcaagagcag    60
gtgtgacgga t                                                        71

<210> SEQ ID NO 364
<211> LENGTH: 71
<212> TYPE: DNA
<213> ORGANISM: Artificial Sequence
<220> FEATURE:
<223> OTHER INFORMATION: chemically synthesized

<400> SEQUENCE: 364
atccgtcaca cctgctcttg accatcacat tgaaaagcat cggtatttag cattggtgtt    60
ggctcccgta t                                                        71

<210> SEQ ID NO 365
<211> LENGTH: 71
<212> TYPE: DNA
<213> ORGANISM: Artificial Sequence
<220> FEATURE:
<223> OTHER INFORMATION: chemically synthesized

<400> SEQUENCE: 365
atacgggagc caacaccaca tagctactac agaactcagg gctaaagtct tatagagcag    60
gtgtgacgga t                                                        71

<210> SEQ ID NO 366
<211> LENGTH: 71
<212> TYPE: DNA
<213> ORGANISM: Artificial Sequence
<220> FEATURE:
<223> OTHER INFORMATION: chemically synthesized

<400> SEQUENCE: 366
atccgtcaca cctgctctat aagactttag ccctgagttc tgtagtagct atgtggtgtt    60
ggctcccgta t                                                        71

<210> SEQ ID NO 367
<211> LENGTH: 70
<212> TYPE: DNA
<213> ORGANISM: Artificial Sequence
<220> FEATURE:
<223> OTHER INFORMATION: chemically synthesized

<400> SEQUENCE: 367
atacgggagc caacaccagc ataccagcaa cggaagctgc ccaaagaatt tcagagcagg    60
tgtgacggat                                                          70
```

<210> SEQ ID NO 368
<211> LENGTH: 70
<212> TYPE: DNA
<213> ORGANISM: Artificial Sequence
<220> FEATURE:
<223> OTHER INFORMATION: chemically synthesized

<400> SEQUENCE: 368

```
atccgtcaca cctgctctga aattctttgg gcagcttccg ttgctggtat gctggtgttg    60
gctcccgtat                                                           70
```

<210> SEQ ID NO 369
<211> LENGTH: 72
<212> TYPE: DNA
<213> ORGANISM: Artificial Sequence
<220> FEATURE:
<223> OTHER INFORMATION: chemically synthesized

<400> SEQUENCE: 369

```
atacgggagc caacaccaga tcgatatatg acaccaggta caccacagac ttgcagagca    60
ggtgtgacgg at                                                        72
```

<210> SEQ ID NO 370
<211> LENGTH: 72
<212> TYPE: DNA
<213> ORGANISM: Artificial Sequence
<220> FEATURE:
<223> OTHER INFORMATION: chemically synthesized

<400> SEQUENCE: 370

```
atccgtcaca cctgctctgc aagtctgtgg tgtacctggt gtcatatatc gatctggtgt    60
tggctcccgt at                                                        72
```

<210> SEQ ID NO 371
<211> LENGTH: 72
<212> TYPE: DNA
<213> ORGANISM: Artificial Sequence
<220> FEATURE:
<223> OTHER INFORMATION: chemically synthesized

<400> SEQUENCE: 371

```
atacgggagc caacaccatc tactcgaaca tcttaaaagc agtctaagca aactagagca    60
ggtgtgacgg at                                                        72
```

<210> SEQ ID NO 372
<211> LENGTH: 72
<212> TYPE: DNA
<213> ORGANISM: Artificial Sequence
<220> FEATURE:
<223> OTHER INFORMATION: chemically synthesized

<400> SEQUENCE: 372

```
atccgtcaca cctgctctag tttgcttaga ctgcttttaa gatgttcgag tagatggtgt    60
tggctcccgt at                                                        72
```

<210> SEQ ID NO 373
<211> LENGTH: 72
<212> TYPE: DNA
<213> ORGANISM: Artificial Sequence
<220> FEATURE:
<223> OTHER INFORMATION: chemically synthesized

<400> SEQUENCE: 373

```
atacgggagc caacaccata gatcttttac gaacaccgcc gaagattatc atttagagca    60
ggtgtgacgg at                                                        72
```

<210> SEQ ID NO 374
<211> LENGTH: 72
<212> TYPE: DNA
<213> ORGANISM: Artificial Sequence
<220> FEATURE:
<223> OTHER INFORMATION: chemically synthesized

<400> SEQUENCE: 374

```
atccgtcaca cctgctctaa atgataatct tcggcggtgt tcgtaaaaga tctatggtgt    60
tggctcccgt at                                                        72
```

<210> SEQ ID NO 375
<211> LENGTH: 72
<212> TYPE: DNA
<213> ORGANISM: Artificial Sequence
<220> FEATURE:
<223> OTHER INFORMATION: chemically synthesized

<400> SEQUENCE: 375

```
atacgggagc caacaccaaa tgatgaatag gcaacttgcg gtgccacgat cttgagagca    60
ggtgtgacgg at                                                        72
```

<210> SEQ ID NO 376
<211> LENGTH: 72
<212> TYPE: DNA
<213> ORGANISM: Artificial Sequence
<220> FEATURE:
<223> OTHER INFORMATION: chemically synthesized

<400> SEQUENCE: 376

```
atccgtcaca cctgctctca agatcgtggc accgcaagtt gcctattcat catttggtgt    60
tggctcccgt at                                                        72
```

<210> SEQ ID NO 377
<211> LENGTH: 72
<212> TYPE: DNA
<213> ORGANISM: Artificial Sequence
<220> FEATURE:
<223> OTHER INFORMATION: chemically synthesized

<400> SEQUENCE: 377

```
atacgggagc caacaccatc ggccgaatag atataattca caaagagtgt ccccagagca    60
ggtgtgacgg at                                                        72
```

<210> SEQ ID NO 378
<211> LENGTH: 72
<212> TYPE: DNA
<213> ORGANISM: Artificial Sequence
<220> FEATURE:
<223> OTHER INFORMATION: chemically synthesized

<400> SEQUENCE: 378

```
atccgtcaca cctgctctgg ggacactctt tgtgaattat atctattcgg ccgatggtgt    60
tggctcccgt at                                                        72
```

<210> SEQ ID NO 379
<211> LENGTH: 71
<212> TYPE: DNA
<213> ORGANISM: Artificial Sequence

```
<220> FEATURE:
<223> OTHER INFORMATION: chemically synthesized

<400> SEQUENCE: 379
atacgggagc caacaccaga aaatgaatac ttcccaagct tgtcaagcaa gtaagagcag    60
gtgtgacgga t                                                        71

<210> SEQ ID NO 380
<211> LENGTH: 71
<212> TYPE: DNA
<213> ORGANISM: Artificial Sequence
<220> FEATURE:
<223> OTHER INFORMATION: chemically synthesized

<400> SEQUENCE: 380
atccgtcaca cctgctctta cttgcttgac aagcttggga agtattcatt ttctggtgtt    60
ggctcccgta t                                                        71

<210> SEQ ID NO 381
<211> LENGTH: 70
<212> TYPE: DNA
<213> ORGANISM: Artificial Sequence
<220> FEATURE:
<223> OTHER INFORMATION: chemically synthesized

<400> SEQUENCE: 381
atacgggagc caacaccaaa caggctgagt gtactgctac cttgcagtat caagagcagg    60
tgtgacggat                                                          70

<210> SEQ ID NO 382
<211> LENGTH: 70
<212> TYPE: DNA
<213> ORGANISM: Artificial Sequence
<220> FEATURE:
<223> OTHER INFORMATION: chemically synthesized

<400> SEQUENCE: 382
atccgtcaca cctgctcttg atactgcaag gtagcagtac actcagcctg tttggtgttg    60
gctcccgtat                                                          70

<210> SEQ ID NO 383
<211> LENGTH: 72
<212> TYPE: DNA
<213> ORGANISM: Artificial Sequence
<220> FEATURE:
<223> OTHER INFORMATION: chemically synthesized

<400> SEQUENCE: 383
atacgggagc caacaccaga ttttccagca aatccagtcc ctatatgtgc ttgaagagca    60
ggtgtgacgg at                                                       72

<210> SEQ ID NO 384
<211> LENGTH: 72
<212> TYPE: DNA
<213> ORGANISM: Artificial Sequence
<220> FEATURE:
<223> OTHER INFORMATION: chemically synthesized

<400> SEQUENCE: 384
atccgtcaca cctgctcttc aagcacatat agggactgga tttgctggaa aatctggtgt    60
tggctcccgt at                                                       72
```

```
<210> SEQ ID NO 385
<211> LENGTH: 72
<212> TYPE: DNA
<213> ORGANISM: Artificial Sequence
<220> FEATURE:
<223> OTHER INFORMATION: chemically synthesized

<400> SEQUENCE: 385
atacgggagc caacaccaac aaccaccagt caagacccaa cgcgtggcga ggaaagagca      60
ggtgtgacgg at                                                         72

<210> SEQ ID NO 386
<211> LENGTH: 72
<212> TYPE: DNA
<213> ORGANISM: Artificial Sequence
<220> FEATURE:
<223> OTHER INFORMATION: chemically synthesized

<400> SEQUENCE: 386
atccgtcaca cctgctcttt cctcgccacg cgttgggtct tgactggtgg ttgttggtgt      60
tggctcccgt at                                                         72

<210> SEQ ID NO 387
<211> LENGTH: 71
<212> TYPE: DNA
<213> ORGANISM: Artificial Sequence
<220> FEATURE:
<223> OTHER INFORMATION: chemically synthesized

<400> SEQUENCE: 387
atacgggagc caacaccagg gatatgctga atatgcattg tcacgctgaa gtcagagcag      60
gtgtgacgga t                                                          71

<210> SEQ ID NO 388
<211> LENGTH: 71
<212> TYPE: DNA
<213> ORGANISM: Artificial Sequence
<220> FEATURE:
<223> OTHER INFORMATION: chemically synthesized

<400> SEQUENCE: 388
atccgtcaca cctgctctga cttcagcgtg acaatgcata ttcagcatat ccctggtgtt      60
ggctcccgta t                                                          71

<210> SEQ ID NO 389
<211> LENGTH: 71
<212> TYPE: DNA
<213> ORGANISM: Artificial Sequence
<220> FEATURE:
<223> OTHER INFORMATION: chemically synthesized

<400> SEQUENCE: 389
atacgggagc caacaccaat acaacaagtc aaaagaaat agaaagttga acgagagcag       60
gtgtgacgga t                                                          71

<210> SEQ ID NO 390
<211> LENGTH: 71
<212> TYPE: DNA
<213> ORGANISM: Artificial Sequence
<220> FEATURE:
<223> OTHER INFORMATION: chemically synthesized

<400> SEQUENCE: 390
atccgtcaca cctgctctcg ttcaactttc tatttctttt tgacttgttg tattggtgtt      60
```

```
ggctcccgta t                                                          71

<210> SEQ ID NO 391
<211> LENGTH: 71
<212> TYPE: DNA
<213> ORGANISM: Artificial Sequence
<220> FEATURE:
<223> OTHER INFORMATION: chemically synthesized

<400> SEQUENCE: 391
atacgggagc caacaccaaa cagacgtttg gggcaatgat ataaagttaa tcaagagcag     60
gtgtgacgga t                                                          71

<210> SEQ ID NO 392
<211> LENGTH: 71
<212> TYPE: DNA
<213> ORGANISM: Artificial Sequence
<220> FEATURE:
<223> OTHER INFORMATION: chemically synthesized

<400> SEQUENCE: 392
atccgtcaca cctgctcttg attaacttta tatcattgcc ccaaacgtct gtttggtgtt     60
ggctcccgta t                                                          71

<210> SEQ ID NO 393
<211> LENGTH: 71
<212> TYPE: DNA
<213> ORGANISM: Artificial Sequence
<220> FEATURE:
<223> OTHER INFORMATION: chemically synthesized

<400> SEQUENCE: 393
atacgggagc caacaccata acggttccct taatgcgcta cccacactat acaagagcag     60
gtgtgacgga t                                                          71

<210> SEQ ID NO 394
<211> LENGTH: 71
<212> TYPE: DNA
<213> ORGANISM: Artificial Sequence
<220> FEATURE:
<223> OTHER INFORMATION: chemically synthesized

<400> SEQUENCE: 394
atccgtcaca cctgctcttg tatagtgtgg gtagcgcatt aagggaaccg ttatggtgtt     60
ggctcccgta t                                                          71

<210> SEQ ID NO 395
<211> LENGTH: 72
<212> TYPE: DNA
<213> ORGANISM: Artificial Sequence
<220> FEATURE:
<223> OTHER INFORMATION: chemically synthesized

<400> SEQUENCE: 395
atacgggagc caacaccagc gctgcctgta tggcagacct acctgaccct ctttagagca     60
ggtgtgacgg at                                                         72

<210> SEQ ID NO 396
<211> LENGTH: 72
<212> TYPE: DNA
<213> ORGANISM: Artificial Sequence
<220> FEATURE:
<223> OTHER INFORMATION: chemically synthesized
```

```
<400> SEQUENCE: 396
atccgtcaca cctgctctaa agagggtcag gtaggtctgc catacaggca gcgctggtgt    60
tggctcccgt at                                                       72

<210> SEQ ID NO 397
<211> LENGTH: 72
<212> TYPE: DNA
<213> ORGANISM: Artificial Sequence
<220> FEATURE:
<223> OTHER INFORMATION: chemically synthesized

<400> SEQUENCE: 397
atacgggagc caacaccaag atgcgagcca atagtgtcac aataattgtc cgaaagagca    60
ggtgtgacgg at                                                       72

<210> SEQ ID NO 398
<211> LENGTH: 72
<212> TYPE: DNA
<213> ORGANISM: Artificial Sequence
<220> FEATURE:
<223> OTHER INFORMATION: chemically synthesized

<400> SEQUENCE: 398
atccgtcaca cctgctcttt cggacaatta ttgtgacact attggctcgc atcttggtgt    60
tggctcccgt at                                                       72

<210> SEQ ID NO 399
<211> LENGTH: 72
<212> TYPE: DNA
<213> ORGANISM: Artificial Sequence
<220> FEATURE:
<223> OTHER INFORMATION: chemically synthesized

<400> SEQUENCE: 399
atacgggagc caacaccaag atatagactc taattgatta ccattcatag gaaaagagca    60
ggtgtgacgg at                                                       72

<210> SEQ ID NO 400
<211> LENGTH: 72
<212> TYPE: DNA
<213> ORGANISM: Artificial Sequence
<220> FEATURE:
<223> OTHER INFORMATION: chemically synthesized

<400> SEQUENCE: 400
atccgtcaca cctgctcttt tcctatgaat ggtaatcaat tagagtctat atcttggtgt    60
tggctcccgt at                                                       72

<210> SEQ ID NO 401
<211> LENGTH: 72
<212> TYPE: DNA
<213> ORGANISM: Artificial Sequence
<220> FEATURE:
<223> OTHER INFORMATION: chemically synthesized

<400> SEQUENCE: 401
atacgggagc caacaccatc cagttccaat tacgcgtaga tagtcacaat ccaaagagca    60
ggtgtgacgg at                                                       72

<210> SEQ ID NO 402
<211> LENGTH: 72
```

```
<212> TYPE: DNA
<213> ORGANISM: Artificial Sequence
<220> FEATURE:
<223> OTHER INFORMATION: chemically synthesized

<400> SEQUENCE: 402
atccgtcaca cctgctcttt ggattgtgac tatctacgcg taattggaac tggatggtgt      60
tggctcccgt at                                                         72

<210> SEQ ID NO 403
<211> LENGTH: 72
<212> TYPE: DNA
<213> ORGANISM: Artificial Sequence
<220> FEATURE:
<223> OTHER INFORMATION: chemically synthesized

<400> SEQUENCE: 403
atacgggagc caacaccact tacctcccct accacacctc caactaaaac ctgaagagca      60
ggtgtgacgg at                                                         72

<210> SEQ ID NO 404
<211> LENGTH: 72
<212> TYPE: DNA
<213> ORGANISM: Artificial Sequence
<220> FEATURE:
<223> OTHER INFORMATION: chemically synthesized

<400> SEQUENCE: 404
atccgtcaca cctgctcttc aggttttagt tggaggtgtg gtaggggagg taagtggtgt      60
tggctcccgt at                                                         72

<210> SEQ ID NO 405
<211> LENGTH: 72
<212> TYPE: DNA
<213> ORGANISM: Artificial Sequence
<220> FEATURE:
<223> OTHER INFORMATION: chemically synthesized

<400> SEQUENCE: 405
atacgggagc caacaccagg atcaaaccac ttgccgtcaa ggcaatggcc cctcagagca      60
ggtgtgacgg at                                                         72

<210> SEQ ID NO 406
<211> LENGTH: 72
<212> TYPE: DNA
<213> ORGANISM: Artificial Sequence
<220> FEATURE:
<223> OTHER INFORMATION: chemically synthesized

<400> SEQUENCE: 406
atccgtcaca cctgctctga ggggccattg ccttgacggc aagtggtttg atcctggtgt      60
tggctcccgt at                                                         72

<210> SEQ ID NO 407
<211> LENGTH: 72
<212> TYPE: DNA
<213> ORGANISM: Artificial Sequence
<220> FEATURE:
<223> OTHER INFORMATION: chemically synthesized

<400> SEQUENCE: 407
atacgggagc caacaccacc cgttttgat ctaatgagga tacaatattc gtctagagca       60
ggtgtgacgg at                                                         72
```

<210> SEQ ID NO 408
<211> LENGTH: 72
<212> TYPE: DNA
<213> ORGANISM: Artificial Sequence
<220> FEATURE:
<223> OTHER INFORMATION: chemically synthesized

<400> SEQUENCE: 408
atccgtcaca cctgctctag acgaatattg tatcctcatt agatcaaaaa cggtggtgt    60 tggctcccgt at    72

<210> SEQ ID NO 409
<211> LENGTH: 72
<212> TYPE: DNA
<213> ORGANISM: Artificial Sequence
<220> FEATURE:
<223> OTHER INFORMATION: chemically synthesized

<400> SEQUENCE: 409
atacgggagc caacaccacc cctccggacc caccctgat gccacgtgcc cctgagagca    60
ggtgtgacgg at    72

<210> SEQ ID NO 410
<211> LENGTH: 72
<212> TYPE: DNA
<213> ORGANISM: Artificial Sequence
<220> FEATURE:
<223> OTHER INFORMATION: chemically synthesized

<400> SEQUENCE: 410
atccgtcaca cctgctctca ggggcacgtg gcatcagggg tgggtccgga ggggtggtgt    60
tggctcccgt at    72

<210> SEQ ID NO 411
<211> LENGTH: 72
<212> TYPE: DNA
<213> ORGANISM: Artificial Sequence
<220> FEATURE:
<223> OTHER INFORMATION: chemically synthesized

<400> SEQUENCE: 411
atacgggagc caacaccaga ccctgcccca gccccttagc cccggcgcgc gacgagagca    60
ggtgtgacgg at    72

<210> SEQ ID NO 412
<211> LENGTH: 72
<212> TYPE: DNA
<213> ORGANISM: Artificial Sequence
<220> FEATURE:
<223> OTHER INFORMATION: chemically synthesized

<400> SEQUENCE: 412
atccgtcaca cctgctctcg tcgcgcgccg gggctaaggg gctggggcag gtctggtgt    60 tggctcccgt at    72

<210> SEQ ID NO 413
<211> LENGTH: 72
<212> TYPE: DNA
<213> ORGANISM: Artificial Sequence
<220> FEATURE:
<223> OTHER INFORMATION: chemically synthesized

<400> SEQUENCE: 413

-continued atacgggagc caacaccaca cacagagcgc catggactca gtcagatgtg atgtagagca    60
ggtgtgacgg at    72

<210> SEQ ID NO 414
<211> LENGTH: 72
<212> TYPE: DNA
<213> ORGANISM: Artificial Sequence
<220> FEATURE:
<223> OTHER INFORMATION: chemically synthesized

<400> SEQUENCE: 414
atccgtcaca cctgctctac atcacatctg actgagtcca tggcgctctg tgtgtggtgt    60
tggctcccgt at    72

<210> SEQ ID NO 415
<211> LENGTH: 72
<212> TYPE: DNA
<213> ORGANISM: Artificial Sequence
<220> FEATURE:
<223> OTHER INFORMATION: chemically synthesized

<400> SEQUENCE: 415
atacgggagc caacaccacg gcacgaagac gaggtgaaaa gtcagcttag tgaaagagca    60
ggtgtgacgg at    72

<210> SEQ ID NO 416
<211> LENGTH: 72
<212> TYPE: DNA
<213> ORGANISM: Artificial Sequence
<220> FEATURE:
<223> OTHER INFORMATION: chemically synthesized

<400> SEQUENCE: 416
atccgtcaca cctgctcttt cactaagctg acttttcacc tcgtcttcgt gccgtggtgt    60
tggctcccgt at    72

<210> SEQ ID NO 417
<211> LENGTH: 72
<212> TYPE: DNA
<213> ORGANISM: Artificial Sequence
<220> FEATURE:
<223> OTHER INFORMATION: chemically synthesized

<400> SEQUENCE: 417
atacgggagc caacaccaca ccccatgaga tcaccattca ctcgcacccc cacgagagca    60
ggtgtgacgg at    72

<210> SEQ ID NO 418
<211> LENGTH: 72
<212> TYPE: DNA
<213> ORGANISM: Artificial Sequence
<220> FEATURE:
<223> OTHER INFORMATION: chemically synthesized

<400> SEQUENCE: 418
atccgtcaca cctgctctcg tgggggtgcg agtgaatggt gatctcatgg ggtgtggtgt    60
tggctcccgt at    72

<210> SEQ ID NO 419
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 419
atacgggagc caacaccagg ctatttgtta gcgctctcta gttccacatg accaagagca      60
ggtgtgacgg at                                                         72

<210> SEQ ID NO 420
<211> LENGTH: 72
<212> TYPE: DNA
<213> ORGANISM: Artificial Sequence
<220> FEATURE:
<223> OTHER INFORMATION: chemically synthesized

<400> SEQUENCE: 420
atccgtcaca cctgctcttg gtcatgtgga actagagagc gctaacaaat agcctggtgt      60
tggctcccgt at                                                         72

<210> SEQ ID NO 421
<211> LENGTH: 72
<212> TYPE: DNA
<213> ORGANISM: Artificial Sequence
<220> FEATURE:
<223> OTHER INFORMATION: chemically synthesized

<400> SEQUENCE: 421
atacgggagc caacaccatg gctggtacac tcccggttcc ctgccgttga gcccagagca      60
ggtgtgacgg at                                                         72

<210> SEQ ID NO 422
<211> LENGTH: 72
<212> TYPE: DNA
<213> ORGANISM: Artificial Sequence
<220> FEATURE:
<223> OTHER INFORMATION: chemically synthesized

<400> SEQUENCE: 422
atccgtcaca cctgctctgg gctcaacggc agggaaccgg gagtgtacca gccatggtgt      60
tggctcccgt at                                                         72

<210> SEQ ID NO 423
<211> LENGTH: 72
<212> TYPE: DNA
<213> ORGANISM: Artificial Sequence
<220> FEATURE:
<223> OTHER INFORMATION: chemically synthesized

<400> SEQUENCE: 423
atacgggagc caacaccacg gggtgggtcg aacccttgtc tgggaggtgc ttctagagca      60
ggtgtgacgg at                                                         72

<210> SEQ ID NO 424
<211> LENGTH: 72
<212> TYPE: DNA
<213> ORGANISM: Artificial Sequence
<220> FEATURE:
<223> OTHER INFORMATION: chemically synthesized

<400> SEQUENCE: 424
atccgtcaca cctgctctag aagcacctcc cagacaaggg ttcgacccac ccgtggtgt       60 tggctcccgt at                                                         72
```

<210> SEQ ID NO 425
<211> LENGTH: 72
<212> TYPE: DNA
<213> ORGANISM: Artificial Sequence
<220> FEATURE:
<223> OTHER INFORMATION: chemically synthesized

<400> SEQUENCE: 425
atacgggagc caacaccaat cttactagtt tgggaaaaaa attaaatata agcaagagca    60
ggtgtgacgg at    72

<210> SEQ ID NO 426
<211> LENGTH: 72
<212> TYPE: DNA
<213> ORGANISM: Artificial Sequence
<220> FEATURE:
<223> OTHER INFORMATION: chemically synthesized

<400> SEQUENCE: 426
atccgtcaca cctgctcttg cttatattta attttttttcc caaactagta agattggtgt    60
tggctcccgt at    72

<210> SEQ ID NO 427
<211> LENGTH: 72
<212> TYPE: DNA
<213> ORGANISM: Artificial Sequence
<220> FEATURE:
<223> OTHER INFORMATION: chemically synthesized

<400> SEQUENCE: 427
atacgggagc caacaccaat tatccactga taacgaaaag atctggacag ttgtagagca    60
ggtgtgacgg at    72

<210> SEQ ID NO 428
<211> LENGTH: 72
<212> TYPE: DNA
<213> ORGANISM: Artificial Sequence
<220> FEATURE:
<223> OTHER INFORMATION: chemically synthesized

<400> SEQUENCE: 428
atccgtcaca cctgctctac aactgtccag atcttttcgt tatcagtgga taattggtgt    60
tggctcccgt at    72

<210> SEQ ID NO 429
<211> LENGTH: 72
<212> TYPE: DNA
<213> ORGANISM: Artificial Sequence
<220> FEATURE:
<223> OTHER INFORMATION: chemically synthesized

<400> SEQUENCE: 429
atacgggagc caacaccagt tgacttaggg tcaaactatg gacactcacc cgtaagagca    60
ggtgtgacgg at    72

<210> SEQ ID NO 430
<211> LENGTH: 72
<212> TYPE: DNA
<213> ORGANISM: Artificial Sequence
<220> FEATURE:
<223> OTHER INFORMATION: chemically synthesized

<400> SEQUENCE: 430
atccgtcaca cctgctctta cgggtgagtg tccatagttt gaccctaagt caactggtgt    60

-continued tggctcccgt at                                                           72

<210> SEQ ID NO 431
<211> LENGTH: 72
<212> TYPE: DNA
<213> ORGANISM: Artificial Sequence
<220> FEATURE:
<223> OTHER INFORMATION: chemically synthesized

<400> SEQUENCE: 431
atacgggagc caacaccact actagacatc gtagcccgac gtccgtggat tgggagagca      60
ggtgtgacgg at                                                           72

<210> SEQ ID NO 432
<211> LENGTH: 72
<212> TYPE: DNA
<213> ORGANISM: Artificial Sequence
<220> FEATURE:
<223> OTHER INFORMATION: chemically synthesized

<400> SEQUENCE: 432
atccgtcaca cctgctctcc caatccacgg acgtcgggct acgatgtcta gtagtggtgt      60
tggctcccgt at                                                           72

<210> SEQ ID NO 433
<211> LENGTH: 72
<212> TYPE: DNA
<213> ORGANISM: Artificial Sequence
<220> FEATURE:
<223> OTHER INFORMATION: chemically synthesized

<400> SEQUENCE: 433
atacgggagc caacaccaga tataccgtaa cattaataga caagttaaat acccagagca      60
ggtgtgacgg at                                                           72

<210> SEQ ID NO 434
<211> LENGTH: 72
<212> TYPE: DNA
<213> ORGANISM: Artificial Sequence
<220> FEATURE:
<223> OTHER INFORMATION: chemically synthesized

<400> SEQUENCE: 434
atccgtcaca cctgctctgg gtatttaact tgtctattaa tgttacggta tatctggtgt      60
tggctcccgt at                                                           72

<210> SEQ ID NO 435
<211> LENGTH: 72
<212> TYPE: DNA
<213> ORGANISM: Artificial Sequence
<220> FEATURE:
<223> OTHER INFORMATION: chemically synthesized

<400> SEQUENCE: 435
atacgggagc caacaccaac atagtgctcg catcctatgg cgtaacgaga ctacagagca      60
ggtgtgacgg at                                                           72

<210> SEQ ID NO 436
<211> LENGTH: 72
<212> TYPE: DNA
<213> ORGANISM: Artificial Sequence
<220> FEATURE:
<223> OTHER INFORMATION: chemically synthesized -continued

<400> SEQUENCE: 436
atccgtcaca cctgctctgt agtctcgtta cgccatagga tgcgagcact atgttggtgt    60
tggctcccgt at    72

<210> SEQ ID NO 437
<211> LENGTH: 72
<212> TYPE: DNA
<213> ORGANISM: Artificial Sequence
<220> FEATURE:
<223> OTHER INFORMATION: chemically synthesized

<400> SEQUENCE: 437
atacgggagc caacaccacc aacgaatact accaggccta gcacaataca caacagagca    60
ggtgtgacgg at    72

<210> SEQ ID NO 438
<211> LENGTH: 66
<212> TYPE: DNA
<213> ORGANISM: Artificial Sequence
<220> FEATURE:
<223> OTHER INFORMATION: chemically synthesized

<400> SEQUENCE: 438
atccgtcaca cctgctctgt tgtgtattgt gctaggcctg gtagtattcg ttgttggctc    60
ccgtat    66

<210> SEQ ID NO 439
<211> LENGTH: 71
<212> TYPE: DNA
<213> ORGANISM: Artificial Sequence
<220> FEATURE:
<223> OTHER INFORMATION: chemically synthesized

<400> SEQUENCE: 439
atacgggagc caacaccatt agaaaagaca tcgctaaatg acgggcacga atgagagcag    60
gtgtgacgga t    71

<210> SEQ ID NO 440
<211> LENGTH: 71
<212> TYPE: DNA
<213> ORGANISM: Artificial Sequence
<220> FEATURE:
<223> OTHER INFORMATION: chemically synthesized

<400> SEQUENCE: 440
atccgtcaca cctgctctca ttcgtgcccg tcatttagcg atgtcttttc taatggtgtt    60
ggctcccgta t    71

<210> SEQ ID NO 441
<211> LENGTH: 72
<212> TYPE: DNA
<213> ORGANISM: Artificial Sequence
<220> FEATURE:
<223> OTHER INFORMATION: chemically synthesized

<400> SEQUENCE: 441
atacgggagc caacaccaca aatgaataaa atttcggaaa aggcaagcag gataagagca    60
ggtgtgacgg at    72

<210> SEQ ID NO 442
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 442
atccgtcaca cctgctctta tcctgcttgc cttttccgaa attttattca tttgtggtgt    60
tggctcccgt at                                                        72

<210> SEQ ID NO 443
<211> LENGTH: 72
<212> TYPE: DNA
<213> ORGANISM: Artificial Sequence
<220> FEATURE:
<223> OTHER INFORMATION: chemically synthesized

<400> SEQUENCE: 443
atacgggagc caacaccatt atgttaacaa aggcatacgg caagctctaa ctgtagagca    60
ggtgtgacgg at                                                        72

<210> SEQ ID NO 444
<211> LENGTH: 72
<212> TYPE: DNA
<213> ORGANISM: Artificial Sequence
<220> FEATURE:
<223> OTHER INFORMATION: chemically synthesized

<400> SEQUENCE: 444
atccgtcaca cctgctctac agttagagct tgccgtatgc ctttgttaac ataatggtgt    60
tggctcccgt at                                                        72

<210> SEQ ID NO 445
<211> LENGTH: 72
<212> TYPE: DNA
<213> ORGANISM: Artificial Sequence
<220> FEATURE:
<223> OTHER INFORMATION: chemically synthesized

<400> SEQUENCE: 445
atacgggagc caacaccata agaaccacca ctccgcgttc gcctcccgag gtgtagagca    60
ggtgtgacgg at                                                        72

<210> SEQ ID NO 446
<211> LENGTH: 72
<212> TYPE: DNA
<213> ORGANISM: Artificial Sequence
<220> FEATURE:
<223> OTHER INFORMATION: chemically synthesized

<400> SEQUENCE: 446
atccgtcaca cctgctctac acctcgggag gcgaacgcgg agtggtggtt cttatggtgt    60
tggctcccgt at                                                        72

<210> SEQ ID NO 447
<211> LENGTH: 72
<212> TYPE: DNA
<213> ORGANISM: Artificial Sequence
<220> FEATURE:
<223> OTHER INFORMATION: chemically synthesized

<400> SEQUENCE: 447
atacgggagc caacaccatc atggcgatac agttatctgc attgttccat ccctagagca    60
ggtgtgacgg at                                                        72
```

<210> SEQ ID NO 448
<211> LENGTH: 72
<212> TYPE: DNA
<213> ORGANISM: Artificial Sequence
<220> FEATURE:
<223> OTHER INFORMATION: chemically synthesized

<400> SEQUENCE: 448
atccgtcaca cctgctctag ggatggaaca atgcagataa ctgtatcgcc atgatggtgt    60
tggctcccgt at                                                        72

<210> SEQ ID NO 449
<211> LENGTH: 72
<212> TYPE: DNA
<213> ORGANISM: Artificial Sequence
<220> FEATURE:
<223> OTHER INFORMATION: chemically synthesized

<400> SEQUENCE: 449
atacgggagc caacaccagc cctgggccag cccgtgactt tccccggcg tccaagagca    60 ggtgtgacgg at                                                        72

<210> SEQ ID NO 450
<211> LENGTH: 72
<212> TYPE: DNA
<213> ORGANISM: Artificial Sequence
<220> FEATURE:
<223> OTHER INFORMATION: chemically synthesized

<400> SEQUENCE: 450
atccgtcaca cctgctcttg dacgccgggg gaaagtcacg ggctggccca gggctggtgt    60
tggctcccgt at                                                        72

<210> SEQ ID NO 451
<211> LENGTH: 71
<212> TYPE: DNA
<213> ORGANISM: Artificial Sequence
<220> FEATURE:
<223> OTHER INFORMATION: chemically synthesized

<400> SEQUENCE: 451
atacgggagc caacaccaaa cggttcagaa ataggaaacg tttgatcgca agaagagcag    60
gtgtgacgga t                                                         71

<210> SEQ ID NO 452
<211> LENGTH: 71
<212> TYPE: DNA
<213> ORGANISM: Artificial Sequence
<220> FEATURE:
<223> OTHER INFORMATION: chemically synthesized

<400> SEQUENCE: 452
atccgtcaca cctgctcttc ttgcgatcaa acgtttccta tttctgaacc gtttggtgtt    60
ggctcccgta t                                                         71

<210> SEQ ID NO 453
<211> LENGTH: 72
<212> TYPE: DNA
<213> ORGANISM: Artificial Sequence
<220> FEATURE:
<223> OTHER INFORMATION: chemically synthesized

<400> SEQUENCE: 453

```
atacgggagc caacaccaga atatctaaaa taaaggaaag acaaccgcgg atgcagagca      60
ggtgtgacgg at                                                          72

<210> SEQ ID NO 454
<211> LENGTH: 72
<212> TYPE: DNA
<213> ORGANISM: Artificial Sequence
<220> FEATURE:
<223> OTHER INFORMATION: chemically synthesized

<400> SEQUENCE: 454
atccgtcaca cctgctctgc atccgcggtt gtctttcctt tattttagat attctggtgt      60
tggctcccgt at                                                          72

<210> SEQ ID NO 455
<211> LENGTH: 72
<212> TYPE: DNA
<213> ORGANISM: Artificial Sequence
<220> FEATURE:
<223> OTHER INFORMATION: chemically synthesized

<400> SEQUENCE: 455
atacgggagc caacaccacg acgggcgtaa agaaataacc aatgctaccg ccacagagca      60
ggtgtgacgg at                                                          72

<210> SEQ ID NO 456
<211> LENGTH: 72
<212> TYPE: DNA
<213> ORGANISM: Artificial Sequence
<220> FEATURE:
<223> OTHER INFORMATION: chemically synthesized

<400> SEQUENCE: 456
atccgtcaca cctgctctgt ggcggtagca ttggttattt ctttacgccc gtcgtggtgt      60
tggctcccgt at                                                          72

<210> SEQ ID NO 457
<211> LENGTH: 72
<212> TYPE: DNA
<213> ORGANISM: Artificial Sequence
<220> FEATURE:
<223> OTHER INFORMATION: chemically synthesized

<400> SEQUENCE: 457
atacgggagc caacaccaac gaataagtat ttaagacaga attagacact tagaagagca      60
ggtgtgacgg at                                                          72

<210> SEQ ID NO 458
<211> LENGTH: 72
<212> TYPE: DNA
<213> ORGANISM: Artificial Sequence
<220> FEATURE:
<223> OTHER INFORMATION: chemically synthesized

<400> SEQUENCE: 458
atccgtcaca cctgctcttc taagtgtcta attctgtctt aaatacttat tcgttggtgt      60
tggctcccgt at                                                          72

<210> SEQ ID NO 459
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 459
atacgggagc caacaccata tacatactcc tcgctacaac cgctgcgccg gatcagagca      60
ggtgtgacgg at                                                         72

<210> SEQ ID NO 460
<211> LENGTH: 72
<212> TYPE: DNA
<213> ORGANISM: Artificial Sequence
<220> FEATURE:
<223> OTHER INFORMATION: chemically synthesized

<400> SEQUENCE: 460
atccgtcaca cctgctctga tccggcgcag cggttgtagc gaggagtatg tatatggtgt      60
tggctcccgt at                                                         72

<210> SEQ ID NO 461
<211> LENGTH: 71
<212> TYPE: DNA
<213> ORGANISM: Artificial Sequence
<220> FEATURE:
<223> OTHER INFORMATION: chemically synthesized

<400> SEQUENCE: 461
atacgggagc caacaccaat ataagcgagg aggaaggcgg cgagctataa gtcagagcag      60
gtgtgacgga t                                                          71

<210> SEQ ID NO 462
<211> LENGTH: 71
<212> TYPE: DNA
<213> ORGANISM: Artificial Sequence
<220> FEATURE:
<223> OTHER INFORMATION: chemically synthesized

<400> SEQUENCE: 462
atccgtcaca cctgctctga cttatagctc gccgccttcc tcctcgctta tattggtgtt      60
ggctcccgta t                                                          71

<210> SEQ ID NO 463
<211> LENGTH: 60
<212> TYPE: DNA
<213> ORGANISM: Artificial Sequence
<220> FEATURE:
<223> OTHER INFORMATION: chemically synthesized

<400> SEQUENCE: 463
catacgggag ccaacaccac aaccattgcg ttactatctt cagagcaggt gtgacggatg      60

<210> SEQ ID NO 464
<211> LENGTH: 60
<212> TYPE: DNA
<213> ORGANISM: Artificial Sequence
<220> FEATURE:
<223> OTHER INFORMATION: chemically synthesized

<400> SEQUENCE: 464
catccgtcac acctgctctg aagatagtaa cgcaatggtt gtggtgttgg ctcccgtatg      60

<210> SEQ ID NO 465
<211> LENGTH: 61
<212> TYPE: DNA
<213> ORGANISM: Artificial Sequence
```

```
<220> FEATURE:
<223> OTHER INFORMATION: chemically synthesized

<400> SEQUENCE: 465
catacgggag ccaacaccac ccgtatcgtt cccaatgcac tcagagcagg tgtgacggat     60
g                                                                    61

<210> SEQ ID NO 466
<211> LENGTH: 61
<212> TYPE: DNA
<213> ORGANISM: Artificial Sequence
<220> FEATURE:
<223> OTHER INFORMATION: chemically synthesized

<400> SEQUENCE: 466
catccgtcac acctgctctg agtgcattgg gaacgatacg ggtggtgttg gctcccgtat     60
g                                                                    61

<210> SEQ ID NO 467
<211> LENGTH: 60
<212> TYPE: DNA
<213> ORGANISM: Artificial Sequence
<220> FEATURE:
<223> OTHER INFORMATION: chemically synthesized

<400> SEQUENCE: 467
catacgggag ccaacaccac gttcccatac aagttactga cagagcaggt gtgacggata    60

<210> SEQ ID NO 468
<211> LENGTH: 60
<212> TYPE: DNA
<213> ORGANISM: Artificial Sequence
<220> FEATURE:
<223> OTHER INFORMATION: chemically synthesized

<400> SEQUENCE: 468
tatccgtcac acctgctctg tcagtaactt gtatgggaac gtggtgttgg ctcccgtatg    60

<210> SEQ ID NO 469
<211> LENGTH: 60
<212> TYPE: DNA
<213> ORGANISM: Artificial Sequence
<220> FEATURE:
<223> OTHER INFORMATION: chemically synthesized

<400> SEQUENCE: 469
catacgggag ccaacaccac aatgtcttgc tcgtgtgtcc cagagcaggt gtgacggatg    60

<210> SEQ ID NO 470
<211> LENGTH: 60
<212> TYPE: DNA
<213> ORGANISM: Artificial Sequence
<220> FEATURE:
<223> OTHER INFORMATION: chemically synthesized

<400> SEQUENCE: 470
catccgtcac acctgctctg ggacacacga gcaagacatt gtggtgttgg ctcccgtatg    60

<210> SEQ ID NO 471
<211> LENGTH: 60
<212> TYPE: DNA
<213> ORGANISM: Artificial Sequence
<220> FEATURE:
<223> OTHER INFORMATION: chemically synthesized

<400> SEQUENCE: 471
```

```
catacgggag ccaacaccac tctcagaatg ggtccaaccc cagagcaggt gtgacggatg    60
```

<210> SEQ ID NO 472
<211> LENGTH: 60
<212> TYPE: DNA
<213> ORGANISM: Artificial Sequence
<220> FEATURE:
<223> OTHER INFORMATION: chemically synthesized

<400> SEQUENCE: 472

```
catccgtcac acctgctctg gggttggacc cattctgaga gtggtgttgg ctcccgtatg    60
```

<210> SEQ ID NO 473
<211> LENGTH: 60
<212> TYPE: DNA
<213> ORGANISM: Artificial Sequence
<220> FEATURE:
<223> OTHER INFORMATION: chemically synthesized

<400> SEQUENCE: 473

```
catacgggag ccaacaccac gtgttgatgc ggggttctcg cagagcaggt gtgacggatg    60
```

<210> SEQ ID NO 474
<211> LENGTH: 60
<212> TYPE: DNA
<213> ORGANISM: Artificial Sequence
<220> FEATURE:
<223> OTHER INFORMATION: chemically synthesized

<400> SEQUENCE: 474

```
catccgtcac acctgctctg cgagaacccc gcatcaacac gtggtgttgg ctcccgtatg    60
```

<210> SEQ ID NO 475
<211> LENGTH: 60
<212> TYPE: DNA
<213> ORGANISM: Artificial Sequence
<220> FEATURE:
<223> OTHER INFORMATION: chemically synthesized

<400> SEQUENCE: 475

```
catacgggag ccaacaccac ccgcagcatc cataaacgag cagagcaggt gtgacggatg    60
```

<210> SEQ ID NO 476
<211> LENGTH: 60
<212> TYPE: DNA
<213> ORGANISM: Artificial Sequence
<220> FEATURE:
<223> OTHER INFORMATION: chemically synthesized

<400> SEQUENCE: 476

```
catccgtcac acctgctctg ctcgtttatg gatgctgcgg gtggtgttgg ctcccgtatg    60
```

<210> SEQ ID NO 477
<211> LENGTH: 72
<212> TYPE: DNA
<213> ORGANISM: Artificial Sequence
<220> FEATURE:
<223> OTHER INFORMATION: chemically synthesized

<400> SEQUENCE: 477

```
atccgtcaca cctgctctat cgtgtcttat ttattctgct caatacgtta cgcttggtgt    60
tggctcccgt at                                                        72
```

<210> SEQ ID NO 478
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 478
atacgggagc caacaccaag cgtaacgtat tgagcagaat aaataagaca cgatagagca    60
ggtgtgacgg at                                                        72

<210> SEQ ID NO 479
<211> LENGTH: 72
<212> TYPE: DNA
<213> ORGANISM: Artificial Sequence
<220> FEATURE:
<223> OTHER INFORMATION: chemically synthesized

<400> SEQUENCE: 479
atacgggagc caacaccaac ctggctatct gcatgcggtc ggtcgccttg ttggagagca    60
ggtgtgacgg at                                                        72

<210> SEQ ID NO 480
<211> LENGTH: 72
<212> TYPE: DNA
<213> ORGANISM: Artificial Sequence
<220> FEATURE:
<223> OTHER INFORMATION: chemically synthesized

<400> SEQUENCE: 480
atccgtcaca cctgctctcc aacaaggcga ccgaccgcat gcagatagcc aggttggtgt    60
tggctcccgt at                                                        72

<210> SEQ ID NO 481
<211> LENGTH: 72
<212> TYPE: DNA
<213> ORGANISM: Artificial Sequence
<220> FEATURE:
<223> OTHER INFORMATION: chemically synthesized

<400> SEQUENCE: 481
atccgtcaca cctgctcttc acgtgtagcg atgacagaat aaggattgaa agactggtgt    60
tggctcccgt at                                                        72

<210> SEQ ID NO 482
<211> LENGTH: 72
<212> TYPE: DNA
<213> ORGANISM: Artificial Sequence
<220> FEATURE:
<223> OTHER INFORMATION: chemically synthesized

<400> SEQUENCE: 482
atacgggagc caacaccagt ctttcaatcc ttattctgtc atcgctacac gtgaagagca    60
ggtgtgacgg at                                                        72

<210> SEQ ID NO 483
<211> LENGTH: 72
<212> TYPE: DNA
<213> ORGANISM: Artificial Sequence
<220> FEATURE:
<223> OTHER INFORMATION: chemically synthesized

<400> SEQUENCE: 483
atccgtcaca cctgctctga ggtcgggtat tagtccgtat aaaccgagac tgaatggtgt    60
tggctcccgt at                                                        72
```

<210> SEQ ID NO 484
<211> LENGTH: 72
<212> TYPE: DNA
<213> ORGANISM: Artificial Sequence
<220> FEATURE:
<223> OTHER INFORMATION: chemically synthesized

<400> SEQUENCE: 484
atacgggagc caacaccatt cagtctcggt ttatacggac taatacccga cctcagagca    60
ggtgtgacgg at    72

<210> SEQ ID NO 485
<211> LENGTH: 72
<212> TYPE: DNA
<213> ORGANISM: Artificial Sequence
<220> FEATURE:
<223> OTHER INFORMATION: chemically synthesized

<400> SEQUENCE: 485
atacgggagc caacaccagc gatacacgtc catcgaacaa gttaaaactt agaaagagca    60
ggtgtgacgg at    72

<210> SEQ ID NO 486
<211> LENGTH: 72
<212> TYPE: DNA
<213> ORGANISM: Artificial Sequence
<220> FEATURE:
<223> OTHER INFORMATION: chemically synthesized

<400> SEQUENCE: 486
atccgtcaca cctgctcttt ctaagttta acttgttcga tggacgtgta tcgctggtgt    60
tggctcccgt at    72

<210> SEQ ID NO 487
<211> LENGTH: 72
<212> TYPE: DNA
<213> ORGANISM: Artificial Sequence
<220> FEATURE:
<223> OTHER INFORMATION: chemically synthesized

<400> SEQUENCE: 487
atacgggagc caacaccacg ggggcatctt ccattaaccc attacctcac cccaagagca    60
ggtgtgacgg at    72

<210> SEQ ID NO 488
<211> LENGTH: 72
<212> TYPE: DNA
<213> ORGANISM: Artificial Sequence
<220> FEATURE:
<223> OTHER INFORMATION: chemically synthesized

<400> SEQUENCE: 488
atccgtcaca cctgctcttg gggtgaggta atgggttaat ggaagatgcc cccgtggtgt    60
tggctcccgt at    72

<210> SEQ ID NO 489
<211> LENGTH: 72
<212> TYPE: DNA
<213> ORGANISM: Artificial Sequence
<220> FEATURE:
<223> OTHER INFORMATION: chemically synthesized

<400> SEQUENCE: 489

```
atacgggagc caacaccacg cccacggcca cgcccgacga gctacccctc atcaagagca    60
ggtgtgacgg at                                                       72
```

<210> SEQ ID NO 490
<211> LENGTH: 72
<212> TYPE: DNA
<213> ORGANISM: Artificial Sequence
<220> FEATURE:
<223> OTHER INFORMATION: chemically synthesized

<400> SEQUENCE: 490

```
atccgtcaca cctgctcttg atgaggggta gctcgtcggg cgtggccgtg ggcgtggtgt    60
tggctcccgt at                                                       72
```

<210> SEQ ID NO 491
<211> LENGTH: 72
<212> TYPE: DNA
<213> ORGANISM: Artificial Sequence
<220> FEATURE:
<223> OTHER INFORMATION: chemically synthesized

<400> SEQUENCE: 491

```
atccgtcaca cctgctctcg catctaacgt ctagactatc aaaagtcgtg ttaatggtgt    60
tggttccggt at                                                       72
```

<210> SEQ ID NO 492
<211> LENGTH: 72
<212> TYPE: DNA
<213> ORGANISM: Artificial Sequence
<220> FEATURE:
<223> OTHER INFORMATION: chemically synthesized

<400> SEQUENCE: 492

```
ataccggaac caacaccatt aacacgactt ttgatagtct agacgttaga tgcgagagca    60
ggtgtgacgg at                                                       72
```

<210> SEQ ID NO 493
<211> LENGTH: 72
<212> TYPE: DNA
<213> ORGANISM: Artificial Sequence
<220> FEATURE:
<223> OTHER INFORMATION: chemically synthesized

<400> SEQUENCE: 493

```
atccgtcaca cctgctcttg gggtgaggta atgggttaat ggaagatgcc cccgtggtgt    60
tggctcccgt at                                                       72
```

<210> SEQ ID NO 494
<211> LENGTH: 72
<212> TYPE: DNA
<213> ORGANISM: Artificial Sequence
<220> FEATURE:
<223> OTHER INFORMATION: chemically synthesized

<400> SEQUENCE: 494

```
atacgggagc caacaccacg ggggcatctt ccattaaccc attacctcac cccaagagca    60
ggtgtgacgg at                                                       72
```

<210> SEQ ID NO 495
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 495
atacgggagc caacaccaca aagtttagcg ttatgcaact cccccttata ctcgagagca    60
ggtgtgacgg at                                                       72

<210> SEQ ID NO 496
<211> LENGTH: 72
<212> TYPE: DNA
<213> ORGANISM: Artificial Sequence
<220> FEATURE:
<223> OTHER INFORMATION: chemically synthesized

<400> SEQUENCE: 496
atccgtcaca cctgctctcg agtataaggg ggagttgcat aacgctaaac tttgtggtgt    60
tggctcccgt at                                                       72

<210> SEQ ID NO 497
<211> LENGTH: 72
<212> TYPE: DNA
<213> ORGANISM: Artificial Sequence
<220> FEATURE:
<223> OTHER INFORMATION: chemically synthesized

<400> SEQUENCE: 497
atacgggagc caacaccagt aattgtcact cacgcagatc ggtgactaca tagcagagca    60
ggtgtgacgg at                                                       72

<210> SEQ ID NO 498
<211> LENGTH: 72
<212> TYPE: DNA
<213> ORGANISM: Artificial Sequence
<220> FEATURE:
<223> OTHER INFORMATION: chemically synthesized

<400> SEQUENCE: 498
atccgtcaca cctgctctgc tatgtagtca ccgatctgcg tgagtgacaa ttactggtgt    60
tggctcccgt at                                                       72

<210> SEQ ID NO 499
<211> LENGTH: 72
<212> TYPE: DNA
<213> ORGANISM: Artificial Sequence
<220> FEATURE:
<223> OTHER INFORMATION: chemically synthesized

<400> SEQUENCE: 499
atccgtcaca cctgctctgt gtactacttg caggaatggc aataggcgga aagtggtgt     60 tggctcccgt at                                                       72

<210> SEQ ID NO 500
<211> LENGTH: 72
<212> TYPE: DNA
<213> ORGANISM: Artificial Sequence
<220> FEATURE:
<223> OTHER INFORMATION: chemically synthesized

<400> SEQUENCE: 500
atacgggagc caacaccacc tttccgccta ttgccattcc tgcaagtagt acacagagca    60
ggtgtgacgg at                                                       72
```

```
<210> SEQ ID NO 501
<211> LENGTH: 71
<212> TYPE: DNA
<213> ORGANISM: Artificial Sequence
<220> FEATURE:
<223> OTHER INFORMATION: chemically synthesized

<400> SEQUENCE: 501
atccgtcaca cctgctctat gttgccggga agatatagtg aaaattcatg atatggtgtt      60
ggctcccgta t                                                           71

<210> SEQ ID NO 502
<211> LENGTH: 71
<212> TYPE: DNA
<213> ORGANISM: Artificial Sequence
<220> FEATURE:
<223> OTHER INFORMATION: chemically synthesized

<400> SEQUENCE: 502
atacgggagc caacaccata tcatgaattt tcactatatc ttcccggcaa catagagcag      60
gtgtgacgga t                                                           71

<210> SEQ ID NO 503
<211> LENGTH: 72
<212> TYPE: DNA
<213> ORGANISM: Artificial Sequence
<220> FEATURE:
<223> OTHER INFORMATION: chemically synthesized

<400> SEQUENCE: 503
atacgggagc caacaccact ggtgaggcgc ctgcgccgac tggccgtccc cccgagagca      60
ggtgtgacgg at                                                          72

<210> SEQ ID NO 504
<211> LENGTH: 72
<212> TYPE: DNA
<213> ORGANISM: Artificial Sequence
<220> FEATURE:
<223> OTHER INFORMATION: chemically synthesized

<400> SEQUENCE: 504
atccgtcaca cctgctctcg gggggacggc cagtcggcgc aggcgcctca ccagtggtgt      60
tggctcccgt at                                                          72

<210> SEQ ID NO 505
<211> LENGTH: 72
<212> TYPE: DNA
<213> ORGANISM: Artificial Sequence
<220> FEATURE:
<223> OTHER INFORMATION: chemically synthesized

<400> SEQUENCE: 505
atccgtcaca cctgctctgg gtgagcgagt cggccccggg agcgaacggc ggcgtggtgt      60
tggctcccgt at                                                          72

<210> SEQ ID NO 506
<211> LENGTH: 72
<212> TYPE: DNA
<213> ORGANISM: Artificial Sequence
<220> FEATURE:
<223> OTHER INFORMATION: chemically synthesized

<400> SEQUENCE: 506
atacgggagc caacaccacg ccgccgttcg ctcccggggc cgactcgctc acccagagca      60
```

```
<210> SEQ ID NO 507
<211> LENGTH: 72
<212> TYPE: DNA
<213> ORGANISM: Artificial Sequence
<220> FEATURE:
<223> OTHER INFORMATION: chemically synthesized

<400> SEQUENCE: 507
atccgtcaca cctgctctca gcggcggcgg gcccgggcga tggaggtcct gacatggtgt    60
tggctcccgt at                                                       72

<210> SEQ ID NO 508
<211> LENGTH: 72
<212> TYPE: DNA
<213> ORGANISM: Artificial Sequence
<220> FEATURE:
<223> OTHER INFORMATION: chemically synthesized

<400> SEQUENCE: 508
atacgggagc caacaccatg tcaggacctc catcgcccgg gcccgccgcc gctgagagca    60
ggtgtgacgg at                                                       72

<210> SEQ ID NO 509
<211> LENGTH: 72
<212> TYPE: DNA
<213> ORGANISM: Artificial Sequence
<220> FEATURE:
<223> OTHER INFORMATION: chemically synthesized

<400> SEQUENCE: 509
atccgtcaca cctgctcttt ccatgtatat tagatactcg gggcaagggg aaactggtgt    60
tggctcccgt at                                                       72

<210> SEQ ID NO 510
<211> LENGTH: 72
<212> TYPE: DNA
<213> ORGANISM: Artificial Sequence
<220> FEATURE:
<223> OTHER INFORMATION: chemically synthesized

<400> SEQUENCE: 510
atacgggagc caacaccagt ttccccttgc cccgagtatc taatatacat ggaaagagca    60
ggtgtgacgg at                                                       72

<210> SEQ ID NO 511
<211> LENGTH: 70
<212> TYPE: DNA
<213> ORGANISM: Artificial Sequence
<220> FEATURE:
<223> OTHER INFORMATION: chemically synthesized

<400> SEQUENCE: 511
atccgtcaca cctgctctgg agcgatctaa ccctttttat caatcaattc ggtggtgttg    60
gctcccgtat                                                          70

<210> SEQ ID NO 512
<211> LENGTH: 70
<212> TYPE: DNA
<213> ORGANISM: Artificial Sequence
<220> FEATURE:
<223> OTHER INFORMATION: chemically synthesized
```

<400> SEQUENCE: 512
atacgggagc caacaccacc gaattgattg ataaaaaggg ttagatcgct ccagagcagg    60
tgtgacggat    70

<210> SEQ ID NO 513
<211> LENGTH: 72
<212> TYPE: DNA
<213> ORGANISM: Artificial Sequence
<220> FEATURE:
<223> OTHER INFORMATION: chemically synthesized

<400> SEQUENCE: 513
atccgtcaca cctgctcttg ggacatttgt agtgcctgtt catgtatcgc agcctggtgt    60
tggctcccgt at    72

<210> SEQ ID NO 514
<211> LENGTH: 72
<212> TYPE: DNA
<213> ORGANISM: Artificial Sequence
<220> FEATURE:
<223> OTHER INFORMATION: chemically synthesized

<400> SEQUENCE: 514
atacgggagc caacaccagg ctgcgataca tgaacaggca ctacaaatgt cccaagagca    60
ggtgtgacgg at    72

<210> SEQ ID NO 515
<211> LENGTH: 72
<212> TYPE: DNA
<213> ORGANISM: Artificial Sequence
<220> FEATURE:
<223> OTHER INFORMATION: chemically synthesized

<400> SEQUENCE: 515
atacgggagc caacaccacc cactctcccc ccgctcccgc tccccgctc cgcgagagca    60 ggtgtgacgg at    72

<210> SEQ ID NO 516
<211> LENGTH: 72
<212> TYPE: DNA
<213> ORGANISM: Artificial Sequence
<220> FEATURE:
<223> OTHER INFORMATION: chemically synthesized

<400> SEQUENCE: 516
atccgtcaca cctgctctcg cggagcgggg gagcgggagc ggggggagag tgggtggtgt    60
tggctcccgt at    72

<210> SEQ ID NO 517
<211> LENGTH: 72
<212> TYPE: DNA
<213> ORGANISM: Artificial Sequence
<220> FEATURE:
<223> OTHER INFORMATION: chemically synthesized

<400> SEQUENCE: 517
atccgtcaca cctgctctac atcacatctg actgagtcca tggcgctctg tgtgtggtgt    60
tggctcccgt at    72

<210> SEQ ID NO 518
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 518
atacgggagc caacaccaca cacagagcgc catggactca gtcagatgtg atgtagagca      60
ggtgtgacgg at                                                          72

<210> SEQ ID NO 519
<211> LENGTH: 72
<212> TYPE: DNA
<213> ORGANISM: Artificial Sequence
<220> FEATURE:
<223> OTHER INFORMATION: chemically synthesized

<400> SEQUENCE: 519
atacgggagc caacaccatc ctcctgcggc gtctggagaa cagcctctac tttaagagca      60
ggtgtgacgg at                                                          72

<210> SEQ ID NO 520
<211> LENGTH: 72
<212> TYPE: DNA
<213> ORGANISM: Artificial Sequence
<220> FEATURE:
<223> OTHER INFORMATION: chemically synthesized

<400> SEQUENCE: 520
atccgtcaca cctgctctta aagtagaggc tgttctccag acgccgcagg aggatggtgt      60
tggctcccgt at                                                          72

<210> SEQ ID NO 521
<211> LENGTH: 72
<212> TYPE: DNA
<213> ORGANISM: Artificial Sequence
<220> FEATURE:
<223> OTHER INFORMATION: chemically synthesized

<400> SEQUENCE: 521
atccgtcaca cctgctcttt ttggtattgt tggcggaagg cggtggttcg tgtctggtgt      60
tggctcccgt at                                                          72

<210> SEQ ID NO 522
<211> LENGTH: 72
<212> TYPE: DNA
<213> ORGANISM: Artificial Sequence
<220> FEATURE:
<223> OTHER INFORMATION: chemically synthesized

<400> SEQUENCE: 522
atacgggagc caacaccaga cacgaaccac cgccttccgc caacaatacc aaaaagagca      60
ggtgtgacgg at                                                          72

<210> SEQ ID NO 523
<211> LENGTH: 72
<212> TYPE: DNA
<213> ORGANISM: Artificial Sequence
<220> FEATURE:
<223> OTHER INFORMATION: chemically synthesized

<400> SEQUENCE: 523
atacgggagc caacaccaat agtaccgcgc ccggcgaaaa agctccttta atacagagca      60
ggtgtgacgg at                                                          72
```

<210> SEQ ID NO 524
<211> LENGTH: 72
<212> TYPE: DNA
<213> ORGANISM: Artificial Sequence
<220> FEATURE:
<223> OTHER INFORMATION: chemically synthesized

<400> SEQUENCE: 524

```
atccgtcaca cctgctctgt attaaaggag cttttcgcc gggcgcggta ctattggtgt    60
tggctcccgt at                                                      72
```

<210> SEQ ID NO 525
<211> LENGTH: 72
<212> TYPE: DNA
<213> ORGANISM: Artificial Sequence
<220> FEATURE:
<223> OTHER INFORMATION: chemically synthesized

<400> SEQUENCE: 525

```
atacgggagc caacaccaat agatggataa gggggaaact gccattcggt tagtagagca    60
ggtgtgacgg at                                                      72
```

<210> SEQ ID NO 526
<211> LENGTH: 72
<212> TYPE: DNA
<213> ORGANISM: Artificial Sequence
<220> FEATURE:
<223> OTHER INFORMATION: chemically synthesized

<400> SEQUENCE: 526

```
atccgtcaca cctgctctac taaccgaatg gcagtttccc ccttatccat ctattggtgt    60
tggctcccgt at                                                      72
```

<210> SEQ ID NO 527
<211> LENGTH: 70
<212> TYPE: DNA
<213> ORGANISM: Artificial Sequence
<220> FEATURE:
<223> OTHER INFORMATION: chemically synthesized

<400> SEQUENCE: 527

```
atccgtcaca cctgctcttg ggtcggccgg gaccagcgcg gcggcctcct ggtggtgttg    60
gctcccgtat                                                         70
```

<210> SEQ ID NO 528
<211> LENGTH: 70
<212> TYPE: DNA
<213> ORGANISM: Artificial Sequence
<220> FEATURE:
<223> OTHER INFORMATION: chemically synthesized

<400> SEQUENCE: 528

```
atacgggagc caacaccacc aggaggccgc cgcgctggtc ccggccgacc caagagcagg    60
tgtgacggat                                                         70
```

<210> SEQ ID NO 529
<211> LENGTH: 72
<212> TYPE: DNA
<213> ORGANISM: Artificial Sequence
<220> FEATURE:
<223> OTHER INFORMATION: chemically synthesized

<400> SEQUENCE: 529

```
atccgtcaca cctgctctat gttacaaccg ccacaagtag gtttgatacc cgggtggtgt    60
tggctcccgt at                                                        72

<210> SEQ ID NO 530
<211> LENGTH: 72
<212> TYPE: DNA
<213> ORGANISM: Artificial Sequence
<220> FEATURE:
<223> OTHER INFORMATION: chemically synthesized

<400> SEQUENCE: 530
atacgggagc caacaccacc cgggtatcaa acctacttgt ggcggttgta acatagagca    60
ggtgtgacgg at                                                        72

<210> SEQ ID NO 531
<211> LENGTH: 71
<212> TYPE: DNA
<213> ORGANISM: Artificial Sequence
<220> FEATURE:
<223> OTHER INFORMATION: chemically synthesized

<400> SEQUENCE: 531
atacgggagc caacaccaca cacagagcgc atggactcag tcagatgtga tgtagagcag    60
gtgtgacgga t                                                         71

<210> SEQ ID NO 532
<211> LENGTH: 71
<212> TYPE: DNA
<213> ORGANISM: Artificial Sequence
<220> FEATURE:
<223> OTHER INFORMATION: chemically synthesized

<400> SEQUENCE: 532
atccgtcaca cctgctctac atcacatctg actgagtcca tgcgctctgt gtgtggtgtt    60
ggctcccgta t                                                         71

<210> SEQ ID NO 533
<211> LENGTH: 72
<212> TYPE: DNA
<213> ORGANISM: Artificial Sequence
<220> FEATURE:
<223> OTHER INFORMATION: chemically synthesized

<400> SEQUENCE: 533
atacgggagc caacaccatc actactttta taatttcatt cttctggcgt ccctagagca    60
ggtgtgacgg at                                                        72

<210> SEQ ID NO 534
<211> LENGTH: 72
<212> TYPE: DNA
<213> ORGANISM: Artificial Sequence
<220> FEATURE:
<223> OTHER INFORMATION: chemically synthesized

<400> SEQUENCE: 534
atccgtcaca cctgctctag ggacgccaga agaatgaaat tataaaagta gtgatggtgt    60
tggctcccgt at                                                        72

<210> SEQ ID NO 535
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 535
atccgtcaca cctgctcttg ttacaaccta gtacccggag ggggacccga ggagtggtgt      60
tggctcccgt at                                                          72

<210> SEQ ID NO 536
<211> LENGTH: 72
<212> TYPE: DNA
<213> ORGANISM: Artificial Sequence
<220> FEATURE:
<223> OTHER INFORMATION: chemically synthesized

<400> SEQUENCE: 536
atacgggagc caacaccact cctcgggtcc ccctccgggt actaggttgt aacaagagca      60
ggtgtgacgg at                                                          72

<210> SEQ ID NO 537
<211> LENGTH: 72
<212> TYPE: DNA
<213> ORGANISM: Artificial Sequence
<220> FEATURE:
<223> OTHER INFORMATION: chemically synthesized

<400> SEQUENCE: 537
atccgtcaca cctgctctgt ttcttcaact tctgccttat ccccggtcgg tacgtggtgt      60
tggctcccgt at                                                          72

<210> SEQ ID NO 538
<211> LENGTH: 72
<212> TYPE: DNA
<213> ORGANISM: Artificial Sequence
<220> FEATURE:
<223> OTHER INFORMATION: chemically synthesized

<400> SEQUENCE: 538
atacgggagc caacaccacg taccgaccgg ggataaggca gaagttgaag aaacagagca      60
ggtgtgacgg at                                                          72

<210> SEQ ID NO 539
<211> LENGTH: 70
<212> TYPE: DNA
<213> ORGANISM: Artificial Sequence
<220> FEATURE:
<223> OTHER INFORMATION: chemically synthesized

<400> SEQUENCE: 539
atacgggagc caacaccatc acggcaatgt ccgataatgt cttgcttcag cgagagcagg      60
tgtgacggat                                                             70

<210> SEQ ID NO 540
<211> LENGTH: 70
<212> TYPE: DNA
<213> ORGANISM: Artificial Sequence
<220> FEATURE:
<223> OTHER INFORMATION: chemically synthesized

<400> SEQUENCE: 540
atccgtcaca cctgctctcg ctgaagcaag acattatcgg acattgccgt gatggtgttg      60
gctcccgtat                                                             70
```

```
<210> SEQ ID NO 541
<211> LENGTH: 72
<212> TYPE: DNA
<213> ORGANISM: Artificial Sequence
<220> FEATURE:
<223> OTHER INFORMATION: chemically synthesized

<400> SEQUENCE: 541
atccgtcaca cctgctctga ggaatatgac gcggcaatag tgaaccagtc aaactggtgt      60
tggctcccgt at                                                         72

<210> SEQ ID NO 542
<211> LENGTH: 72
<212> TYPE: DNA
<213> ORGANISM: Artificial Sequence
<220> FEATURE:
<223> OTHER INFORMATION: chemically synthesized

<400> SEQUENCE: 542
atacgggagc caacaccagt ttgactggtt cactattgcc gcgtcatatt cctcagagca      60
ggtgtgacgg at                                                         72

<210> SEQ ID NO 543
<211> LENGTH: 72
<212> TYPE: DNA
<213> ORGANISM: Artificial Sequence
<220> FEATURE:
<223> OTHER INFORMATION: chemically synthesized

<400> SEQUENCE: 543
atccgtcaca cctgctctgc atggccatcc agattagtct tgcagcacat tcggtggtgt      60
tggctcccgt at                                                         72

<210> SEQ ID NO 544
<211> LENGTH: 72
<212> TYPE: DNA
<213> ORGANISM: Artificial Sequence
<220> FEATURE:
<223> OTHER INFORMATION: chemically synthesized

<400> SEQUENCE: 544
atacgggagc caacaccacc gaatgtgctg caagactaat ctggatggcc atgcagagca      60
ggtgtgacgg at                                                         72

<210> SEQ ID NO 545
<211> LENGTH: 72
<212> TYPE: DNA
<213> ORGANISM: Artificial Sequence
<220> FEATURE:
<223> OTHER INFORMATION: chemically synthesized

<400> SEQUENCE: 545
atacgggagc caacaccaca cctggtaaat ttaccacggc ttacttgctc agatagagca      60
ggtgtgacgg at                                                         72

<210> SEQ ID NO 546
<211> LENGTH: 72
<212> TYPE: DNA
<213> ORGANISM: Artificial Sequence
<220> FEATURE:
<223> OTHER INFORMATION: chemically synthesized

<400> SEQUENCE: 546
atccgtcaca cctgctctat ctgagcaagt aagccgtggt aaatttacca ggtgtggtgt      60
```

```
tggctcccgt at                                                          72

<210> SEQ ID NO 547
<211> LENGTH: 71
<212> TYPE: DNA
<213> ORGANISM: Artificial Sequence
<220> FEATURE:
<223> OTHER INFORMATION: chemically synthesized

<400> SEQUENCE: 547
atacgggagc caacaccagc acacggcacg ccctccgaa ccacgccccc gaaagagcag        60
gtgtgacgga t                                                           71

<210> SEQ ID NO 548
<211> LENGTH: 71
<212> TYPE: DNA
<213> ORGANISM: Artificial Sequence
<220> FEATURE:
<223> OTHER INFORMATION: chemically synthesized

<400> SEQUENCE: 548
atccgtcaca cctgctcttt cggggcgtg gttcggaggg gcgtgccgtg tgctggtgtt        60
ggctcccgta t                                                           71

<210> SEQ ID NO 549
<211> LENGTH: 72
<212> TYPE: DNA
<213> ORGANISM: Artificial Sequence
<220> FEATURE:
<223> OTHER INFORMATION: chemically synthesized

<400> SEQUENCE: 549
atacgggagc caacaccatc caatgaggcc atggaccggt aaactcggac gcgcagagca       60
ggtgtgacgg at                                                          72

<210> SEQ ID NO 550
<211> LENGTH: 72
<212> TYPE: DNA
<213> ORGANISM: Artificial Sequence
<220> FEATURE:
<223> OTHER INFORMATION: chemically synthesized

<400> SEQUENCE: 550
atccgtcaca cctgctctgc gcgtccgagt ttaccggtcc atggcctcat tggatggtgt       60
tggctcccgt at                                                          72

<210> SEQ ID NO 551
<211> LENGTH: 72
<212> TYPE: DNA
<213> ORGANISM: Artificial Sequence
<220> FEATURE:
<223> OTHER INFORMATION: chemically synthesized

<400> SEQUENCE: 551
atacgggagc caacaccaca cgccacaaac cccactccgt gccgtgcccg ccccagagca       60
ggtgtgacgg at                                                          72

<210> SEQ ID NO 552
<211> LENGTH: 72
<212> TYPE: DNA
<213> ORGANISM: Artificial Sequence
<220> FEATURE:
<223> OTHER INFORMATION: chemically synthesized
```

```
<400> SEQUENCE: 552
atccgtcaca cctgctctgg ggcgggcacg gcacggagtg gggtttgtgg cgtgtggtgt    60
tggctcccgt at                                                       72

<210> SEQ ID NO 553
<211> LENGTH: 72
<212> TYPE: DNA
<213> ORGANISM: Artificial Sequence
<220> FEATURE:
<223> OTHER INFORMATION: chemically synthesized

<400> SEQUENCE: 553
atacgggagc caacaccacc tggagcccag cctgtactca tctcaccgcc gtccagagca    60
ggtgtgacgg at                                                       72

<210> SEQ ID NO 554
<211> LENGTH: 72
<212> TYPE: DNA
<213> ORGANISM: Artificial Sequence
<220> FEATURE:
<223> OTHER INFORMATION: chemically synthesized

<400> SEQUENCE: 554
atccgtcaca cctgctctgg acggcggtga gatgagtaca ggctgggctc caggtggtgt    60
tggctcccgt at                                                       72

<210> SEQ ID NO 555
<211> LENGTH: 72
<212> TYPE: DNA
<213> ORGANISM: Artificial Sequence
<220> FEATURE:
<223> OTHER INFORMATION: chemically synthesized

<400> SEQUENCE: 555
atacgggagc caacaccagg cgccgtacag cggtccgcta ccgacctatt gtgtagagca    60
ggtgtgacgg at                                                       72

<210> SEQ ID NO 556
<211> LENGTH: 72
<212> TYPE: DNA
<213> ORGANISM: Artificial Sequence
<220> FEATURE:
<223> OTHER INFORMATION: chemically synthesized

<400> SEQUENCE: 556
atccgtcaca cctgctctac acaataggtc ggtagcggac cgctgtacgg cgcctggtgt    60
tggctcccgt at                                                       72

<210> SEQ ID NO 557
<211> LENGTH: 71
<212> TYPE: DNA
<213> ORGANISM: Artificial Sequence
<220> FEATURE:
<223> OTHER INFORMATION: chemically synthesized

<400> SEQUENCE: 557
atacgggagc caacaccata cgtcccacaa agcgatcggc tggatacttc gtcagagcag    60
gtgtgacgga t                                                        71

<210> SEQ ID NO 558
<211> LENGTH: 71
```

```
<212> TYPE: DNA
<213> ORGANISM: Artificial Sequence
<220> FEATURE:
<223> OTHER INFORMATION: chemically synthesized

<400> SEQUENCE: 558
atccgtcaca cctgctctga cgaagtatcc agccgatcgc tttgtgggac gtatggtgtt    60
ggctcccgta t                                                         71

<210> SEQ ID NO 559
<211> LENGTH: 72
<212> TYPE: DNA
<213> ORGANISM: Artificial Sequence
<220> FEATURE:
<223> OTHER INFORMATION: chemically synthesized

<400> SEQUENCE: 559
atacgggagc caacaccaca gaatgtcgat gcacagggga attcggtgcg cccgagagca    60
ggtgtgacgg at                                                        72

<210> SEQ ID NO 560
<211> LENGTH: 72
<212> TYPE: DNA
<213> ORGANISM: Artificial Sequence
<220> FEATURE:
<223> OTHER INFORMATION: chemically synthesized

<400> SEQUENCE: 560
atccgtcaca cctgctctcg ggcgcaccga attccctgt gcatcgacat tctgtggtgt    60
tggctcccgt at                                                        72

<210> SEQ ID NO 561
<211> LENGTH: 72
<212> TYPE: DNA
<213> ORGANISM: Artificial Sequence
<220> FEATURE:
<223> OTHER INFORMATION: chemically synthesized

<400> SEQUENCE: 561
atacgggagc caacaccact ctagctgaca ggtgcatacg atacccgacg cttcagagca    60
ggtgtgacgg at                                                        72

<210> SEQ ID NO 562
<211> LENGTH: 72
<212> TYPE: DNA
<213> ORGANISM: Artificial Sequence
<220> FEATURE:
<223> OTHER INFORMATION: chemically synthesized

<400> SEQUENCE: 562
atccgtcaca cctgctctga agcgtcgggt atcgtatgca cctgtcagct agagtggtgt    60
tggctcccgt at                                                        72

<210> SEQ ID NO 563
<211> LENGTH: 72
<212> TYPE: DNA
<213> ORGANISM: Artificial Sequence
<220> FEATURE:
<223> OTHER INFORMATION: chemically synthesized

<400> SEQUENCE: 563
atacgggagc caacaccagg tccgtcaaac gttacgtagg aggcatatca cggtagagca    60
ggtgtgacgg at                                                        72
```

<210> SEQ ID NO 564
<211> LENGTH: 72
<212> TYPE: DNA
<213> ORGANISM: Artificial Sequence
<220> FEATURE:
<223> OTHER INFORMATION: chemically synthesized

<400> SEQUENCE: 564
atccgtcaca cctgctctac cgtgatatgc ctcctacgta acgtttgacg gacctggtgt    60
tggctcccgt at                                                         72

<210> SEQ ID NO 565
<211> LENGTH: 72
<212> TYPE: DNA
<213> ORGANISM: Artificial Sequence
<220> FEATURE:
<223> OTHER INFORMATION: chemically synthesized

<400> SEQUENCE: 565
atacgggagc caacaccatg catacgaggc caccactcag aaagatatgt gggcagagca    60
ggtgtgacgg at                                                         72

<210> SEQ ID NO 566
<211> LENGTH: 72
<212> TYPE: DNA
<213> ORGANISM: Artificial Sequence
<220> FEATURE:
<223> OTHER INFORMATION: chemically synthesized

<400> SEQUENCE: 566
atccgtcaca cctgctctgc ccacatatct ttctgagtgg tggcctcgta tgcatggtgt    60
tggctcccgt at                                                         72

<210> SEQ ID NO 567
<211> LENGTH: 72
<212> TYPE: DNA
<213> ORGANISM: Artificial Sequence
<220> FEATURE:
<223> OTHER INFORMATION: chemically synthesized

<400> SEQUENCE: 567
atacgggagc caacaccagc ccactgccac gatatatgcg caaccgttgt ccgcagagca    60
ggtgtgacgg at                                                         72

<210> SEQ ID NO 568
<211> LENGTH: 72
<212> TYPE: DNA
<213> ORGANISM: Artificial Sequence
<220> FEATURE:
<223> OTHER INFORMATION: chemically synthesized

<400> SEQUENCE: 568
atccgtcaca cctgctctgc ggacaacggt tgcgcatata tcgtggcagt gggctggtgt    60
tggctcccgt at                                                         72

<210> SEQ ID NO 569
<211> LENGTH: 72
<212> TYPE: DNA
<213> ORGANISM: Artificial Sequence
<220> FEATURE:
<223> OTHER INFORMATION: chemically synthesized

<400> SEQUENCE: 569

```
atacgggagc caacaccaac cgacaccccc gcccagcccc atcctgcccg gtccagagca    60
ggtgtgacgg at                                                        72
```

<210> SEQ ID NO 570
<211> LENGTH: 72
<212> TYPE: DNA
<213> ORGANISM: Artificial Sequence
<220> FEATURE:
<223> OTHER INFORMATION: chemically synthesized
<400> SEQUENCE: 570

```
atccgtcaca cctgctctgg accgggcagg atggggctgg gcggggggtgt cggttggtgt    60 tggctcccgt at                                                        72
```

<210> SEQ ID NO 571
<211> LENGTH: 72
<212> TYPE: DNA
<213> ORGANISM: Artificial Sequence
<220> FEATURE:
<223> OTHER INFORMATION: chemically synthesized
<400> SEQUENCE: 571

```
atacgggagc caacaccatg cggggagcaa tgtaggtctt agtaccacgt ggccagagca    60
ggtgtgacgg at                                                        72
```

<210> SEQ ID NO 572
<211> LENGTH: 72
<212> TYPE: DNA
<213> ORGANISM: Artificial Sequence
<220> FEATURE:
<223> OTHER INFORMATION: chemically synthesized
<400> SEQUENCE: 572

```
atccgtcaca cctgctctgg ccacgtggta ctaagaccta cattgctccc cgcatggtgt    60
tggctcccgt at                                                        72
```

<210> SEQ ID NO 573
<211> LENGTH: 72
<212> TYPE: DNA
<213> ORGANISM: Artificial Sequence
<220> FEATURE:
<223> OTHER INFORMATION: chemically synthesized
<400> SEQUENCE: 573

```
atacgggagc caacaccagc cgtactaggc ccgaagtcag gtgtaggatt ggccagagca    60
ggtgtgacgg at                                                        72
```

<210> SEQ ID NO 574
<211> LENGTH: 72
<212> TYPE: DNA
<213> ORGANISM: Artificial Sequence
<220> FEATURE:
<223> OTHER INFORMATION: chemically synthesized
<400> SEQUENCE: 574

```
atccgtcaca cctgctctgg ccaatcctac acctgacttc gggcctagta cggctggtgt    60
tggctcccgt at                                                        72
```

<210> SEQ ID NO 575
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 575
atacgggagc caacaccaca tcccacacac gaacagtacc ttgccacccc cgccagagca    60
ggtgtgacgg at                                                       72

<210> SEQ ID NO 576
<211> LENGTH: 72
<212> TYPE: DNA
<213> ORGANISM: Artificial Sequence
<220> FEATURE:
<223> OTHER INFORMATION: chemically synthesized

<400> SEQUENCE: 576
atccgtcaca cctgctctgg cgggggtggc aaggtactgt tcgtgtgtgg gatgtggtgt    60
tggctcccgt at                                                       72

<210> SEQ ID NO 577
<211> LENGTH: 72
<212> TYPE: DNA
<213> ORGANISM: Artificial Sequence
<220> FEATURE:
<223> OTHER INFORMATION: chemically synthesized

<400> SEQUENCE: 577
atacgggagc caacaccacc tgtccacttt ggcacgcgcg ccactcagtc ctccagagca    60
ggtgtgacgg at                                                       72

<210> SEQ ID NO 578
<211> LENGTH: 72
<212> TYPE: DNA
<213> ORGANISM: Artificial Sequence
<220> FEATURE:
<223> OTHER INFORMATION: chemically synthesized

<400> SEQUENCE: 578
atccgtcaca cctgctctgg aggactgagt ggcgcgcgtg ccaaagtgga caggtggtgt    60
tggctcccgt at                                                       72

<210> SEQ ID NO 579
<211> LENGTH: 72
<212> TYPE: DNA
<213> ORGANISM: Artificial Sequence
<220> FEATURE:
<223> OTHER INFORMATION: chemically synthesized

<400> SEQUENCE: 579
atacgggagc caacaccagt ccgttatgac atgtccggac ccgtacgcgt gtcaagagca    60
ggtgtgacgg at                                                       72

<210> SEQ ID NO 580
<211> LENGTH: 72
<212> TYPE: DNA
<213> ORGANISM: Artificial Sequence
<220> FEATURE:
<223> OTHER INFORMATION: chemically synthesized

<400> SEQUENCE: 580
atccgtcaca cctgctcttg acacgcgtac gggtccggac atgtcataac ggactggtgt    60
tggctcccgt at                                                       72
```

```
<210> SEQ ID NO 581
<211> LENGTH: 72
<212> TYPE: DNA
<213> ORGANISM: Artificial Sequence
<220> FEATURE:
<223> OTHER INFORMATION: chemically synthesized

<400> SEQUENCE: 581
atacgggagc caacaccagt ccgttatgac atgtccggac ccgtacgcgt gtcaagagca      60
ggtgtgacgg at                                                         72

<210> SEQ ID NO 582
<211> LENGTH: 72
<212> TYPE: DNA
<213> ORGANISM: Artificial Sequence
<220> FEATURE:
<223> OTHER INFORMATION: chemically synthesized

<400> SEQUENCE: 582
atccgtcaca cctgctcttg acacgcgtac gggtccggac atgtcataac ggactggtgt      60
tggctcccgt at                                                         72

<210> SEQ ID NO 583
<211> LENGTH: 59
<212> TYPE: DNA
<213> ORGANISM: Artificial Sequence
<220> FEATURE:
<223> OTHER INFORMATION: chemically synthesized

<400> SEQUENCE: 583
atacgggagc caacaccaca agcaggaata agcgccggtc cagagcaggt gtgacggat       59

<210> SEQ ID NO 584
<211> LENGTH: 59
<212> TYPE: DNA
<213> ORGANISM: Artificial Sequence
<220> FEATURE:
<223> OTHER INFORMATION: chemically synthesized

<400> SEQUENCE: 584
atccgtcaca cctgctctgg accggcgctt attcctgctt gtggtgttgg ctcccgtat       59

<210> SEQ ID NO 585
<211> LENGTH: 71
<212> TYPE: DNA
<213> ORGANISM: Artificial Sequence
<220> FEATURE:
<223> OTHER INFORMATION: chemically synthesized

<400> SEQUENCE: 585
atacgggagc caacaccagc gaactgaaaa cgcttaaagg agaccaatga ccgaagagca      60
ggtgtgacgg a                                                          71

<210> SEQ ID NO 586
<211> LENGTH: 72
<212> TYPE: DNA
<213> ORGANISM: Artificial Sequence
<220> FEATURE:
<223> OTHER INFORMATION: chemically synthesized

<400> SEQUENCE: 586
atccgtcaca cctgctcttc ggtcattggt ctcctttaag cgttttcagt tcgctggtgt      60
tggctcccgt at                                                         72
```

-continued

```
<210> SEQ ID NO 587
<211> LENGTH: 72
<212> TYPE: DNA
<213> ORGANISM: Artificial Sequence
<220> FEATURE:
<223> OTHER INFORMATION: chemically synthesized

<400> SEQUENCE: 587
atacgggagc caacaccaag tcatgccgaa gtagggtaac gtctgaatgg tagaagagca      60
ggtgtgacgg at                                                         72

<210> SEQ ID NO 588
<211> LENGTH: 72
<212> TYPE: DNA
<213> ORGANISM: Artificial Sequence
<220> FEATURE:
<223> OTHER INFORMATION: chemically synthesized

<400> SEQUENCE: 588
atccgtcaca cctgctcttc taccattcag acgttaccct acttcggcat gacttggtgt      60
tggctcccgt at                                                         72

<210> SEQ ID NO 589
<211> LENGTH: 72
<212> TYPE: DNA
<213> ORGANISM: Artificial Sequence
<220> FEATURE:
<223> OTHER INFORMATION: chemically synthesized

<400> SEQUENCE: 589
atacgggagc caacaccact cgtaatcctt aatacacct attgcaacaa tgctagagca       60
ggtgtgacgg at                                                         72

<210> SEQ ID NO 590
<211> LENGTH: 72
<212> TYPE: DNA
<213> ORGANISM: Artificial Sequence
<220> FEATURE:
<223> OTHER INFORMATION: chemically synthesized

<400> SEQUENCE: 590
atccgtcaca cctgctctag cattgttgca ataggtgtat taaaggatta cgagtggtgt      60
tggctcccgt at                                                         72

<210> SEQ ID NO 591
<211> LENGTH: 72
<212> TYPE: DNA
<213> ORGANISM: Artificial Sequence
<220> FEATURE:
<223> OTHER INFORMATION: chemically synthesized

<400> SEQUENCE: 591
atacgggagc caacaccagt ccgttatgac atgtccggac ccgtacgcgt gtcaagagca      60
ggtgtgacgg at                                                         72

<210> SEQ ID NO 592
<211> LENGTH: 72
<212> TYPE: DNA
<213> ORGANISM: Artificial Sequence
<220> FEATURE:
<223> OTHER INFORMATION: chemically synthesized

<400> SEQUENCE: 592
atccgtcaca cctgctcttg acacgcgtac gggtccggac atgtcataac ggactggtgt      60
```

```
tggctcccgt at                                                          72

<210> SEQ ID NO 593
<211> LENGTH: 72
<212> TYPE: DNA
<213> ORGANISM: Artificial Sequence
<220> FEATURE:
<223> OTHER INFORMATION: chemically synthesized

<400> SEQUENCE: 593
atacgggagc caacaccagt ccgttatgac atgtccggac ccgtacgcgt gtcaagagca      60
ggtgtgacgg at                                                          72

<210> SEQ ID NO 594
<211> LENGTH: 72
<212> TYPE: DNA
<213> ORGANISM: Artificial Sequence
<220> FEATURE:
<223> OTHER INFORMATION: chemically synthesized

<400> SEQUENCE: 594
atccgtcaca cctgctcttg acacgcgtac gggtccggac atgtcataac ggactggtgt      60
tggctcccgt at                                                          72

<210> SEQ ID NO 595
<211> LENGTH: 72
<212> TYPE: DNA
<213> ORGANISM: Artificial Sequence
<220> FEATURE:
<223> OTHER INFORMATION: chemically synthesized

<400> SEQUENCE: 595
atacgggagc caacaccagt ccgttatgac atgtccggac ccgtacgcgt gtcaagagca      60
ggtgtgacgg at                                                          72

<210> SEQ ID NO 596
<211> LENGTH: 72
<212> TYPE: DNA
<213> ORGANISM: Artificial Sequence
<220> FEATURE:
<223> OTHER INFORMATION: chemically synthesized

<400> SEQUENCE: 596
atccgtcaca cctgctcttg acacgcgtac gggtccggac atgtcataac ggactggtgt      60
tggctcccgt at                                                          72

<210> SEQ ID NO 597
<211> LENGTH: 71
<212> TYPE: DNA
<213> ORGANISM: Artificial Sequence
<220> FEATURE:
<223> OTHER INFORMATION: chemically synthesized

<400> SEQUENCE: 597
atacgggagc caacaccaca ctaccgtccc accccctccc agctcctccg gccgagagca      60
ggtgtgacgg a                                                           71

<210> SEQ ID NO 598
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 598
atccgtcaca cctgctctcg gccggaggag ctgggagggg gtgggacggt agtgtggtgt    60
tggctcccgt at                                                       72

<210> SEQ ID NO 599
<211> LENGTH: 72
<212> TYPE: DNA
<213> ORGANISM: Artificial Sequence
<220> FEATURE:
<223> OTHER INFORMATION: chemically synthesized

<400> SEQUENCE: 599
atacgggagc caacaccaag gggcaactcg aacccgggcg ataccgagac tgacagagca    60
ggtgtgacgg at                                                       72

<210> SEQ ID NO 600
<211> LENGTH: 72
<212> TYPE: DNA
<213> ORGANISM: Artificial Sequence
<220> FEATURE:
<223> OTHER INFORMATION: chemically synthesized

<400> SEQUENCE: 600
atccgtcaca cctgctctgt cagtctcggt atcgcccggg ttcgagttgc cccttggtgt    60
tggctcccgt at                                                       72

<210> SEQ ID NO 601
<211> LENGTH: 72
<212> TYPE: DNA
<213> ORGANISM: Artificial Sequence
<220> FEATURE:
<223> OTHER INFORMATION: chemically synthesized

<400> SEQUENCE: 601
atacgggagc caacaccacg atcctactca tacggagccc tggctgactc gcgcagagca    60
ggtgtgacgg at                                                       72

<210> SEQ ID NO 602
<211> LENGTH: 72
<212> TYPE: DNA
<213> ORGANISM: Artificial Sequence
<220> FEATURE:
<223> OTHER INFORMATION: chemically synthesized

<400> SEQUENCE: 602
atccgtcaca cctgctctgc gcgagtcagc cagggctccg tatgagtagg atcgtggtgt    60
tggctcccgt at                                                       72

<210> SEQ ID NO 603
<211> LENGTH: 72
<212> TYPE: DNA
<213> ORGANISM: Artificial Sequence
<220> FEATURE:
<223> OTHER INFORMATION: chemically synthesized

<400> SEQUENCE: 603
atacgggagc caacaccagt ccgttatgac atgtccggac ccgtacgcgt gtcaagagca    60
ggtgtgacgg at                                                       72

<210> SEQ ID NO 604
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 604
atccgtcaca cctgctcttg acacgcgtac gggtccggac atgtcataac ggactggtgt    60
tggctcccgt at                                                        72

<210> SEQ ID NO 605
<211> LENGTH: 72
<212> TYPE: DNA
<213> ORGANISM: Artificial Sequence
<220> FEATURE:
<223> OTHER INFORMATION: chemically synthesized

<400> SEQUENCE: 605
atacgggagc caacaccagt ccgttatgac atgtccggac ccgtacgcgt gtcaagagca    60
ggtgtgacgg at                                                        72

<210> SEQ ID NO 606
<211> LENGTH: 72
<212> TYPE: DNA
<213> ORGANISM: Artificial Sequence
<220> FEATURE:
<223> OTHER INFORMATION: chemically synthesized

<400> SEQUENCE: 606
atccgtcaca cctgctcttg acacgcgtac gggtccggac atgtcataac ggactggtgt    60
tggctcccgt at                                                        72

<210> SEQ ID NO 607
<211> LENGTH: 72
<212> TYPE: DNA
<213> ORGANISM: Artificial Sequence
<220> FEATURE:
<223> OTHER INFORMATION: chemically synthesized

<400> SEQUENCE: 607
atacgggagc caacaccact gaaaacttat gaaatgccgg tcgcagattt tgtcagagca    60
ggtgtgacgg at                                                        72

<210> SEQ ID NO 608
<211> LENGTH: 72
<212> TYPE: DNA
<213> ORGANISM: Artificial Sequence
<220> FEATURE:
<223> OTHER INFORMATION: chemically synthesized

<400> SEQUENCE: 608
atccgtcaca cctgctctga caaaatctgc gaccggcatt tcataagttt tcagtggtgt    60
tggctcccgt at                                                        72

<210> SEQ ID NO 609
<211> LENGTH: 71
<212> TYPE: DNA
<213> ORGANISM: Artificial Sequence
<220> FEATURE:
<223> OTHER INFORMATION: chemically synthesized

<400> SEQUENCE: 609
atacgggagc caacaccagt ccgttatgac atgtccggac ccgtacgcgt gtcagagcag    60
gtgtgacgga t                                                         71
```

<210> SEQ ID NO 610
<211> LENGTH: 71
<212> TYPE: DNA
<213> ORGANISM: Artificial Sequence
<220> FEATURE:
<223> OTHER INFORMATION: chemically synthesized

<400> SEQUENCE: 610
atccgtcaca cctgctctga cacgcgtacg ggtccggaca tgtcataacg gactggtgtt     60
ggctcccgta t                                                         71

<210> SEQ ID NO 611
<211> LENGTH: 72
<212> TYPE: DNA
<213> ORGANISM: Artificial Sequence
<220> FEATURE:
<223> OTHER INFORMATION: chemically synthesized

<400> SEQUENCE: 611
atacgggagc caacaccaca ctaccgtccc accccctccc agctcctccg gccgagagca     60
ggtgtgacgg at                                                        72

<210> SEQ ID NO 612
<211> LENGTH: 72
<212> TYPE: DNA
<213> ORGANISM: Artificial Sequence
<220> FEATURE:
<223> OTHER INFORMATION: chemically synthesized

<400> SEQUENCE: 612
atccgtcaca cctgctctcg gccggaggag ctgggagggg gtgggacggt agtgtggtgt     60
tggctcccgt at                                                        72

<210> SEQ ID NO 613
<211> LENGTH: 72
<212> TYPE: DNA
<213> ORGANISM: Artificial Sequence
<220> FEATURE:
<223> OTHER INFORMATION: chemically synthesized

<400> SEQUENCE: 613
atacgggagc caacaccagt ccgttatgac atgtccggac ccgtacgcgt gtcaagagca     60
ggtgtgacgg at                                                        72

<210> SEQ ID NO 614
<211> LENGTH: 72
<212> TYPE: DNA
<213> ORGANISM: Artificial Sequence
<220> FEATURE:
<223> OTHER INFORMATION: chemically synthesized

<400> SEQUENCE: 614
atccgtcaca cctgctcttg acacgcgtac gggtccggac atgtcataac ggactggtgt     60
tggctcccgt at                                                        72

<210> SEQ ID NO 615
<211> LENGTH: 72
<212> TYPE: DNA
<213> ORGANISM: Artificial Sequence
<220> FEATURE:
<223> OTHER INFORMATION: chemically synthesized

<400> SEQUENCE: 615

```
atacgggagc caacaccagt ccgttatgac atgtccggac ccgtacgcgt gtcaagagca      60
ggtgtgacgg at                                                          72
```

<210> SEQ ID NO 616
<211> LENGTH: 72
<212> TYPE: DNA
<213> ORGANISM: Artificial Sequence
<220> FEATURE:
<223> OTHER INFORMATION: chemically synthesized

<400> SEQUENCE: 616

```
atccgtcaca cctgctcttg acacgcgtac gggtccggac atgtcataac ggactggtgt      60
tggctcccgt at                                                          72
```

<210> SEQ ID NO 617
<211> LENGTH: 58
<212> TYPE: DNA
<213> ORGANISM: Artificial Sequence
<220> FEATURE:
<223> OTHER INFORMATION: chemically synthesized

<400> SEQUENCE: 617

```
atacgggagc caacaccacc gcaacacact atccacgacc agagcaggtg tgacggat        58
```

<210> SEQ ID NO 618
<211> LENGTH: 58
<212> TYPE: DNA
<213> ORGANISM: Artificial Sequence
<220> FEATURE:
<223> OTHER INFORMATION: chemically synthesized

<400> SEQUENCE: 618

```
atccgtcaca cctgctctgg tcgtggatag tgtgttgcgg tggtgttggc tcccgtat        58
```

<210> SEQ ID NO 619
<211> LENGTH: 72
<212> TYPE: DNA
<213> ORGANISM: Artificial Sequence
<220> FEATURE:
<223> OTHER INFORMATION: chemically synthesized

<400> SEQUENCE: 619

```
atacgggagc caacaccacc gcccgcctcc tggcgccaca ccccgccgc agcgagagca       60 ggtgtgacgg at                                                          72
```

<210> SEQ ID NO 620
<211> LENGTH: 72
<212> TYPE: DNA
<213> ORGANISM: Artificial Sequence
<220> FEATURE:
<223> OTHER INFORMATION: chemically synthesized

<400> SEQUENCE: 620

```
atccgtcaca cctgctctcg ctgcggcggg ggtgtggcgc caggaggcgg gcggtggtgt      60
tggctcccgt at                                                          72
```

<210> SEQ ID NO 621
<211> LENGTH: 72
<212> TYPE: DNA
<213> ORGANISM: Artificial Sequence
<220> FEATURE:
<223> OTHER INFORMATION: chemically synthesized

<400> SEQUENCE: 621

```
atacgggagc caacaccaaa tacagtgcct aataggtatg aaaattatag taatagagca      60
ggtgtgacgg at                                                          72

<210> SEQ ID NO 622
<211> LENGTH: 72
<212> TYPE: DNA
<213> ORGANISM: Artificial Sequence
<220> FEATURE:
<223> OTHER INFORMATION: chemically synthesized

<400> SEQUENCE: 622
atccgtcaca cctgctctat tactataatt ttcataccta ttaggcactg tatttggtgt      60
tggctcccgt at                                                          72

<210> SEQ ID NO 623
<211> LENGTH: 72
<212> TYPE: DNA
<213> ORGANISM: Artificial Sequence
<220> FEATURE:
<223> OTHER INFORMATION: chemically synthesized

<400> SEQUENCE: 623
atacgggagc caacaccaca ctaccgtccc accccctccc agctcctccg gccgagagca      60
ggtgtgacgg at                                                          72

<210> SEQ ID NO 624
<211> LENGTH: 72
<212> TYPE: DNA
<213> ORGANISM: Artificial Sequence
<220> FEATURE:
<223> OTHER INFORMATION: chemically synthesized

<400> SEQUENCE: 624
atccgtcaca cctgctctcg gccggaggag ctgggagggg gtgggacggt agtgtggtgt      60
tggctcccgt at                                                          72

<210> SEQ ID NO 625
<211> LENGTH: 72
<212> TYPE: DNA
<213> ORGANISM: Artificial Sequence
<220> FEATURE:
<223> OTHER INFORMATION: chemically synthesized

<400> SEQUENCE: 625
atacgggagc caacaccact agttatttca tagggaaat taacaaattt tgacagagca       60
ggtgtgacgg at                                                          72

<210> SEQ ID NO 626
<211> LENGTH: 72
<212> TYPE: DNA
<213> ORGANISM: Artificial Sequence
<220> FEATURE:
<223> OTHER INFORMATION: chemically synthesized

<400> SEQUENCE: 626
atccgtcaca cctgctctgt caaaatttgt taatttcccc tatgaaataa ctagtggtgt      60
tggctcccgt at                                                          72

<210> SEQ ID NO 627
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 627
atacgggagc caacaccacg gacaatctgg tagtagtaaa caatatataa gtatagagca      60
ggtgtgacgg at                                                         72

<210> SEQ ID NO 628
<211> LENGTH: 72
<212> TYPE: DNA
<213> ORGANISM: Artificial Sequence
<220> FEATURE:
<223> OTHER INFORMATION: chemically synthesized

<400> SEQUENCE: 628
atccgtcaca cctgctctat acttatatat tgtttactac taccagattg tccgtggtgt      60
tggctcccgt at                                                         72

<210> SEQ ID NO 629
<211> LENGTH: 72
<212> TYPE: DNA
<213> ORGANISM: Artificial Sequence
<220> FEATURE:
<223> OTHER INFORMATION: chemically synthesized

<400> SEQUENCE: 629
atacgggagc caacaccagt actcgctgtg gcaaaagcag catttcgtct atctagagca      60
ggtgtgacgg at                                                         72

<210> SEQ ID NO 630
<211> LENGTH: 72
<212> TYPE: DNA
<213> ORGANISM: Artificial Sequence
<220> FEATURE:
<223> OTHER INFORMATION: chemically synthesized

<400> SEQUENCE: 630
atccgtcaca cctgctctag atagacgaaa tgctgctttt gccacagcga gtactggtgt      60
tggctcccgt at                                                         72

<210> SEQ ID NO 631
<211> LENGTH: 72
<212> TYPE: DNA
<213> ORGANISM: Artificial Sequence
<220> FEATURE:
<223> OTHER INFORMATION: chemically synthesized

<400> SEQUENCE: 631
atacgggagc caacaccaaa gctccccccc tcatccctgg catctccgct aaccagagca      60
ggtgtgacgg at                                                         72

<210> SEQ ID NO 632
<211> LENGTH: 72
<212> TYPE: DNA
<213> ORGANISM: Artificial Sequence
<220> FEATURE:
<223> OTHER INFORMATION: chemically synthesized

<400> SEQUENCE: 632
atccgtcaca cctgctctgg ttagcggaga tgccagggat gagggggggga gctttggtgt      60 tggctcccgt at                                                         72
```

```
<210> SEQ ID NO 633
<211> LENGTH: 72
<212> TYPE: DNA
<213> ORGANISM: Artificial Sequence
<220> FEATURE:
<223> OTHER INFORMATION: chemically synthesized

<400> SEQUENCE: 633
atacgggagc caacaccagt ccgttatgac atgtccggac ccgtacgcgt gtcaagagca    60
ggtgtgacgg at                                                       72

<210> SEQ ID NO 634
<211> LENGTH: 72
<212> TYPE: DNA
<213> ORGANISM: Artificial Sequence
<220> FEATURE:
<223> OTHER INFORMATION: chemically synthesized

<400> SEQUENCE: 634
atccgtcaca cctgctcttg acacgcgtac gggtccggac atgtcataac ggactggtgt    60
tggctcccgt at                                                       72

<210> SEQ ID NO 635
<211> LENGTH: 72
<212> TYPE: DNA
<213> ORGANISM: Artificial Sequence
<220> FEATURE:
<223> OTHER INFORMATION: chemically synthesized

<400> SEQUENCE: 635
atacgggagc caacaccatt aacgtcgcaa tagcgctcat ctaacgtcaa gggcagagca    60
ggtgtgacgg at                                                       72

<210> SEQ ID NO 636
<211> LENGTH: 72
<212> TYPE: DNA
<213> ORGANISM: Artificial Sequence
<220> FEATURE:
<223> OTHER INFORMATION: chemically synthesized

<400> SEQUENCE: 636
atccgtcaca cctgctctgc ccttgacgtt agatgagcgc tattgcgacg ttaatggtgt    60
tggctcccgt at                                                       72

<210> SEQ ID NO 637
<211> LENGTH: 72
<212> TYPE: DNA
<213> ORGANISM: Artificial Sequence
<220> FEATURE:
<223> OTHER INFORMATION: chemically synthesized

<400> SEQUENCE: 637
atacgggagc caacaccaaa gtgtcgtaat ttaagatgca tacgcatgcc gttaagagca    60
ggtgtgacgg at                                                       72

<210> SEQ ID NO 638
<211> LENGTH: 72
<212> TYPE: DNA
<213> ORGANISM: Artificial Sequence
<220> FEATURE:
<223> OTHER INFORMATION: chemically synthesized

<400> SEQUENCE: 638
atccgtcaca cctgctctta acggcatgcg tatgcatctt aaattacgac actttggtgt    60
```

```
tggctcccgt at                                                        72

<210> SEQ ID NO 639
<211> LENGTH: 72
<212> TYPE: DNA
<213> ORGANISM: Artificial Sequence
<220> FEATURE:
<223> OTHER INFORMATION: chemically synthesized

<400> SEQUENCE: 639
atacgggagc caacaccagt gtcttatgaa tgtagatgag ctcagatcgg aattagagca    60
ggtgtgacgg at                                                        72

<210> SEQ ID NO 640
<211> LENGTH: 72
<212> TYPE: DNA
<213> ORGANISM: Artificial Sequence
<220> FEATURE:
<223> OTHER INFORMATION: chemically synthesized

<400> SEQUENCE: 640
atccgtcaca cctgctctaa ttccgatctg agctcatcta cattcataag acactggtgt    60
tggctcccgt at                                                        72

<210> SEQ ID NO 641
<211> LENGTH: 78
<212> TYPE: DNA
<213> ORGANISM: Artificial Sequence
<220> FEATURE:
<223> OTHER INFORMATION: chemically synthesized

<400> SEQUENCE: 641
atacgggagc caacaccaca catcacatac cttcaagagc gatgacggcc ctttataggc    60
agagcaggtg tgacggat                                                  78

<210> SEQ ID NO 642
<211> LENGTH: 78
<212> TYPE: DNA
<213> ORGANISM: Artificial Sequence
<220> FEATURE:
<223> OTHER INFORMATION: chemically synthesized

<400> SEQUENCE: 642
atccgtcaca cctgctctgc ctataaaggg ccgtcatcgc tcttgaaggt atgtgatgtg    60
tggtgttggc tcccgtat                                                  78

<210> SEQ ID NO 643
<211> LENGTH: 72
<212> TYPE: DNA
<213> ORGANISM: Artificial Sequence
<220> FEATURE:
<223> OTHER INFORMATION: chemically synthesized

<400> SEQUENCE: 643
atacgggagc caacaccaca ctaccgtccc acccctccc agctcctccg gccgagagca    60
ggtgtgacgg at                                                        72

<210> SEQ ID NO 644
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 644
atccgtcaca cctgctctcg gccggaggag ctgggagggg gtgggacggt agtgtggtgt    60
tggctcccgt at                                                        72

<210> SEQ ID NO 645
<211> LENGTH: 72
<212> TYPE: DNA
<213> ORGANISM: Artificial Sequence
<220> FEATURE:
<223> OTHER INFORMATION: chemically synthesized

<400> SEQUENCE: 645
atacgggagc caacaccagt ccgttatgac atgtccggac ccgtacgcgt gtcaagagca    60
ggtgtgacgg at                                                        72

<210> SEQ ID NO 646
<211> LENGTH: 72
<212> TYPE: DNA
<213> ORGANISM: Artificial Sequence
<220> FEATURE:
<223> OTHER INFORMATION: chemically synthesized

<400> SEQUENCE: 646
atccgtcaca cctgctcttg acacgcgtac gggtccggac atgtcataac ggactggtgt    60
tggctcccgt at                                                        72

<210> SEQ ID NO 647
<211> LENGTH: 72
<212> TYPE: DNA
<213> ORGANISM: Artificial Sequence
<220> FEATURE:
<223> OTHER INFORMATION: chemically synthesized

<400> SEQUENCE: 647
atacgggagc caacaccaat gtggtggata gcaaaccccc gacgattgag gattagagca    60
ggtgtgacgg at                                                        72

<210> SEQ ID NO 648
<211> LENGTH: 72
<212> TYPE: DNA
<213> ORGANISM: Artificial Sequence
<220> FEATURE:
<223> OTHER INFORMATION: chemically synthesized

<400> SEQUENCE: 648
atccgtcaca cctgctctaa tcctcaatcg tcggggtttt gctatccacc acattggtgt    60
tggctcccgt at                                                        72

<210> SEQ ID NO 649
<211> LENGTH: 72
<212> TYPE: DNA
<213> ORGANISM: Artificial Sequence
<220> FEATURE:
<223> OTHER INFORMATION: chemically synthesized

<400> SEQUENCE: 649
atacgggagc caacaccagt tgaagctagt actgcggaag catagtccat aagtagagca    60
ggtgtgacgg at                                                        72

<210> SEQ ID NO 650
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 650
atccgtcaca cctgctctac ttatggacta tgcttccgca gtactagctt caactggtgt    60
tggctcccgt at                                                         72

<210> SEQ ID NO 651
<211> LENGTH: 72
<212> TYPE: DNA
<213> ORGANISM: Artificial Sequence
<220> FEATURE:
<223> OTHER INFORMATION: chemically synthesized

<400> SEQUENCE: 651
atacgggagc caacaccagc gaaatgaagg tatgtttttg aataataatg tggcagagca    60
ggtgtgacgg at                                                         72

<210> SEQ ID NO 652
<211> LENGTH: 72
<212> TYPE: DNA
<213> ORGANISM: Artificial Sequence
<220> FEATURE:
<223> OTHER INFORMATION: chemically synthesized

<400> SEQUENCE: 652
atccgtcaca cctgctctgc cacattatta ttcaaaaaca taccttcatt tcgctggtgt    60
tggctcccgt at                                                         72

<210> SEQ ID NO 653
<211> LENGTH: 73
<212> TYPE: DNA
<213> ORGANISM: Artificial Sequence
<220> FEATURE:
<223> OTHER INFORMATION: chemically synthesized

<400> SEQUENCE: 653
atacgggagc caacaccaaa atagatcaaa accgcatgct ggagcagttt tagcaagagc    60
aggtgtgacg gat                                                        73

<210> SEQ ID NO 654
<211> LENGTH: 73
<212> TYPE: DNA
<213> ORGANISM: Artificial Sequence
<220> FEATURE:
<223> OTHER INFORMATION: chemically synthesized

<400> SEQUENCE: 654
atccgtcaca cctgctcttg ctaaaactgc tccagcatgc ggttttgatc tattttggtg    60
ttggctcccg tat                                                        73

<210> SEQ ID NO 655
<211> LENGTH: 72
<212> TYPE: DNA
<213> ORGANISM: Artificial Sequence
<220> FEATURE:
<223> OTHER INFORMATION: chemically synthesized

<400> SEQUENCE: 655
atacgggagc caaccaat aattgctcgt tgatacttat ataaagtaca ggcaagagca      60
ggtgtgacgg at                                                         72
```

<210> SEQ ID NO 656
<211> LENGTH: 72
<212> TYPE: DNA
<213> ORGANISM: Artificial Sequence
<220> FEATURE:
<223> OTHER INFORMATION: chemically synthesized

<400> SEQUENCE: 656
atccgtcaca cctgctcttg cctgtactttt atataagtat caacgagcaa ttattggtgt    60
tggctcccgt at    72

<210> SEQ ID NO 657
<211> LENGTH: 72
<212> TYPE: DNA
<213> ORGANISM: Artificial Sequence
<220> FEATURE:
<223> OTHER INFORMATION: chemically synthesized

<400> SEQUENCE: 657
atacgggagc caacaccatc caatgaggcc atggaccggt aaactcggac gcgcagagca    60
ggtgtgacgg at    72

<210> SEQ ID NO 658
<211> LENGTH: 72
<212> TYPE: DNA
<213> ORGANISM: Artificial Sequence
<220> FEATURE:
<223> OTHER INFORMATION: chemically synthesized

<400> SEQUENCE: 658
atccgtcaca cctgctctgc gcgtccgagt ttaccggtcc atggcctcat tggatggtgt    60
tggctcccgt at    72

<210> SEQ ID NO 659
<211> LENGTH: 72
<212> TYPE: DNA
<213> ORGANISM: Artificial Sequence
<220> FEATURE:
<223> OTHER INFORMATION: chemically synthesized

<400> SEQUENCE: 659
atacgggagc caacaccagt ccgttatgac atgtccggac ccgtacgcgt gtcaagagca    60
ggtgtgacgg at    72

<210> SEQ ID NO 660
<211> LENGTH: 72
<212> TYPE: DNA
<213> ORGANISM: Artificial Sequence
<220> FEATURE:
<223> OTHER INFORMATION: chemically synthesized

<400> SEQUENCE: 660
atccgtcaca cctgctcttg acacgcgtac gggtccggac atgtcataac ggactggtgt    60
tggctcccgt at    72

<210> SEQ ID NO 661
<211> LENGTH: 71
<212> TYPE: DNA
<213> ORGANISM: Artificial Sequence
<220> FEATURE:
<223> OTHER INFORMATION: chemically synthesized

<400> SEQUENCE: 661

```
atacgggagc caacaccaag acgataagaa taatatcgaa aatatatgtt ttcagagcag    60
gtgtgacgga t                                                        71

<210> SEQ ID NO 662
<211> LENGTH: 71
<212> TYPE: DNA
<213> ORGANISM: Artificial Sequence
<220> FEATURE:
<223> OTHER INFORMATION: chemically synthesized

<400> SEQUENCE: 662
atccgtcaca cctgctctga aaacatatat tttcgatatt attcttatcg tcttggtgtt    60
ggctcccgta t                                                        71

<210> SEQ ID NO 663
<211> LENGTH: 72
<212> TYPE: DNA
<213> ORGANISM: Artificial Sequence
<220> FEATURE:
<223> OTHER INFORMATION: chemically synthesized

<400> SEQUENCE: 663
atacgggagc caacaccagc ctcgccttca gatgttcact gctgtttatt gcatagagca    60
ggtgtgacgg at                                                       72

<210> SEQ ID NO 664
<211> LENGTH: 72
<212> TYPE: DNA
<213> ORGANISM: Artificial Sequence
<220> FEATURE:
<223> OTHER INFORMATION: chemically synthesized

<400> SEQUENCE: 664
atccgtcaca cctgctctat gcaataaaca gcagtgaaca tctgaaggcg aggctggtgt    60
tggctcccgt at                                                       72

<210> SEQ ID NO 665
<211> LENGTH: 72
<212> TYPE: DNA
<213> ORGANISM: Artificial Sequence
<220> FEATURE:
<223> OTHER INFORMATION: chemically synthesized

<400> SEQUENCE: 665
atacgggagc caacaccaat agatggataa gggggaaact gccattcggt tagtagagca    60
ggtgtgacgg at                                                       72

<210> SEQ ID NO 666
<211> LENGTH: 72
<212> TYPE: DNA
<213> ORGANISM: Artificial Sequence
<220> FEATURE:
<223> OTHER INFORMATION: chemically synthesized

<400> SEQUENCE: 666
atccgtcaca cctgctctac taaccgaatg gcagtttccc ccttatccat ctattggtgt    60
tggctcccgt at                                                       72

<210> SEQ ID NO 667
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 667
atacgggagc caacaccagt ccgttatgac atgtccggac ccgtacgcgt gtcaagagca    60
ggtgtgacgg at                                                       72

<210> SEQ ID NO 668
<211> LENGTH: 72
<212> TYPE: DNA
<213> ORGANISM: Artificial Sequence
<220> FEATURE:
<223> OTHER INFORMATION: chemically synthesized

<400> SEQUENCE: 668
atccgtcaca cctgctcttg acacgcgtac gggtccggac atgtcataac ggactggtgt    60
tggctcccgt at                                                       72

<210> SEQ ID NO 669
<211> LENGTH: 71
<212> TYPE: DNA
<213> ORGANISM: Artificial Sequence
<220> FEATURE:
<223> OTHER INFORMATION: chemically synthesized

<400> SEQUENCE: 669
atacgggagc caacaccagg actcgcgcaa ataatttta tacgcaccac ttcagagcag     60
gtgtgacgga t                                                        71

<210> SEQ ID NO 670
<211> LENGTH: 71
<212> TYPE: DNA
<213> ORGANISM: Artificial Sequence
<220> FEATURE:
<223> OTHER INFORMATION: chemically synthesized

<400> SEQUENCE: 670
atccgtcaca cctgctctga agtggtgcgt ataaaaatta tttgcgcgag tcctggtgtt    60
ggctcccgta t                                                        71

<210> SEQ ID NO 671
<211> LENGTH: 73
<212> TYPE: DNA
<213> ORGANISM: Artificial Sequence
<220> FEATURE:
<223> OTHER INFORMATION: chemically synthesized

<400> SEQUENCE: 671
atacgggagc caacaccagt ccgttatgac atgtccggac cccgtacgcg tgtcaagagc    60
aggtgtgacg gat                                                      73

<210> SEQ ID NO 672
<211> LENGTH: 73
<212> TYPE: DNA
<213> ORGANISM: Artificial Sequence
<220> FEATURE:
<223> OTHER INFORMATION: chemically synthesized

<400> SEQUENCE: 672
atccgtcaca cctgctcttg acacgcgtac ggggtccgga catgtcataa cggactggtg    60
ttggctcccg tat                                                      73
```

```
<210> SEQ ID NO 673
<211> LENGTH: 72
<212> TYPE: DNA
<213> ORGANISM: Artificial Sequence
<220> FEATURE:
<223> OTHER INFORMATION: chemically synthesized

<400> SEQUENCE: 673
atacgggagc caacaccata aagctcgtat tgccaccccc ctgttattta atacagagca      60
ggtgtgacgg at                                                          72

<210> SEQ ID NO 674
<211> LENGTH: 72
<212> TYPE: DNA
<213> ORGANISM: Artificial Sequence
<220> FEATURE:
<223> OTHER INFORMATION: chemically synthesized

<400> SEQUENCE: 674
atccgtcaca cctgctctgt attaaataac agggggtgg caatacgagc tttatggtgt       60
tggctcccgt at                                                          72

<210> SEQ ID NO 675
<211> LENGTH: 71
<212> TYPE: DNA
<213> ORGANISM: Artificial Sequence
<220> FEATURE:
<223> OTHER INFORMATION: chemically synthesized

<400> SEQUENCE: 675
atacgggagc caacaccatc acggcaatgt cccgataatg tcttgcttca gcgagagcag      60
gtgtgacgga t                                                           71

<210> SEQ ID NO 676
<211> LENGTH: 71
<212> TYPE: DNA
<213> ORGANISM: Artificial Sequence
<220> FEATURE:
<223> OTHER INFORMATION: chemically synthesized

<400> SEQUENCE: 676
atccgtcaca cctgctctcg ctgaagcaag acattatcgg acattgccg tgatggtgtt       60 ggctcccgta t                                                           71

<210> SEQ ID NO 677
<211> LENGTH: 71
<212> TYPE: DNA
<213> ORGANISM: Artificial Sequence
<220> FEATURE:
<223> OTHER INFORMATION: chemically synthesized

<400> SEQUENCE: 677
atacgggagc caacaccagc agtactaacc ccccttacca tatatatcac acgagagcag      60
gtgtgacgga t                                                           71

<210> SEQ ID NO 678
<211> LENGTH: 71
<212> TYPE: DNA
<213> ORGANISM: Artificial Sequence
<220> FEATURE:
<223> OTHER INFORMATION: chemically synthesized

<400> SEQUENCE: 678
atccgtcaca cctgctctcg tgtgatatat atggtaaggg gggttagtac tgctggtgtt      60
```

```
ggctcccgta t                                                          71

<210> SEQ ID NO 679
<211> LENGTH: 72
<212> TYPE: DNA
<213> ORGANISM: Artificial Sequence
<220> FEATURE:
<223> OTHER INFORMATION: chemically synthesized

<400> SEQUENCE: 679
atacgggagc caacaccacc ctaaattcca gagtgtacaa gagaacgaac taccagagca    60
ggtgtgacgg at                                                         72

<210> SEQ ID NO 680
<211> LENGTH: 72
<212> TYPE: DNA
<213> ORGANISM: Artificial Sequence
<220> FEATURE:
<223> OTHER INFORMATION: chemically synthesized

<400> SEQUENCE: 680
atccgtcaca cctgctctgg tagttcgttc tcttgtacac tctggaattt agggtggtgt    60
tggctcccgt at                                                         72

<210> SEQ ID NO 681
<211> LENGTH: 71
<212> TYPE: DNA
<213> ORGANISM: Artificial Sequence
<220> FEATURE:
<223> OTHER INFORMATION: chemically synthesized

<400> SEQUENCE: 681
atacgggagc caacaccata gcgacttggc aaaaaattta catccattac tccagagcag    60
gtgtgacgga t                                                          71

<210> SEQ ID NO 682
<211> LENGTH: 71
<212> TYPE: DNA
<213> ORGANISM: Artificial Sequence
<220> FEATURE:
<223> OTHER INFORMATION: chemically synthesized

<400> SEQUENCE: 682
atccgtcaca cctgctctgg agtaatggat gtaaattttt tgccaagtcg ctatggtgtt    60
ggctcccgta t                                                          71

<210> SEQ ID NO 683
<211> LENGTH: 71
<212> TYPE: DNA
<213> ORGANISM: Artificial Sequence
<220> FEATURE:
<223> OTHER INFORMATION: chemically synthesized

<400> SEQUENCE: 683
atacgggagc caacaccacg tacacaaacc aaatacgcac cttcccaccc tccagagcag    60
gtgtgacgga t                                                          71

<210> SEQ ID NO 684
<211> LENGTH: 71
<212> TYPE: DNA
<213> ORGANISM: Artificial Sequence
<220> FEATURE:
<223> OTHER INFORMATION: chemically synthesized
```

<400> SEQUENCE: 684
atccgtcaca cctgctctgg agggtgggaa ggtgcgtatt tggtttgtgt acgtggtgtt     60
ggctcccgta t                                                         71

<210> SEQ ID NO 685
<211> LENGTH: 59
<212> TYPE: DNA
<213> ORGANISM: Artificial Sequence
<220> FEATURE:
<223> OTHER INFORMATION: chemically synthesized

<400> SEQUENCE: 685
atacgggagc caacaccaca tctagcacga gaccctatcc cagagcaggt gtgacggat     59

<210> SEQ ID NO 686
<211> LENGTH: 59
<212> TYPE: DNA
<213> ORGANISM: Artificial Sequence
<220> FEATURE:
<223> OTHER INFORMATION: chemically synthesized

<400> SEQUENCE: 686
atccgtcaca cctgctctgg atagggtct cgtgctagat gtggtgttgg ctcccgtat      59

<210> SEQ ID NO 687
<211> LENGTH: 72
<212> TYPE: DNA
<213> ORGANISM: Artificial Sequence
<220> FEATURE:
<223> OTHER INFORMATION: chemically synthesized

<400> SEQUENCE: 687
atacgggagc caacaccaaa tcgtcaacag ccctgcgcca cttatctttt tgccagagca     60
ggtgtgacgg at                                                        72

<210> SEQ ID NO 688
<211> LENGTH: 72
<212> TYPE: DNA
<213> ORGANISM: Artificial Sequence
<220> FEATURE:
<223> OTHER INFORMATION: chemically synthesized

<400> SEQUENCE: 688
atccgtcaca cctgctctgg caaaaagata agtggcgcag gctgttgac gatttggtgt     60 tggctcccgt at                                                        72

<210> SEQ ID NO 689
<211> LENGTH: 73
<212> TYPE: DNA
<213> ORGANISM: Artificial Sequence
<220> FEATURE:
<223> OTHER INFORMATION: chemically synthesized

<400> SEQUENCE: 689
atacgggagc caacaccaac agatggataa gggggaaact gcccattcgg ttagtagagc     60
aggtgtgacg gat                                                       73

<210> SEQ ID NO 690
<211> LENGTH: 73
<212> TYPE: DNA
<213> ORGANISM: Artificial Sequence
<220> FEATURE:
<223> OTHER INFORMATION: chemically synthesized -continued

<400> SEQUENCE: 690
atccgtcaca cctgctctac taaccgaatg ggcagtttcc cccttatcca tctgttggtg    60
ttggctcccg tat    73

<210> SEQ ID NO 691
<211> LENGTH: 71
<212> TYPE: DNA
<213> ORGANISM: Artificial Sequence
<220> FEATURE:
<223> OTHER INFORMATION: chemically synthesized

<400> SEQUENCE: 691
atacgggagc caacaccacg cagttataac ggcaggcccc atatcgttta accagagcag    60
gtgtgacgga t    71

<210> SEQ ID NO 692
<211> LENGTH: 71
<212> TYPE: DNA
<213> ORGANISM: Artificial Sequence
<220> FEATURE:
<223> OTHER INFORMATION: chemically synthesized

<400> SEQUENCE: 692
atccgtcaca cctgctctgg ttaaacgata tggggcctgc cgttataact gcgtggtgtt    60
ggctcccgta t    71

<210> SEQ ID NO 693
<211> LENGTH: 68
<212> TYPE: DNA
<213> ORGANISM: Artificial Sequence
<220> FEATURE:
<223> OTHER INFORMATION: chemically synthesized

<400> SEQUENCE: 693
atacgggagc caacaccatg tcaggacctc catcgcccgg gcccgccgcc gctgagagca    60
ggtgtgac    68

<210> SEQ ID NO 694
<211> LENGTH: 68
<212> TYPE: DNA
<213> ORGANISM: Artificial Sequence
<220> FEATURE:
<223> OTHER INFORMATION: chemically synthesized

<400> SEQUENCE: 694
gtcacacctg ctctcagcgg cggcgggccc gggcgatgga ggtcctgaca tggtgttggc    60
tcccgtat    68

<210> SEQ ID NO 695
<211> LENGTH: 70
<212> TYPE: DNA
<213> ORGANISM: Artificial Sequence
<220> FEATURE:
<223> OTHER INFORMATION: chemically synthesized

<400> SEQUENCE: 695
atacgggagc caacaccata acaaataacc accctcaatg ctagatagtg gcagagcagg    60
tgtgacggat    70

<210> SEQ ID NO 696
<211> LENGTH: 70

<212> TYPE: DNA
<213> ORGANISM: Artificial Sequence
<220> FEATURE:
<223> OTHER INFORMATION: chemically synthesized

<400> SEQUENCE: 696
atccgtcaca cctgctctgc cactatctag cattgagggt ggttatttgt tatggtgttg    60
gctcccgtat    70

<210> SEQ ID NO 697
<211> LENGTH: 72
<212> TYPE: DNA
<213> ORGANISM: Artificial Sequence
<220> FEATURE:
<223> OTHER INFORMATION: chemically synthesized

<400> SEQUENCE: 697
atacggcagc caacaccaca cacatagcgc tttgtattca gccggatgtg atgtagagca    60
ggtgtgacgg at    72

<210> SEQ ID NO 698
<211> LENGTH: 72
<212> TYPE: DNA
<213> ORGANISM: Artificial Sequence
<220> FEATURE:
<223> OTHER INFORMATION: chemically synthesized

<400> SEQUENCE: 698
atccgtcaca cctgctctac atcacatccg gctgaataca aagcgctatg tgtgtggtgt    60
tggctgccgt aa    72

<210> SEQ ID NO 699
<211> LENGTH: 72
<212> TYPE: DNA
<213> ORGANISM: Artificial Sequence
<220> FEATURE:
<223> OTHER INFORMATION: chemically synthesized

<400> SEQUENCE: 699
atacgggagc caacaccaca cacagagcgc catggactca gtcagatgtg atgtagagca    60
ggtgtgacgg at    72

<210> SEQ ID NO 700
<211> LENGTH: 72
<212> TYPE: DNA
<213> ORGANISM: Artificial Sequence
<220> FEATURE:
<223> OTHER INFORMATION: chemically synthesized

<400> SEQUENCE: 700
atccgtcaca cctgctctac atcacatctg actgagtcca tggcgctctg tgtgtggtgt    60
tggctcccgt at    72

<210> SEQ ID NO 701
<211> LENGTH: 71
<212> TYPE: DNA
<213> ORGANISM: Artificial Sequence
<220> FEATURE:
<223> OTHER INFORMATION: chemically synthesized

<400> SEQUENCE: 701
atacgggagc caacgccaca ggcgtgacat cacccgtacc ctaccttagt gccagagcag    60
gtgtgacgga t    71

<210> SEQ ID NO 702
<211> LENGTH: 71
<212> TYPE: DNA
<213> ORGANISM: Artificial Sequence
<220> FEATURE:
<223> OTHER INFORMATION: chemically synthesized

<400> SEQUENCE: 702
atccgtcaca cctgctctgg cactaaggta gggtacgggt gatgtcacgc ctgtggcgtt    60
ggctcccgta t                                                        71

<210> SEQ ID NO 703
<211> LENGTH: 71
<212> TYPE: DNA
<213> ORGANISM: Artificial Sequence
<220> FEATURE:
<223> OTHER INFORMATION: chemically synthesized

<400> SEQUENCE: 703
atacgggagc caacaccata attcaagagg attcctcaaa atatgaagct tccagagcag    60
gtgtgacgga t                                                        71

<210> SEQ ID NO 704
<211> LENGTH: 71
<212> TYPE: DNA
<213> ORGANISM: Artificial Sequence
<220> FEATURE:
<223> OTHER INFORMATION: chemically synthesized

<400> SEQUENCE: 704
atccgtcaca cctgctctgg aagcttcata ttttgaggaa tcctcttgaa ttatggtgtt    60
ggctcccgta t                                                        71

<210> SEQ ID NO 705
<211> LENGTH: 73
<212> TYPE: DNA
<213> ORGANISM: Artificial Sequence
<220> FEATURE:
<223> OTHER INFORMATION: chemically synthesized

<400> SEQUENCE: 705
atacgggagc caacaccagt ccgttatgac atgtccggac ccgtacgcgt gtcaaagagc    60
aggtgtgacg gat                                                      73

<210> SEQ ID NO 706
<211> LENGTH: 73
<212> TYPE: DNA
<213> ORGANISM: Artificial Sequence
<220> FEATURE:
<223> OTHER INFORMATION: chemically synthesized

<400> SEQUENCE: 706
atccgtcaca cctgctcttt gacacgcgta cgggtccgga catgtcataa cggactggtg    60
ttggctcccg tat                                                      73

<210> SEQ ID NO 707
<211> LENGTH: 72
<212> TYPE: DNA
<213> ORGANISM: Artificial Sequence
<220> FEATURE:
<223> OTHER INFORMATION: chemically synthesized

<400> SEQUENCE: 707

```
atacgggagc caacaccata tcttatcata atgtgatgct aagaaggatc ctttagagca    60
ggtgtgacgg at                                                         72
```

<210> SEQ ID NO 708
<211> LENGTH: 72
<212> TYPE: DNA
<213> ORGANISM: Artificial Sequence
<220> FEATURE:
<223> OTHER INFORMATION: chemically synthesized

<400> SEQUENCE: 708

```
atccgtcaca cctgctctaa aggatccttc ttagcatcac attatgataa gatatggtgt    60
tggctcccgt at                                                         72
```

<210> SEQ ID NO 709
<211> LENGTH: 72
<212> TYPE: DNA
<213> ORGANISM: Artificial Sequence
<220> FEATURE:
<223> OTHER INFORMATION: chemically synthesized

<400> SEQUENCE: 709

```
atacgggagc caacaccaga ttgatgtaag tagccctcaa atgatttaaa gtttagagca    60
ggtgtgacgg at                                                         72
```

<210> SEQ ID NO 710
<211> LENGTH: 72
<212> TYPE: DNA
<213> ORGANISM: Artificial Sequence
<220> FEATURE:
<223> OTHER INFORMATION: chemically synthesized

<400> SEQUENCE: 710

```
atccgtcaca cctgctctaa actttaaatc atttgagggc tacttacatc aatctggtgt    60
tggctcccgt at                                                         72
```

<210> SEQ ID NO 711
<211> LENGTH: 72
<212> TYPE: DNA
<213> ORGANISM: Artificial Sequence
<220> FEATURE:
<223> OTHER INFORMATION: chemically synthesized

<400> SEQUENCE: 711

```
atacgggagc caacaccaca ctaatttatc gcatgcatcg cccgctgatg cccaagagca    60
ggtgtgacgg at                                                         72
```

<210> SEQ ID NO 712
<211> LENGTH: 72
<212> TYPE: DNA
<213> ORGANISM: Artificial Sequence
<220> FEATURE:
<223> OTHER INFORMATION: chemically synthesized

<400> SEQUENCE: 712

```
atccgtcaca cctgctcttg ggcatcagcg ggcgatgcat gcgataaatt agtgtggtgt    60
tggctcccgt at                                                         72
```

<210> SEQ ID NO 713
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 713
atacgggagc caacaccaca gaagttattt tgagaacgcg acccaaatag gttaagagca      60
ggtgtgacgg at                                                         72

<210> SEQ ID NO 714
<211> LENGTH: 72
<212> TYPE: DNA
<213> ORGANISM: Artificial Sequence
<220> FEATURE:
<223> OTHER INFORMATION: chemically synthesized

<400> SEQUENCE: 714
atccgtcaca cctgctctta acctatttgg gtcgcgttct caaataact tctgtggtgt      60 tggctcccgt at                                                         72

<210> SEQ ID NO 715
<211> LENGTH: 72
<212> TYPE: DNA
<213> ORGANISM: Artificial Sequence
<220> FEATURE:
<223> OTHER INFORMATION: chemically synthesized

<400> SEQUENCE: 715
atacgggagc caacaccatt aatgtagaac accactctta ttgacaagcc tattagagca     60
ggtgtgacgg at                                                         72

<210> SEQ ID NO 716
<211> LENGTH: 72
<212> TYPE: DNA
<213> ORGANISM: Artificial Sequence
<220> FEATURE:
<223> OTHER INFORMATION: chemically synthesized

<400> SEQUENCE: 716
atccgtcaca cctgctctaa taggcttgtc aataagagtg gtgttctaca ttaatggtgt     60
tggctcccgt at                                                         72

<210> SEQ ID NO 717
<211> LENGTH: 72
<212> TYPE: DNA
<213> ORGANISM: Artificial Sequence
<220> FEATURE:
<223> OTHER INFORMATION: chemically synthesized

<400> SEQUENCE: 717
atacgggagc caacaccagt ccgttatgac atgtccggac ccgtacgcgt gtcaagagca     60
ggtgtgacgg at                                                         72

<210> SEQ ID NO 718
<211> LENGTH: 72
<212> TYPE: DNA
<213> ORGANISM: Artificial Sequence
<220> FEATURE:
<223> OTHER INFORMATION: chemically synthesized

<400> SEQUENCE: 718
atccgtcaca cctgctcttg acacgcgtac gggtccggac atgtcataac ggactggtgt     60
tggctcccgt at                                                         72
```

```
<210> SEQ ID NO 719
<211> LENGTH: 72
<212> TYPE: DNA
<213> ORGANISM: Artificial Sequence
<220> FEATURE:
<223> OTHER INFORMATION: chemically synthesized

<400> SEQUENCE: 719
atacgggagc caacaccaca gtttgtagtg taacaatgct agataataat gaaaagagca    60
ggtgtgacgg at                                                       72

<210> SEQ ID NO 720
<211> LENGTH: 72
<212> TYPE: DNA
<213> ORGANISM: Artificial Sequence
<220> FEATURE:
<223> OTHER INFORMATION: chemically synthesized

<400> SEQUENCE: 720
atccgtcaca cctgctcttt tcattattat ctagcattgt tacactacaa actgtggtgt    60
tggctcccgt at                                                       72

<210> SEQ ID NO 721
<211> LENGTH: 72
<212> TYPE: DNA
<213> ORGANISM: Artificial Sequence
<220> FEATURE:
<223> OTHER INFORMATION: chemically synthesized

<400> SEQUENCE: 721
atacgggagc caacaccaag caaatcacca gaaatctttt aacaatctat tgacagagca    60
ggtgtgacgg at                                                       72

<210> SEQ ID NO 722
<211> LENGTH: 72
<212> TYPE: DNA
<213> ORGANISM: Artificial Sequence
<220> FEATURE:
<223> OTHER INFORMATION: chemically synthesized

<400> SEQUENCE: 722
atccgtcaca cctgctctgt caatagattg ttaaaagatt tctggtgatt tgcttggtgt    60
tggctcccgt at                                                       72

<210> SEQ ID NO 723
<211> LENGTH: 72
<212> TYPE: DNA
<213> ORGANISM: Artificial Sequence
<220> FEATURE:
<223> OTHER INFORMATION: chemically synthesized

<400> SEQUENCE: 723
atacgggagc caacaccaca caggaactag aagaaagtat ctttttttcga tttaagagca    60 ggtgtgacgg at                                                       72

<210> SEQ ID NO 724
<211> LENGTH: 72
<212> TYPE: DNA
<213> ORGANISM: Artificial Sequence
<220> FEATURE:
<223> OTHER INFORMATION: chemically synthesized

<400> SEQUENCE: 724
atccgtcaca cctgctctta aatcgaaaaa agatactttc ttctagttcc tgtgtggtgt    60
```

```
tggctcccgt at                                                          72

<210> SEQ ID NO 725
<211> LENGTH: 59
<212> TYPE: DNA
<213> ORGANISM: Artificial Sequence
<220> FEATURE:
<223> OTHER INFORMATION: chemically synthesized

<400> SEQUENCE: 725
atacgggagc caacaccaca tctagcacga gaccctatcc cagagcaggt gtgacggat      59

<210> SEQ ID NO 726
<211> LENGTH: 59
<212> TYPE: DNA
<213> ORGANISM: Artificial Sequence
<220> FEATURE:
<223> OTHER INFORMATION: chemically synthesized

<400> SEQUENCE: 726
atccgtcaca cctgctctgg datagggtct cgtgctagat gtggtgttgg ctcccgtat      59

<210> SEQ ID NO 727
<211> LENGTH: 72
<212> TYPE: DNA
<213> ORGANISM: Artificial Sequence
<220> FEATURE:
<223> OTHER INFORMATION: chemically synthesized

<400> SEQUENCE: 727
atacgggagc cagcaccatt ccgttatgac gtgtccggac ccgttcgcgc gtcaagagca     60
ggtgtgacgg at                                                          72

<210> SEQ ID NO 728
<211> LENGTH: 72
<212> TYPE: DNA
<213> ORGANISM: Artificial Sequence
<220> FEATURE:
<223> OTHER INFORMATION: chemically synthesized

<400> SEQUENCE: 728
atccgtcaca cctgctcttg acgcgcgaac gggtccggac acgtcataac ggaatggtgc     60
tggctcccgt aa                                                          72

<210> SEQ ID NO 729
<211> LENGTH: 71
<212> TYPE: DNA
<213> ORGANISM: Artificial Sequence
<220> FEATURE:
<223> OTHER INFORMATION: chemically synthesized

<400> SEQUENCE: 729
atacgggagc caacaccatc acggcaatgt cccgataatg tcttgcttca gcgagagcag     60
gtgtgacgga t                                                           71

<210> SEQ ID NO 730
<211> LENGTH: 71
<212> TYPE: DNA
<213> ORGANISM: Artificial Sequence
<220> FEATURE:
<223> OTHER INFORMATION: chemically synthesized

<400> SEQUENCE: 730
atccgtcaca cctgctctcg ctgaagcaag acattatcgg gacattgccg tgatggtgtt     60
```

```
ggctcccgta t                                                       71

<210> SEQ ID NO 731
<211> LENGTH: 55
<212> TYPE: DNA
<213> ORGANISM: Artificial Sequence
<220> FEATURE:
<223> OTHER INFORMATION: chemically synthesized

<400> SEQUENCE: 731
atacgggagc caacaccagt ccgttatgac attgtcaaga gcaggtgtga cggat      55

<210> SEQ ID NO 732
<211> LENGTH: 55
<212> TYPE: DNA
<213> ORGANISM: Artificial Sequence
<220> FEATURE:
<223> OTHER INFORMATION: chemically synthesized

<400> SEQUENCE: 732
atccgtcaca cctgctcttg acaatgtcat aacggactgg tgttggctcc cgtat      55

<210> SEQ ID NO 733
<211> LENGTH: 71
<212> TYPE: DNA
<213> ORGANISM: Artificial Sequence
<220> FEATURE:
<223> OTHER INFORMATION: chemically synthesized

<400> SEQUENCE: 733
atacgggagc caacaccaca tactcagacg attacccagc gcatgcttgt aacagagcag  60
gtgtgacgga t                                                       71

<210> SEQ ID NO 734
<211> LENGTH: 71
<212> TYPE: DNA
<213> ORGANISM: Artificial Sequence
<220> FEATURE:
<223> OTHER INFORMATION: chemically synthesized

<400> SEQUENCE: 734
atccgtcaca cctgctctgt tacaagcatg cgctgggtaa tcgtctgagt atgtggtgtt  60
ggctcccgta t                                                       71

<210> SEQ ID NO 735
<211> LENGTH: 71
<212> TYPE: DNA
<213> ORGANISM: Artificial Sequence
<220> FEATURE:
<223> OTHER INFORMATION: chemically synthesized

<400> SEQUENCE: 735
atacgggagc caacaccact ctctagccca cggcggggtt ttctcgcaag tccagagcag  60
gtgtgacgga t                                                       71

<210> SEQ ID NO 736
<211> LENGTH: 71
<212> TYPE: DNA
<213> ORGANISM: Artificial Sequence
<220> FEATURE:
<223> OTHER INFORMATION: chemically synthesized

<400> SEQUENCE: 736
atccgtcaca cctgctctgg acttgcgaga aaaccccgcc gtgggctaga gagtggtgtt  60
```

```
ggctcccgta t                                                          71

<210> SEQ ID NO 737
<211> LENGTH: 71
<212> TYPE: DNA
<213> ORGANISM: Artificial Sequence
<220> FEATURE:
<223> OTHER INFORMATION: chemically synthesized

<400> SEQUENCE: 737
atacgggagc caacaccaat tgcgccctaa ggctacccac attacccatg tgtagagcag     60
gtgtgacgga t                                                          71

<210> SEQ ID NO 738
<211> LENGTH: 71
<212> TYPE: DNA
<213> ORGANISM: Artificial Sequence
<220> FEATURE:
<223> OTHER INFORMATION: chemically synthesized

<400> SEQUENCE: 738
atccgtcaca cctgctctac acatgggtaa tgtgggtagc cttagggcgc aattggtgtt     60
ggctcccgta t                                                          71

<210> SEQ ID NO 739
<211> LENGTH: 71
<212> TYPE: DNA
<213> ORGANISM: Artificial Sequence
<220> FEATURE:
<223> OTHER INFORMATION: chemically synthesized

<400> SEQUENCE: 739
atacgggagc caacaccagc tgctgcttca acgaaatccc aggcaccctg acaagagcag     60
gtgtgacgga t                                                          71

<210> SEQ ID NO 740
<211> LENGTH: 71
<212> TYPE: DNA
<213> ORGANISM: Artificial Sequence
<220> FEATURE:
<223> OTHER INFORMATION: chemically synthesized

<400> SEQUENCE: 740
atccgtcaca cctgctcttg tcagggtgcc tgggatttcg ttgaagcagc agctggtgtt     60
ggctcccgta t                                                          71

<210> SEQ ID NO 741
<211> LENGTH: 71
<212> TYPE: DNA
<213> ORGANISM: Artificial Sequence
<220> FEATURE:
<223> OTHER INFORMATION: chemically synthesized

<400> SEQUENCE: 741
atacgggagc caacaccagt acctgatacc ggggtacata aacaccaaca tctagagcag     60
gtgtgacgga t                                                          71

<210> SEQ ID NO 742
<211> LENGTH: 71
<212> TYPE: DNA
<213> ORGANISM: Artificial Sequence
<220> FEATURE:
<223> OTHER INFORMATION: chemically synthesized
```

<400> SEQUENCE: 742
atccgtcaca cctgctctag atgttggtgt ttatgtaccc cggtatcagg tactggtgtt    60
ggctcccgta t    71

<210> SEQ ID NO 743
<211> LENGTH: 71
<212> TYPE: DNA
<213> ORGANISM: Artificial Sequence
<220> FEATURE:
<223> OTHER INFORMATION: chemically synthesized

<400> SEQUENCE: 743
atacgggagc caacaccaga taccgtgaat atactaattt cgcaatagtt aatagagcag    60
gtgtgacgga t    71

<210> SEQ ID NO 744
<211> LENGTH: 71
<212> TYPE: DNA
<213> ORGANISM: Artificial Sequence
<220> FEATURE:
<223> OTHER INFORMATION: chemically synthesized

<400> SEQUENCE: 744
atccgtcaca cctgctctat taactattgc gaaattagta tattcacggt atctggtgtt    60
ggctcccgta t    71

<210> SEQ ID NO 745
<211> LENGTH: 72
<212> TYPE: DNA
<213> ORGANISM: Artificial Sequence
<220> FEATURE:
<223> OTHER INFORMATION: chemically synthesized

<400> SEQUENCE: 745
atacgggagc caacaccagt ccgttatgac atgtccggac ccgtacgcgt gtcaagagca    60
ggtgtgacgg at    72

<210> SEQ ID NO 746
<211> LENGTH: 72
<212> TYPE: DNA
<213> ORGANISM: Artificial Sequence
<220> FEATURE:
<223> OTHER INFORMATION: chemically synthesized

<400> SEQUENCE: 746
atccgtcaca cctgctcttg acacgcgtac gggtccggac atgtcataac ggactggtgt    60
tggctcccgt at    72

<210> SEQ ID NO 747
<211> LENGTH: 72
<212> TYPE: DNA
<213> ORGANISM: Artificial Sequence
<220> FEATURE:
<223> OTHER INFORMATION: chemically synthesized

<400> SEQUENCE: 747
atacgggagc caacaccagt ccgttatgac atgtccggac ccgtacgcgt gtcaagagca    60
ggtgtgacgg at    72

<210> SEQ ID NO 748
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 748
atccgtcaca cctgctcttg acacgcgtac gggtccggac atgtcataac ggactggtgt      60
tggctcccgt at                                                          72

<210> SEQ ID NO 749
<211> LENGTH: 71
<212> TYPE: DNA
<213> ORGANISM: Artificial Sequence
<220> FEATURE:
<223> OTHER INFORMATION: chemically synthesized

<400> SEQUENCE: 749
atacgggagc caacaccagt ccgtttgaca tgtccggacc cgtacgcgtg tcaagagcag      60
gtgtgacgga t                                                           71

<210> SEQ ID NO 750
<211> LENGTH: 71
<212> TYPE: DNA
<213> ORGANISM: Artificial Sequence
<220> FEATURE:
<223> OTHER INFORMATION: chemically synthesized

<400> SEQUENCE: 750
atccgtcaca cctgctcttg acacgcgtac gggtccggac atgtcaaacg gactggtgtt      60
ggctcccgta t                                                           71

<210> SEQ ID NO 751
<211> LENGTH: 71
<212> TYPE: DNA
<213> ORGANISM: Artificial Sequence
<220> FEATURE:
<223> OTHER INFORMATION: chemically synthesized

<400> SEQUENCE: 751
atacgggagc caacaccatc acggcaatgt cccgataatg tcttgcttca gcagagcag       60 gtgtgacgga t                                                           71

<210> SEQ ID NO 752
<211> LENGTH: 71
<212> TYPE: DNA
<213> ORGANISM: Artificial Sequence
<220> FEATURE:
<223> OTHER INFORMATION: chemically synthesized

<400> SEQUENCE: 752
atccgtcaca cctgctctcg ctgaagcaag acattatcgg gacattgccg tgatggtgtt     60
ggctcccgta t                                                           71

<210> SEQ ID NO 753
<211> LENGTH: 65
<212> TYPE: DNA
<213> ORGANISM: Artificial Sequence
<220> FEATURE:
<223> OTHER INFORMATION: chemically synthesized

<400> SEQUENCE: 753
atacgggagc caacaccagt ccgttatgac atgtccggac cgtacaaga gcaggtgtga      60 cggat                                                                 65
```

<210> SEQ ID NO 754
<211> LENGTH: 65
<212> TYPE: DNA
<213> ORGANISM: Artificial Sequence
<220> FEATURE:
<223> OTHER INFORMATION: chemically synthesized

<400> SEQUENCE: 754
atccgtcaca cctgctcttg tacgggtccg gacatgtcat aacggactgg tgttggctcc    60
cgtat    65

<210> SEQ ID NO 755
<211> LENGTH: 72
<212> TYPE: DNA
<213> ORGANISM: Artificial Sequence
<220> FEATURE:
<223> OTHER INFORMATION: chemically synthesized

<400> SEQUENCE: 755
atacgggagc caacaccaag tccaagccaa acaagagcat aacaccaaat ctggagagca    60
ggtgtgacgg at    72

<210> SEQ ID NO 756
<211> LENGTH: 72
<212> TYPE: DNA
<213> ORGANISM: Artificial Sequence
<220> FEATURE:
<223> OTHER INFORMATION: chemically synthesized

<400> SEQUENCE: 756
atccgtcaca cctgctctcc agatttggtg ttatgctctt gtttggcttg gacttggtgt    60
tggctcccgt at    72

<210> SEQ ID NO 757
<211> LENGTH: 72
<212> TYPE: DNA
<213> ORGANISM: Artificial Sequence
<220> FEATURE:
<223> OTHER INFORMATION: chemically synthesized

<400> SEQUENCE: 757
atacgggagc caacaccact cggcaccgcc cttccgtatc ggcgagtaac gtacagagca    60
ggtgtgacgg at    72

<210> SEQ ID NO 758
<211> LENGTH: 72
<212> TYPE: DNA
<213> ORGANISM: Artificial Sequence
<220> FEATURE:
<223> OTHER INFORMATION: chemically synthesized

<400> SEQUENCE: 758
atccgtcaca cctgctctgt acgttactcg ccgatacgga agggcggtgc cgagtggtgt    60
tggctcccgt at    72

<210> SEQ ID NO 759
<211> LENGTH: 72
<212> TYPE: DNA
<213> ORGANISM: Artificial Sequence
<220> FEATURE:
<223> OTHER INFORMATION: chemically synthesized

<400> SEQUENCE: 759

```
atacgggagc caacaccacc gcaggagtcc atcaggggtt ggcagtcagc gctcagagca    60
ggtgtgacgg at                                                       72

<210> SEQ ID NO 760
<211> LENGTH: 72
<212> TYPE: DNA
<213> ORGANISM: Artificial Sequence
<220> FEATURE:
<223> OTHER INFORMATION: chemically synthesized

<400> SEQUENCE: 760
atccgtcaca cctgctctga gcgctgactg ccaaccsctg atggactcct gcggtggtgt    60
tggctcccgt at                                                       72

<210> SEQ ID NO 761
<211> LENGTH: 72
<212> TYPE: DNA
<213> ORGANISM: Artificial Sequence
<220> FEATURE:
<223> OTHER INFORMATION: chemically synthesized

<400> SEQUENCE: 761
atacgggagc caacaccaca cgaacggagt gcaccgggga agatactcca acgcagagca    60
ggtgtgacgg at                                                       72

<210> SEQ ID NO 762
<211> LENGTH: 72
<212> TYPE: DNA
<213> ORGANISM: Artificial Sequence
<220> FEATURE:
<223> OTHER INFORMATION: chemically synthesized

<400> SEQUENCE: 762
atccgtcaca cctgctctgc gttggagtat cttccccggt gcactccgtt cgtgtggtgt    60
tggctcccgt at                                                       72

<210> SEQ ID NO 763
<211> LENGTH: 72
<212> TYPE: DNA
<213> ORGANISM: Artificial Sequence
<220> FEATURE:
<223> OTHER INFORMATION: chemically synthesized

<400> SEQUENCE: 763
atacgggagc caacaccagc caattataca ggtaggtcaa aaaagtttag gggaagagca    60
ggtgtgacgg at                                                       72

<210> SEQ ID NO 764
<211> LENGTH: 72
<212> TYPE: DNA
<213> ORGANISM: Artificial Sequence
<220> FEATURE:
<223> OTHER INFORMATION: chemically synthesized

<400> SEQUENCE: 764
atccgtcaca cctgctcttc ccctaaactt ttttgaccta cctgtataat tggctggtgt    60
tggctcccgt at                                                       72

<210> SEQ ID NO 765
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 765
atacgggagc caacaccacc atgccccttt aagtgaatag actagtggcc gttgagagca      60
ggtgtgacgg at                                                         72

<210> SEQ ID NO 766
<211> LENGTH: 72
<212> TYPE: DNA
<213> ORGANISM: Artificial Sequence
<220> FEATURE:
<223> OTHER INFORMATION: chemically synthesized

<400> SEQUENCE: 766
atccgtcaca cctgctctca acggccacta gtctattcac ttaaaggggc atggtggtgt      60
tggctcccgt at                                                         72

<210> SEQ ID NO 767
<211> LENGTH: 72
<212> TYPE: DNA
<213> ORGANISM: Artificial Sequence
<220> FEATURE:
<223> OTHER INFORMATION: chemically synthesized

<400> SEQUENCE: 767
atacgggagc caacaccaga gacgtcttag cctcgcgatc ccgtccgttg gcccagagca      60
ggtgtgacgg at                                                         72

<210> SEQ ID NO 768
<211> LENGTH: 72
<212> TYPE: DNA
<213> ORGANISM: Artificial Sequence
<220> FEATURE:
<223> OTHER INFORMATION: chemically synthesized

<400> SEQUENCE: 768
atccgtcaca cctgctctgg ccaacggac gggatcgcga ggctaagacg tctctggtgt       60
tggctcccgt at                                                         72

<210> SEQ ID NO 769
<211> LENGTH: 72
<212> TYPE: DNA
<213> ORGANISM: Artificial Sequence
<220> FEATURE:
<223> OTHER INFORMATION: chemically synthesized

<400> SEQUENCE: 769
atacgggagc caacaccatc ctcccgcgac gtctggagaa cagcctctac tttaagagca      60
ggtgtgacgg at                                                         72

<210> SEQ ID NO 770
<211> LENGTH: 72
<212> TYPE: DNA
<213> ORGANISM: Artificial Sequence
<220> FEATURE:
<223> OTHER INFORMATION: chemically synthesized

<400> SEQUENCE: 770
atccgtcaca cctgctctta aagtagaggc tgttctccag acgtcgcggg aggatggtgt      60
tggctcccgt at                                                         72
```

```
<210> SEQ ID NO 771
<211> LENGTH: 72
<212> TYPE: DNA
<213> ORGANISM: Artificial Sequence
<220> FEATURE:
<223> OTHER INFORMATION: chemically synthesized

<400> SEQUENCE: 771
atacgggagc caacaccaca cacagagcgc catggactca gtcagatgtg atgtagagca      60
ggtgtgacgg at                                                         72

<210> SEQ ID NO 772
<211> LENGTH: 72
<212> TYPE: DNA
<213> ORGANISM: Artificial Sequence
<220> FEATURE:
<223> OTHER INFORMATION: chemically synthesized

<400> SEQUENCE: 772
atccgtcaca cctgctctac atcacatctg actgagtcca tggcgctctg tgtgtggtgt      60
tggctcccgt at                                                         72

<210> SEQ ID NO 773
<211> LENGTH: 72
<212> TYPE: DNA
<213> ORGANISM: Artificial Sequence
<220> FEATURE:
<223> OTHER INFORMATION: chemically synthesized

<400> SEQUENCE: 773
atacgggagc caacaccatt gacttggccg tctctgaccc ctagcacccc tcgcagagca      60
ggtgtgacgg at                                                         72

<210> SEQ ID NO 774
<211> LENGTH: 72
<212> TYPE: DNA
<213> ORGANISM: Artificial Sequence
<220> FEATURE:
<223> OTHER INFORMATION: chemically synthesized

<400> SEQUENCE: 774
atccgtcaca cctgctctgc gaggggtgct aggggtcaga gacggccaag tcaatggtgt      60
tggctcccgt at                                                         72
```

METHODS AND COMPOSITIONS OF DNA LIGANDS FOR ARTHROPOD-BORNE PATHOGEN DETECTION AND PROPHYLAXIS OR THERAPY

This application is based upon and claims priority from U.S. Provisional application Ser. No. 61/401,731 filed on Aug. 18, 2010, which is incorporated herein by reference.

BACKGROUND OF THE INVENTION

1. Field of the Invention

The present invention pertains to the field of nucleic acid (especially DNA) ligand-based diagnostics and prophylaxis or passive "immunity" (i.e., binding and blocking infectious agents from infecting or progressing throughout the body). In particular, the application relates to single-stranded deoxyribonucleic acid ("DNA") and ribonucleic acid ("RNA") ligand sequences, whether individual or linked together to form longer multiple binding site "receptors," that specifically target and bind to arthropod-borne bacteria and viruses (arboviruses). Such arthropod-borne bacteria include the *Rickettsia* genus that can cause typhus or spotted fevers and deadly hemorrhagic fevers or other lethal diseases such as Crimean-Congo Hemorrhagic Fever ("CCHF") viruses, Chikungunya ("CHIK") viruses, Dengue viruses, and West Nile Viruses ("WNV") or parasites such as various species of *Leishmania* . The arthropod vectors can include mosquitoes, ticks, lice, mites, midges, fleas, flies and sandflies.

These individual or linked DNA ligand (aptamer) sequences represent valuable target analyte-responsive components of diagnostic devices or biosensors. A biosensor can be defined as any device that employs a biologically-derived molecule as the sensing component and transduces a target analyte binding event into a detectable physical signal (including, but not limited to, changes in light intensity, absorbance, emission, wavelength, color, electrical conduction, electrical resistance, or other electrical properties, etc). Once bonded with the target, these DNA ligand sequences can be used to qualitatively determine the presence of target analyte, as well as to quantify the target analyte amount, in a sample using a broad variety of assay types and diagnostic or sensor platforms including, but not limited to: affinity-based lateral flow test strips, enzyme-linked ("ELISA-like") microplate assays, membrane blotting, surface plasmon resonance ("SPR"), surface acoustic wave ("SAW") or surface transverse wave ("STW") sensors, magnetic bead ("MB")-based capture, plastic-adherent sandwich assays, electrochemiluminescence ("ECL"), radioisotopic, fluorescence intensity assays including quantum dot ("QD") or other fluorescent nanoparticle ("NP")-based assays, fluorescence lifetime, and fluorescence polarization ("FP") assays.

The invention includes general DNA ligand or aptamer-based methods of detection and quantification of these arthropod-borne diseases or related pathogens in homogenized or chemically (chaotrope or detergent)-extracted arthropods or animal or human body fluids such as whole blood, plasma, serum, sputum or saliva, interstitial, synovial, or cerebrospinal fluid aspirates, mucus, and urine or solid biopsy samples.

In addition, these DNA ligand sequences are valuable in competitive displacement assays which are not solely dependent on affinity or avidity to produce sensitive detection. Such assays would include competitive displacement fluorescence or Förster resonance energy transfer ("FRET") assays or DNA ligand "beacon" FRET assays. Each of these types of assays and detection platforms has different applications in either central laboratories or as a component of portable detectors to identify infected arthropods (homogenates or extracts) or human or animal body fluids.

It has been established that aptamers can replace antibodies in lateral flow or chromatographic test strip assay formats and may enhance detection sensitivity by virtue of higher affinity versus comparable antibodies. Such test strips or dipsticks represent rapid, inexpensive and convenient visual detection formats. The user can add various human body fluids or arthropod homogenates or extracts (proteins removed from arthropod guts by low levels of detergents or chaotropes including guanidinium or metal salts) and obtain a positive or negative result by visualizing a red colloidal gold-aptamer conjugate line. Use of fluorescent nanoparticle ("FNP")- or quantum dot ("QD")-DNA aptamer conjugates on the test line of a lateral flow test strip in combination with a handheld UV penlight or common laser pointer to illuminate the fluorescent test and control lines appears to confer even greater sensitivity to the assay.

These individual or linked DNA ligand (concatamer-like aptamer) sequences represent valuable target analyte-responsive components of diagnostic devices or "biosensors." A biosensor is defined as any sensor device that employs a biologically-derived molecule as the sensing component and transduces a target analyte binding event into a detectable physical signal, including, but not limited to, changes in light intensity, absorbance, transmittance, refraction (Surface Plasmon Resonance or SPR), wavelength, color, agglutination of cells or particles, fluorescence intensity, fluorescence lifetime, fluorescence polarization or anisotropy, fluorescence correlation spectroscopy ("FCS"), fluorescence or Förster resonance energy transfer (FRET; nonradiative dipole-dipole coupling of fluorophores or fluorophores and quenchers), upconverting phosphor (anti-Stokes shifts), two-photon interaction phenomena, Raman spectroscopy or surface-enhanced Raman spectroscopy ("SERS"), electrical conduction, electrical resistance or other electrical properties, mass, photon or radioactive particle emissions, etc.

Once bonded with the target, these DNA ligand sequences can be used to qualitatively determine the presence of analyte, as well as to quantify or semi-quantify the target analyte amount in a sample using a broad variety of assay types and diagnostic or sensor platforms including, but not limited to, affinity-based lateral flow test strips, membrane blotting, surface plasmon resonance ("SPR"), surface acoustic waveguides ("SAW") or surface transverse waveguides ("STW") devices, magnetic bead ("MB")-based capture, plastic-adherent sandwich assays ("PASA"), chemiluminescence ("CL"), electrochemiluminescence ("ECL"), radioisotopic, fluorescence intensity, including quantum dot ("QD") or other fluorescent nanoparticle ("FNP") of dye-based, fluorescence lifetime, and fluorescence polarization ("FP") assays, or enzyme-linked ("ELISA-like") microplate assays.

Finally, since envelope- or capsid-protruding spike proteins on viral surfaces control binding to and invasion of host cells, the DNA ligands may have prophylactic or therapeutic value by simply binding or coating the viral spike proteins to prevent attachment to host cell surfaces and inhibiting virus entry into host cells. The prophylactic effect has been demonstrated for H5N1 influenza virus with similar DNA ligand or aptamer sequences that coated the H5N1 viruses and prevented or severely inhibited invasion of host cells and slowed or stopped subsequent viral replication.

2. Background Information

The DNA ligand sequences listed herein were derived by iterative cycles of affinity-based selection of DNA ligands from a randomized library using rickettsial or leishmanial surface molecules (cold 1.5M $MgCl_2$-extracted outer membrane proteins; OMPs), recombinant surface proteins or synthetic peptide epitopes derived from the known amino acid sequences of viral envelope protein spikes or other surface epitopes as defined in Table 1. After affinity-based selection, the DNA ligands were subjected to polymerase chain reaction ("PCR") amplification followed by cloning and traditional Sanger dideoxynucleotide DNA sequencing. The utility of many of the sequences in ELISA-like plate assays as well as fluorescence (intensity) assays have been used and verified as illustrated by Tables 2-7 and FIGS. 2-7 and FIG. 9.

Some of the sequences function more effectively in affinity-based (ELISA-like, lateral flow strips, or fluorescence intensity) assays, while other DNA ligand sequences against the same pathogen targets have functioned better in competitive FRET assays). Therefore, all of the listed sequences have potential utility in some assay format for use in one or more tests or types of sensors for arthropod-borne pathogens and their therapy or prevention.

Arthropod-borne pathogens can present serious threats to human health in the form of alphaviruses or flaviviruses (arboviruses) that can cause encephalitis or hemorrhagic fevers or shock syndromes and death. Similarly, untreated rickettsial infections can lead to serious cases of spotted fevers or typhus with significant mortality. Finally, visceral and non-visceral leishmaniasis are serious conditions which are difficult to treat and can be fatal. All of these diseases are transferred to man by arthropod vectors (flying or other insects including mosquitoes, fleas, mites, midges, ticks, lice, flies and sandflies).

Rapid, accurate, and ultrasensitive detection of arthropod-borne diseases aids physicians by supplying key diagnostic information in the early phases of infection. This in turn allows administration of the proper antibiotic or anti-viral agent to treat these potentially deadly diseases before they become life-threatening. Current methods of detection such as lateral flow immunochromatographic test strips, although rapid, are not very sensitive and miss early stage disease detection or rely on detection of antibodies against the disease agent which may take weeks to emerge in the patient's serum. The same is true for many slower and more tedious ELISA tests which are somewhat more sensitive than lateral flow test strips, but often rely on detection of antibodies slowly made by the patient against the infectious pathogen over a period of weeks to months. In addition, there are no truly effective therapies for some of the arboviruses.

The DNA ligands disclosed herein can potentially and directly detect many arthropod-borne pathogenic microbes with greater sensitivity and speed than conventional antibodies. These same DNA ligands or aptamers may also have value as high affinity and highly specific binding agents against arboviruses, rickettsia and parasites to block or slow disease progression.

SUMMARY OF THE INVENTION

The present invention provides specific DNA sequence information for nucleic acid ligands selected and amplified from randomized pools to bind arthropod-borne pathogenic rickettsia, arboviruses and parasites in a variety of assay formats and sensor or diagnostic platforms. In addition, the DNA ligands may bind and slow or block infection and inhibit disease progression due to these pathogens, thereby functioning as prophylactics or therapeutics in vivo.

BRIEF DESCRIPTION OF THE DRAWINGS

FIG. 2 illustrates fluorescence spectra from titration of a plastic-adherent DNA ligand-magnetic bead and fluorescent nanoparticle assay.

FIG. 6 illustrates similar plastic-adherent (PASA) DNA ligand-magnetic bead and DNA ligand-fluorescent nanoparticle sandwich assay fluorescence results.

FIG. 7 illustrates the plastic-adherent (PASA) sandwich assay results for three different combinations of capture and reporter DNA ligands for detection of *Rickettsia typhi*.

FIG. 8 illustrates the probe scheme used for the test and control lines on successful lateral flow nitrocellulose aptamer chromatographic test strips.

FIG. 9 shows several successful attempts to detect either gamma-irradiated viruses or purified BSA-glutaraldehyde-viral spike peptide conjugates on lateral flow strips.

DETAILED DESCRIPTION OF THE PREFERRED EMBODIMENTS

There is no single preferred embodiment for use of the DNA ligand sequences in assay or biosensor formats identified herein. Rather, as is the case with monoclonal antibodies, the sequences are useful to varying extents in a variety of assay formats and sensors or diagnostic devices chosen from the following non-comprehensive and non-exclusive list: lateral flow or chromatographic test strips or "dipsticks," ELISA-like enzyme-linked microplate assays, magnetic bead-based capture assays, ECL or other chemiluminescence assays, radioisotopic assays and a variety of fluorescence assays including, but not limited to, fluorescence intensity or spectrofluorometry, lifetime, fluorescence polarization ("FP") and fluorescence resonance energy transfer ("FRET") assays (both end-labeled beacons and competitive FRET), SAW and STW-based detection, SPR.

Referring to the figures, FIG. 1A illustrates the general structure of an IgG antibody showing the linkage of hypervariable ("HV") amino acid regions used for actual binding to target epitopes on complex antigens. Linear linkage of HV binding sites adds affinity, avidity and specificity to the antibody binding to complex targets. FIG. 1A is a Porter stick model of an antibody revealing the multiple hypervariable antigen combining or binding sites on both the heavy and light chains.

FIG. 1B illustrates the concept of linking aptamers or their binding sites in a linear fashion (although 2-D and 3-D dendrimer-like linkages are also possible) to mimic the linkage of multiple HV regions in antigen combining sites of antibody chains to enhance affinity, avidity, and specificity against complex target antigens ("Ag") containing two or more distinct epitopes. The linked DNA ligands or aptamers are somewhat like concatamers, but can vary in the composition of DNA molecules that are linked together (i.e., can be non-repetitive versus repetitive concatamers). DNA ligands or aptamers or their shorter (5-10 base) binding sites can be linked during chemical or biochemical (enzymatic) synthesis to enhance aptamer binding affinity, avidity or specificity for improved assay sensitivity and selectivity.

Figure 1:
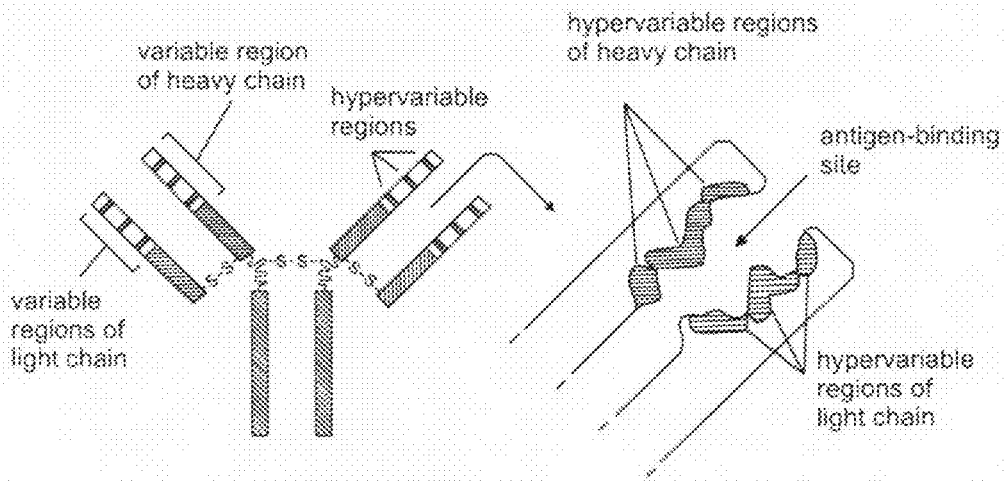
FIG. 1A illustrates the general structure of an IgG antibody showing the linkage of hypervariable (HV) amino acid regions used for actual binding to target epitopes on complex antigens.
FIG. 1B illustrates nucleotide segments designed into the cDNA template.
Figure 1:
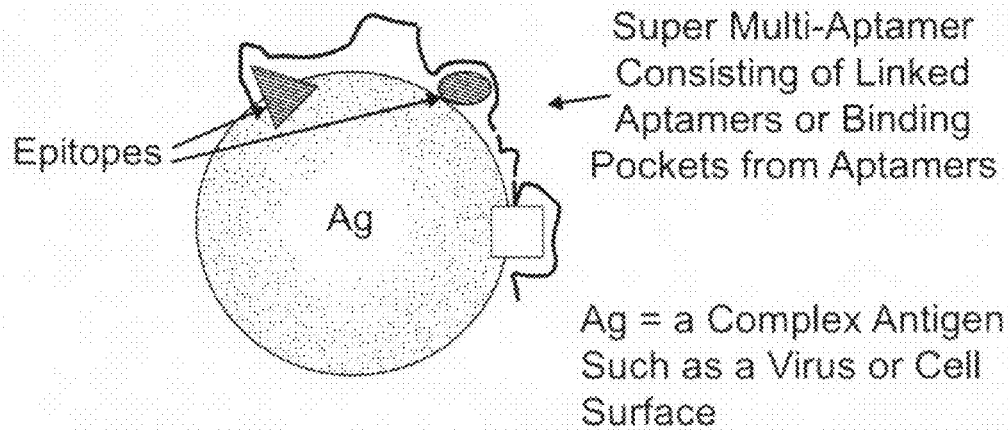

As nature, immunology, and FIG. 1 suggest, the linkage of binding sites is beneficial in terms of enhancing receptor affinity, avidity (tensile binding strength), and selectivity versus complex targets with two or more distinct epitopes. This linkage can be sequential and linear (one-dimensional as in antibody heavy and light chain linkage of HV regions, FIG. 1A) or could be expanded into two or three dimensions much like DNA dendrimers or other more complex structures known to those skilled in the art. The linked DNA ligands or aptamers are somewhat like concatamers, but can vary in the composition of DNA molecules or subunits that are linked together (i.e., can be non-repetitive versus repetitive concatamers).

Linear linkage by chemical synthesis is quite facile, if one already knows the aptamer DNA sequences or shorter (approximately 5-10 base) binding site sequences to be linked. One can simply design one long sequence to incorporate the desired aptamers or binding sites with repetitive poly-adenine (A), poly-cytosine (C), poly-guanine (G), poly-thymine (T), poly-uridine (U), or other intervening sequences that are unlikely to bind the target epitopes. The length of the composite aptamer construct will be limited by current chemical synthesis technology to about 200 bases. However, cellular biosynthesis or enzymatic synthesis by polymerase chain reaction or asymmetric PCR (producing predominately single-stranded ss-DNA from a template) would not be so limited and should produce aptamer constructs up to 2,000 bases before the Taq polymerase or other thermostable DNA polymerase falls off the template DNA. The 2 kilobase Taq polymerase limit is the basis for the well-known Random Amplification of Polymorphic DNA ("RAPD") method of DNA or genetic "fingerprint" analyses in which primers greater than 2 kilobases apart fail to produce a PCR product or amplicon, because Taq becomes disengaged from the template DNA before traveling 2,000 bases. In this way, lengthy aptamer constructs of less than 2 kilobases could be made from complementary DNA templates that would enable binding of different epitopes that are distal on the surface of relatively large objects such as viruses and whole bacteria, rickettsia, or eukaryotic parasites and other cells. Again, poly-A, C, G, T, or U or other linker nucleotide segments (similar to the concept of genetic "introns") could be designed into the cDNA template to produce the resultant nascent strand to ligate aptamers or aptamer binding sites together into one contiguous linear chain with intervening linkers as shown in FIG. 1B.

For 2-D or 3-D linked aptamer structures a variety of linker chemistries are available, but the preferred embodiment is probably addition of a UniLink™ primary amine group somewhere in the mid-section of a larger multi-aptamer construct followed by covalent linkage and branching of two or more such multi-aptamer constructs by means of bifunctional linkers such as low levels (≤1%) of glutaraldehyde, carbodiimides, sulfo-EGS, sulfo-SMCC or other such bifunctional linkers familiar to those skilled in conjugate chemistry. This strategy would result in larger flower-like or dendrimer-like 2-D or 3-D structures consisting of two or more lengthy multi-aptamer structures.

Figure 2:
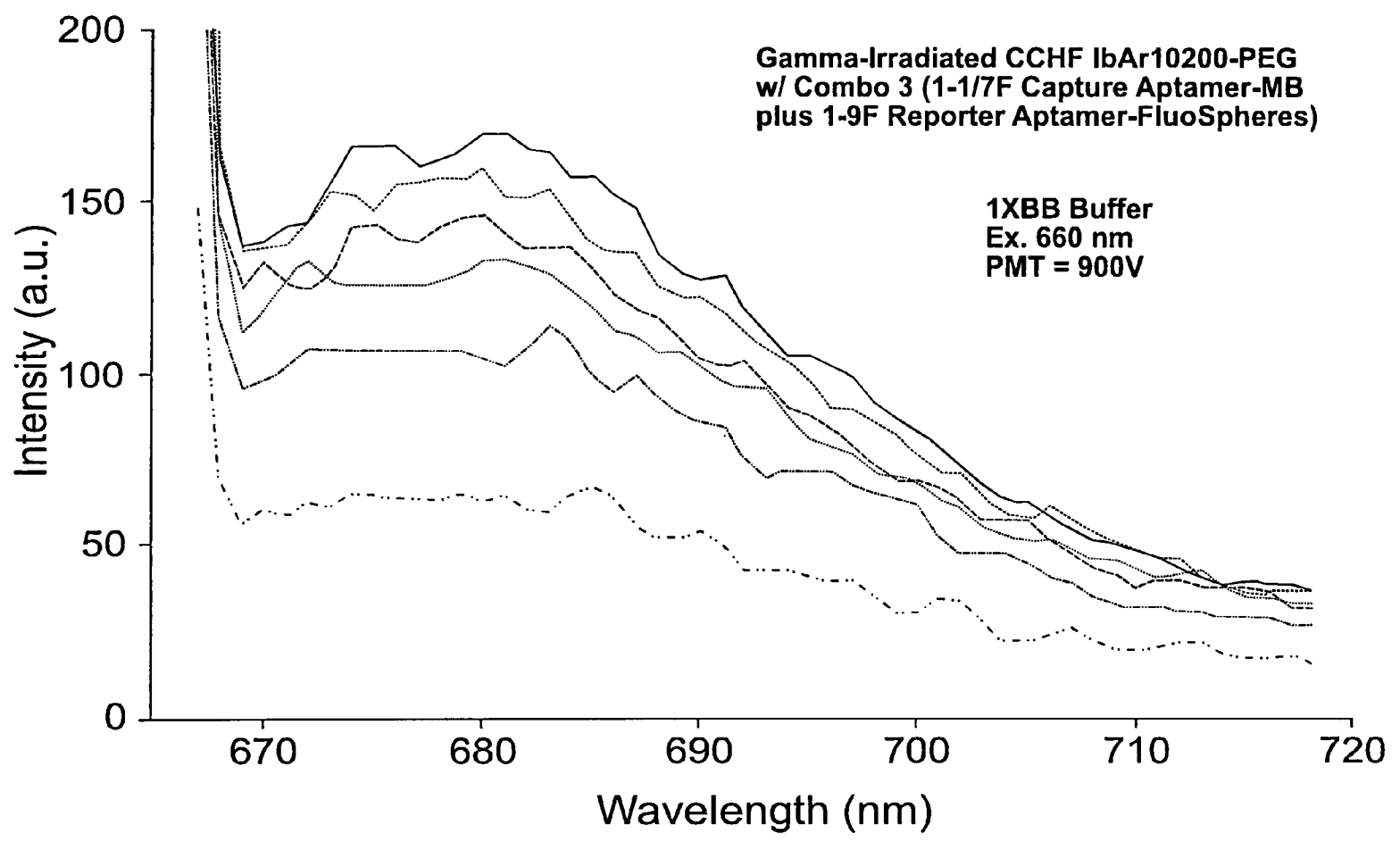

FIG. 2 shows fluorescence spectra from titration of a plastic-adherent DNA ligand-magnetic bead and fluorescent nanoparticle assay for detection of gamma-irradiated (inactivated) Crimean-Congo Hemorrhagic Fever (CCHF) viruses. The spectra or curves each represent fluorescence intensity results as a function of wavelength elicited by interaction with various virus dilutions after collection on aptamer or DNA ligand-biotin-streptavidin-magnetic microbeads of 2.8 microns in diameter (Dynal brand from Invitrogen Corp.), exposure to red-emitting fluorescent nanoparticles (FNPs) or Fluospheres (Invitrogen, Inc.) and two washes in 1× binding buffer (1XBB; 0.5M NaCl, 10 mM Tris and 1 mM $MgCl_2$ at pH 7.6). Excitation was at 660 nm and the photomultiplier tube of the spectrofluorometer was set at 900 V. The spectra were obtained using DNA ligands for capture on magnetic beads and red fluorophore-labeled reporter DNA ligands selected from the pool of aptamers represented by SEQ ID NOs. 1-168. In particular, aptamer C1-1/7F (SEQ ID NO. 3) was used for gamma-irradiated viral capture on magnetic beads and 5'-amino aptamer C1-9F (SEQ ID NO. 15) was conjugated to red FNPs by means of a carbodiimide bond, purified and used as the reporter reagent. The clear detection of the 1; 6400 dilution above the background curve suggests detection of as few as 150 CCHF virus particles.

Figure 3:
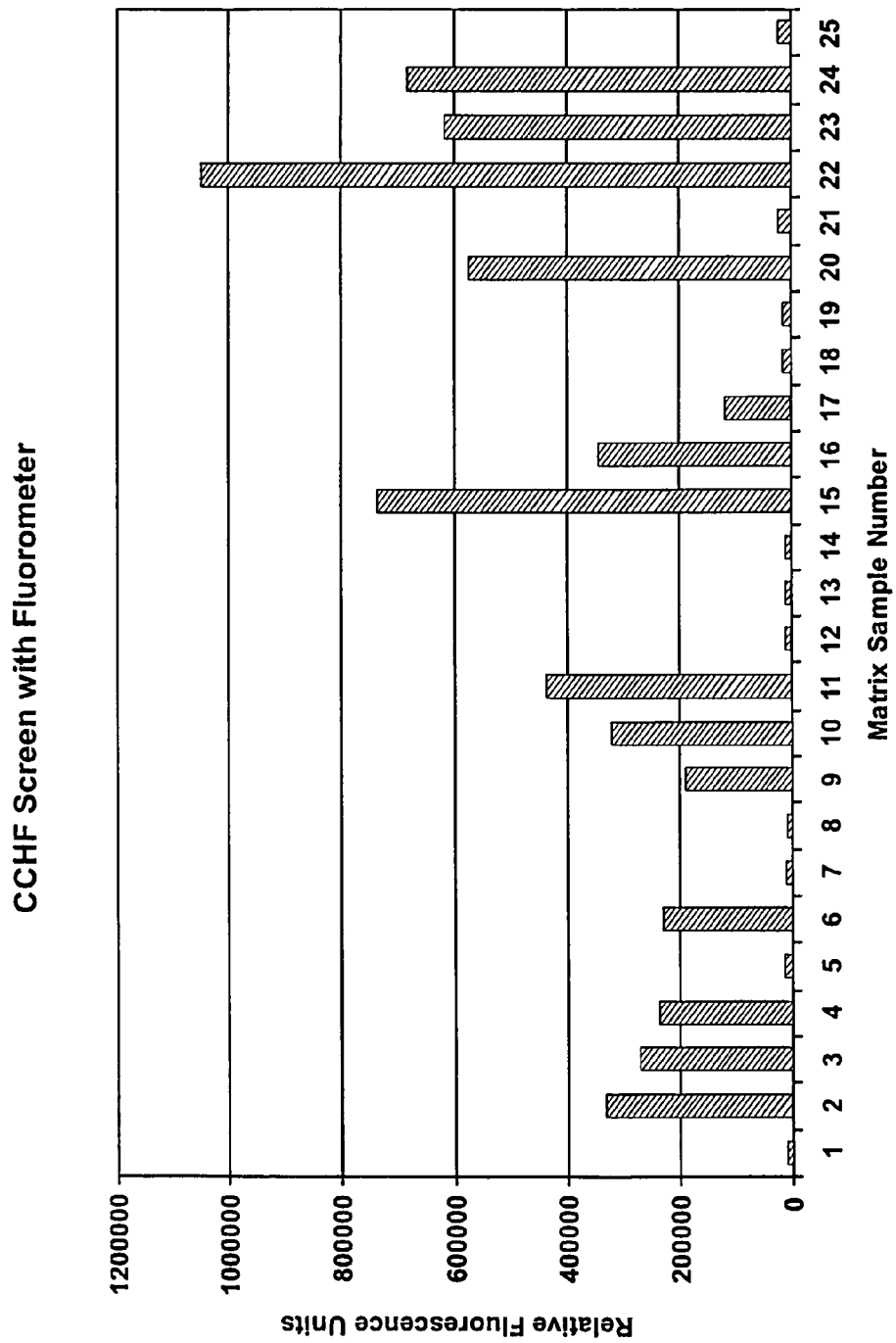
FIG. 3 illustrates the results of screening a matrix of 5-biotinylated capture aptamer-magnetic beads and TYE 665 dye-5'-labeled reporter aptamers from the Crimean-Congo viral aptamer pool represented by SEQ ID NOs. 663-756.

FIG. 3 shows the results of screening another matrix of 5-biotinylated capture aptamer-magnetic beads and TYE 665 dye-5'-labeled reporter aptamers from the Crimean-Congo (CCHF) viral aptamer pool represented by SEQ ID NOs. 663-756. The top 5 capture and reporter sandwich assay aptamer combinations were evaluated in all 25 (5 capture×5 reporter) possible combinations using a handheld Picofluor™ fluorometer set to its highest sensitivity (STD VAL=999.0). After washing in buffer on a permanent magnetic collection rack and reading this plastic-adherent assay in the polystyrene cuvettes, combination 22 (Gn6-25R; SEQ ID NO. 98) capture aptamer-biotin on streptavidin magnetic beads combined with E7A-18F; SEQ ID NO. 689) 5'-TYE 665-labeled reporter aptamer) was shown to be the strongest or most intense possible assay combination for further development.

Figure 4:
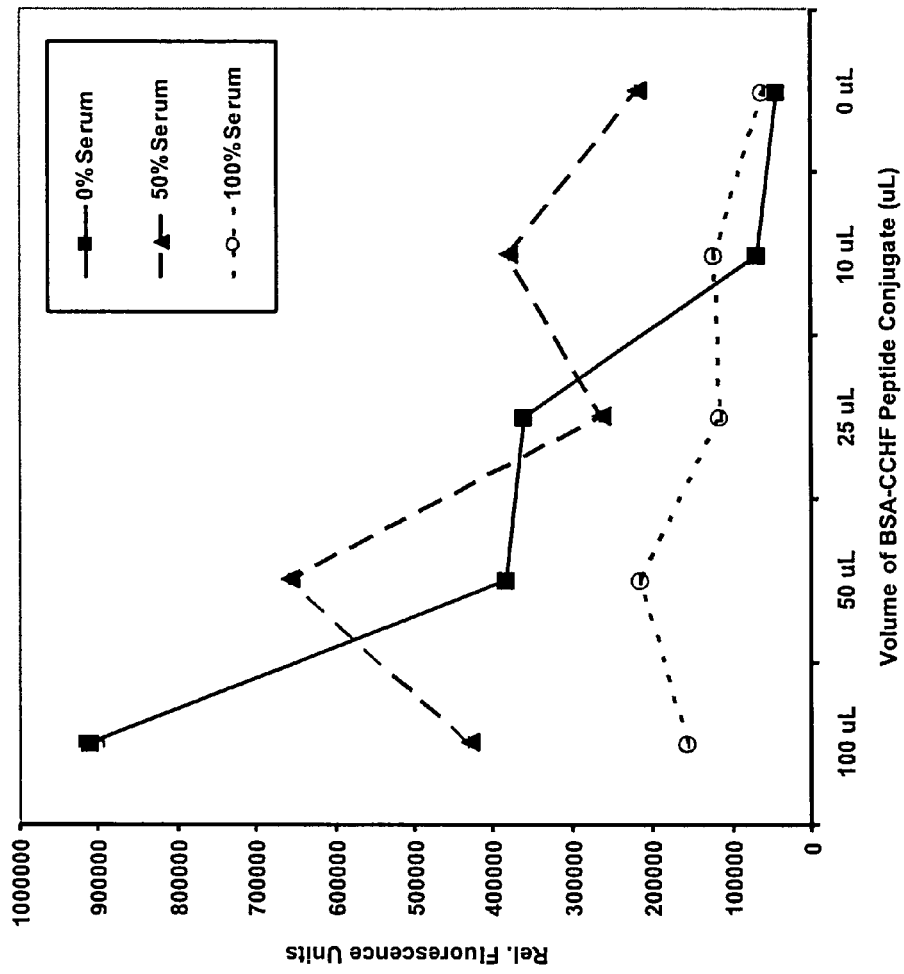
FIG. 4 illustrates titration of CCHF viral peptides conjugated with 1% glutaraldehyde to bovine serum albumin.

FIG. 4 illustrates titration of CCHF viral peptides conjugated with 1% glutaraldehyde to bovine serum albumin (BSA) and purified by size-exclusion chromatography in the void volume of a Sephadex G25 column to emulate CCHF virus particles in pure phosphate buffered saline (PBS), a 50:50 PBS to human serum mix or 100% human serum matrix to test detection with the CCHF combination 22 assay using the Picofluor™ handheld fluorometer at its highest sensitivity setting. Clearly CCHF combination 22 detected the viral stimulant quite well in buffer and continued to detect the simulant even in pure human serum, albeit with less intense fluorescence output.

Figure 5:
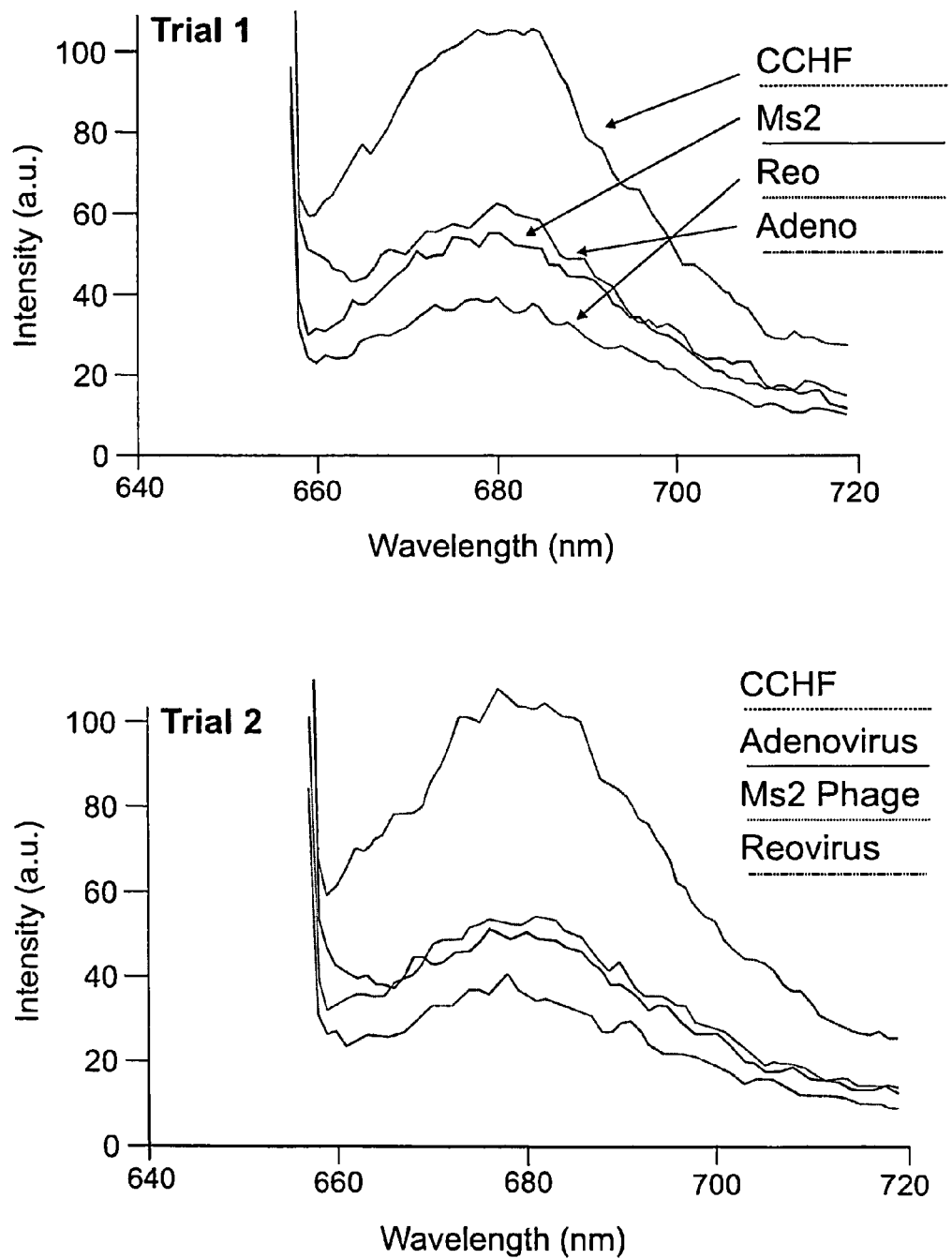
FIG. 5 illustrates the specificity of the combination 22 CCHF plastic-adherent assay which detects gamma-irradiated CCHF viruses.

FIG. 5 shows the specificity of the combination 22 CCHF plastic-adherent assay which detects gamma-irradiated CCHF viruses of a comparable concentration much more intensely than unrelated Adenovirus, MS-2 bacteriophage, or Reovirus Type 3 Abney strain viruses.

Figure 6C:
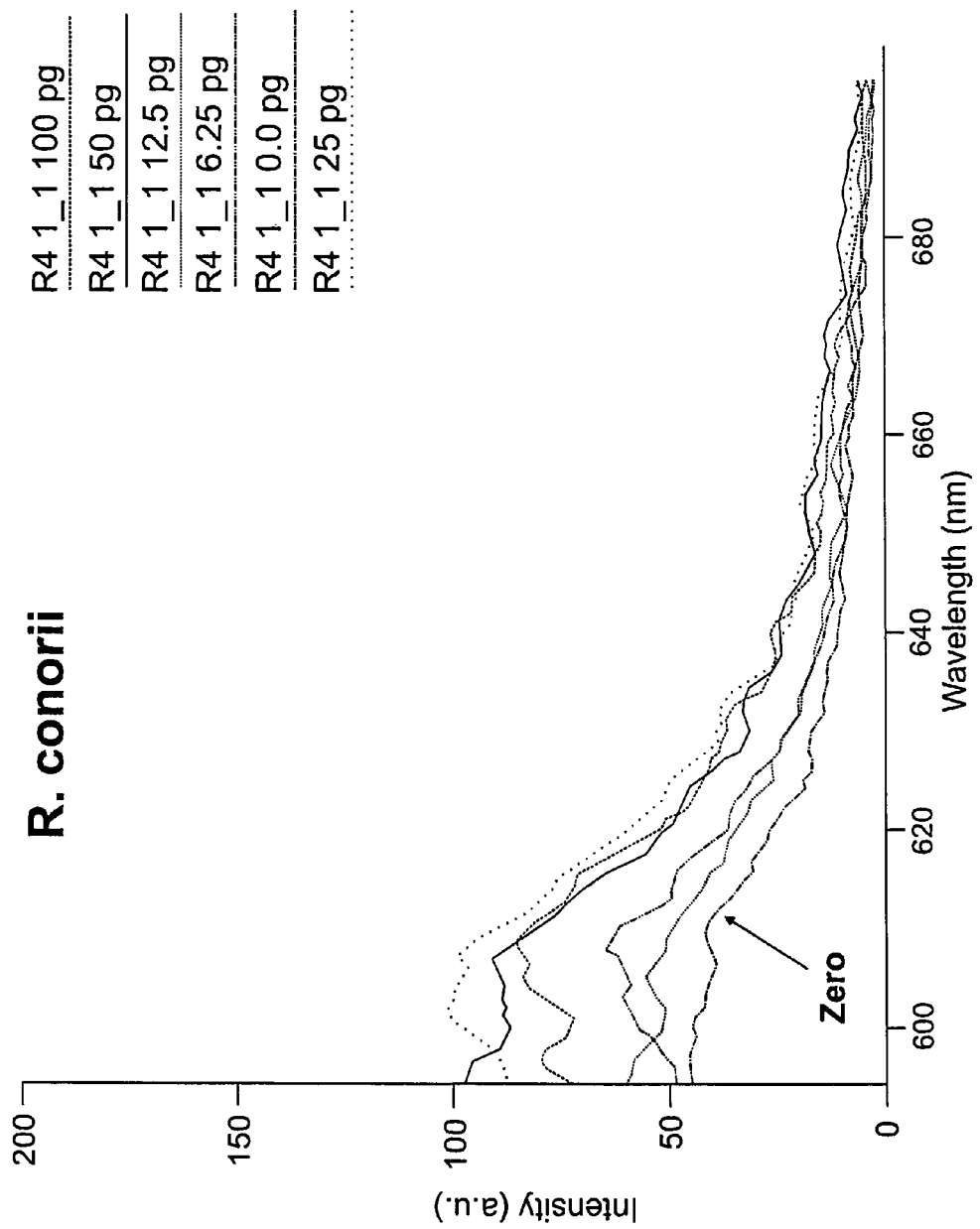
Figure 6D:
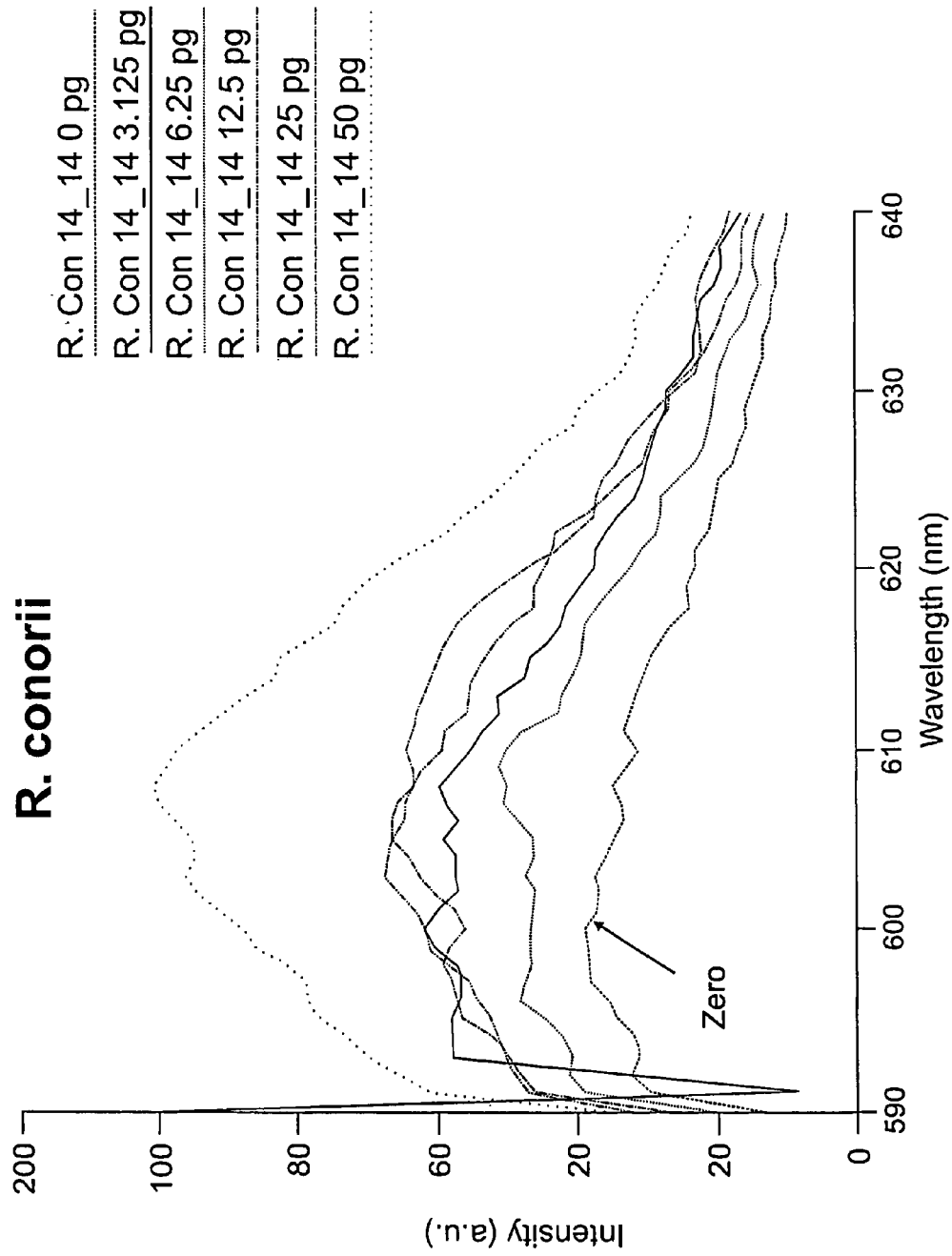

FIG. 6 illustrates similar plastic-adherent (PASA) DNA ligand-magnetic bead and DNA ligand-fluorescent nanoparticle sandwich assay fluorescence results for the detection of *Rickettsia conorii* to a level of approximately 3 μL or 75 cells in some cases. Various DNA ligand sequences are used in capture and reporter roles in the four different experiments from the pool of SEQ ID NOs. 549-662.

Figure 7A:
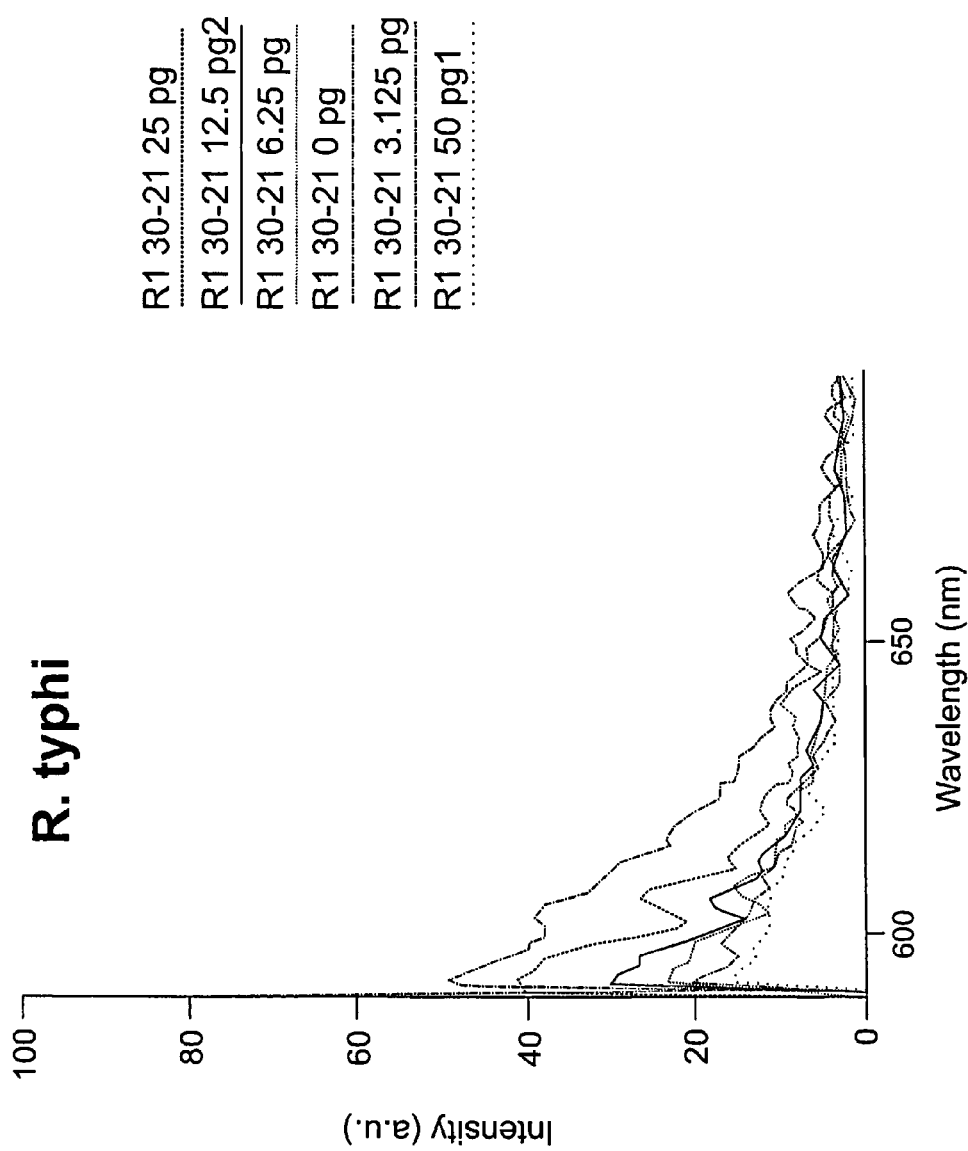
Figure 7B:
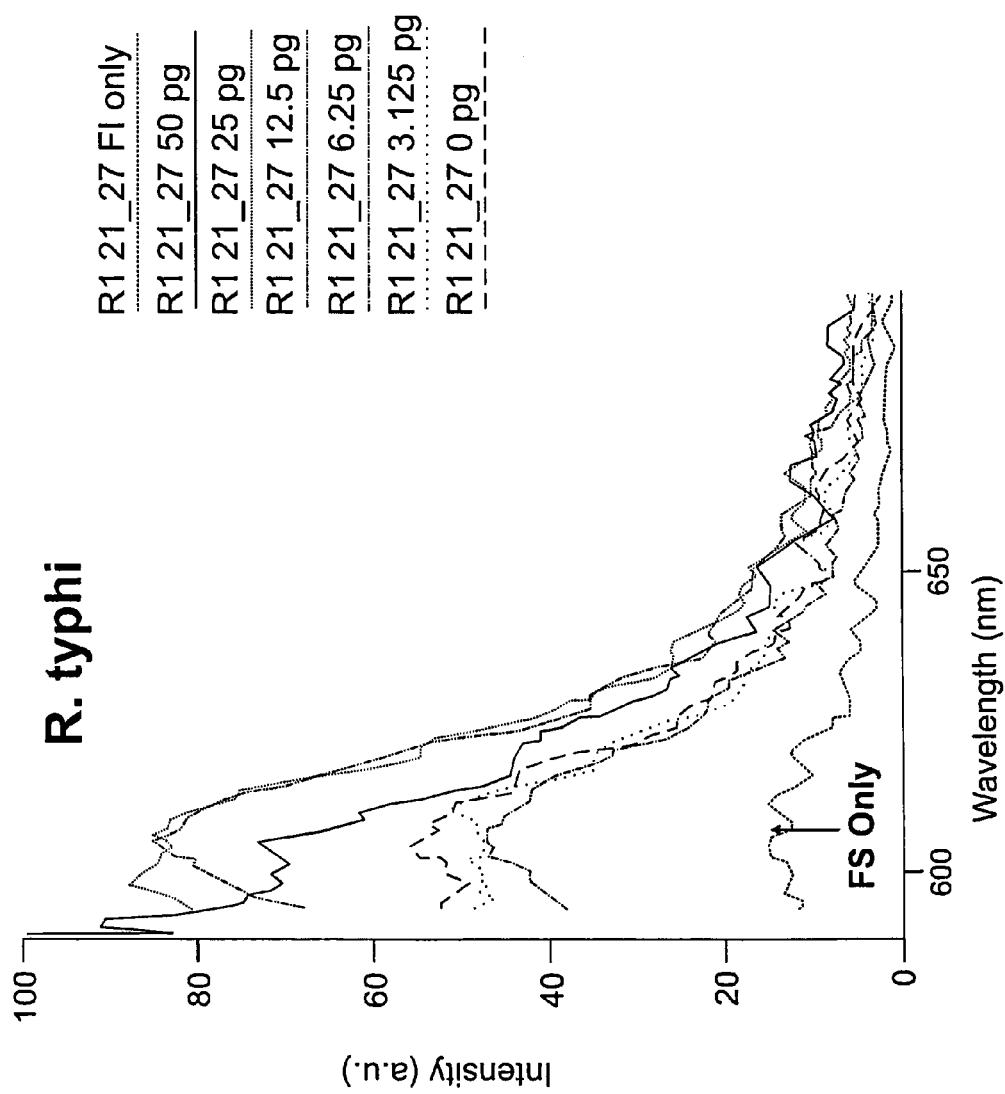

FIG. 7 illustrates the plastic-adherent (PASA) sandwich assay results for three different combinations of capture and reporter DNA ligands for detection of *Rickettsia typhi*. Serial dilutions of the rickettsia were evaluated using a spectrofluorometer and red-emitting fluorescent nanoparticles. Again, these sandwich assay aptamer combinations were drawn from the pool of SEQ ID NOs. 549-662.

Figure 8:
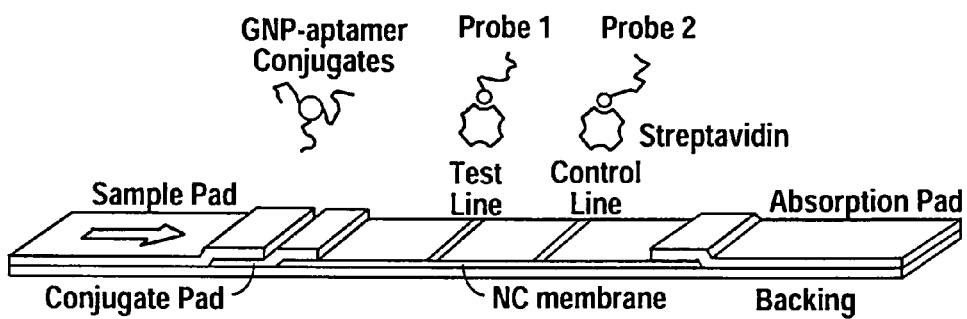
Figure 8:
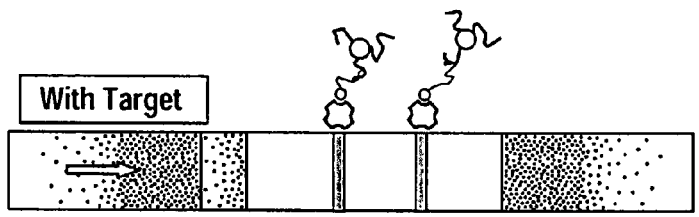
Figure 8:
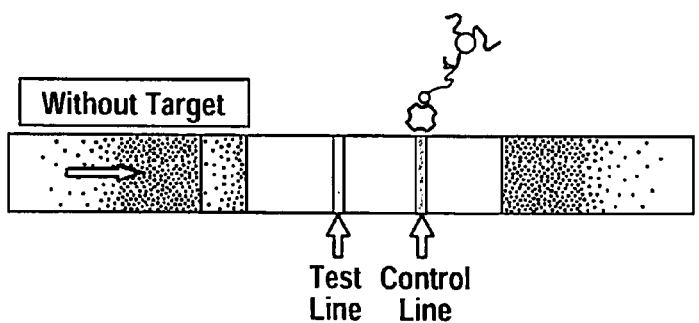

FIG. 8 illustrates the aptamer-5'-biotin-streptavidin-gold nanoparticle (GNP) or fluorescent nanoparticle (FNP) and streptavidin-biotin-5'-primer probe (to grab the complementary 18 base constant primer regions on the DNA ligand ends) scheme used for the test and control lines on successful lateral flow nitrocellulose aptamer chromatographic test strips displayed in FIG. 9 and described in the specifications or main text.

FIG. 9 documents several successful attempts to detect either gamma-irradiated viruses or purified BSA-glutaraldehyde-viral spike peptide conjugates on lateral flow strips using the method shown in FIG. 8. In particular, panel A shows a strong visible red spot indicating detection of the Chikungunya envelope peptide (ChE) with aptamer ChE 20R (SEQ ID NO. 204) and much fainter detection at the spot where ChE 17R aptamer was laid down and immobilized. Panel B shows similar positive red GNP detection spots for the C1-9F aptamer (SEQ ID NO. 15) detecting two different strains of actual gamma-irradiated CCHF virus, while the CCHF or C3-6R aptamer did not detect the viruses despite its strong performances and evidence of very high affinity in ELISA-like microplate assays and SPR analyses (Tables 2 and 3). Panel C illustrates two successful tests for West Nile Virus (WNV) envelope peptide-BSA conjugates using the WNV-18R and 19R aptamers which correspond to SEQ ID NOs. 306 and 307, respectively. Arrows in each of the panels point to the locations where capture dots or lines of DNA ligands were laid down.

TABLE 1

Targets for DNA Ligand Selection and Development

Chikungunya (ChE) E1a Virus Surface Peptide
(one letter amino acid-coded sequence)

GDIQSRTPESKDVYANTQLVLQRPAVGTVHVPYSQAPSGFKYWLKERGAS

Crimean-Congo Hemmorhagic Fever (CCHF) Virus
Surface Peptide Targets (one-letter amino acid
coded sequences)

CCHF Peptide 1: RRLL

CCHF Peptide 2: RKPL

CCHF Peptide 3: GQGKTIEAYRAREG

CCHF Peptide 4: GQGKTIEAYRAREGNAST GQGKTIEAYRAREG

CCHF Altamura Gn 611: TQEGRGHVKLSRGSE

CCHF 11E7-a: GLKFASLTCTGCYACSSGISCKVRIHVDEPDE

CCHF 11E7-b: VAASSSLMARKLEFGTDSTFKAFSAMPKTSLCFYIV EREY

CCHF 11E7-c: EDTQKCVNTKLEQPQSILIEHKGTIIGK

Dengue Viruses
Recombinant Envelope Proteins Serotypes 1-4 from Virostat Corp., Portland, Me., Cat. Nos. 8812-8815.

*Leishmania* promastigotes
L. donovani, L. major WR2885 and other species of live cell surface cold (4° C.) overnight 1.5M $MgCl_2$-protein extracts obtained from the U.S. Army, Walter Reed Army Institute of Research (WRAIR).
Rickettsia
R. belli, R. conorii, R. parkeri, R. rickettsii, and R. typhi frozen cell protein extracts obtained from the U.S Navy Medical Research Command at WRAIR.
Tick-borne Encephalitis Viruses (TBEV)
Recombinant TBEV CE/gE from Feldan Bio Corp. (Boston, Mass. and Quebec, Canada) Cat. No. FB03-80-149.
West Nile Virus (WNV)
Recombinant Envelope Protein from GenWay Biotech Corp. San Diego, Calif., Cat. No. 10-511-248224.

EXAMPLE 1

ELISA-Like and SPR Affinity-Based Screening of Arthropod-Borne Pathogen DNA Ligands Table 2 illustrates diversity of affinities for several different CCHF envelope peptide epitopes using two methods (0.1M bicarbonate buffer at pH 8.5 or N-oxy-succinimide-coated microwells) to immobilize the peptides and then carry out a traditional ELISA-like assay with 100 µL of 5'biotinylated DNA ligands for one hour at room temperature (RT, followed by a wash step, addition of 100 µL of 1:2,000 dilution of streptavidin-peroxidase (1 mg/mL stock) for 30 minutes at RT, three more wash steps and finally treatment with one-step ABTS substrate for 10 minutes at RT and reading of absorbance at 405 nm on a microplate reader. Tables 2 and 5-7 show ELISA-like rankings of the various top 3 to 10 DNA ligands by SEQ ID NOs for each of the general arthropod disease categories.
The highest ranking or highest affinity DNA ligands register the highest absorbance at 405 nm values and can be used in other types of affinity-based assays besides the ELISA-formatted assays. The highest affinity or highest ranking CCHF DNA ligands such as CCHF1-9F and CCHF3-6R also yielded very high affinity constants of greater $10^8$ to $4.23 \times 10^{11}$ by surface plasmon resonance (SPR) using a Biacore X-100 sensor as documented in Tables 3 and 4. The same or similar ELISA-like methods were used to screen and rank DNA ligand affinities against cognate arboviral, rickettsial and *Leishmania* targets as shown in Tables 5-7. Table 8 chronicles all of the actual candidate DNA ligand nucleotide sequences and corresponding SEQ ID NOs for all of the arthropod-borne pathogen-binding DNA ligands.

TABLE 2

ELISA-Like Rankings for Absorbance of Highest Affinity CCHF DNA Ligands

| | $NaHCO_3$-Immobilized | | | | NOS-Immobilized | | |
|---|---|---|---|---|---|---|---|
| Rank | Abs 405 | SEQ ID NO. | Aptamer | Rank | Abs 405 | SEQ ID NO. | Aptamer |
| 1 | 2.669 | 31 | CCHF3-4F | 1 | 2.219 | 15 | CCHF1-9F |
| 2 | 2.478 | 36 | CCHF3-6R | 2 | 2.141 | 36 | CCHF3-6R |
| 3 | 2.473 | 32 | CCHF3-4R | 3 | 2.048 | 4 | CCHF1-1/7R |
| 4 | 2.243 | 15 | CCHF1-9F | 4 | 1.987 | 32 | CCHF3-4F |
| 5 | 1.657 | 28 | CCHF2-10R | 5 | 1.987 | 16 | CCHF1-9R |
| 6 | 1.645 | 25 | CCHF2-8F | 6 | 1.987 | 2 | CCHF1-1R |
| 7 | 1.618 | 18 | CCHF1-10R | 7 | 1.949 | 14 | CCHF1-6R |
| 8 | 1.561 | 16 | CCHF1-9R | 8 | 1.903 | 3 | CCHF1-1/7F |
| 9 | 1.505 | 38 | CCHF3-7R | 9 | 1.853 | 7 | CCHF1-3F |
| 10 | 1.483 | 40 | CCHF3-8R | 10 | 1.848 | 25 | CCHF2-8F |

TABLE 3

Summary of CCHF DNA Ligand SPR Data

| CCHF DNA Ligand | vs. Peptide | $K_a$ | $K_d$ (picoM) |
|---|---|---|---|
| 1-9F | Peptide 1 | $1.23 \times 10^8$ | 8.13 |
| 1-9F | Peptide 3 | $3.06 \times 10^6$ | 327 |
| 1-9F | Peptide 4 | $3.2 \times 10^{10}$ | 0.31 |
| 3-4R | Peptide 3 | $8.85 \times 10^7$ | 11.3 |
| 3-4R | Peptide 4 | $3.1 \times 10^6$ | 322 |
| 3-6R | Peptide 3 | $4.23 \times 10^{11}$ | 0.24 |
| 3-6R | Peptide 4 | $2.19 \times 10^4$ | 45,700 |

TABLE 4

Summary of Aptamer $K_A$ Values vs. 11E7 CCHF Envelope Peptides by SPR

| DNA Ligands or Aptamers | 11E7A | 11E7B | 11E7C |
|---|---|---|---|
| E7A-11R | $4.62 \times 10^8$ | $7.34 \times 10^7$ | $3.11 \times 10^9$ |
| Drosdov 4-7/10R | $5.39 \times 10^9$ | $1.27 \times 10^7$ | Not done |
| Drosdov 17R | $2.09 \times 10^9$ | $6.08 \times 10^8$ | Not done |
| E7B-14R | $5.2 \times 10^8$ | $9.37 \times 10^7$ | $3.72 \times 10^7$ |
| Gn6-25R | $5.5 \times 10^8$ | $2.07 \times 10^8$ | $1.48 \times 10^{10}$ |
| E7A-18F | $1.39 \times 10^7$ | $3.48 \times 10^9$ | $1.92 \times 10^7$ |

TABLE 5

ELISA-Like Rankings of Various Arthropod-borne Virus DNA Ligands

| Sequence | SEQ ID NO. | A 405 nm |
|---|---|---|
| TBEV-2 R | 760 | 2.601 |
| TBEV-8 R | 772 | 2.430 |
| TBEV-2 F | 759 | 2.314 |
| TBEV-1 R | 758 | 2.150 |
| TBEV-4 R | 764 | 2.124 |
| TBEV-6 R | 768 | 2.124 |
| TBEV-6 F | 767 | 2.067 |
| TBEV-5 F | 765 | 2.057 |
| TBEV-7 F | 769 | 2.021 |
| TBEV-7 R | 770 | 1.972 |
| TBEV-10F | 773 | 1.951 |
| TBEV-1 F | 757 | 1.935 |
| TBEV-5 R | 766 | 1.925 |
| TBEV-3 R | 762 | 1.908 |
| TBEV-4 F | 763 | 1.881 |
| TBEV-8 F | 771 | 1.847 |
| TBEV-10R | 774 | 1.823 |
| TBEV-3 F | 761 | 1.797 |
| ChE - 16F | 195 | 2.594 |
| ChE - 20R | 204 | 2.562 |
| ChE - 17R | 198 | 2.510 |
| ChE - 19F | 201 | 2.474 |
| ChE - 16R | 196 | 2.464 |
| ChE - 19R | 202 | 2.459 |
| ChE - 17F | 197 | 2.431 |
| ChE - 18F | 199 | 2.388 |
| ChE - 20F | 203 | 2.364 |
| ChE - 18R | 200 | 2.246 |
| WNV 19F | 307 | 2.727 |
| WNV 18R | 306 | 2.654 |
| WNV 20F | 309 | 2.538 |
| WNV 20R | 310 | 2.467 |
| WNV 16F | 303 | 2.450 |
| WNV 16R | 304 | 2.255 |
| WNV 19R | 308 | 2.177 |
| WNV 18F | 305 | 1.997 |

TABLE 6

ELISA-Like Rankings of Leishmania parasite DNA Ligands

| Sequence | SEQ ID NO. | A 405 nm | Sequence | SEQ ID NO. | A 405 nm |
|---|---|---|---|---|---|
| Lm 49,50R | 548 | 2.501 | Lm 29R | | 1.516 |
| Lm 25R | 516 | 2.406 | Lm 34F | | 1.516 |
| Lm 1147R | 494 | 2.238 | Lm 9R | | 1.504 |
| Lm 610F | 487 | 2.212 | Lm 610R | | 1.466 |
| Lm 16F | 501 | 2.166 | Lm 18R | | 1.446 |
| Lm 19R | 508 | 2.141 | Lm 19F | | 1.442 |
| Lm 17R | 504 | 2.091 | Lm 23R | | 1.442 |
| Lm 3240F | 525 | 2.045 | Lm 16R | | 1.437 |
| Lm 38F | 535 | 1.979 | Lm 45R | | 1.435 |
| Lm 13R | 496 | 1.935 | Lm 35R | | 1.433 |
| Lm 22R | | 1.916 | Lm 32/40R | | 1.411 |
| Lm 31R | | 1.899 | Lm 17F | | 1.410 |
| Lm 2643F | | 1.854 | Lm 44F | | 1.391 |
| Lm 241R | | 1.850 | Lm 45F | | 1.380 |
| Lm 241F | | 1.849 | Lm 1F | | 1.378 |
| Lm 46F | | 1.845 | Lm 18F | | 1.367 |
| Lm 34R | | 1.838 | Lm 37F | | 1.366 |
| Lm 42R | | 1.835 | Lm 15F | | 1.365 |
| Lm 4950F | | 1.806 | Lm 35F | | 1.305 |
| Lm 7F | | 1.791 | Lm 1R | | 1.261 |
| Lm 25F | | 1.787 | Lm 21R | | 1.261 |
| Lm 36R | | 1.709 | Lm 5F | | 1.252 |
| Lm 15R | | 1.698 | Lm 39F | | 1.224 |
| Lm 13F | | 1.684 | Lm 9F | | 1.219 |
| Lm 39F | | 1.679 | Lm 4R | | 1.217 |
| Lm 21F | | 1.659 | Lm 1147F | | 1.216 |
| Lm 38R | | 1.653 | Lm 27R | | 1.207 |
| Lm 23F | | 1.644 | Lm 14F | | 1.182 |
| Lm 46R | | 1.634 | Lm 36F | | 1.181 |
| Lm 2643R | | 1.626 | Lm 3R | | 1.179 |
| Lm 27F | | 1.598 | Lm 44R | | 1.157 |
| Lm 42F | | 1.596 | Lm 29F | | 1.125 |
| Lm 22F | | 1.576 | Lm 4F | | 1.095 |
| Lm 31F | | 1.569 | Lm 3F | | 1.092 |
| Lm 5R | | 1.537 | Lm 37R | | 1.048 |
| Lm 7R | | 1.516 | Lm 14R | | 0.984 |

TABLE 7

ELISA-Like Rankings of Rickettisia DNA Ligands

| Type | Species | Aptamer Clone | SEQ ID NO. | Avg. Absorbance at 405 nm |
|---|---|---|---|---|
| Whole Cell | R. parkeri | Rp-7R | 556 | 1.33 |
| | | Rp-14R | 568 | 1.34 |
| | | Rp-20F | 577 | 1.37 |
| | R. rickettsii | Rr-8/14/22R | 584 | 1.21 |
| | | Rr-17F | 599 | 1.18 |
| | | Rr-23R | 610 | 1.22 |
| | R. typhi | Rt-3R | 620 | 1.48 |
| | | Rt-5/16F | 623 | 1.53 |
| | | Rt-18R | 648 | 1.45 |
| OMPs | R. belli | R5-23F | 317 | 2.93 |
| | | R5-39F | 347 | 1.95 |
| | | R5-21bR | 316 | 1.89 |
| | R. conorii | R4-1R | 352 | 2.12 |
| | | R4-14R | 362 | 2.05 |
| | | R4-1F | 351 | 1.99 |
| | R. parkeri | R2-14F | 393 | 2.08 |
| | | R2-17R | 400 | 2.05 |
| | | R2-5F | 379 | 1.95 |
| | R. rickettsii | R3-39F | 413 | 2.12 |
| | | R3-39R | 414 | 2.05 |
| | | R3-40R | 416 | 1.99 |
| | R. typhi | R1-21R | 426 | 2.88 |
| | | R1-30R | 444 | 2.85 |
| | | R1-27bF | 437 | 2.62 |

EXAMPLE 2

Ultrasensitive Detection of CCHF Virus and Rickettsia by Plastic-Adherent Sandwich Assay The DNA ligand sequences have repeatedly been reduced to practice and used to detect low levels of CCHF viral envelope epitopes in neat buffer or animal sera as shown in FIG. 2. In this assay, two different CCHF sequences (CCHF 1-1/7F and 1-9F) from the SEQ ID NO. 3 and SEQ ID NO. 15 were 5'-biotin or 5'-amine modified upon synthesis and attached to either $10^6$ streptavidin-M280 (2.8 micron diameter) Dynal (Invitrogen, Inc.) MBs for virus capture or custom-made red-emitting carboxyl-coated FNPs (Invitrogen, Inc.) for reporting per test. The lower limit of detection (LLOD or 1:6400 dilution) for this assay was approximately 150 viral particles according to plaque assay data obtained from the U.S. Army at USAMRIID, Ft. Detrick, Md. Excitation was at 600 nm and the photomultiplier tube ("PMT") was set at 900V.

Similarly sensitive plastic-adherent sandwich fluorescence assay results for two species of rickettsia cells with LLOD or about 75 cells are shown in FIGS. 5 and 6. These assays also sandwich rickettsial cells between magnetic bead-DNA ligand capture elements and DNA ligand-quantum dot or FNP-labeled reporter aptamers drawn from the SEQ ID NOs given in Table 8.

EXAMPLE 3

Lateral Flow (LF) Aptamer Sandwich Assays for Arthropod-Borne Bacteria or Viruses Using Colloidal Gold or Fluorescent Nanoparticles Aptamer-based LF test strips are assembled much like traditional immunochromatographic strips by combining a Whatman GB002 sample pad, a Whatman Standard 17 conjugate pad, Millipore High Flow 240 analytical membrane (for slower migration and greatest sensitivity) and a Whatman 470 wicking or absorbent applied to a pressure sensitive sticky laminate backing. The sample pad is soaked in 0.05M Tris-HCl (pH 8.03) with 0.15 mM NaCl and 0.25% Triton X-100 for 30 minutes followed by air drying of the sample pad strip at 37° C. for several hours until completely dry. The components are assembled with the sample pad overlapping the conjugate pad and both the conjugate pad and wicking pads overlapping onto the nitrocellulose analytical membrane at each end of the analytical membrane as shown in FIG. 8. Thereafter, 4 mm wide strips are cut with a sharp paper cutter and laid into plastic cassettes for protection.

The streptavidin-colloidal gold for use in conjugates was obtained from DCN at 10 O.D. units per mL and 100 µL of this reagent was added to 100 µL of each 5'-biotinylated aptamer (1.3 to 1.5 mg/mL). Similarly, 100 µL of each 5'-biotin aptamer were added to 100 µL of simple streptavidin at (0.5 mL, Sigma Chemical Co.) and reagents were gently mixed at RT (20-25° C.) for 30 minutes. Any unbound aptamers were removed by use of sterile 30 kD molecular weight cut off spin columns which were centrifuged at 5,000×g for 10 minutes. The retentate was resuspended or rehydrated in 1004 of sterile 1 XBB and used in LF test strip experiments. The capture lines or "dots" (droplets) were laid down as 1 µL droplets a few millimeters from the conjugate pad on Millipore High Flow (HF) 240 nitrocellulose analytical membranes, sometimes in series, and air dried prior to baking in a UV oven for 15 minutes. The conjugate pads were loaded with 10-15 µL of colloidal gold-streptavidin-biotin-aptamer conjugates and target analytes were added in 100 µL of 1 XBB at the indicated amounts in each figure. All colloidal gold LF tests were conducted and evaluated after 5 minutes of run time to enable the HF 240 membranes time to fully develop. FIG. 9 specifically illustrates examples of successful lateral flow DNA ligand (aptamer) tests with the Chikungunya virus aptamer ChE 20R (SEQ ID NO. 204), Crimean-Congo (CCHF) virus aptamer C1-9F (SEQ ID NO. 15) and the West Nile virus (WNV) aptamers 18R and 19F (SEQ ID NOs. 306 and 307 respectively). Interestingly, some other aptamers used for the experiments represented in FIG. 9 such as ChE 17R and CCHF C3-6R which performed well in ELISA-like plate assays or SPR analysis for affinity assessment (Tables 2, 3, and 5), did not perform well in the lateral flow format, thereby further underscoring a basic tenet of this patent application that not all high-affinity DNA ligands from a given group will perform well in all assay formats.

DNA aptamer-quantum dot and aptamer-fluorescent nanoparticle (FluoSpheres™; "FS" from Invitrogen) conjugates were initially adhering rather tightly to glass fiber conjugate pads and not releasing well or not migrating as far as unconjugated particles, but these obstacles were overcome by switching to a larger porosity HighFlow ("HF") 75 analytical membrane and 40 nm streptavidin-FS to obtain the successful proof-of-concept data shown in FIG. 9C.

Although the invention and DNA ligand sequences listed in Table 8 have been described with reference to specific embodiments, this description is not meant to be construed in a limited sense. Various modifications of the disclosed embodiments, as well as alternative embodiments of the inventions will become apparent to persons skilled in the art upon reference to the description of the invention. It is, therefore, contemplated that the appended claims will cover such modifications that fall within the scope of the invention.

TABLE 8

DNA Ligand Sequence ID Nos.
Arthropod Aptamer Sequences 2011-Final

```
<SEQ ID NO. 1 C1 - 1 F; DNA; ARTIFICIAL>
ATACGGGAGCCAACACCAATAAAGAGCGGAACTTTTAGAACTGGATAGACTCATAGAGCAGGTGTGACGGAT

<SEQ ID NO. 2 C1 - 1 R; DNA; Artificial>
ATCCGTCACACCTGCTCTATGAGTCTATCCAGTTCTAAAAGTTCCGCTCTTTATTGGTGTTGGCTCCCGTAT <SEQ ID NO. 3 C1 - 1/7 F; DNA; ARTIFICIAL>
ATACGGGAGCCAACACCATAGTGTTGGGCCAATACGGTAACGTGTCCTTGGAGAGCAGGTGTGACGGAT <SEQ ID NO. 4 C1 - 1/7 R; DNA; Artificial>
ATCCGTCACACCTGCTCTCCAAGGACACGTTACCGTATTGGCCCAACACTATGGTGTTGGCTCCCGTAT
```

TABLE 8-continued

DNA Ligand Sequence ID Nos.
Arthropod Aptamer Sequences 2011-Final

<SEQ ID NO. 5 C1 - 2 F; DNA; ARTIFICIAL>
ATACGGGAGCCAACACCACTAACTTGTTGCTGATCTTATCCAGAGCAGGTGTGACGGAT

<SEQ ID NO. 6 C1 - 2 R; DNA; Artificial>
ATCCGTCACACCTGCTCTGGATAAGATCAGCAACAAGTTAGTGGTGTTGGCTCCCGTAT <SEQ ID NO. 7 C1 - 3 F; DNA; ARTIFICIAL>
ATACGGGAGCCAACACCAATGAGAGCAAAGATCCCAGGATACACTAATCCCTGTAGAGCAGGTGTGACGGAT <SEQ ID NO. 8 C1 - 3 R; DNA; Artificial>
ATCCGTCACACCTGCTCTACAGGGATTAGTGTATCCTGGGATCTTTGCTCTCATTGGTGTTGGCTCCCGTAT <SEQ ID NO. 9 C1 - 4 F; DNA; ARTIFICIAL>
ATACGGGAGCCAACACCACCTAGTGTTGAATCTGACCACAAGCTAAGTCTTCGGAGAGCAGGTGTGACGGAT <SEQ ID NO. 10 C1 - 4 R; DNA; Artificial>
ATCCGTCACACCTGCTCTCCGAAGACTTAGCTTGTGGTCAGATTCAACACTAGGTGGTGTTGGCTCCCGTAT <SEQ ID NO. 11 C1 - 5 F; DNA; ARTIFICIAL>
ATACGGGAGCCAACACCAAGCACGGAAAGAGGGTCGCCTGATAGCCCGCCAATCAGAGCAGGTGTGACGGAT <SEQ ID NO. 12 C1 - 5 R; DNA; Artificial>
ATCCGTCACACCTGCTCTGATTGGCGGGCTATCAGGCGACCCTCTTTCCGTGCTTGGTGTTGGCTCCCGTAT <SEQ ID NO. 13 C1 - 6 F; DNA; ARTIFICIAL>
ATACGGGAGCCAACACCAAGAAATGCCAACACAACGACACCGGTAGTGCTGCCCAGAGCAGGTGTGACGGAT <SEQ ID NO. 14 C1 - 6 R; DNA; Artificial>
ATCCGTCACACCTGCTCTGGGCAGCACTACCGGTGTCGTTGTGTTGGCATTTCTTGGTGTTGGCTCCCGTAT <SEQ ID NO. 15 C1 - 9 F; DNA; ARTIFICIAL>
ATACGGGAGCCAACACCATGGTGACGGACCTTGAGAGCAAGACCGCTACGATTCAGAGCAGGTGTGACGGAT <SEQ ID NO. 16 C1 - 9 R; DNA; Artificial>
ATCCGTCACACCTGCTCTGAATCGTAGCGGTCTTGCTCTCAAGGTCCGTCACCATGGTGTTGGCTCCCGTAT <SEQ ID NO. 17 C1 - 10 F; DNA; ARTIFICIAL>
ATACGGGAGCCAACACCAGAAGAACACTGCCTAGAATAAGTGGTGCAGGGCCGTAGAGCAGGTGTGACGGAT <SEQ ID NO. 18 C1 - 10 R; DNA; Artificial>
ATCCGTCACACCTGCTCTACGGCCCTGCACCACTTATTCTAGGCAGTGTTCTTCTGGTGTTGGCTCCCGTAT <SEQ ID NO. 19 C2 - 4 F; DNA; ARTIFICIAL>
ATACGGGAGCCAACACCATTAGGTGGTAGACTGTAGGTTACAGATAGCCGGGGAGAGCAGGTGTGACGGAT <SEQ ID NO. 20 C2 - 4 R; DNA; Artificial>
ATCCGTCACACCTGCTCTCCCCGGCTATCTGTAACCTACAGTCTACCACCTAATGGTGTTGGCTCCCGTAT <SEQ ID NO. 21 C2 - 5 F; DNA; ARTIFICIAL>
ATACGGGAGCCAACACCATCTGGCGCCGACCCTGTGGATTGCAGTCGCGGTTACAGAGCAGGTGTGACGGAT <SEQ ID NO. 22 C2 - 5 R; DNA; Artificial>
ATCCGTCACACCTGCTCTGTAACCGCGACTGCAATCCACAGGGTCGGCGCCAGATGGTGTTGGCTCCCGTAT <SEQ ID NO. 23 C2 - 6/9 F; DNA; ARTIFICIAL>
ATACGGGAGCCAACACCATAGTGTTGGGCCAATACGGTAACGTGTCCTTGGAGAGCAGGTGTGACGGAT <SEQ ID NO. 24 C2 - 6/9 R; DNA; Artificial>
ATCCGTCACACCTGCTCTCCAAGGACACGTTACCGTATTGGCCCAACACTATGGTGTTGGCTCCCGTAT <SEQ ID NO. 25 C2 - 8 F; DNA; ARTIFICIAL>
ATACGGGAGCCAACACCACAGACACCGAATGAGCAACACAACAACGGGACCCGTAGAGCAGGTGTGACGGAT <SEQ ID NO. 26 C2 - 8 R; DNA; Artificial>
ATCCGTCACACCTGCTCTACGGGTCCCGTTGTTGTGTTGCTCATTCGGTGTCTGTGGTGTTGGCTCCCGTAT <SEQ ID NO. 27 C2 - 10 F; DNA; ARTIFICIAL>
ATACGGGAGCCAACACCAGGTATCCGACCGGACACGGCACTACGACCTCTTTGCAGAGCAGGTGTGACGGAT <SEQ ID NO. 28 C2 - 10 R; DNA; Artificial>
ATCCGTCACACCTGCTCTGCAAAGAGGTCGTAGTGCCGTGTCCGGTCGGATACCTGGTGTTGGCTCCCGTAT <SEQ ID NO. 29 C3 - 3 F; DNA; ARTIFICIAL>
ATACGGGAGCCAACACCAGGGTTGGTGTAAAGTGGCCAGCCCTTTACGCTAAGTAGAGCAGGTGTGACGGAT <SEQ ID NO. 30 C3 - 3 R; DNA; Artificial>
ATCCGTCACACCTGCTCTACTTAGCGTAAAGGGCTGGCCACTTTACACCAACCCTGGTGTTGGCTCCCGTAT TABLE 8-continued DNA Ligand Sequence ID Nos.
Arthropod Aptamer Sequences 2011-Final <SEQ ID NO. 31 C3 - 4 F; DNA; ARTIFICIAL>
ATACGGGAGCCAACACCACAGCTGACAATAGAAGGATATCCTGGGTACCGATGCAGAGCAGGTGTGACGGAT <SEQ ID NO. 32 C3 - 4 R; DNA; Artificial>
ATCCGTCACACCTGCTCTGCATCGGTACCCAGGATATCCTTCTATTGTCAGCTGTGGTGTTGGCTCCCGTAT <SEQ ID NO. 33 C3 - 5 F; DNA; ARTIFICIAL>
ATACGGGAGCCAACACCACTGTGTATAACCCTAACGCTCTATGTTCGTTATGCAAGAGCAGGTGTGACGGAT <SEQ ID NO. 34 C3 - 5 R; DNA; Artificial>
ATCCGTCACACCTGCTCTTGCATAACGAACATAGAGCGTTAGGGTTATACACAGTGGTGTTGGCTCCCGTAT <SEQ ID NO. 35 C3 - 6 F; DNA; ARTIFICIAL>
ATACGGGAGCCAACACCAGCCCCCGCCTGGTTCCCGCAGGCCGCTCGCGTCCCGAGAGCAGGTGTGACGGAT <SEQ ID NO. 36 C3 - 6 R; DNA; Artificial>
ATCCGTCACACCTGCTCTCGGGACGCGAGCGGCCTGCGGGAACCAGGCGGGGGCTGGTGTTGGCTCCCGTAT <SEQ ID NO. 37 C3 - 7 F; DNA; ARTIFICIAL>
ATACGGGAGCCAACACCACGGGCGTCACTAGCTCAGACCGTCCCCCGTTGGTATAGAGCAGGTGTGACGGAT <SEQ ID NO. 38 C3 - 7 R; DNA; Artificial>
ATCCGTCACACCTGCTCTATACCAACGGGGACGGTCTGAGCTAGTGACGCCCGTGGTGTTGGCTCCCGTAT <SEQ ID NO. 39 C3 - 8 F; DNA; ARTIFICIAL>
ATACGGGAGCCAACACCATAGTGTTGGGCCAATACGGTGACGTGTCCTTGGAGAGCAGGTGTGACGGAT <SEQ ID NO. 40 C3 - 8 R; DNA; Artificial>
ATCCGTCACACCTGCTCTCCAAGGACACGTCACCGTATTGGCCCAACACTATGGTGTTGGCTCCCGTAT <SEQ ID NO. 41 C3 - 9 F; DNA; ARTIFICIAL>
ATACGGGAGCCAACACCAATGTCCTCGTTACAAGAATATTTCCTGTTACGCACCAGAGCAGGTGTGACGGAT <SEQ ID NO. 42 C3 - 9 R; DNA; Artificial>
ATCCGTCACACCTGCTCTGGTGCGTAACAGGAAATATTCTTGTAACGAGGACATTGGTGTTGGCTCCCGTAT <SEQ ID NO. 43 C4 - 7/10/20 F; DNA; ARTIFICIAL>
ATACGGGAGCCAACACCATAGTGTTGGGCCAATACGGTAACGTGTCCTTGGAGAGCAGGTGTGACGGAT <SEQ ID NO. 44 C4 - 7/10/20 R; DNA; Artificial>
ATCCGTCACACCTGCTCTCCAAGGACACGTTACCGTATTGGCCCAACACTATGGTGTTGGCTCCCGTAT <SEQ ID NO. 45 Gn6 - 1F; DNA; ARTIFICIAL>
ATACGGGAGCCAACACCAACTGAAAACTAAGACTTGGTTCCAAATCCTTTCTCTAGAGCAGGTGTGACGGAT <SEQ ID NO. 46 Gn6 - 1R; DNA; ARTIFICIAL>
ATCCGTCACACCTGCTCTAGAGAAAGGATTTGGAACCAAGTCTTAGTTTTCAGTTGGTGTTGGCTCCCGTAT <SEQ ID NO. 47 Gn6 - 2F; DNA; ARTIFICIAL>
ATACGGGAGCCAACACCAGGCCGGAGACTAGCCGAACCCTACTTTTTACTGTGTAGAGCAGGTGTGACGGAT <SEQ ID NO. 48 Gn6 - 2R; DNA; ARTIFICIAL>
ATCCGTCACACCTGCTCTACACAGTAAAAAGTAGGGTTCGGCTAGTCTCCGGCCTGGTGTTGGCTCCCGTAT <SEQ ID NO. 49 Gn6 - 4F; DNA; ARTIFICIAL>
ATACGGGAGCCAACACCACGTGCTGACTATACTATTCAAAAACAACACCCTAGGAGAGCAGGTGTGACGGAT <SEQ ID NO. 50 Gn6 - 4R; DNA; Artificial>
ATCCGTCACACCTGCTCTCCTAGGGTGTTGTTTTGAATAGTATAGTCAGCACGTGGTGTTGGCTCCCGTAT <SEQ ID NO. 51 Gn6 - 5F; DNA; ARTIFICIAL>
ATACGGGAGCCAACACCACGCCTTGTCTATTCTCTTAGTTTCCTGCTACTCCACAGAGCAGGTGTGACGGAT <SEQ ID NO. 52 Gn6 - 5R; DNA; Artificial>
ATCCGTCACACCTGCTCTGTGGAGTAGCAGGAAACTAAGAGAATAGACAAGGCGTGGTGTTGGCTCCCGTAT <SEQ ID NO. 53 Gn6 - 6F; DNA; ARTIFICIAL>
ATACGGGAGCCAACACCAGGATAGTTACCAGTCCCTTGTTAAAAATTTATATGCAGAGCAGGTGTGACGGAT <SEQ ID NO. 54 Gn6 - 6R; DNA; Artificial>
ATCCGTCACACCTGCTCTGCATATAAATTTTTAACAAGGGACTGGTAACTATCCTGGTGTTGGCTCCCGTAT <SEQ ID NO. 55 Gn6 - 7aF; DNA; ARTIFICIAL>
ATACGGGAGCCAACACCATAGCTTTAGGTTACTTTTCAGACACTATATGTCCCAGAGCAGGTGTGACGGAT <SEQ ID NO. 56 Gn6 - 7aR; DNA; Artificial>
ATCCGTCACACCTGCTCTGGGACATATAGTGTCTGAAAAGTAACCTAAAGCTATGGTGTTGGCTCCCGTAT TABLE 8-continued DNA Ligand Sequence ID Nos.
Arthropod Aptamer Sequences 2011-Final <SEQ ID NO. 57 Gn6 - 7bF; DNA; ARTIFICIAL>
ATACGGGAGCCAACACCAATGCCCGCCTCGATAGAGACTGACCAGTATGTGAGAGCAGGTGTGACGGAT <SEQ ID NO. 58 Gn6 - 7bR; DNA; Artificial>
ATCCGTCACACCTGCTCTCACATACTGGTCAGTCTCTATCGAGGCGGGCATTGGTGTTGGCTCCCGTAT <SEQ ID NO. 59 Gn6 - 7cF; DNA; ARTIFICIAL>
ATACGGGAGCCAACACCACCTCATAGTTATGTAATAACGCTTATCTTGTCCGGCAGAGCAGGTGTGACGGAT <SEQ ID NO. 60 Gn6 - 7cR; DNA; Artificial>
ATCCGTCACACCTGCTCTGCCGGACAAGATAAGCGTTATTACATAACTATGAGGTGGTGTTGGCTCCCGTAT <SEQ ID NO. 61 Gn6 - 8F; DNA; ARTIFICIAL>
ATACGGGAGCCAACACCACCCATCTCAACCACCGTACCTCACTCGGCGACTTACAGAGCAGGTGTGACGGAT <SEQ ID NO. 62 Gn6 - 8R; DNA; Artificial>
ATCCGTCACACCTGCTCTGTAAGTCGCCGAGTGAGGTACGGTGGTTGAGATGGGTGGTGTTGGCTCCCGTAT <SEQ ID NO. 63 Gn6 - 9F; DNA; ARTIFICIAL>
ATACGGGAGCCAACACCACGCTGTCCCCAAGACATTCAGTCTTTGCAACCCGGTAGAGCAGGTGTGACGGAT <SEQ ID NO. 64 Gn6 - 9R; DNA; Artificial>
ATCCGTCACACCTGCTCTACCGGGTTGCAAAGACTGAATGTCTTGGGGACAGCGTGGTGTTGGCTCCCGTAT <SEQ ID NO. 65 Gn6 - 10F; DNA; ARTIFICIAL>
ATACGGGAGCCAACACCACGCCATCCCCTTGACACTACCACTAAATCGGCGGTCAGAGCAGGTGTGACGGAT <SEQ ID NO. 66 Gn6 - 10R; DNA; Artificial>
ATCCGTCACACCTGCTCTGACCGCCGATTTAGTGGTAGTGTCAAGGGGATGGCGTGGTGTTGGCTCCCGTAT <SEQ ID NO. 67 Gn6 - 11F; DNA; ARTIFICIAL>
ATACGGGAGCCAACACCAATAGATGGATAAGGGGGAAACTGCCATTCGGTTAGTAGAGCAGGTGTGACGGAT <SEQ ID NO. 68 Gn6 - 11R; DNA; Artificial>
ATCCGTCACACCTGCTCTACTAACCGAATGGCAGTTTCCCCCTTATCCATCTATTGGTGTTGGCTCCCGTAT <SEQ ID NO. 69 Gn6 - 12F; DNA; ARTIFICIAL>
ATACGGGAGCCAACACCATTACCAGGACTAACTCGTTTTGCACTGGTCTCAGTCAGAGCAGGTGTGACGGAT <SEQ ID NO. 70 Gn6 - 12R; DNA; Artificial>
ATCCGTCACACCTGCTCTGACTGAGACCAGTGCAAAACGAGTTAGTCCTGGTAATGGTGTTGGCTCCCGTAT <SEQ ID NO. 71 Gn6 - 13F; DNA; ARTIFICIAL>
ATACGGGAGCCAACACCACGGACGCGTACAGAGTTTATTCCTGAGATCCGTGCTAGAGCAGGTGTGACGGAT <SEQ ID NO. 72 Gn6 - 13R; DNA; Artificial>
ATCCGTCACACCTGCTCTAGCACGGATCTCAGGAATAAACTCTGTACGCGTCCGTGGTGTTGGCTCCCGTAT <SEQ ID NO. 73 Gn6 - 14F; DNA; ARTIFICIAL>
ATACGGGAGCCAACACCAGAAAAAAACAAACCCAAGGAATTACACCACAAAAGTAGAGCAGGTGTGACGGAT <SEQ ID NO. 74 Gn6 - 14R; DNA; Artificial>
ATCCGTCACACCTGCTCTACTTTTGTGGTGTAATTCCTTGGGTTTGTTTTTTCTGGTGTTGGCTCCCGTAT <SEQ ID NO. 75 Gn6 - 15F; DNA; ARTIFICIAL>
ATACGGGAGCCAACACCACATGTATTACACAGCTCGCATCTTCTTACCTGGCCCAGAGCAGGTGTGACGGAT <SEQ ID NO. 76 Gn6 - 15R; DNA; Artificial>
ATCCGTCACACCTGCTCTGGGCCAGGTAAGAAGATGCGAGCTGTGTAATACATGGTGTTGGCTCCCGTAT <SEQ ID NO. 77 Gn6 - 16aF; DNA; ARTIFICIAL>
ATACGGGAGCCAACACCAGCCTTTCCACCTACACTAGCTATCTTATCTCCTTATAGAGCAGGTGTGACGGAT <SEQ ID NO. 78 Gn6 - 16aR; DNA; Artificial>
ATCCGTCACACCTGCTCTATAAGGAGATAAGATAGCTAGTGTAGGTGGAAAGGCTGGTGTTGGCTCCCGTAT <SEQ ID NO. 79 Gn6 - 16bF; DNA; ARTIFICIAL>
ATACGGGAGCCAACACCATTAGGTTGGAATTTACATTCATGTTCTGTGGTCATAAGAGCAGGTGTGACGGAT <SEQ ID NO. 80 Gn6 - 16bR; DNA; Artificial>
ATCCGTCACACCTGCTCTTATGACCACAGAACATGAATGTAAATTCCAACCTAATGGTGTTGGCTCCCGTAT <SEQ ID NO. 81 Gn6 - 16cF; DNA; ARTIFICIAL>
ATACGGGAGCCAACACCAGAGCACACTAATCATGGCGGCCCGGCGCATCCCGACAGAGCAGGTGTGACGGAT TABLE 8-continued DNA Ligand Sequence ID Nos.
Arthropod Aptamer Sequences 2011-Final <SEQ ID NO. 82 Gn6 - 16cR; DNA; Artificial>
ATCCGTCACACCTGCTCTGTCGGGATGCGCCGGGCCGCCATGATTAGTGTGCTCTGGTGTTGGCTCCCGTAT <SEQ ID NO. 83 Gn6 - 17F; DNA; ARTIFICIAL>
ATACGGGAGCCAACACCAAACTAGACAACCGCCCTTATACACACTGTACCAGTAGAGCAGGTGTGACGGAT <SEQ ID NO. 84 Gn6 17R; DNA; Artificial>
ATCCGTCACACCTGCTCTACTGGTACAGTGTGTATAAGGGCGGTTGTCTAGTTTGGTGTTGGCTCCCGTAT <SEQ ID NO. 85 Gn6 - 19F; DNA; ARTIFICIAL>
ATACGGGAGCCAACACCAGCATCCCCGAATAAATAATGCTGCGCTGTTAAAGATAGAGCAGGTGTGACGGAT <SEQ ID NO. 86 Gn6 - 19R; DNA; Artificial>
ATCCGTCACACCTGCTCTATCTTTAACAGCGCAGCATTATTTATTCGGGGATGCTGGTGTTGGCTCCCGTAT <SEQ ID NO. 87 Gn6 - 20F; DNA; ARTIFICIAL>
ATACGGGAGCCAACACCAAATTCCTCGTTGACCCCTAACTGTACTCTTAGCCAGAGCAGGTGTGACGGAT <SEQ ID NO. 88 Gn6 - 20R; DNA; Artificial>
ATCCGTCACACCTGCTCTGGCTAAGAGTACAGTTAGGGGTCAACGAGGAATTTGGTGTTGGCTCCCGTAT <SEQ ID NO. 89 Gn6 - 21F; DNA; ARTIFICIAL>
ATACGGGAGCCAACACCACCCATTCTGAGACCCCCCGCGCATGTATTGGTCTTGAGAGCAGGTGTGACGGAT <SEQ ID NO. 90 Gn6 - 21R; DNA; Artificial>
ATCCGTCACACCTGCTCTCAAGACCAATACATGCGCGGGGGGTCTCAGAATGGGTGGTGTTGGCTCCCGTAT <SEQ ID NO. 91 Gn6 - 22F; DNA; ARTIFICIAL>
ATACGGGAGCCAACACCATGCTAGTGCCCCCACAGACGCACACTAAAGTATTCCAGAGCAGGTGTGACGGAT <SEQ ID NO. 92 Gn6 - 22R; DNA; Artificial>
ATCCGTCACACCTGCTCTGGAATACTTTAGTGTGCGTCTGTGGGGGCACTAGCATGGTGTTGGCTCCCGTAT <SEQ ID NO. 93 Gn6 - 23F; DNA; ARTIFICIAL>
ATACGGGAGCCAACACCAGGCCGTGCGCGCTCATTTTGAGAACCACTGCCCCCAGAGCAGGTGTGACGGAT <SEQ ID NO. 94 Gn6 - 23R; DNA; Artificial>
ATCCGTCACACCTGCTCTGGGGGCAGTGGTTCTCAAAATGAGCGCGCACGGCCTGGTGTTGGCTCCCGTAT <SEQ ID NO. 95 Gn6 - 24F; DNA; ARTIFICIAL>
ATACGGGAGCCAACACCAGTACTACCCACGGGCTTATTACCCCCTCATCCTTGCAGAGCAGGTGTGACGGAT <SEQ ID NO. 96 Gn6 - 24R; DNA; Artificial>
ATCCGTCACACCTGCTCTGCAAGGATGAGGGGGTAATAAGCCCGTGGGTAGTACTGGTGTTGGCTCCCGTAT <SEQ ID NO. 97 Gn6 - 25F; DNA; ARTIFICIAL>
ATACGGGAGCCAACACCATTATGTTAACAAAGGCATACGGCAAGCTCTAACTGTAGAGCAGGTGTGACGGAT <SEQ ID NO. 98 Gn6 - 25R; DNA; Artificial>
ATCCGTCACACCTGCTCTACAGTTAGAGCTTGCCGTATGCCTTTGTTAACATAATGGTGTTGGCTCCCGTAT <SEQ ID NO. 99 Gn6 - 27F; DNA; ARTIFICIAL>
ATACGGGAGCCAACACCACCTCAAGATAGCCGTTCATCCGACTGTCGCCATTGTAGAGCAGGTGTGACGGAT <SEQ ID NO. 100 Gn6 - 27R; DNA; Artificial>
ATCCGTCACACCTGCTCTACAATGGCGACAGTCGGATGAACGGCTATCTTGAGGTGGTGTTGGCTCCCGTAT <SEQ ID NO. 101 Gn6 - 28F; DNA; ARTIFICIAL>
ATACGGGAGCCAACACCACATAATGGACAATCCCACTGGGCACGTTCTATAACCAGAGCAGGTGTGACGGAT <SEQ ID NO. 102 Gn6 - 28R; DNA; Artificial>
ATCCGTCACACCTGCTCTGGTTATAGAACGTGCCCAGTGGGATTGTCCATTATGTGGTGTTGGCTCCCGTAT <SEQ ID NO. 103 Gn6 - 29F; DNA; ARTIFICIAL>
ATACGGGAGCCAACACCAAGCCCGAGCCCGCCGTTATATCCCATCGAGTTCCCCAGAGCAGGTGTGACGGAT <SEQ ID NO. 104 Gn6 - 29R; DNA; Artificial>
ATCCGTCACACCTGCTCTGGGGAACTCGATGGGATATAACGGCGGGCTCGGGCTTGGTGTTGGCTCCCGTAT <SEQ ID NO. 105 Gn6 - 30F; DNA; ARTIFICIAL>
ATACGGGAGCCAACACCATCCCACCGAATATCCGCTTTCCTCGTCCTCCTTTCAGAGCAGGTGTGACGGAT <SEQ ID NO. 106 Gn6 - 30R; DNA; Artificial>
ATCCGTCACACCTGCTCTGAAAGGAGGACGAGGAAAGCGGATATTCGGTGGGATGGTGTTGGCTCCCGTAT <SEQ ID NO. 107 E7c - 1aF; DNA; ARTIFICIAL>
ATACGGGAGCCAACACCAATAGATGGATAAGGGGGAAACTGCCCATTCGGTTAGTAGAGCAGGTGTGACGGAT

TABLE 8-continued

DNA Ligand Sequence ID Nos.
Arthropod Aptamer Sequences 2011-Final

<SEQ ID NO. 108 E7c - 1aR; DNA; Artificial>
ATCCGTCACACCTGCTCTACTAACCGAATGGCAGTTTCCCCCTTATCCATCTATTGGTGTTGGCTCCCGTAT <SEQ ID NO. 109 E7c - 1bF; DNA; ARTIFICIAL>
ATACGGGAGCCAACACCACATCTACGCCCAAGCCTCTATGTACAAGTAGCAACAAGAGCAGGTGTGACGGAT <SEQ ID NO. 110 E7c - 1bR; DNA; Artificial>
ATCCGTCACACCTGCTCTTGTTGCTACTTGTACATAGAGGCTTGGGCGTAGATGTGGTGTTGGCTCCCGTAT <SEQ ID NO. 111 E7c - 2F; DNA; ARTIFICIAL>
ATACGGGAGCCAACACCAATCTCCACTGTGAACCTTATCGAGTTTTTTGTACGAGAGCAGGTGTGACGGAT <SEQ ID NO. 112 E7c - 2R; DNA; Artificial>
ATCCGTCACACCTGCTCTCGTACAAAAAACTCGATAAGGTTCACAGTGGAGATTGGTGTTGGCTCCCGTAT <SEQ ID NO. 113 E7c - 3F; DNA; ARTIFICIAL>
ATACGGGAGCCAACACCATAGGCTATACCGCGTTAGACTTTCTGAGTCGTCCTCAGAGCAGGTGTGACGGAT <SEQ ID NO. 114 E7c - 3R; DNA; Artificial>
ATCCGTCACACCTGCTCTGAGGACGACTCAGAAAGTCTAACGCGGTATAGCCTATGGTGTTGGCTCCCGTAT <SEQ ID NO. 115 E7c - 4aF; DNA; ARTIFICIAL>
ATACGGGAGCCAACACCAGCACGCCCTTTTAGTGTCCAACTGAATCTTCACCTAAGAGCAGGTGTGACGGAT <SEQ ID NO. 116 E7c - 4aR; DNA; Artificial>
ATCCGTCACACCTGCTCTTAGGTGAAGATTCAGTTGGACACTAAAAGGGCGTGCTGGTGTTGGCTCCCGTAT <SEQ ID NO. 117 E7c - 4bF; DNA; ARTIFICIAL>
ATACGGGAGCCAACACCATGCTTTTGGAGTATTTCGCCTCCAAGCTACTCCCCTAGAGCAGGTGTGACGGAT <SEQ ID NO. 118 E7c - 4bR; DNA; Artificial>
ATCCGTCACACCTGCTCTAGGGGAGTAGCTTGGAGGCGAAATACTCCAAAAGCATGGTGTTGGCTCCCGTAT <SEQ ID NO. 119 E7c - 5F; DNA; ARTIFICIAL>
ATACGGGAGCCAACACCATTGATCCTGCCGGTTCGCCCCTTGTTCCCACCTTTTAGAGCAGGTGTGACGGAT <SEQ ID NO. 120 E7c - 5R; DNA; Artificial>
ATCCGTCACACCTGCTCTAAAAGGTGGGAACAAGGGGCGAACCGGCAGGATCAATGGTGTTGGCTCCCGTAT <SEQ ID NO. 121 E7c - 6F; DNA; ARTIFICIAL>
ATACGGGAGCCAACACCACCACTGTTTAGGCACAACTTGCTTTCTTAGCCCCGCAGAGCAGGTGTGACGGAT <SEQ ID NO. 122 E7c - 6R; DNA; Artificial>
ATCCGTCACACCTGCTCTGCGGGGCTAAGAAAGCAAGTTGTGCCTAAACAGTGGTGGTGTTGGCTCCCGTAT <SEQ ID NO. 123 E7c - 7aF; DNA; ARTIFICIAL>
ATACGGGAGCCAACACCACGCGTTTATTATGTTCCCCATGATTGCCACGGCTACAGAGCAGGTGTGACGGAT <SEQ ID NO. 124 E7c - 7aR; DNA; Artificial>
ATCCGTCACACCTGCTCTGTAGCCGTGGCAATCATGGGGAACATAATAAACGCGTGGTGTTGGCTCCCGTAT <SEQ ID NO. 125 E7c - 7bF; DNA; ARTIFICIAL>
ATACGGGAGCCAACACCATATACTGCCGCAGTTTGGGCCCGCAGTCCATGGGCAAGAGCAGGTGTGACGGAT <SEQ ID NO. 126 E7c - 7bR; DNA; Artificial>
ATCCGTCACACCTGCTCTTGCCCATGGACTGCGGGCCCAAACTGCGGCAGTATATGGTGTTGGCTCCCGTAT <SEQ ID NO. 127 E7c - 8F; DNA; ARTIFICIAL>
ATACGGGAGCCAACACCACCTAAGTAATGCCAAAAACAACTCGGGTACGCAATGAGAGCAGGTGTGACGGAT <SEQ ID NO. 128 E7c - 8R; DNA; Artificial>
ATCCGTCACACCTGCTCTCATTGCGTACCCGAGTTGTTTTTGGCATTACTTAGGTGGTGTTGGCTCCCGTAT <SEQ ID NO. 129 E7c - 9F; DNA; ARTIFICIAL>
ATACGGGAGCCAACACCACTTCTCTGTGACCAGTATACGTCCCATTTCCCTATTAGAGCAGGTGTGACGGAT <SEQ ID NO. 130 E7c - 9R; DNA; Artificial>
ATCCGTCACACCTGCTCTAATAGGGAAATGGGACGTATACTGGTCACAGAGAAGTGGTGTTGGCTCCCGTAT <SEQ ID NO. 131 E7c - 10F; DNA; ARTIFICIAL>
ATACGGGAGCCAACACCAGGATACGTTCCGTGCATGGATGTGCTGCCCCATGTTAGAGCAGGTGTGACGGAT <SEQ ID NO. 132 E7c - 10R; DNA; Artificial>
ATCCGTCACACCTGCTCTAACATGGGGCAGCACATCCATGCACGGAACGTATCCTGGTGTTGGCTCCCGTAT TABLE 8-continued DNA Ligand Sequence ID Nos.
Arthropod Aptamer Sequences 2011-Final <SEQ ID NO. 133 E7c - 11F; DNA; ARTIFICIAL>
ATACGGGAGCCAACACCACCATTTTCGTTTTTCTTGAGTATTTCGACCTTAGTGAGAGCAGGTGTGACGGAT <SEQ ID NO. 134 E7c - 11R; DNA; Artificial>
ATCCGTCACACCTGCTCTCACTAAGGTCGAAATACTCAAGAAAAACGAAAATGGTGGTGTTGGCTCCCGTAT <SEQ ID NO. 135 E7c - 12F; DNA; ARTIFICIAL>
ATACGGGAGCCAACACCATTCGAAACCCATAATCTTTTCCTCACTCTGCGTATTAGAGCAGGTGTGACGGAT <SEQ ID NO. 136 E7c - 12R; DNA; Artificial>
ATCCGTCACACCTGCTCTAATACGCAGAGTGAGGAAAAGATTATGGGTTTCGAATGGTGTTGGCTCCCGTAT <SEQ ID NO. 137 E7c - 13F; DNA; ARTIFICIAL>
ATACGGGAGCCAACACCACGCATGGGGCTCTCCCTATTACGCAATCCGTTGTAGAGAGCAGGTGTGACGGAT <SEQ ID NO. 138 E7c - 13R; DNA; Artificial>
ATCCGTCACACCTGCTCTACAACGGATTGCGTAATAGGGAGAGCCCCATGCGTGGTGTTGGCTCCCGTAT <SEQ ID NO. 139 E7c - 14F; DNA; ARTIFICIAL>
ATACGGGAGCCAACACCATCTTGTCCTCGGTCCGTCTTTGCATTCTGGTCTAAAAGAGCAGGTGTGACGGAT <SEQ ID NO. 140 E7c - 14R; DNA; Artificial>
ATCCGTCACACCTGCTCTTTTAGACCAGAATGCAAAGACGGACCGAGGACAAGATGGTGTTGGCTCCCGTAT <SEQ ID NO. 141 E7c - 15F; DNA; ARTIFICIAL>
ATACGGGAGCCAACACCACCGCTGTAAGTGCTTGGGTCGACCGCGCCCGCTGCCAGAGCAGGTGTGACGGAT <SEQ ID NO. 142 E7c - 15R; DNA; Artificial>
ATCCGTCACACCTGCTCTGGCAGCGGGCGCGGTCGACCCAAGCACTTACAGCGGTGGTGTTGGCTCCCGTAT <SEQ ID NO. 143 E7C - 17F; DNA; ARTIFICIAL>
ATACGGGAGCCAACACCAGGTGACGCAGGTGAGTCTGCCTCCCCATGTGCTCCCAGAGCAGGTGTGACGGAT <SEQ ID NO. 144 E7C - 17R; DNA; Artificial>
ATCCGTCACACCTGCTCTGGGAGCACATGGGGAGGCAGACTCACCTGCGTCACCTGGTGTTGGCTCCCGTAT <SEQ ID NO. 145 E7C - 18R; DNA; Artificial>
ATACGGGAGCCAACACCAATAGATGGATAAGGGGGAAACTGCCATTCGGTTAGTAGAGCAGGTGTGACGGAT <SEQ ID NO. 146 E7C - 18F; DNA; ARTIFICIAL>
ATCCGTCACACCTGCTCTACTAACCGAATGGCAGTTTCCCCCTTATCCATCTATTGGTGTTGGCTCCCGTAT <SEQ ID NO. 147 E7C - 19F; DNA; ARTIFICIAL>
ATACGGGAGCCAACACCACTTCCGGGCTATACCGGGGCTCGCGCAATTCTGACCAGAGCAGGTGTGACGGAT <SEQ ID NO. 148 E7C - 19R; DNA; Artificial>
ATCCGTCACACCTGCTCTGGTCAGAATTGCGCGAGCCCCGGTATAGCCCGGAAGTGGTGTTGGCTCCCGTAT <SEQ ID NO. 149 E7C - 20F; DNA; ARTIFICIAL>
ATACGGGAGCCAACACCAATAGATGGATAAGGGGGAAACTGCCATTCGGTTAGTAGAGCAGGTGTGACGGAT <SEQ ID NO. 150 E7C - 20R; DNA; Artificial>
ATCCGTCACACCTGCTCTACTAACCGAATGGCAGTTTCCCCCTTATCCATCTATTGGTGTTGGCTCCCGTAT <SEQ ID NO. 151 E7C - 21F; DNA; ARTIFICIAL>
ATACGGGAGCCAACACCAGTCTTTTATTCATCATGATCGCTGACCTACACCCCAAGAGCAGGTGTGACGGAT <SEQ ID NO. 152 E7C - 21R; DNA; Artificial>
ATCCGTCACACCTGCTCTTGGGGTGTAGGTCAGCGATCATGATGAATAAAAGACTGGTGTTGGCTCCCGTAT <SEQ ID NO. 153 E7C - 22F; DNA; ARTIFICIAL>
ATACGGGAGCCAACACCACTTCAAAAGTCAGATACAAAGACAGAGATTGGACTTAGAGCAGGTGTGACGGAT <SEQ ID NO. 154 E7C - 22R; DNA; Artificial>
ATCCGTCACACCTGCTCTAAGTCCAATCTCTGTCTTTGTATCTGACTTTTGAAGTGGTGTTGGCTCCCGTAT <SEQ ID NO. 155 E7C - 23F; DNA; ARTIFICIAL>
ATACGGGAGCCAACACCATTATGTTAACAAAGGCATACGGCAAGCTCTAACTGTAGAGCAGGTGTGACGGAT <SEQ ID NO. 156 E7C - 23R; DNA; Artificial>
ATCCGTCACACCTGCTCTACAGTTAGAGCTTGCCGTATGCCTTTGTTAACATAATGGTGTTGGCTCCCGTAT <SEQ ID NO. 157 E7C - 24F; DNA; ARTIFICIAL>
ATACGGGAGCCAACACCATAATATTACAATGCCAGAATCTACACATAATCCTATAGAGCAGGTGTGACGGAT <SEQ ID NO. 158 E7C - 24R; DNA; Artificial>
ATCCGTCACACCTGCTCTATAGGATTATGTGTAGATTCTGGCATTGTAATATTATGGTGTTGGCTCCCGTAT TABLE 8-continued DNA Ligand Sequence ID Nos.
Arthropod Aptamer Sequences 2011-Final <SEQ ID NO. 159 E7C - 25F; DNA; ARTIFICIAL>
ATACGGGAGCCAACACCATTATGTTAACAAAGGCATACGGCAAGCTCTAACTGTAGAGCAGGTGTGACGGAT <SEQ ID NO. 160 E7C - 25R; DNA; Artificial>
ATCCGTCACACCTGCTCTACAGTTAGAGCTTGCCGTATGCCTTTGTTAACATAATGGTGTTGGCTCCCGTAT <SEQ ID NO. 161 E7C - 26F; DNA; ARTIFICIAL>
ATACGGGAGCCAACACCACTTGACGCCGTGGCAACACGCTGACGAGCTTTACCCAGAGCAGGTGTGACGGAT <SEQ ID NO. 162 E7C - 26R; DNA; Artificial>
ATCCGTCACACCTGCTCTGGGTAAAGCTCGTCAGCGTGTTGCCACGGCGTCAAGTGGTGTTGGCTCCCGTAT <SEQ ID NO. 163 E7C - 27F; DNA; ARTIFICIAL>
ATACGGGAGCCAACACCAGCCAACTCACTATTACTTAGTAACCCTAACGATGGCAGAGCAGGTGTGACGGAT <SEQ ID NO. 164 E7C - 27R; DNA; Artificial>
ATCCGTCACACCTGCTCTGCCATCGTTAGGGTTACTAAGTAATAGTGAGTTGGCTGGTGTTGGCTCCCGTAT <SEQ ID NO. 165 E7C - 29F; DNA; ARTIFICIAL>
ATACGGGAGCCAACACCATACGATCCAATGATGGACCCGTGCGGACTGATTTACAGAGCAGGTGTGACGGAT <SEQ ID NO. 166 E7C - 29F; DNA; ARTIFICIAL>
ATCCGTCACACCTGCTCTGTAAATCAGTCCGCACGGGTCCATCATTGGATCGTATGGTGTTGGCTCCCGTAT <SEQ ID NO. 167 E7C - 30F; DNA; ARTIFICIAL>
ATACGGGAGCCAACACCATTCCATCTCCATGTAGCTAAAGTCGATACTCCATCCAGAGCAGGTGTGACGGAT <SEQ ID NO. 168 E7C - 30R; DNA; Artificial>
ATCCGTCACACCTGCTCTGGATGGAGTATCGACTTTAGCTACATGGAGATGGAATGGTGTTGGCTCCCGTAT <SEQ ID NO. 169 ChE -1F; DNA; ARTIFICIAL>
ATACGGGAGCCAACACCACAGAGGACGGTTCGTCAGATGCCGTTTGCCACGAAGAGCAGGTGTGACGGAT <SEQ ID NO. 170 ChE -1F; DNA; ARTIFICIAL>
ATCCGTCACACCTGCTCTTCGTGGCAAACGGCATCTGACGAACCGTCCTCTGTGTGGTGTTGGCTCCCGTAT <SEQ ID NO. 171 ChE 2F; DNA; ARTIFICIAL>
ATACGGGAGCCAACACCAAAAAAGGTCTTCTCCCACGATGTGTCCAATGCATCCAGAGCAGGTGTGACGGAT <SEQ ID NO. 172 ChE - 2R; DNA; Artificial>
ATCCGTCACACCTGCTCTGGATGCATTGGACACATCGTGGGAGAAGACCTTTTTTGGTGTTGGCTCCCGTAT <SEQ ID NO. 173 ChE 3F; DNA; ARTIFICIAL>
ATACGGGAGCCAACACCACCGCCTCGACCGCTCGGGGCCCTTACCCTAGCTTCAGAGCAGGTGTGACGGAT <SEQ ID NO. 174 ChE 3R; DNA; Artificial>
ATCCGTCACACCTGCTCTGAAGCTAGGGTAAGGGCCCCGAGCGGTCGAGGCGGTGGTGTTGGCTCCCGTAT <SEQ ID NO. 175 ChE 4F; DNA; ARTIFICIAL>
ATACGGGAGCCAACACCACCACAACCGTAGGGACCCGCCTGGTCCCCAACCTAGAGAGCAGGTGTGACGGAT <SEQ ID NO. 176 ChE 4R; DNA; Artificial>
ATCCGTCACACCTGCTCTCTAGGTTGGGGACCAGGCGGGTCCCTACGGTTGTGGTGGTGTTGGCTCCCGTAT <SEQ ID NO. 177 ChE 6F; DNA; ARTIFICIAL>
ATACGGGAGCCAACACCACCTCGGATGGTTATGATATAGTTTACAATCATGAAGAGCAGGTGTGACGGAT <SEQ ID NO. 178 ChE 6R; DNA; Artificial>
ATCCGTCACACCTGCTCTCTTCATGATTGTAAACTATATCATAACCATCCGAGGTGGTGTTGGCTCCCGTAT <SEQ ID NO. 179 ChE 7F; DNA; ARTIFICIAL>
ATACGGGAGCCAACACCACATAGCCAACCTCAGCCACACCGACTACGCTTGGCCAGAGCAGGTGTGACGGAT <SEQ ID NO. 180 ChE 7R; DNA; Artificial>
ATCCGTCACACCTGCTCTGGCCAAGCGTAGTCGGTGTGGCTGAGGTTGGCTATGTGGTGTTGGCTCCCGTAT <SEQ ID NO. 181 ChE 8F; DNA; ARTIFICIAL>
ATACGGGAGCCAACACCATTTATCTAATGGCAACTAGGGATAGTGAAAACTACCAGAGCAGGTGTGACGGAT <SEQ ID NO. 182 ChE 8R; DNA; Artificial>
ATCCGTCACACCTGCTCTCCTCCTAGGAATGTAGTCGGGCGGATAAAGTGACAATGGTGTTGGCTCCCGTAT <SEQ ID NO. 183 ChE 9F; DNA; ARTIFICIAL>
ATACGGGAGCCAACACCATTGTCACTTTATCCGCCCGACTACATTCCTAGGAGGAGAGCAGGTGTGACGGAT TABLE 8-continued DNA Ligand Sequence ID Nos.
Arthropod Aptamer Sequences 2011-Final <SEQ ID NO. 184 ChE 9R; DNA; Artificial>
ATCCGTCACACCTGCTCTCCTCCTAGGAATGTAGTCGGGCGGATAAAGTGACAATGGTGTTGGCTCCCGTAT <SEQ ID NO. 185 ChE 10F; DNA; ARTIFICIAL>
ATACGGGAGCCAACACCACCTTCGACGCCAACGACGAACGGCTTTGAAAGGCTAAGAGCAGGTGTGACGGAT <SEQ ID NO. 186 ChE 10R; DNA; Artificial>
ATCCGTCACACCTGCTCTTAGCCTTTCAAAGCCGTTCGTCGTTGGCGTCGAAGGTGGTGTTGGCTCCCGTAT <SEQ ID NO. 187 ChE 11F; DNA; ARTIFICIAL>
ATACGGGAGCCAACACCAATGGAAGCCGTACCTTCACACCCGTTATTTAAAAACAGAGCAGGTGTGACGGAT <SEQ ID NO. 188 ChE 11R; DNA; Artificial>
ATCCGTCACACCTGCTCTGTTTTTAAATAACGGGTGTGAAGGTACGGCTTCCATTGGTGTTGGCTCCCGTAT <SEQ ID NO. 189 ChE 12F; DNA; ARTIFICIAL>
ATACGGGAGCCAACACCACGCTGGCCGGGAGGCCCGTCCAAGCCATTACCGTCAAGAGCAGGTGTGACGGAT <SEQ ID NO. 190 ChE 12R; DNA; Artificial>
ATCCGTCACACCTGCTCTTGACGGTAATGGCTTGGACGGGCCTCCCGGCCAGCGTGGTGTTGGCTCCCGTAT <SEQ ID NO. 191 ChE 13F; DNA; ARTIFICIAL>
ATACGGGAGCCAACACCACATATCACCGCACGCCTATTCCATGTGACGAATCTAAGAGCAGGTGTGACGGAT <SEQ ID NO. 192 ChE 13R; DNA; Artificial>
ATCCGTCACACCTGCTCTTAGATTCGTCACATGGAATAGGCGTGCGGTGATATGTGGTGTTGGCTCCCGTAT <SEQ ID NO. 193 ChE 15F; DNA; ARTIFICIAL>
ATACGGGAGCCAACACCACGGCGGGCGGGGCATCTCGTGGGGGACGAAGGCGCAAGAGCAGGTGTGACGGAT <SEQ ID NO. 194 ChE 15R; DNA; Artificial>
ATCCGTCACACCTGCTCTTGCGCCTTCGTCCCCCACGAGATGCCCCGCCCGCCGTGGTGTTGGCTCCCGTAT <SEQ ID NO. 195 ChE 16F; DNA; ARTIFICIAL>
ATACGGGAGCCAACACCATCCTCCTGCGACGTCTGGAGAACAGCCTCTACTTTAAGAGCAGGTGTGACGGAT <SEQ ID NO. 196 ChE 16R; DNA; Artificial>
ATCCGTCACACCTGCTCTTAAAGTAGAGGCTGTTCTCCAGACGTCGCAGGAGGATGGTGTTGGCTCCCGTAT <SEQ ID NO. 197 ChE 17F; DNA; ARTIFICIAL>
ATACGGGAGCCAACACCAAAACCCGCACTACATCTCCTCTGCCCCCTTCTGATAAGAGCAGGTGTGACGGAT <SEQ ID NO. 198 ChE 17R; DNA; Artificial>
ATCCGTCACACCTGCTCTTATCAGAAGGGGGCAGAGGAGATGTAGTGCGGGTTTTGGTGTTGGCTCCCGTAT <SEQ ID NO. 199 ChE 18F; DNA; ARTIFICIAL>
ATACGGGAGCCAACACCAGTGGTCTTGTTTTGGATGTTTAGTGATGCGGGTTCTAGAGCAGGTGTGACGGAT <SEQ ID NO. 200 ChE 18R; DNA; Artificial>
ATCCGTCACACCTGCTCTAGAACCCGCATCACTAAACATCCAAAACAAGACCACTGGTGTTGGCTCCCGTAT <SEQ ID NO. 201 ChE 19F; DNA; ARTIFICIAL>
ATACGGGAGCCAACACCATCTTTCGTGATAGCTATTAAGGCCTATTCGTATCGTAGAGCAGGTGTGACGGAT <SEQ ID NO. 202 ChE 19R; DNA; Artificial>
ATCCGTCACACCTGCTCTACGATACGAATAGGCCTTAATAGCTATCACGAAAGATGGTGTTGGCTCCCGTAT <SEQ ID NO. 203 ChE 20F; DNA; ARTIFICIAL>
ATACGGGAGCCAACACCATACTGAAGCCATACGTCTGTCCAACCGTCATAACTTAGAGCAGGTGTGACGGAT <SEQ ID NO. 204 ChE 20R; DNA; Artificial>
ATCCGTCACACCTGCTCTAAGTTATGACGGTTGGACAGACGTATGGCTTCAGTATGGTGTTGGCTCCCGTAT <SEQ ID NO. 205 D1-3F; DNA; ARTIFICIAL>
ATACGGGAGCCAACACCACCCTAAATTCCAGAGTGTACAAGAGAACGAACTACCAGAGCAGGTGTGACGGAT <SEQ ID NO. 206 D1-3R; DNA; Artificial>
ATCCGTCACACCTGCTCTGGTAGTTCGTTCTCTTGTACACTCTGGAATTTAGGGTGGTGTTGGCTCCCGTAT <SEQ ID NO. 207 D1-4F; DNA; ARTIFICIAL>
ATACGGGAGCCAACACCACTACTCATATACCTTATACTATAAACAATCTGCGCGAGAGCAGGTGTGACGGAT <SEQ ID NO. 208 D1-4R; DNA; Artificial>
ATCCGTCACACCTGCTCTCGCGCAGATTGTTTATAGTATAAGGTATATGAGTAGTGGTGTTGGCTCCCGTAT <SEQ ID NO. 209 D1-5aF; DNA; ARTIFICIAL>
ATACGGGAGCCAACACCACATTCGTACTAGCCCCGGTTGCCCGTCGACCGGACAAGAGCAGGTGTGACGGAT TABLE 8-continued DNA Ligand Sequence ID Nos.
Arthropod Aptamer Sequences 2011-Final <SEQ ID NO. 210 D1-5bF; DNA; ARTIFICIAL>
ATACGGGAGCCAACACCAGGAGGGCGCGCCTATTTCGCCAATTCGTCCGCAGCGAGAGCAGGTGTGACGGAT <SEQ ID NO. 211 D1-5aR; DNA; Artificial>
ATCCGTCACACCTGCTCTTGTCCGGTCGACGGGCAACCGGGGCTAGTACGAATGTGGTGTTGGCTCCCGTAT <SEQ ID NO. 212 D1-5bR; DNA; Artificial>
ATCCGTCACACCTGCTCTCGCTGCGGACGAATTGGCGAAATAGGCGCGCCCTCCTGGTGTTGGCTCCCGTAT <SEQ ID NO. 213 D1-6F; DNA; ARTIFICIAL>
ATACGGGAGCCAACACCACACATTATCGGCAACTGGCAAGGCTAAGGTACTGGTAGAGCAGGTGTGACGGAT <SEQ ID NO. 214 D1-6R; DNA; Artificial>
ATCCGTCACACCTGCTCTACCAGTACCTTAGCCTTGCCAGTTGCCGATAATGTGTGGTGTTGGCTCCCGTAT <SEQ ID NO. 215 D1-8F; DNA; ARTIFICIAL>
ATACGGGAGCCAACACCACTGGCGACCCACTCCCCTGGTACGTCACCACAGCCTAGAGCAGGTGTGACGGAT <SEQ ID NO. 216 D1-8R; DNA; Artificial>
ATCCGTCACACCTGCTCTAGGCTGTGGTGACGTACCAGGGGAGTGGGTCGCCAGTGGTGTTGGCTCCCGTAT <SEQ ID NO. 217 D1-9F; DNA; ARTIFICIAL>
ATACGGGAGCCAACACCAAGACAACCGAGCTAATAGGCATTTCAACACCTGTCCAGAGCAGGTGTGACGGAT <SEQ ID NO. 218 D1-9R; DNA; Artificial>
ATCCGTCACACCTGCTCTGGACAGGTGTTGAAATGCCTATTAGCTCGGTTGTCTTGGTGTTGGCTCCCGTAT <SEQ ID NO. 219 D1-10F; DNA; ARTIFICIAL>
ATACGGGAGCCAACACCAGAAGACCATGTGAAGTAAAGACTTCAATTATCAGTCAGAGCAGGTGTGACGGAT <SEQ ID NO. 220 D1-10R; DNA; Artificial>
ATCCGTCACACCTGCTCTGACTGATAATTGAAGTCTTTACTTCACATGGTCTTCTGGTGTTGGCTCCCGTAT <SEQ ID NO. 221 D2-2F; DNA; ARTIFICIAL>
ATACGGGAGCCAACACCACAATAAATCCGTGCGCGTGACGCGTTTCATACAGTCAGAGCAGGTGTGACGGAT <SEQ ID NO. 222 D2-2R; DNA; Artificial>
ATCCGTCACACCTGCTCTGACTGTATGAAACGCGTCACGCGCACGGATTTATTGTGGTGTTGGCTCCCGTAT <SEQ ID NO. 223 D2-4F; DNA; ARTIFICIAL>
ATACGGGAGCCAACACCACTATTGGCTATACATTCGTTGTGAGAAACGCACCGCAGAGCAGGTGTGACGGAT <SEQ ID NO. 224 D2-4R; DNA; Artificial>
ATCCGTCACACCTGCTCTGCGGTGCGTTTCTCACAACGAATGTATAGCCAATAGTGGTGTTGGCTCCCGTAT <SEQ ID NO. 225 D2-5aF; DNA; ARTIFICIAL>
ATACGGGAGCCAACACCATGGGACCAACTGTCCGGAGAGAGTCCTGTCGAGGGAGAGCAGGTGTGACGGAT <SEQ ID NO. 226 D2-5bF; DNA; ARTIFICIAL>
ATACGGGAGCCAACACCACATAGACACAAGATATATCATATATTGCTCGCAGAGCAGGTGTGACGGAT <SEQ ID NO. 227 D2-5bR; DNA; Artificial>
ATCCGTCACACCTGCTCTCCCTCGACAGGACTCTCTCCGGACAGTTGGTCCCCATGGTGTTGGCTCCCGTAT <SEQ ID NO. 228 D2-5bR; DNA; Artificial>
ATCCGTCACACCTGCTCTGCGAGCAATATATGATATATCTTGTGTCTATGTGGTGTTGGCTCCCGTAT <SEQ ID NO. 229 D2-6F; DNA; ARTIFICIAL>
ATACGGGAGCCAACACCATTGTAGCTGACAACTGTTTTACATGAACACTTCAGAGCAGGTGTGACGGAT <SEQ ID NO. 230 D2-6R; DNA; Artificial>
ATCCGTCACACCTGCTCTGAAGTGTTCATGTAAAACAGTTGTCAGCTACAATGGTGTTGGCTCCCGTAT <SEQ ID NO. 231 D2-7F; DNA; ARTIFICIAL>
ATACGGGAGCCAACACCAGGGTGCCAGCAGATTATAATTGAACAAACCAGCGATAGAGCAGGTGTGACGGAT <SEQ ID NO. 232 D2-7R; DNA; Artificial>
ATCCGTCACACCTGCTCTATCGCTGGTTTGTTCAATTATAATCTGCTGGCACCCTGGTGTTGGCTCCCGTAT <SEQ ID NO. 233 D2-8F; DNA; ARTIFICIAL>
ATACGGGAGCCAACACCAGCACATAGAAAAAAAATACAACCACATCGATTGACCAGAGCAGGTGTGACGGAT <SEQ ID NO. 234 D2-8R; DNA; Artificial>
ATCCGTCACACCTGCTCTGGTCAATCGATGTGGTTGTATTTTTTTTCTATGTGCTGGTGTTGGCTCCCGTAT <SEQ ID NO. 235 D2-9F; DNA; ARTIFICIAL>
ATACGGGAGCCAACACCAACCAGGTATTGTCCAAAATGGAAACAAATGAGGAATAGAGCAGGTGTGACGGAT TABLE 8-continued DNA Ligand Sequence ID Nos.
Arthropod Aptamer Sequences 2011-Final <SEQ ID NO. 236 D2-9R; DNA; Artificial>
ATCCGTCACACCTGCTCTATTCCTCATTTGTTTCCATTTTGGACAATACCTGGTTGGTGTTGGCTCCCGTAT <SEQ ID NO. 237 D2-10F; DNA; ARTIFICIAL>
ATACGGGAGCCAACACCACACACAAAAGGAATTGTATACTCGCATAAGGCCGCCAGAGCAGGTGTGACGGAT <SEQ ID NO. 238 D2-10R; DNA; Artificial>
ATCCGTCACACCTGCTCTGGCGGCCTTATGCGAGTATACAATTCCTTTTGTGTGTGGTGTTGGCTCCCGTAT <SEQ ID NO. 239 D3-1F; DNA; ARTIFICIAL>
ATACGGGAGCCAACACCAGAAACGTGGACTGTGTAGGCAAACCTATTATTTTCTAGAGCAGGTGTGACGGAT <SEQ ID NO. 240 D3-1R; DNA; Artificial>
ATCCGTCACACCTGCTCTAGAAAATAATAGGTTTGCCTACACAGTCCACGTTTCTGGTGTTGGCTCCCGTAT <SEQ ID NO. 241 D3-2F; DNA; ARTIFICIAL>
ATACGGGAGCCAACACCAGCGCAATTGATGACTACCCTAAGAAATCTATTGGCCAGAGCAGGTGTGACGGAT <SEQ ID NO. 242 D3-2R; DNA; Artificial>
ATCCGTCACACCTGCTCTGGCCAATAGATTTCTTAGGGTAGTCATCAATTGCGCTGGTGTTGGCTCCCGTAT <SEQ ID NO. 243 D3-3aF; DNA; ARTIFICIAL>
ATACGGGAGCCAACACCACGGCCGAGGTCCACTACCCCTATGGCTGGCCCTTCCAGAGCAGGTGTGACGGAT <SEQ ID NO. 244 D3-3bF; DNA; ARTIFICIAL>
ATACGGGAGCCAACACCAGCCTACGGGTGGATGATCCGCGGTGTTCGAGTGTTAGAGCAGGTGTGACGG <SEQ ID NO. 245 D3-3aR; DNA; Artificial>
ATCCGTCACACCTGCTCTGGAAGGGCCAGCCATAGGGGTAGTGGACCTCGGCCGTGGTGTTGGCTCCCGTAT <SEQ ID NO. 246 D3-3bR; DNA; Artificial>
CCGTCACACCTGCTCTAACACTCGAACACCGCGGATCATCCACCCGTAGGCTGGTGTTGGCTCCCGTAT <SEQ ID NO. 247 D3-4aF; DNA; ARTIFICIAL>
ATACGGGAGCCAACACCATGCAGTATCCACCTTCTCTTTTTTCTCACTCCACTGAGAGCAGGTGTGACGGAT <SEQ ID NO. 248 D3-4aR; DNA; Artificial>
ATCCGTCACACCTGCTCTCAGTGGAGTGAGAAAAAAGAGAAGGTGGATACTGCATGGTGTTGGCTCCCGTAT <SEQ ID NO. 249 D3-4bF; DNA; ARTIFICIAL>
ATCCGTCACACCTGCTCTCGAATGGGACAACTTCTCGATATCTACTATGGTTGGTGGTGTTGGCTCCCGTAT <SEQ ID NO. 250 D3-4bR; DNA; Artificial>
ATACGGGAGCCAACACCACCAACCATAGTAGATATCGAGAAGTTGTCCCATTCGAGAGCAGGTGTGACGGAT <SEQ ID NO. 251 D3-6F; DNA; ARTIFICIAL>
ATACGGGAGCCAACACCAGGGATGGGTAAAGAAAGTCGCGAGACGATGATGCCAGAGCAGGTGTGACGGAT <SEQ ID NO. 252 D3-6R; DNA; Artificial>
ATCCGTCACACCTGCTCTGGCATCATCGTCTCGCGACTTTCTTTACCCATCCCTGGTGTTGGCTCCCGTAT <SEQ ID NO. 253 D3-9F; DNA; ARTIFICIAL>
ATACGGGAGCCAACACCACGACATCCGTTCTGAACACACGATAGTGATGATTGTAGAGCAGGTGTGACGGAT <SEQ ID NO. 254 D3-9R; DNA; Artificial>
ATCCGTCACACCTGCTCTACAATCATCACTATCGTGTGTTCAGAACGGATGTCGTGGTGTTGGCTCCCGTAT <SEQ ID NO. 255 D3-10F; DNA; ARTIFICIAL>
ATACGGGAGCCAACACCACGGTATTGTAAAGAAATGAAATCAGTAATATATTCCAGAGCAGGTGTGACGGAT <SEQ ID NO. 256 D3-10R; DNA; Artificial>
ATCCGTCACACCTGCTCTGGAATATATTACTGATTTCATTTCTTTACAATACCGTGGTGTTGGCTCCCGTAT <SEQ ID NO. 257 D4-2F; DNA; ARTIFICIAL>
ATACGGGAGCCAACACCATACAAAAATCCGAAGTTAAGACAGCTCACGCTTATCAGAGCAGGTGTGACGGAT <SEQ ID NO. 258 D4-2R; DNA; Artificial>
ATCCGTCACACCTGCTCTGATAAGCGTGAGCTGTCTTAACTTCGGATTTTTGTATGGTGTTGGCTCCCGTAT <SEQ ID NO. 259 D4-3F; DNA; ARTIFICIAL>
ATACGGGAGCCAACACCATACATGGCAGCTCCTACAGATCACCACTCTAAGAGTAGAGCAGGTGTGACGGAT <SEQ ID NO. 260 D4-3R; DNA; Artificial>
ATCCGTCACACCTGCTCTACTCTTAGAGTGGTGATCTGTAGGAGCTGCCATGTATGGTGTTGGCTCCCGTAT TABLE 8-continued DNA Ligand Sequence ID Nos.
Arthropod Aptamer Sequences 2011-Final <SEQ ID NO. 261 D4-4F; DNA; ARTIFICIAL>
ATACGGGAGCCAACACCACAACTCACCAGGACACTCGGCCGCCCGGTCCCCAATAGAGCAGGTGTGACGGAT <SEQ ID NO. 262 D4-4R; DNA; Artificial>
ATCCGTCACACCTGCTCTATTGGGGACCGGGCGGCCGAGTGTCCTGGTGAGTTGTGGTGTTGGCTCCCGTAT <SEQ ID NO. 263 D4-5F; DNA; ARTIFICIAL>
ATACGGGAGCCAACACCAGTTGACAACACATGACTCTACACGATATGTCACACAAGAGCAGGTGTGACGGAT <SEQ ID NO. 264 D4-5R; DNA; Artificial>
ATCCGTCACACCTGCTCTTGTGTGACATATCGTGTAGAGTCATGTGTTGTCAACTGGTGTTGGCTCCCGTAT <SEQ ID NO. 265 D4-6F; DNA; ARTIFICIAL>
ATACGGGAGCCAACACCAGGCTATGAAGAAAGAAAAATGAGTAACACATAACGCAGAGCAGGTGTGACGGAT <SEQ ID NO. 266 D4-6R; DNA; Artificial>
ATCCGTCACACCTGCTCTGCGTTATGTGTTACTCATTTTTCTTTCTTCATAGCCTGGTGTTGGCTCCCGTAT <SEQ ID NO. 267 D4-7F; DNA; ARTIFICIAL>
ATACGGGAGCCAACACCACGCCCCCCCTCACTACTGTCCCGCCCCCCGCCGTGGAGAGCAGGTGTGACGGAT <SEQ ID NO. 268 D4-7R; DNA; Artificial>
ATCCGTCACACCTGCTCTCCACGGCGGGGGCGGGACAGTAGTGAGGGGGGCGTGGTGTTGGCTCCCGTAT <SEQ ID NO. 269 D4-9aF; DNA; ARTIFICIAL>
ATACGGGAGCCAACACCACCGGCCAACGAAAGACCTCGCTCACTAGACACCCCTAGAGCAGGTGTGACGGAT <SEQ ID NO. 270 D4-9bF; DNA; ARTIFICIAL>
ATACGGGAGCCAACACCACCAGAAAATCAATATAACAACGTATGCTGGCTCCGAGAGCAGGTGTGACGGAT <SEQ ID NO. 271 D4-9aR; DNA; Artificial>
ATCCGTCACACCTGCTCTAGGGGTGTCTAGTGAGCGAGGTCTTTCGTTGGCCGGTGGTGTTGGCTCCCGTAT <SEQ ID NO. 272 D4-9bR; DNA; Artificial>
ATCCGTCACACCTGCTCTCGGAGCCAGCATACGTTGTTATATTGATTTTCTGGTGGTGTTGGCTCCCGTAT <SEQ ID NO. 273 WNV -1F; DNA; ARTIFICIAL>
ATACGGGAGCCAACACCAATAGATGGATAAGGGGGAAACTGCCATTCGGTTAGTAGAGCAGGTGTGACGGAT <SEQ ID NO. 274 WNV -1R; DNA; Artificial>
ATCCGTCACACCTGCTCTACTAACCGAATGGCAGTTTCCCCCTTATCCATCTATTGGTGTTGGCTCCCGTAT <SEQ ID NO. 275 WNV - 2F; DNA; ARTIFICIAL>
ATACGGGAGCCAACACCAGATTGAAGCTCAAGCCTAAAGGTGACCAAAGGTAGAA TABLE 8-continued DNA Ligand Sequence ID Nos.
Arthropod Aptamer Sequences 2011-Final <SEQ ID NO. 287 WNV 8F; DNA; ARTIFICIAL>
ATACGGGAGCCAACACCACGAGGATTACAACTTTATGCGTGCAACCAGACACCAAGAGCAGGTGTGACGGAT <SEQ ID NO. 288 WNV 8R; DNA; Artificial>
ATCCGTCACACCTGCTCTTGGTGTCTGGTTGCACGCATAAAGTTGTAATCCTCGTGGTGTTGGCTCCCGTAT <SEQ ID NO. 289 WNV 9F; DNA; ARTIFICIAL>
ATACGGGAGCCAACACCACCTACAGATCCGCGAACCAGCCGACTACTCGTCCACAGAGCAGGTGTGACGGAT <SEQ ID NO. 290 WNV -9R; DNA; Artificial>
ATCCGTCACACCTGCTCTGTGGACGAGTAGTCGGCTGGTTCGCGGATCTGTAGGTGGTGTTGGCTCCCGTAT <SEQ ID NO. 291 WNV 10F; DNA; ARTIFICIAL>
ATACGGGAGCCAACACCACAGCTGATATTGGATGGTCCGGCAGAGCAGGTGTGACGGAT <SEQ ID NO. 292 WNV 10R; DNA; Artificial>
ATCCGTCACACCTGCTCTGCCGGACCATCCAATATCAGCTGTGGTGTTGGCTCCCGTAT <SEQ ID NO. 293 WNV 11F; DNA; ARTIFICIAL>
ATACGGGAGCCAACACCACAGGAGAGGCAGTAAAAGGGTTGGCTGCCTGGGTAGAGAGCAGGTGTGACGGAT <SEQ ID NO. 294 WNV 11R; DNA; Artificial>
ATCCGTCACACCTGCTCTCTACCCAGGCAGCCAACCCTTTTACTGCCTCTCCTGTGGTGTTGGCTCCCGTAT <SEQ ID NO. 295 WNV 12F; DNA; ARTIFICIAL>
ATACGGGAGCCAACACCAAGCTCTCACGTGACACAGTGCTCCGCCGTCAAAATGAGAGCAGGTGTGACGGAT <SEQ ID NO. 296 WNV 12R; DNA; Artificial>
ATCCGTCACACCTGCTCTCATTTTGACGGCGGAGCACTGTGTCACGTGAGAGCTTGGTGTTGGCTCCCGTAT <SEQ ID NO. 297 WNV 13F; DNA; ARTIFICIAL>
ATACGGGAGCCAACACCATCCCGCGCCCACTGCTTGTCACCTCTTAGCCCCCGCAGAGCAGGTGTGACGGAT <SEQ ID NO. 298 WNV 13R; DNA; Artificial>
ATCCGTCACACCTGCTCTGCGGGGGCTAAGAGGTGACAAGCAGTGGGCGCGGGATGGTGTTGGCTCCCGTAT <SEQ ID NO. 299 WNV 14F; DNA; ARTIFICIAL>
ATACGGGAGCCAACACCAACCCAATAAACTTATTGGACCTACGCTTTGATGATTAGAGCAGGTGTGACGGAT <SEQ ID NO. 300 WNV 14R; DNA; Artificial>
ATCCGTCACACCTGCTCTAATCATCAAAGCGTAGGTCCAATAAGTTTATTGGGTTGGTGTTGGCTCCCGTAT <SEQ ID NO. 301 WNV 15F; DNA; ARTIFICIAL>
ATACGGGAGCCAACACCACACTGCATCCCTCTACCGTACTTACATTCCTGACATAGAGCAGGTGTGACGGAT <SEQ ID NO. 302 WNV 15R; DNA; Artificial>
ATCCGTCACACCTGCTCTATGTCAGGAATGTAAGTACGGTAGAGGGATGCAGTGTGGTGTTGGCTCCCGTAT <SEQ ID NO. 303 WNV 16F; DNA; ARTIFICIAL>
ATACGGGAGCCAACACCATGTCAGGACCTCCATCGCCCGGGCCCGCCGCCGCTGAGAGCAGGTGTGACGGAT <SEQ ID NO. 304 WNV 16R; DNA; Artificial>
ATCCGTCACACCTGCTCTCAGCGGCGGCGGGCCCGGGCGATGGAGGTCCTGACATGGTGTTGGCTCCCGTAT <SEQ ID NO. 305 WNV 18F; DNA; ARTIFICIAL>
ATACGGGAGCCAACACCACCCCGTCGCCAAGCACTTGGCTGGGCTCTAACGGCCAGAGCAGGTGTGACGGAT <SEQ ID NO. 306 WNV 18R; DNA; Artificial>
ATCCGTCACACCTGCTCTGGCCGTTAGAGCCCAGCCAAGTGCTTGGCGACGGGGTGGTGTTGGCTCCCGTAT <SEQ ID NO. 307 WNV 19F; DNA; ARTIFICIAL>
ATACGGGAGCCAACACCACAGCTGATATCGGATGGTCCGGCAGAGCAGGTGTGACGGAT <SEQ ID NO. 308 WNV 19R; DNA; Artificial>
ATCCGTCACACCTGCTCTGCCGGACCATCCGATATCAGCTGTGGTGTTGGCTCCCGTAT <SEQ ID NO. 309 WNV 20F; DNA; ARTIFICIAL>
ATACGGGAGCCAACACCACCCGTGGCCTTCACCCAGCCAGGGGCCCCGTCTCTGAGAGCAGGTGTGACGGAT <SEQ ID NO. 310 WNV 20R; DNA; Artificial>
ATCCGTCACACCTGCTCTCAGAGACGGGGCCCCTGGCTGGGTGAAGGCCACGGGTGGTGTTGGCTCCCGTAT <SEQ ID NO. 311 R; DNA; Artificial>B-5F; DNA; ARTIFICIAL>
ATACGGGAGCCAACACCATGTCTCTTAGGATACAAAGCCAAACTGAGCCCGTGCAGAGCAGGTGTGACGGAT <SEQ ID NO. 312 R; DNA; Artificial>B-5R; DNA; Artificial>
ATCCGTCACACCTGCTCTGCACGGGCTCAGTTTGGCTTTGTATCCTAAGAGACATGGTGTTGGCTCCCGTAT TABLE 8-continued DNA Ligand Sequence ID Nos.
Arthropod Aptamer Sequences 2011-Final <SEQ ID NO. 313 21aF; DNA; ARTIFICIAL>
ATACGGGAGCCAACACCAGTCACAGTGTCTGGCCAGAATGCCAAGGGAATCGTTAGAGCAGGTGTGACGGAT <SEQ ID NO. 314 21aR; DNA; Artificial>
ATCCGTCACACCTGCTCTAACGATTCCCTTGGCATTCTGGCCAGACACTGTGACTGGTGTTGGCTCCCGTAT <SEQ ID NO. 315 21bF; DNA; ARTIFICIAL>
ATACGGGAGCCAACACCAACACTAATACTAATGCCATTATGCGTGATCTATTTAGAGCAGGTGTGACGGAT <SEQ ID NO. 316 21bR; DNA; Artificial>
ATCCGTCACACCTGCTCTAAATAGATCACGCATAATGGCATTAGTATTAGTGTTGGTGTTGGCTCCCGTAT <SEQ ID NO. 317 23F; DNA; ARTIFICIAL>
ATACGGGAGCCAACACCATAACAAATAACCACCCTCAATGCTAGATAGTGGCTTAGAGCAGGTGTGACGGAT <SEQ ID NO. 318 23R; DNA; Artificial>
ATCCGTCACACCTGCTCTAAGCCACTATCTAGCATTGAGGGTGGTTATTTGTTATGGTGTTGGCTCCCGTAT <SEQ ID NO. 319 25F; DNA; ARTIFICIAL>
ATACGGGAGCCAACACCAGCACTTACCCACCTATAAGGAATATTCTAGATCGGAAGAGCAGGTGTGACGGAT <SEQ ID NO. 320 25R; DNA; Artificial>
ATCCGTCACACCTGCTCTTCCGATCTAGAATATTCCTTATAGGTGGGTAAGTGCTGGTGTTGGCTCCCGTAT <SEQ ID NO. 321 26F; DNA; ARTIFICIAL>
ATACGGGAGCCAACACCATCGGGCATTAACATGGAATATCCTTCCCCAGCGTCTAGAGCAGGTGTGACGGAT <SEQ ID NO. 322 26R; DNA; Artificial>
ATCCGTCACACCTGCTCTAGACGCTGGGGAAGGATATTCCATGTTAATGCCCGATGGTGTTGGCTCCCGTAT <SEQ ID NO. 323 27F; DNA; ARTIFICIAL>
ATACGGGAGCCAACACCAGTCCACACTTGACCACAAAACATAATCCCATATTGTAGAGCAGGTGTGACGGAT <SEQ ID NO. 324 27R; DNA; Artificial>
ATCCGTCACACCTGCTCTACAATATGGGATTATGTTTTGTGGTCAAGTGTGGACTGGTGTTGGCTCCCGTAT <SEQ ID NO. 325 28F; DNA; ARTIFICIAL>
ATACGGGAGCCAACACCATAAGATAGTAAAGCTAGAGACATCTCAGAGCAGGAGAGAGCAGGTGTGACGGAT <SEQ ID NO. 326 28R; DNA; Artificial>
ATCCGTCACACCTGCTCTCTCCTGCTCTGAGATGTCTCTAGCTTTACTATCTTATGGTGTTGGCTCCCGTAT <SEQ ID NO. 327 29F; DNA; ARTIFICIAL>
ATACGGGAGCCAACACCAAAGGCAACAGTCTCTTCCTACTATTAAAACGAAACGAGAGCAGGTGTGACGGAT <SEQ ID NO. 328 29R; DNA; Artificial>
ATCCGTCACACCTGCTCTCGTTTCGTTTTAATAGTAGGAAGAGACTGTTGCCTTTGGTGTTGGCTCCCGTAT <SEQ ID NO. 329 30F; DNA; ARTIFICIAL>
ATACGGGAGCCAACACCAGCGTCATAATATTCCTGTTGTGGCCCTATTGGACGGAGAGCAGGTGTGACGGAT <SEQ ID NO. 330 30R; DNA; Artificial>
ATCCGTCACACCTGCTCTCCGTCCAATAGGGCCACAACAGGAATATTATGACGCTGGTGTTGGCTCCCGTAT <SEQ ID NO. 331 31F; DNA; ARTIFICIAL>
ATACGGGAGCCAACACCAAATATCTAACCATACATTTATACAAGTGGTTCATAGAGAGCAGGTGTGACGGAT <SEQ ID NO. 332 31R; DNA; Artificial>
ATCCGTCACACCTGCTCTCTATGAACCACTTGTATAAATGTATGGTTAGATATTTGGTGTTGGCTCCCGTAT <SEQ ID NO. 333 32F; DNA; ARTIFICIAL>
ATACGGGAGCCAACACCACAAGTTCAACGAGTTGATAACACAACATGACCGCCCAGAGCAGGTGTGACGGAT <SEQ ID NO. 334 32R; DNA; Artificial>
ATCCGTCACACCTGCTCTGGGCGGTCATGTTGTGTTATCAACTCGTTGAACTTGTGGTGTTGGCTCCCGTAT <SEQ ID NO. 335 33F; DNA; ARTIFICIAL>
ATACGGGAGCCAACACCACTAATAAAAATGAAAAACACCCCTCAACACCCATGAGAGCAGGTGTGACGGAT <SEQ ID NO. 336 33R; DNA; Artificial>
ATCCGTCACACCTGCTCTCATGGGTGTTGAGGGGTGTTTTTCATTTTTATTAGTGGTGTTGGCTCCCGTAT <SEQ ID NO. 337 34F; DNA; ARTIFICIAL>
ATACGGGAGCCAACACCACATTGAGCGTAAGCACCACGCCTTCTAGGTCGAGCTAGAGCAGGTGTGACGGAT <SEQ ID NO. 338 34R; DNA; Artificial>
ATCCGTCACACCTGCTCTAGCTCGACCTAGAAGGCGTGGTGCTTACGCTCAATGTGGTGTTGGCTCCCGTAT TABLE 8-continued DNA Ligand Sequence ID Nos.
Arthropod Aptamer Sequences 2011-Final <SEQ ID NO. 339 35F; DNA; ARTIFICIAL>
ATACGGGAGCCAACACCATAGTCGTTCTGACATGTACTTTTGAGGAAATGGTGCAGAGCAGGTGTGACGGAT <SEQ ID NO. 340 35; DNA; Artificial>R
ATCCGTCACACCTGCTCTGCACCATTTCCTCAAAAGTACATGTCAGAACGACTATGGTGTTGGCTCCCGTAT <SEQ ID NO. 341 36F; DNA; ARTIFICIAL>
ATACGGGAGCCAACACCATTACTCGCTCTGTATGCGCCTCCCACCCTCTGATAGAGAGCAGGTGTGACGGAT <SEQ ID NO. 342 36R; DNA; Artificial>
ATCCGTCACACCTGCTCTCTATCAGAGGGTGGGAGGCGCATACAGAGCGAGTAATGGTGTTGGCTCCCGTAT <SEQ ID NO. 343 37F; DNA; ARTIFICIAL>
ATACGGGAGCCAACACCAGAGTCGGCTACAGAGGTCTGATGTTAAAGCGATGGTAGAGCAGGTGTGACGGAT <SEQ ID NO. 344 37R; DNA; Artificial>
ATCCGTCACACCTGCTCTACCATCGCTTTAACATCAGACCTCTGTAGCCGACTCTGGTGTTGGCTCCCGTAT <SEQ ID NO. 345 38F; DNA; ARTIFICIAL>
ATACGGGAGCCAACACCACACCATTCTGGCCCCCTCCCCTTCACCGATCCTCTCAGAGCAGGTGTGACGGAT <SEQ ID NO. 346 38R; DNA; Artificial>
ATCCGTCACACCTGCTCTGAGAGGATCGGTGAAGGGGAGGGGGCCAGAATGGTGTGGTGTTGGCTCCCGTAT <SEQ ID NO. 347 39F; DNA; ARTIFICIAL>
ATACGGGAGCCAACACCAGCACTGCAGTTAACATTTACGAAGAGGCTTTAATGCAGAGCAGGTGTGACGGAT <SEQ ID NO. 348 39R; DNA; Artificial>
ATCCGTCACACCTGCTCTGCATTAAAGCCTCTTCGTAAATGTTAACTGCAGTGCTGGTGTTGGCTCCCGTAT <SEQ ID NO. 349 40F; DNA; ARTIFICIAL>
ATACGGGAGCCAACACCAACCCGGCGTTATATCACCTCATGGAGAAAAGTGCGTAGAGCAGGTGTGACGGAT <SEQ ID NO. 350 40R; DNA; Artificial>
ATCCGTCACACCTGCTCTACGCACTTTTCTCCATGAGGTGATATAACGCCGGGTTGGTGTTGGCTCCCGTAT <SEQ ID NO. 351 1F; DNA; ARTIFICIAL>
ATACGGGAGCCAACACCAGCACAACTTAAGTGCAAGCAAATTCGGATTAACCAAAGAGCAGGTGTGACGGAT <SEQ ID NO. 352 1R; DNA; Artificial>
ATCCGTCACACCTGCTCTTTGGTTAATCCGAATTTGCTTGCACTTAAGTTGTGCTGGTGTTGGCTCCCGTAT <SEQ ID NO. 353 4F; DNA; ARTIFICIAL>
ATACGGGAGCCAACACCACGACTACATTGTGTTCAAGCGCCGAAGACGCTATCAAGAGCAGGTGTGACGGAT <SEQ ID NO. 354 4R; DNA; Artificial>
ATCCGTCACACCTGCTCTTGATAGCGTCTTCGGCGCTTGAACACAATGTAGTCGTGGTGTTGGCTCCCGTAT <SEQ ID NO. 355 8F; DNA; ARTIFICIAL>
ATACGGGAGCCAACACCAGCATACCAGCAACGGAAGCTGCCCAAAGAATTTCAGAGCAGGTGTGACGGAT <SEQ ID NO. 356 8R; DNA; Artificial>
ATCCGTCACACCTGCTCTGAAATTCTTTGGGCAGCTTCCGTTGCTGGTATGCTGGTGTTGGCTCCCGTAT <SEQ ID NO. 357 9F; DNA; ARTIFICIAL>
ATACGGGAGCCAACACCAATGCTAAATACCGATGCTTTTCAATGTGATGGTCAAGAGCAGGTGTGACGGAT <SEQ ID NO. 358 9R; DNA; Artificial>
ATCCGTCACACCTGCTCTTGACCATCACATTGAAAAGCATCGGTATTTAGCATTGGTGTTGGCTCCCGTAT <SEQ ID NO. 359 12F; DNA; ARTIFICIAL>
ATACGGGAGCCAACACCATCCGGGCCATGGTAGAGTGTTATAATCGAACAAAAGAGCAGGTGTGACGGAT <SEQ ID NO. 360 12R; DNA; Artificial>
ATCCGTCACACCTGCTCTTTTGTTCGATTATAACACTCTACCATGGCCCGGATGGTGTTGGCTCCCGTAT <SEQ ID NO. 361 14F; DNA; ARTIFICIAL>
ATACGGGAGCCAACACCAAGTCCAAGCCAAACAAGAGCATAACACCAAATCTGGAGAGCAGGTGTGACGGAT <SEQ ID NO. 362 14R; DNA; Artificial>
ATCCGTCACACCTGCTCTCCAGATTTGGTGTTATGCTCTTGTTTGGCTTGGACTTGGTGTTGGCTCCCGTAT <SEQ ID NO. 363 17F; DNA; ARTIFICIAL>
ATACGGGAGCCAACACCAATGCTAAATACCGATGCTTTTCAATGTGATGGTCAAGAGCAGGTGTGACGGAT <SEQ ID NO. 364 17R; DNA; Artificial>
ATCCGTCACACCTGCTCTTGACCATCACATTGAAAAGCATCGGTATTTAGCATTGGTGTTGGCTCCCGTAT TABLE 8-continued DNA Ligand Sequence ID Nos.
Arthropod Aptamer Sequences 2011-Final <SEQ ID NO. 365 18F; DNA; ARTIFICIAL>
ATACGGGAGCCAACACCACATAGCTACTACAGAACTCAGGGCTAAAGTCTTATAGAGCAGGTGTGACGGAT <SEQ ID NO. 366 18R; DNA; Artificial>
ATCCGTCACACCTGCTCTATAAGACTTTAGCCCTGAGTTCTGTAGTAGCTATGTGGTGTTGGCTCCCGTAT <SEQ ID NO. 367 19F; DNA; ARTIFICIAL>
ATACGGGAGCCAACACCAGCATACCAGCAACGGAAGCTGCCCAAAGAATTTCAGAGCAGGTGTGACGGAT <SEQ ID NO. 368 19R; DNA; Artificial>
ATCCGTCACACCTGCTCTGAAATTCTTTGGGCAGCTTCCGTTGCTGGTATGCTGGTGTTGGCTCCCGTAT <SEQ ID NO. 369 20F; DNA; ARTIFICIAL>
ATACGGGAGCCAACACCAGATCGATATATGACACCAGGTACACCACAGACTTGCAGAGCAGGTGTGACGGAT <SEQ ID NO. 370 20R; DNA; Artificial>
ATCCGTCACACCTGCTCTGCAAGTCTGTGGTGTACCTGGTGTCATATATCGATCTGGTGTTGGCTCCCGTAT <SEQ ID NO. 371 1F; DNA; ARTIFICIAL>
ATACGGGAGCCAACACCATCTACTCGAACATCTTAAAAGCAGTCTAAGCAAACTAGAGCAGGTGTGACGGAT <SEQ ID NO. 372 1R; DNA; Artificial>
ATCCGTCACACCTGCTCTAGTTTGCTTAGACTGCTTTTAAGATGTTCGAGTAGATGGTGTTGGCTCCCGTAT <SEQ ID NO. 373 3aF; DNA; ARTIFICIAL>
ATACGGGAGCCAACACCATAGATCTTTTACGAACACCGCCGAAGATTATCATTTAGAGCAGGTGTGACGGAT <SEQ ID NO. 374 3aR; DNA; Artificial>
ATCCGTCACACCTGCTCTAAATGATAATCTTCGGCGGTGTTCGTAAAAGATCTATGGTGTTGGCTCCCGTAT <SEQ ID NO. 375 3bF; DNA; ARTIFICIAL>
ATACGGGAGCCAACACCAAATGATGAATAGGCAACTTGCGGTGCCACGATCTTGAGAGCAGGTGTGACGGAT <SEQ ID NO. 376 3bR; DNA; Artificial>
ATCCGTCACACCTGCTCTCAAGATCGTGGCACCGCAAGTTGCCTATTCATCATTTGGTGTTGGCTCCCGTAT <SEQ ID NO. 377 4F; DNA; ARTIFICIAL>
ATACGGGAGCCAACACCATCGGCCGAATAGATATAATTCACAAAGAGTGTCCCCAGAGCAGGTGTGACGGAT <SEQ ID NO. 378 4R; DNA; Artificial>
ATCCGTCACACCTGCTCTGGGGACACTCTTTGTGAATTATATCTATTCGGCCGATGGTGTTGGCTCCCGTAT <SEQ ID NO. 379 5F; DNA; ARTIFICIAL>
ATACGGGAGCCAACACCAGAAAATGAATACTTCCCAAGCTTGTCAAGCAAGTAAGAGCAGGTGTGACGGAT <SEQ ID NO. 380 5R; DNA; Artificial>
ATCCGTCACACCTGCTCTTACTTGCTTGACAAGCTTGGGAAGTATTCATTTTCTGGTGTTGGCTCCCGTAT <SEQ ID NO. 381 6F; DNA; ARTIFICIAL>
ATACGGGAGCCAACACCAAACAGGCTGAGTGTACTGCTACCTTGCAGTATCAAGAGCAGGTGTGACGGAT <SEQ ID NO. 382 6R; DNA; Artificial>
ATCCGTCACACCTGCTCTTGATACTGCAAGGTAGCAGTACACTCAGCCTGTTTGGTGTTGGCTCCCGTAT <SEQ ID NO. 383 9F; DNA; ARTIFICIAL>
ATACGGGAGCCAACACCAGATTTTCCAGCAAATCCAGTCCCTATATGTGCTTGAAGAGCAGGTGTGACGGAT <SEQ ID NO. 384 9R; DNA; Artificial>
ATCCGTCACACCTGCTCTTCAAGCACATATAGGGACTGGATTTGCTGGAAAATCTGGTGTTGGCTCCCGTAT <SEQ ID NO. 385 10F; DNA; ARTIFICIAL>
ATACGGGAGCCAACACCAACAACCACCAGTCAAGACCCAACGCGTGGCGAGGAAAGAGCAGGTGTGACGGAT <SEQ ID NO. 386 10R; DNA; Artificial>
ATCCGTCACACCTGCTCTTTCCTCGCCACGCGTTGGGTCTTGACTGGTGGTTGTTGGTGTTGGCTCCCGTAT <SEQ ID NO. 387 11F; DNA; ARTIFICIAL>
ATACGGGAGCCAACACCAGGGATATGCTGAATATGCATTGTCACGCTGAAGTCAGAGCAGGTGTGACGGAT <SEQ ID NO. 388 11R; DNA; Artificial>
ATCCGTCACACCTGCTCTGACTTCAGCGTGACAATGCATATTCAGCATATCCCTGGTGTTGGCTCCCGTAT <SEQ ID NO. 389 12F; DNA; ARTIFICIAL>
ATACGGGAGCCAACACCAATACAACAAGTCAAAAAGAAATAGAAAGTTGAACGAGAGCAGGTGTGACGGAT TABLE 8-continued DNA Ligand Sequence ID Nos.
Arthropod Aptamer Sequences 2011-Final <SEQ ID NO. 390 12R; DNA; Artificial>
ATCCGTCACACCTGCTCTCGTTCAACTTTCTATTTCTTTTTGACTTGTTGTATTGGTGTTGGCTCCCGTAT <SEQ ID NO. 391 13F; DNA; ARTIFICIAL>
ATACGGGAGCCAACACCAAACAGACGTTTGGGGCAATGATATAAAGTTAATCAAGAGCAGGTGTGACGGAT <SEQ ID NO. 392 13R; DNA; Artificial>
ATCCGTCACACCTGCTCTTGATTAACTTTATATCATTGCCCCAAACGTCTGTTTGGTGTTGGCTCCCGTAT <SEQ ID NO. 393 14F; DNA; ARTIFICIAL>
ATACGGGAGCCAACACCATAACGGTTCCCTTAATGCGCTACCCACACTATACAAGAGCAGGTGTGACGGAT <SEQ ID NO. 394 14R; DNA; Artificial>
ATCCGTCACACCTGCTCTTGTATAGTGTGGGTAGCGCATTAAGGGAACCGTTATGGTGTTGGCTCCCGTAT <SEQ ID NO. 395 15F; DNA; ARTIFICIAL>
ATACGGGAGCCAACACCAGCGCTGCCTGTATGGCAGACCTACCTGACCCTCTTTAGAGCAGGTGTGACGGAT <SEQ ID NO. 396 15R; DNA; Artificial>
ATCCGTCACACCTGCTCTAAAGAGGGTCAGGTAGGTCTGCCATACAGGCAGCGCTGGTGTTGGCTCCCGTAT <SEQ ID NO. 397 16F; DNA; ARTIFICIAL>
ATACGGGAGCCAACACCAAGATGCGAGCCAATAGTGTCACAATAATTGTCCGAAAGAGCAGGTGTGACGGAT <SEQ ID NO. 398 16R; DNA; Artificial>
ATCCGTCACACCTGCTCTTTCGGACAATTATTGTGACACTATTGGCTCGCATCTTGGTGTTGGCTCCCGTAT <SEQ ID NO. 399 17F; DNA; ARTIFICIAL>
ATACGGGAGCCAACACCAAGATATAGACTCTAATTGATTACCATTCATAGGAAAAGAGCAGGTGTGACGGAT <SEQ ID NO. 400 17R; DNA; Artificial>
ATCCGTCACACCTGCTCTTTTCCTATGAATGGTAATCAATTAGAGTCTATATCTTGGTGTTGGCTCCCGTAT <SEQ ID NO. 401 18F; DNA; ARTIFICIAL>
ATACGGGAGCCAACACCATCCAGTTCCAATTACGCGTAGATAGTCACAATCCAAAGAGCAGGTGTGACGGAT <SEQ ID NO. 402 18R; DNA; Artificial>
ATCCGTCACACCTGCTCTTTGGATTGTGACTATCTACGCGTAATTGGAACTGGATGGTGTTGGCTCCCGTAT <SEQ ID NO. 403 19F; DNA; ARTIFICIAL>
ATACGGGAGCCAACACCACTTACCTCCCCTACCACACCTCCAACTAAAACCTGAAGAGCAGGTGTGACGGAT <SEQ ID NO. 404 19R; DNA; Artificial>
ATCCGTCACACCTGCTCTTCAGGTTTTAGTTGGAGGTGTGGTAGGGGAGGTAAGTGGTGTTGGCTCCCGTAT <SEQ ID NO. 405 20F; DNA; ARTIFICIAL>
ATACGGGAGCCAACACCAGGATCAAACCACTTGCCGTCAAGGCAATGGCCCCTCAGAGCAGGTGTGACGGAT <SEQ ID NO. 406 20R; DNA; Artificial>
ATCCGTCACACCTGCTCTGAGGGGCCATTGCCTTGACGGCAAGTGGTTTGATCCTGGTGTTGGCTCCCGTAT <SEQ ID NO. 407 31F; DNA; ARTIFICIAL>
ATACGGGAGCCAACACCACCCGTTTTTGATCTAATGAGGATACAATATTCGTCTAGAGCAGGTGTGACGGAT <SEQ ID NO. 408 31R; DNA; Artificial>
ATCCGTCACACCTGCTCTAGACGAATATTGTATCCTCATTAGATCAAAAACGGGTGGTGTTGGCTCCCGTAT <SEQ ID NO. 409 36F; DNA; ARTIFICIAL>
ATACGGGAGCCAACACCACCCCTCCGGACCCACCCCTGATGCCACGTGCCCCTGAGAGCAGGTGTGACGGAT <SEQ ID NO. 410 36R; DNA; Artificial>
ATCCGTCACACCTGCTCTCAGGGGCACGTGGCATCAGGGGTGGGTCCGGAGGGGTGGTGTTGGCTCCCGTAT <SEQ ID NO. 411 37F; DNA; ARTIFICIAL>
ATACGGGAGCCAACACCAGACCCTGCCCCAGCCCCTTAGCCCCGGCGCGCGACGAGAGCAGGTGTGACGGAT <SEQ ID NO. 412 37R; DNA; Artificial>
ATCCGTCACACCTGCTCTCGTCGCGCGCCGGGGCTAAGGGGCTGGGGCAGGGTCTGGTGTTGGCTCCCGTAT <SEQ ID NO. 413 39F; DNA; ARTIFICIAL>
ATACGGGAGCCAACACCACACACAGAGCGCCATGGACTCAGTCAGATGTGATGTAGAGCAGGTGTGACGGAT <SEQ ID NO. 414 39R; DNA; Artificial>
ATCCGTCACACCTGCTCTACATCACATCTGACTGAGTCCATGGCGCTCTGTGTGTGGTGTTGGCTCCCGTAT <SEQ ID NO. 415 40F; DNA; ARTIFICIAL>
ATACGGGAGCCAACACCACGGCACGAAGACGAGGTGAAAAGTCAGCTTAGTGAAAGAGCAGGTGTGACGGAT TABLE 8-continued DNA Ligand Sequence ID Nos.
Arthropod Aptamer Sequences 2011-Final <SEQ ID NO. 416 40R; DNA; Artificial>
ATCCGTCACACCTGCTCTTTCACTAAGCTGACTTTTCACCTCGTCTTCGTGCCGTGGTGTTGGCTCCCGTAT <SEQ ID NO. 417 41F; DNA; ARTIFICIAL>
ATACGGGAGCCAACACCACACCCCATGAGATCACCATTCACTCGCACCCCCACGAGAGCAGGTGTGACGGAT <SEQ ID NO. 418 41R; DNA; Artificial>
ATCCGTCACACCTGCTCTCGTGGGGGTGCGAGTGAATGGTGATCTCATGGGGTGTGGTGTTGGCTCCCGTAT <SEQ ID NO. 419 43F; DNA; ARTIFICIAL>
ATACGGGAGCCAACACCAGGCTATTTGTTAGCGCTCTCTAGTTCCACATGACCAAGAGCAGGTGTGACGGAT <SEQ ID NO. 420 43R; DNA; Artificial>
ATCCGTCACACCTGCTCTTGGTCATGTGGAACTAGAGAGCGCTAACAAATAGCCTGGTGTTGGCTCCCGTAT <SEQ ID NO. 421 44F; DNA; ARTIFICIAL>
ATACGGGAGCCAACACCATGGCTGGTACACTCCCGGTTCCCTGCCGTTGAGCCCAGAGCAGGTGTGACGGAT <SEQ ID NO. 422 44R; DNA; Artificial>
ATCCGTCACACCTGCTCTGGGCTCAACGGCAGGGAACCGGGAGTGTACCAGCCATGGTGTTGGCTCCCGTAT <SEQ ID NO. 423 45F; DNA; ARTIFICIAL>
ATACGGGAGCCAACACCACGGGGTGGGTCGAACCCTTGTCTGGGAGGTGCTTCTAGAGCAGGTGTGACGGAT <SEQ ID NO. 424 45R; DNA; Artificial>
ATCCGTCACACCTGCTCTAGAAGCACCTCCCAGACAAGGGTTCGACCCACCCCGTGGTGTTGGCTCCCGTAT <SEQ ID NO. 425 21F; DNA; ARTIFICIAL>
ATACGGGAGCCAACACCAATCTTACTAGTTTGGGAAAAAAATTAAATATAAGCAAGAGCAGGTGTGACGGAT <SEQ ID NO. 426 21R; DNA; Artificial>
ATCCGTCACACCTGCTCTTGCTTATATTTAATTTTTTTCCCAAACTAGTAAGATTGGTGTTGGCTCCCGTAT <SEQ ID NO. 427 22F; DNA; ARTIFICIAL>
ATACGGGAGCCAACACCAATTATCCACTGATAACGAAAAGATCTGGACAGTTGTAGAGCAGGTGTGACGGAT <SEQ ID NO. 428 22R; DNA; Artificial>
ATCCGTCACACCTGCTCTACAACTGTCCAGATCTTTTCGTTATCAGTGGATAATTGGTGTTGGCTCCCGTAT <SEQ ID NO. 429 24F; DNA; ARTIFICIAL>
ATACGGGAGCCAACACCAGTTGACTTAGGGTCAAACTATGGACACTCACCCGTAAGAGCAGGTGTGACGGAT <SEQ ID NO. 430 24R; DNA; Artificial>
ATCCGTCACACCTGCTCTTACGGGTGAGTGTCCATAGTTTGACCCTAAGTCAACTGGTGTTGGCTCCCGTAT <SEQ ID NO. 431 25F; DNA; ARTIFICIAL>
ATACGGGAGCCAACACCACTACTAGACATCGTAGCCCGACGTCCGTGGATTGGGAGAGCAGGTGTGACGGAT <SEQ ID NO. 432 25R; DNA; Artificial>
ATCCGTCACACCTGCTCTCCCAATCCACGGACGTCGGGCTACGATGTCTAGTAGTGGTGTTGGCTCCCGTAT <SEQ ID NO. 433 26F; DNA; ARTIFICIAL>
ATACGGGAGCCAACACCAGATATACCGTAACATTAATAGACAAGTTAAATACCCAGAGCAGGTGTGACGGAT <SEQ ID NO. 434 26R; DNA; Artificial>
ATCCGTCACACCTGCTCTGGGTATTTAACTTGTCTATTAATGTTACGGTATATCTGGTGTTGGCTCCCGTAT <SEQ ID NO. 435 27aF; DNA; ARTIFICIAL>
ATACGGGAGCCAACACCAACATAGTGCTCGCATCCTATGGCGTAACGAGACTACAGAGCAGGTGTGACGGAT <SEQ ID NO. 436 27aR; DNA; Artificial>
ATCCGTCACACCTGCTCTGTAGTCTCGTTACGCCATAGGATGCGAGCACTATGTTGGTGTTGGCTCCCGTAT <SEQ ID NO. 437 27bF; DNA; ARTIFICIAL>
ATACGGGAGCCAACACCACCAACGAATACTACCAGGCCTAGCACAATACACAACAGAGCAGGTGTGACGGAT <SEQ ID NO. 438 27bR; DNA; Artificial>
ATCCGTCACACCTGCTCTGTTGTGTATTGTGCTAGGCCTGGTAGTATTCGTTGTTGGCTCCCGTAT <SEQ ID NO. 439 28F; DNA; ARTIFICIAL>
ATACGGGAGCCAACACCATTAGAAAAGACATCGCTAAATGACGGGCACGAATGAGAGCAGGTGTGACGGAT <SEQ ID NO. 440 28R; DNA; Artificial>
ATCCGTCACACCTGCTCTCATTCGTGCCCGTCATTTAGCGATGTCTTTTCTAATGGTGTTGGCTCCCGTAT <SEQ ID NO. 441 29F; DNA; ARTIFICIAL>
ATACGGGAGCCAACACCACAAATGAATAAAATTTCGGAAAAGGCAAGCAGGATAAGAGCAGGTGTGACGGAT TABLE 8-continued DNA Ligand Sequence ID Nos.
Arthropod Aptamer Sequences 2011-Final <SEQ ID NO. 442 29R; DNA; Artificial>
ATCCGTCACACCTGCTCTTATCCTGCTTGCCTTTTCCGAAATTTTATTCATTTGTGGTGTTGGCTCCCGTAT <SEQ ID NO. 443 30F; DNA; ARTIFICIAL>
ATACGGGAGCCAACACCATTATGTTAACAAAGGCATACGGCAAGCTCTAACTGTAGAGCAGGTGTGA CGGAT <SEQ ID NO. 444 30R; DNA; Artificial>
ATCCGTCACACCTGCTCTACAGTTAGAGCTTGCCGTATGCCTTTGTTAACATAATGGTGTTGGCTCCCGTAT <SEQ ID NO. 445 31F; DNA; ARTIFICIAL>
ATACGGGAGCCAACACCATAAGAACCACCACTCCGCGTTCGCCTCCCGAGGTGTAGAGCAGGTGTGACGGAT <SEQ ID NO. 446 31R; DNA; Artificial>
ATCCGTCACACCTGCTCTACACCTCGGGAGGCGAACGCGGAGTGGTGGTTCTTATGGTGTTGGCTCCCGTAT <SEQ ID NO. 447 33F; DNA; ARTIFICIAL>
ATACGGGAGCCAACACCATCATGGCGATACAGTTATCTGCATTGTTCCATCCCTAGAGCAGGTGTGACGGAT <SEQ ID NO. 448 33R; DNA; Artificial>
ATCCGTCACACCTGCTCTAGGGATGGAACAATGCAGATAACTGTATCGCCATGATGGTGTTGGCTCCCGTAT <SEQ ID NO. 449 34F; DNA; ARTIFICIAL>
ATACGGGAGCCAACACCAGCCCTGGGCCAGCCCGTGACTTTCCCCCGGCGTCCAAGAGCAGGTGTGACGGAT <SEQ ID NO. 450 34R; DNA; Artificial>
ATCCGTCACACCTGCTCTTGGACGCCGGGGGAAAGTCACGGGCTGGCCCAGGGCTGGTGTTGGCTCCCGTAT <SEQ ID NO. 451 35F; DNA; ARTIFICIAL>
ATACGGGAGCCAACACCAAACGGTTCAGAAATAGGAAACGTTTGATCGCAAGAAGAGCAGGTGTGACGGAT <SEQ ID NO. 452 35R; DNA; Artificial>
ATCCGTCACACCTGCTCTTCTTGCGATCAAACGTTTCCTATTTCTGAACCGTTTGGTGTTGGCTCCCGTAT <SEQ ID NO. 453 36F; DNA; ARTIFICIAL>
ATACGGGAGCCAACACCAGAATATCTAAAATAAAGGAAAGACAACCGCGGATGCAGAGCAGGTGTGACGGAT <SEQ ID NO. 454 36R; DNA; Artificial>
ATCCGTCACACCTGCTCTGCATCCGCGGTTGTCTTTCCTTTATTTTAGATATTCTGGTGTTGGCTCCCGTAT <SEQ ID NO. 455 37F; DNA; ARTIFICIAL>
ATACGGGAGCCAACACCACGACGGGCGTAAAGAAATAACCAATGCTACCGCCACAGAGCAGGTGTGACGGAT <SEQ ID NO. 456 37R; DNA; Artificial>
ATCCGTCACACCTGCTCTGTGGCGGTAGCATTGGTTATTTCTTTACGCCCGTCGTGGTGTTGGCTCCCGTAT <SEQ ID NO. 457 38F; DNA; ARTIFICIAL>
ATACGGGAGCCAACACCAACGAATAAGTATTTAAGACAGAATTAGACACTTAGAAGAGCAGGTGTGACGGAT <SEQ ID NO. 458 38R; DNA; Artificial>
ATCCGTCACACCTGCTCTTCTAAGTGTCTAATTCTGTCTTAAATACTTATTCGTTGGTGTTGGCTCCCGTAT <SEQ ID NO. 459 39F; DNA; ARTIFICIAL>
ATACGGGAGCCAACACCATATACATACTCCTCGCTACAACCGCTGCGCCGGATCAGAGCAGGTGTGACGGAT <SEQ ID NO. 460 39R; DNA; Artificial>
ATCCGTCACACCTGCTCTGATCCGGCGCAGCGGTTGTAGCGAGGAGTATGTATATGGTGTTGGCTCCCGTAT <SEQ ID NO. 461 40F; DNA; ARTIFICIAL>
ATACGGGAGCCAACACCAATATAAGCGAGGAGGAAGGCGGCGAGCTATAAGTCAGAGCAGGTGTGACGGAT <SEQ ID NO. 462 40R; DNA; Artificial>
ATCCGTCACACCTGCTCTGACTTATAGCTCGCCGCCTTCCTCCTCGCTTATATTGGTGTTGGCTCCCGTAT <SEQ ID NO. 463 LP 21F; DNA; ARTIFICIAL>
CATACGGGAGCCAACACCACAACCATTGCGTTACTATCTTCAGAGCAGGTGTGACGGATG <SEQ ID NO. 464 LP 21R; DNA; Artificial>
CATCCGTCACACCTGCTCTGAAGATAGTAACGCAATGGTTGTGGTGTTGGCTCCCGTATG <SEQ ID NO. 465 L. major LRC 940 3F; DNA; ARTIFICIAL>
CATACGGGAGCCAACACCACCCGTATCGTTCCCAATGCACTCAGAGCAGGTGTGACGGATG <SEQ ID NO. 466 L. major LRC 940 3R; DNA; Artificial>
CATCCGTCACACCTGCTCTGAGTGCATTGGGAACGATACGGGTGGTGTTGGCTCCCGTATG <SEQ ID NO. 467 L. major LRC 940-5F; DNA; ARTIFICIAL>
CATACGGGAGCCAACACCACGTTCCCATACAAGTTACTGACAGAGCAGGTGTGACGGATA TABLE 8-continued DNA Ligand Sequence ID Nos.
Arthropod Aptamer Sequences 2011-Final <SEQ ID NO. 468 L. major LRC 940-5R; DNA; Artificial>
TATCCGTCACACCTGCTCTGTCAGTAACTTGTATGGGAACGTGGTGTTGGCTCCCGTATG <SEQ ID NO. 469 L. major LRC 940-6F; DNA; ARTIFICIAL>
CATACGGGAGCCAACACCACAATGTCTTGCTCGTGTGTCCCAGAGCAGGTGTGACGGATG <SEQ ID NO. 470 L. major LRC 940-6R; DNA; Artificial>
CATCCGTCACACCTGCTCTGGGACACACGAGCAAGACATTGTGGTGTTGGCTCCCGTATG <SEQ ID NO. 471 L. major LRC 940 18.2F; DNA; ARTIFICIAL>
CATACGGGAGCCAACACCACTCTCAGAATGGGTCCAACCCCAGAGCAGGTGTGACGGATG <SEQ ID NO. 472 L. major LRC 940 18.2R; DNA; Artificial>
CATCCGTCACACCTGCTCTGGGGTTGGACCCATTCTGAGAGTGGTGTTGGCTCCCGTATG <SEQ ID NO. 473 25F; DNA; ARTIFICIAL>
CATACGGGAGCCAACACCACGTGTTGATGCGGGGTTCTCGCAGAGCAGGTGTGACGGATG <SEQ ID NO. 474 25R; DNA; Artificial>
CATCCGTCACACCTGCTCTGCGAGAACCCCGCATCAACACGTGGTGTTGGCTCCCGTATG <SEQ ID NO. 475 29F; DNA; ARTIFICIAL>
CATACGGGAGCCAACACCACCCGCAGCATCCATAAACGAGCAGAGCAGGTGTGACGGATG <SEQ ID NO. 476 29R; DNA; Artificial>
CATCCGTCACACCTGCTCTGCTCGTTTATGGATGCTGCGGGTGGTGTTGGCTCCCGTATG <SEQ ID NO. 477 Lm 1F; DNA; ARTIFICIAL>
ATCCGTCACACCTGCTCTATCGTGTCTTATTTATTCTGCTCAATACGTTACGCTTGGTGTTGGCTCCCGTAT <SEQ ID NO. 478 Lm 1R; DNA; Artificial>
ATACGGGAGCCAACACCAAGCGTAACGTATTGAGCAGAATAAATAAGACACGATAGAGCAGGTGTGACGGAT <SEQ ID NO. 479 Lm 2/41F; DNA; ARTIFICIAL>
ATACGGGAGCCAACACCAACCTGGCTATCTGCATGCGGTCGGTCGCCTTGTTGGAGAGCAGGTGTGACGGAT <SEQ ID NO. 480 Lm 2/41R; DNA; Artificial>
ATCCGTCACACCTGCTCTCCAACAAGGCGACCGACCGCATGCAGATAGCCAGGTTGGTGTTGGCTCCCGTAT <SEQ ID NO. 481 Lm 3F; DNA; ARTIFICIAL>
ATCCGTCACACCTGCTCTTCACGTGTAGCGATGACAGAATAAGGATTGAAAGACTGGTGTTGGCTCCCGTAT <SEQ ID NO. 482 Lm 3R; DNA; Artificial>
ATACGGGAGCCAACACCAGTCTTTCAATCCTTATTCTGTCATCGCTACACGTGAAGAGCAGGTGTGACGGAT <SEQ ID NO. 483 Lm 4F; DNA; ARTIFICIAL>
ATCCGTCACACCTGCTCTGAGGTCGGGTATTAGTCCGTATAAACCGAGACTGAATGGTGTTGGCTCCCGTAT <SEQ ID NO. 484 Lm 4R; DNA; Artificial>
ATACGGGAGCCAACACCATTCAGTCTCGGTTTATACGGACTAATACCCGACCTCAGAGCAGGTGTGACGGAT <SEQ ID NO. 485 Lm 5F; DNA; ARTIFICIAL>
ATACGGGAGCCAACACCAGCGATACACGTCCATCGAACAAGTTAAAACTTAGAAAGAGCAGGTGTGACGGAT <SEQ ID NO. 486 Lm 5R; DNA; Artificial>
ATCCGTCACACCTGCTCTTTCTAAGTTTTAACTTGTTCGATGGACGTGTATCGCTGGTGTTGGCTCCCGTAT <SEQ ID NO. 487 Lm 6/10F; DNA; ARTIFICIAL>
ATACGGGAGCCAACACCACGGGGGCATCTTCCATTAACCCATTACCTCACCCCAAGAGCAGGTGTGACGGAT <SEQ ID NO. 488 Lm 6/10R; DNA; Artificial>
ATCCGTCACACCTGCTCTTGGGGTGAGGTAATGGGTTAATGGAAGATGCCCCCGTGGTGTTGGCTCCCGTAT <SEQ ID NO. 489 Lm 7F; DNA; ARTIFICIAL>
ATACGGGAGCCAACACCACGCCCACGGCCACGCCCGACGAGCTACCCCTCATCAAGAGCAGGTGTGACGGAT <SEQ ID NO. 490 Lm 7R; DNA; Artificial>
ATCCGTCACACCTGCTCTTGATGAGGGGTAGCTCGTCGGGCGTGGCCGTGGGCGTGGTGTTGGCTCCCGTAT <SEQ ID NO. 491 Lm 9F; DNA; ARTIFICIAL>
ATCCGTCACACCTGCTCTCGCATCTAACGTCTAGACTATCAAAAGTCGTGTTAATGGTGTTGGTTCCGGTAT <SEQ ID NO. 492 Lm 9R; DNA; Artificial>
ATACCGGAACCAACACCATTAACACGACTTTTGATAGTCTAGACGTTAGATGCGAGAGCAGGTGTGACGGAT <SEQ ID NO. 493 Lm 11/47F; DNA; ARTIFICIAL>
ATCCGTCACACCTGCTCTTGGGGTGAGGTAATGGGTTAATGGAAGATGCCCCCGTGGTGTTGGCTCCCGTAT TABLE 8-continued DNA Ligand Sequence ID Nos.
Arthropod Aptamer Sequences 2011-Final

```
<SEQ ID NO. 494 Lm 11/47R; DNA; Artificial>
ATACGGGAGCCAACACCACGGGGGCATCTTCCATTAACCCATTACCTCACCCCAAGAGCAGGTGTGACGGAT <SEQ ID NO. 495 Lm 13F; DNA; ARTIFICIAL>
ATACGGGAGCCAACACCACAAAGTTTAGCGTTATGCAACTCCCCCTTATACTCGAGAGCAGGTGTGACGGAT <SEQ ID NO. 496 Lm 13R; DNA; Artificial>
ATCCGTCACACCTGCTCTCGAGTATAAGGGGGAGTTGCATAACGCTAAACTTTGTGGTGTTGGCTCCCGTAT <SEQ ID NO. 497 Lm 14F; DNA; ARTIFICIAL>
ATACGGGAGCCAACACCAGTAATTGTCACTCACGCAGATCGGTGACTACATAGCAGAGCAGGTGTGACGGAT <SEQ ID NO. 498 Lm 14R; DNA; Artificial>
ATCCGTCACACCTGCTCTGCTATGTAGTCACCGATCGCGTGAGTGACAATTACTGGTGTTGGCTCCCGTAT <SEQ ID NO. 499 Lm 15F; DNA; ARTIFICIAL>
ATCCGTCACACCTGCTCTGTGTACTACTTGCAGGAATGGCAATAGGCGGAAAGGTGGTGTTGGCTCCCGTAT <SEQ ID NO. 500 Lm 15R; DNA; Artificial>
ATACGGGAGCCAACACCACCTTTCCGCCTATTGCCATTCCTGCAAGTAGTACACAGAGCAGGTGTGACGGAT <SEQ ID NO. 501 Lm 16F; DNA; ARTIFICIAL>
ATCCGTCACACCTGCTCTATGTTGCCGGGAAGATATAGTGAAAATTCATGATATGGTGTTGGCTCCCGTAT <SEQ ID NO. 502 Lm 16R; DNA; Artificial>
ATACGGGAGCCAACACCATATCATGAATTTTCACTATATCTTCCCGGCAACATAGAGCAGGTGTGACGGAT <SEQ ID NO. 503 Lm 17F; DNA; ARTIFICIAL>
ATACGGGAGCCAACACCACTGGTGAGGCGCCTGCGCCGACTGGCCGTCCCCCCGAGAGCAGGTGTGACGGAT <SEQ ID NO. 504 Lm 17R; DNA; Artificial>
ATCCGTCACACCTGCTCTCGGGGGACGGCCAGTCGGCGCAGGCGCCTCACCAGTGGTGTTGGCTCCCGTAT <SEQ ID NO. 505 Lm 18F; DNA; ARTIFICIAL>
ATCCGTCACACCTGCTCTGGGTGAGCGAGTCGGCCCCGGGAGCGAACGGCGGCGTGGTGTTGGCTCCCGTAT <SEQ ID NO. 506 Lm 18R; DNA; Artificial>
ATACGGGAGCCAACACCACGCCGCCGTTCGCTCCCGGGGCCGACTCGCTCACCCAGAGCAGGTGTGACGGAT <SEQ ID NO. 507 Lm 19F; DNA; ARTIFICIAL>
ATCCGTCACACCTGCTCTCAGCGGCGGCGGGCCCGGGCGATGGAGGTCCTGACATGGTGTTGGCTCCCGTAT <SEQ ID NO. 508 Lm 19R; DNA; Artificial>
ATACGGGAGCCAACACCATGTCAGGACCTCCATCGCCCGGGCCCGCCGCCGCTGAGAGCAGGTGTGACGGAT <SEQ ID NO. 509 Lm 21F; DNA; ARTIFICIAL>
ATCCGTCACACCTGCTCTTTCCATGTATATTAGATACTCGGGGCAAGGGGAAACTGGTGTTGGCTCCCGTAT <SEQ ID NO. 510 Lm 21R; DNA; Artificial>
ATACGGGAGCCAACACCAGTTTCCCCTTGCCCCGAGTATCTAATATACATGGAAAGAGCAGGTGTGACGGAT <SEQ ID NO. 511 Lm 22F; DNA; ARTIFICIAL>
ATCCGTCACACCTGCTCTGGAGCGATCTAACCCTTTTTATCAATCAATTCGGTGGTGTTGGCTCCCGTAT <SEQ ID NO. 512 Lm 22R; DNA; Artificial>
ATACGGGAGCCAACACCACCGAATTGATTGATAAAAAGGGTTAGATCGCTCCAGAGCAGGTGTGACGGAT <SEQ ID NO. 513 Lm 23F; DNA; ARTIFICIAL>
ATCCGTCACACCTGCTCTTGGGACATTTGTAGTGCCTGTTCATGTATCGCAGCCTGGTGTTGGCTCCCGTAT <SEQ ID NO. 514 Lm 23R; DNA; Artificial>
ATACGGGAGCCAACACCAGGCTGCGATACATGAACAGGCACTACAAATGTCCCAAGAGCAGGTGTGACGGAT <SEQ ID NO. 515 Lm 25F; DNA; ARTIFICIAL>
ATACGGGAGCCAACACCACCCACTCTCCCCCCGCTCCCGCTCCCCCGCTCCGCGAGAGCAGGTGTGACGGAT <SEQ ID NO. 516 Lm 25R; DNA; Artificial>
ATCCGTCACACCTGCTCTCGCGGAGCGGGGGAGCGGGAGCGGGGGAGAGTGGGTGGTGTTGGCTCCCGTAT <SEQ ID NO. 517 Lm 26/43F; DNA; ARTIFICIAL>
ATCCGTCACACCTGCTCTACATACACATCTGACTGAGTCCATGGCGCTCTGTGTGTGGTGTTGGCTCCCGTAT <SEQ ID NO. 518 Lm 26/43R; DNA; Artificial>
ATACGGGAGCCAACACCACACACAGAGCGCCATGGACTCAGTCAGATGTGATGTAGAGCAGGTGTGACGGAT <SEQ ID NO. 519 Lm 27F; DNA; ARTIFICIAL>
ATACGGGAGCCAACACCATCCTCCTGCGGCGTCTGGAGAACAGCCTCTACTTTAAGAGCAGGTGTGACGGAT
```

TABLE 8-continued

DNA Ligand Sequence ID Nos.
Arthropod Aptamer Sequences 2011-Final

<SEQ ID NO. 520 Lm 27R; DNA; Artificial>
ATCCGTCACACCTGCTCTTAAAGTAGAGGCTGTTCTCCAGACGCCGCAGGAGGATGGTGTTGGCTCCCGTAT <SEQ ID NO. 521 Lm 29F; DNA; ARTIFICIAL>
ATCCGTCACACCTGCTCTTTTTGGTATTGTTGGCGGAAGGCGGTGGTTCGTGTCTGGTGTTGGCTCCCGTAT <SEQ ID NO. 522 Lm 29R; DNA; Artificial>
ATACGGGAGCCAACACCAGACACGAACCACCGCCTTCCGCCAACAATACCAAAAAGAGCAGGTGTGACGGAT <SEQ ID NO. 523 Lm 31F; DNA; ARTIFICIAL>
ATACGGGAGCCAACACCAATAGTACCGCGCCCGGCGAAAAAGCTCCTTTAATACAGAGCAGGTGTGACGGAT <SEQ ID NO. 524 Lm 31R; DNA; Artificial>
ATCCGTCACACCTGCTCTGTATTAAAGGAGCTTTTTCGCCGGGCGCGGTACTATTGGTGTTGGCTCCCGTAT <SEQ ID NO. 525 Lm 32/40F; DNA; ARTIFICIAL>
ATACGGGAGCCAACACCAATAGATGGATAAGGGGGAAACTGCCATTCGGTTAGTAGAGCAGGTGTGACGGAT <SEQ ID NO. 526 Lm 32/40R; DNA; Artificial>
ATCCGTCACACCTGCTCTACTAACCGAATGGCAGTTTCCCCCTTATCCATCTATTGGTGTTGGCTCCCGTAT <SEQ ID NO. 527 Lm 34F; DNA; ARTIFICIAL>
ATCCGTCACACCTGCTCTTGGGTCGGCCGGGACCAGCGCGGCGGCCTCCTGGTGGTGTTGGCTCCCGTAT <SEQ ID NO. 528 Lm 34R; DNA; Artificial>
ATACGGGAGCCAACACCACCAGGAGGCCGCCGCGCTGGTCCCGGCCGACCCAAGAGCAGGTGTGACGGAT <SEQ ID NO. 529 Lm 35F; DNA; ARTIFICIAL>
ATCCGTCACACCTGCTCTATGTTACAACCGCCACAAGTAGGTTTGATACCCGGGTGGTGTTGGCTCCCGTAT <SEQ ID NO. 530 Lm 35R; DNA; Artificial>
ATACGGGAGCCAACACCACCCGGGTATCAAACCTACTTGTGGCGGTTGTAACATAGAGCAGGTGTGACGGAT <SEQ ID NO. 531 Lm 36F; DNA; ARTIFICIAL>
ATACGGGAGCCAACACCACACAGAGCGCATGGACTCAGTCAGATGTGATGTAGAGCAGGTGTGACGGAT <SEQ ID NO. 532 Lm 36R; DNA; Artificial>
ATCCGTCACACCTGCTCTACATCACATCTGACTGAGTCCATGCGCTCTGTGTGTGGTGTTGGCTCCCGTAT <SEQ ID NO. 533 Lm 37F; DNA; ARTIFICIAL>
ATACGGGAGCCAACACCATCACTACTTTTATAATTTCATTCTTCTGGCGTCCCTAGAGCAGGTGTGACGGAT <SEQ ID NO. 534 Lm 37R; DNA; Artificial>
ATCCGTCACACCTGCTCTAGGGACGCCAGAAGAATGAAATTATAAAAGTAGTGATGGTGTTGGCTCCCGTAT <SEQ ID NO. 535 Lm 38F; DNA; ARTIFICIAL>
ATCCGTCACACCTGCTCTTGTTACAACCTAGTACCCGGAGGGGGACCCGAGGAGTGGTGTTGGCTCCCGTAT <SEQ ID NO. 536 Lm 38R; DNA; Artificial>
ATACGGGAGCCAACACCACTCCTCGGGTCCCCCTCCGGGTACTAGGTTGTAACAAGAGCAGGTGTGACGGAT <SEQ ID NO. 537 Lm 39F; DNA; ARTIFICIAL>
ATCCGTCACACCTGCTCTGTTTCTTCAACTTCTGCCTTATCCCCGGTCGGTACGTGGTGTTGGCTCCCGTAT <SEQ ID NO. 538 Lm 39R; DNA; Artificial>
ATACGGGAGCCAACACCACGTACCGACCGGGGATAAGGCAGAAGTTGAAGAAACAGAGCAGGTGTGACGGAT <SEQ ID NO. 539 Lm 42F; DNA; ARTIFICIAL>
ATACGGGAGCCAACACCATCACGGCAATGTCCGATAATGTCTTGCTTCAGCGAGAGCAGGTGTGACGGAT <SEQ ID NO. 540 Lm 42R; DNA; Artificial>
ATCCGTCACACCTGCTCTCGCTGAAGCAAGACATTATCGGACATTGCCGTGATGGTGTTGGCTCCCGTAT <SEQ ID NO. 541 Lm 44F; DNA; ARTIFICIAL>
ATCCGTCACACCTGCTCTGAGGAATATGACGCGGCAATAGTGAACCAGTCAAACTGGTGTTGGCTCCCGTAT <SEQ ID NO. 542 Lm 44R; DNA; Artificial>
ATACGGGAGCCAACACCAGTTTGACTGGTTCACTATTGCCGCGTCATATTCCTCAGAGCAGGTGTGACGGAT <SEQ ID NO. 543 Lm 45F; DNA; ARTIFICIAL>
ATCCGTCACACCTGCTCTGCATGGCCATCCAGATTAGTCTTGCAGCACATTCGGTGGTGTTGGCTCCCGTAT <SEQ ID NO. 544 Lm 45R; DNA; Artificial>
ATACGGGAGCCAACACCACCGAATGTGCTGCAAGACTAATCTGGATGGCCATGCAGAGCAGGTGTGACGGAT <SEQ ID NO. 545 Lm 46F; DNA; ARTIFICIAL>
ATACGGGAGCCAACACCACACCTGGTAAATTTACCACGGCTTACTTGCTCAGATAGAGCAGGTGTGACGGAT TABLE 8-continued DNA Ligand Sequence ID Nos.
Arthropod Aptamer Sequences 2011-Final <SEQ ID NO. 546 Lm 46R; DNA; Artificial>
ATCCGTCACACCTGCTCTATCTGAGCAAGTAAGCCGTGGTAAATTTACCAGGTGTGGTGTTGGCTCCCGTAT <SEQ ID NO. 547 Lm 49/49F; DNA; ARTIFICIAL>
ATACGGGAGCCAACACCAGCACACGGCACGCCCCTCCGAACCACGCCCCCGAAAGAGCAGGTGTGACGGAT <SEQ ID NO. 548 Lm 49/49R; DNA; Artificial>
ATCCGTCACACCTGCTCTTTCGGGGGCGTGGTTCGGAGGGGCGTGCCGTGTGCTGGTGTTGGCTCCCGTAT <SEQ ID NO. 549 Rp-1/4/6/12F; DNA; Artificial>
ATACGGGAGCCAACACCATCCAATGAGGCCATGGACCGGTAAACTCGGACGCGCAGAGCAGGTGTGACGGAT <SEQ ID NO. 550 Rp-1/4/6/12R; DNA; Artificial>
ATCCGTCACACCTGCTCTGCGCGTCCGAGTTTACCGGTCCATGGCCTCATTGGATGGTGTTGGCTCCCGTAT <SEQ ID NO. 551 Rp-3F; DNA; Artificial>
ATACGGGAGCCAACACCACACGCCACAAACCCCACTCCGTGCCGTGCCCGCCCCAGAGCAGGTGTGACGGAT <SEQ ID NO. 552 Rp-3R; DNA; Artificial>
ATCCGTCACACCTGCTCTGGGGCGGGCACGGCACGGAGTGGGGTTTGTGGCGTGTGGTGTTGGCTCCCGTAT <SEQ ID NO. 553 Rp-5F; DNA; Artificial>
ATACGGGAGCCAACACCACCTGGAGCCCAGCCTGTACTCATCTCACCGCCGTCCAGAGCAGGTGTGACGGAT <SEQ ID NO. 554 Rp-5R; DNA; Artificial>
ATCCGTCACACCTGCTCTGGACGGCGGTGAGATGAGTACAGGCTGGGCTCCAGGTGGTGTTGGCTCCCGTAT <SEQ ID NO. 555 Rp-7F; DNA; Artificial>
ATACGGGAGCCAACACCAGGCGCCGTACAGCGGTCCGCTACCGACCTATTGTGTAGAGCAGGTGTGACGGAT <SEQ ID NO. 556 Rp-7R; DNA; Artificial>
ATCCGTCACACCTGCTCTACACAATAGGTCGGTAGCGGACCGCTGTACGGCGCCTGGTGTTGGCTCCCGTAT <SEQ ID NO. 557 Rp-8F; DNA; Artificial>
ATACGGGAGCCAACACCATACGTCCCACAAAGCGATCGGCTGGATACTTCGTCAGAGCAGGTGTGACGGAT <SEQ ID NO. 558 Rp-8R; DNA; Artificial>
ATCCGTCACACCTGCTCTGACGAAGTATCCAGCCGATCGCTTTGTGGGACGTATGGTGTTGGCTCCCGTAT <SEQ ID NO. 559 Rp-9F; DNA; Artificial>
ATACGGGAGCCAACACCACAGAATGTCGATGCACAGGGGAATTCGGTGCGCCCGAGAGCAGGTGTGACGGAT <SEQ ID NO. 560 Rp-9R; DNA; Artificial>
ATCCGTCACACCTGCTCTCGGGCGCACCGAATTCCCCTGTGCATCGACATTCTGTGGTGTTGGCTCCCGTAT <SEQ ID NO. 561 Rp-10F; DNA; Artificial>
ATACGGGAGCCAACACCACTCTAGCTGACAGGTGCATACGATACCCGACGCTTCAGAGCAGGTGTGACGGAT <SEQ ID NO. 562 Rp-10R; DNA; Artificial>
ATCCGTCACACCTGCTCTGAAGCGTCGGGTATCGTATGCACCTGTCAGCTAGAGTGGTGTTGGCTCCCGTAT <SEQ ID NO. 563 Rp-11F; DNA; Artificial>
ATACGGGAGCCAACACCAGGTCCGTCAAACGTTACGTAGGAGGCATATCACGGTAGAGCAGGTGTGACGGAT <SEQ ID NO. 564 Rp-11R; DNA; Artificial>
ATCCGTCACACCTGCTCTACCGTGATATGCCTCCTACGTAACGTTTGACGGACCTGGTGTTGGCTCCCGTAT <SEQ ID NO. 565 Rp-13F; DNA; Artificial>
ATACGGGAGCCAACACCATGCATACGAGGCCACCACTCAGAAAGATATGTGGGCAGAGCAGGTGTGACGGAT <SEQ ID NO. 566 Rp-13R; DNA; Artificial>
ATCCGTCACACCTGCTCTGCCCACATATCTTTCTGAGTGGTGGCCTCGTATGCATGGTGTTGGCTCCCGTAT <SEQ ID NO. 567 Rp-14F; DNA; Artificial>
ATACGGGAGCCAACACCAGCCCACTGCCACGATATATGCGCAACCGTTGTCCGCAGAGCAGGTGTGACGGAT <SEQ ID NO. 568 Rp-14R; DNA; Artificial>
ATCCGTCACACCTGCTCTGCGGACAACGGTTGCGCATATATCGTGGCAGTGGGCTGGTGTTGGCTCCCGTAT <SEQ ID NO. 569 Rp-15F; DNA; Artificial>
ATACGGGAGCCAACACCAACCGACACCCCCGCCCAGCCCCATCCTGCCCGGTCCAGAGCAGGTGTGACGGAT <SEQ ID NO. 570 Rp-15R; DNA; Artificial>
ATCCGTCACACCTGCTCTGGACCGGGCAGGATGGGGCTGGGCGGGGGTGTCGGTTGGTGTTGGCTCCCGTAT <SEQ ID NO. 571 Rp-16F; DNA; Artificial>
ATACGGGAGCCAACACCATGCGGGGAGCAATGTAGGTCTTAGTACCACGTGGCCAGAGCAGGTGTGACGGAT TABLE 8-continued DNA Ligand Sequence ID Nos.
Arthropod Aptamer Sequences 2011-Final <SEQ ID NO. 572 Rp-16R; DNA; Artificial>
ATCCGTCACACCTGCTCTGGCCACGTGGTACTAAGACCTACATTGCTCCCCGCATGGTGTTGGCTCCCGTAT <SEQ ID NO. 573 Rp-17F; DNA; Artificial>
ATACGGGAGCCAACACCAGCCGTACTAGGCCCGAAGTCAGGTGTAGGATTGGCCAGAGCAGGTGTGACGGAT <SEQ ID NO. 574 Rp-17R; DNA; Artificial>
ATCCGTCACACCTGCTCTGGCCAATCCTACACCTGACTTCGGGCCTAGTACGGCTGGTGTTGGCTCCCGTAT <SEQ ID NO. 575 Rp-19F; DNA; Artificial>
ATACGGGAGCCAACACCACATCCCACACACGAACAGTACCTTGCCACCCCCGCCAGAGCAGGTGTGACGGAT <SEQ ID NO. 576 Rp-19R; DNA; Artificial>
ATCCGTCACACCTGCTCTGGCGGGGGTGGCAAGGTACTGTTCGTGTGTGGGATGTGGTGTTGGCTCCCGTAT <SEQ ID NO. 577 Rp-20F; DNA; Artificial>
ATACGGGAGCCAACACCACCTGTCCACTTTGGCACGCGCGCCACTCAGTCCTCCAGAGCAGGTGTGACGGAT <SEQ ID NO. 578 Rp-20R; DNA; Artificial>
ATCCGTCACACCTGCTCTGGAGGACTGAGTGGCGCGCGTGCCAAAGTGGACAGGTGGTGTTGGCTCCCGTAT <SEQ ID NO. 579 Rr-3F; DNA; Artificial>
ATACGGGAGCCAACACCAGTCCGTTATGACATGTCCGGACCCGTACGCGTGTCAAGAGCAGGTGTGACGGAT <SEQ ID NO. 580 Rr-3R; DNA; Artificial>
ATCCGTCACACCTGCTCTTGACACGCGTACGGGTCCGGACATGTCATAACGGACTGGTGTTGGCTCCCGTAT <SEQ ID NO. 581 Rr-7F; DNA; Artificial>
ATACGGGAGCCAACACCAGTCCGTTATGACATGTCCGGACCCGTACGCGTGTCAAGAGCAGGTGTGACGGAT <SEQ ID NO. 582 Rr-7R; DNA; Artificial>
ATCCGTCACACCTGCTCTTGACACGCGTACGGGTCCGGACATGTCATAACGGACTGGTGTTGGCTCCCGTAT <SEQ ID NO. 583 Rr-8/14/22F; DNA; Artificial>
ATACGGGAGCCAACACCACAAGCAGGAATAAGCGCCGGTCCAGAGCAGGTGTGACGGAT <SEQ ID NO. 584 Rr-8/14/22R; DNA; Artificial>
ATCCGTCACACCTGCTCTGGACCGGCGCTTATTCCTGCTTGTGGTGTTGGCTCCCGTAT <SEQ ID NO. 585 Rr-9F; DNA; Artificial>
ATACGGGAGCCAACACCAGCGAACTGAAAACGCTTAAAGGAGACCAATGACCGAAGAGCAGGTGTGACGGA <SEQ ID NO. 586 Rr-9R; DNA; Artificial>
ATCCGTCACACCTGCTCTTCGGTCATTGGTCTCCTTTAAGCGTTTTCAGTTCGCTGGTGTTGGCTCCCGTAT <SEQ ID NO. 587 Rr-10F; DNA; Artificial>
ATACGGGAGCCAACACCAAGTCATGCCGAAGTAGGGTAACGTCTGAATGGTAGAAGAGCAGGTGTGACGGAT <SEQ ID NO. 588 Rr-10R; DNA; Artificial>
ATCCGTCACACCTGCTCTTCTACCATTCAGACGTTACCCTACTTCGGCATGACTTGGTGTTGGCTCCCGTAT <SEQ ID NO. 589 Rr-11F; DNA; Artificial>
ATACGGGAGCCAACACCACTCGTAATCCTTTAATACACCTATTGCAACAATGCTAGAGCAGGTGTGACGGAT <SEQ ID NO. 590 Rr-11R; DNA; Artificial>
ATCCGTCACACCTGCTCTAGCATTGTTGCAATAGGTGTATTAAAGGATTACGAGTGGTGTTGGCTCCCGTAT <SEQ ID NO. 591 Rr-12F; DNA; Artificial>
ATACGGGAGCCAACACCAGTCCGTTATGACATGTCCGGACCCGTACGCGTGTCAAGAGCAGGTGTGACGGAT <SEQ ID NO. 592 Rr-12R; DNA; Artificial>
ATCCGTCACACCTGCTCTTGACACGCGTACGGGTCCGGACATGTCATAACGGACTGGTGTTGGCTCCCGTAT <SEQ ID NO. 593 Rr-13F; DNA; Artificial>
ATACGGGAGCCAACACCAGTCCGTTATGACATGTCCGGACCCGTACGCGTGTCAAGAGCAGGTGTGACGGAT <SEQ ID NO. 594 Rr-13R; DNA; Artificial>
ATCCGTCACACCTGCTCTTGACACGCGTACGGGTCCGGACATGTCATAACGGACTGGTGTTGGCTCCCGTAT <SEQ ID NO. 595 Rr-15F; DNA; Artificial>
ATACGGGAGCCAACACCAGTCCGTTATGACATGTCCGGACCCGTACGCGTGTCAAGAGCAGGTGTGACGGAT <SEQ ID NO. 596 Rr-15R; DNA; Artificial>
ATCCGTCACACCTGCTCTTGACACGCGTACGGGTCCGGACATGTCATAACGGACTGGTGTTGGCTCCCGTAT <SEQ ID NO. 597 Rr-16F; DNA; Artificial>
ATACGGGAGCCAACACCACACTACCGTCCCACCCCCTCCCAGCTCCTCCGGCCGAGAGCAGGTGTGACGGA TABLE 8-continued DNA Ligand Sequence ID Nos.
Arthropod Aptamer Sequences 2011-Final <SEQ ID NO. 598 Rr-16R; DNA; Artificial>
ATCCGTCACACCTGCTCTCGGCCGGAGGAGCTGGGAGGGGGTGGGACGGTAGTGTGGTGTTGGCTCCCGTAT <SEQ ID NO. 599 Rr-17F; DNA; Artificial>
ATACGGGAGCCAACACCAAGGGGCAACTCGAACCCGGGCGATACCGAGACTGACAGAGCAGGTGTGACGGAT <SEQ ID NO. 600 Rr-17R; DNA; Artificial>
ATCCGTCACACCTGCTCTGTCAGTCTCGGTATCGCCCGGGTTCGAGTTGCCCCTTGGTGTTGGCTCCCGTAT <SEQ ID NO. 601 Rr-18F; DNA; Artificial>
ATACGGGAGCCAACACCACGATCCTACTCATACGGAGCCCTGGCTGACTCGCGCAGAGCAGGTGTGACGGAT <SEQ ID NO. 602 Rr-18R; DNA; Artificial>
ATCCGTCACACCTGCTCTGCGCGAGTCAGCCAGGGCTCCGTATGAGTAGGATCGTGGTGTTGGCTCCCGTAT <SEQ ID NO. 603 Rr-19F; DNA; Artificial>
ATACGGGAGCCAACACCAGTCCGTTATGACATGTCCGGACCCGTACGCGTGTCAAGAGCAGGTGTGACGGAT <SEQ ID NO. 604 Rr-19R; DNA; Artificial>
ATCCGTCACACCTGCTCTTGACACGCGTACGGGTCCGGACATGTCATAACGGACTGGTGTTGGCTCCCGTAT <SEQ ID NO. 605 Rr-20F; DNA; Artificial>
ATACGGGAGCCAACACCAGTCCGTTATGACATGTCCGGACCCGTACGCGTGTCAAGAGCAGGTGTGACGGAT <SEQ ID NO. 606 Rr-20R; DNA; Artificial>
ATCCGTCACACCTGCTCTTGACACGCGTACGGGTCCGGACATGTCATAACGGACTGGTGTTGGCTCCCGTAT <SEQ ID NO. 607 Rr-21F; DNA; Artificial>
ATACGGGAGCCAACACCACTGAAAACTTATGAAATGCCGGTCGCAGATTTTGTCAGAGCAGGTGTGACGGAT <SEQ ID NO. 608 Rr-21R; DNA; Artificial>
ATCCGTCACACCTGCTCTGACAAAATCTGCGACCGGCATTTCATAAGTTTTCAGTGGTGTTGGCTCCCGTAT <SEQ ID NO. 609 Rr-23F; DNA; Artificial>
ATACGGGAGCCAACACCAGTCCGTTATGACATGTCCGGACCCGTACGCGTGTCAGAGCAGGTGTGACGGAT <SEQ ID NO. 610 Rr-23R; DNA; Artificial>
ATCCGTCACACCTGCTCTGACACGCGTACGGGTCCGGACATGTCATAACGGACTGGTGTTGGCTCCCGTAT <SEQ ID NO. 611 Rr-24F; DNA; Artificial>
ATACGGGAGCCAACACCACACTACCGTCCCACCCCCTCCCAGCTCCTCCGGCCGAGAGCAGGTGTGACGGAT <SEQ ID NO. 612 Rr-24R; DNA; Artificial>
ATCCGTCACACCTGCTCTCGGCCGGAGGAGCTGGGAGGGGGTGGGACGGTAGTGTGGTGTTGGCTCCCGTAT <SEQ ID NO. 613 Rr-25F; DNA; Artificial>
ATACGGGAGCCAACACCAGTCCGTTATGACATGTCCGGACCCGTACGCGTGTCAAGAGCAGGTGTGACGGAT <SEQ ID NO. 614 Rr-25R; DNA; Artificial>
ATCCGTCACACCTGCTCTTGACACGCGTACGGGTCCGGACATGTCATAACGGACTGGTGTTGGCTCCCGTAT <SEQ ID NO. 615 Rt-1F; DNA; Artificial>
ATACGGGAGCCAACACCAGTCCGTTATGACATGTCCGGACCCGTACGCGTGTCAAGAGCAGGTGTGACGGAT <SEQ ID NO. 616 Rt-1R; DNA; Artificial>
ATCCGTCACACCTGCTCTTGACACGCGTACGGGTCCGGACATGTCATAACGGACTGGTGTTGGCTCCCGTAT <SEQ ID NO. 617 Rt-2F; DNA; Artificial>
ATACGGGAGCCAACACCACCGCAACACACTATCCACGACCAGAGCAGGTGTGACGGAT <SEQ ID NO. 618 Rt-2R; DNA; Artificial>
ATCCGTCACACCTGCTCTGGTCGTGGATAGTGTGTTGCGGTGGTGTTGGCTCCCGTAT <SEQ ID NO. 619 Rt-3F; DNA; Artificial>
ATACGGGAGCCAACACCACCGCCCGCCTCCTGGCGCCACACCCCGCCGCAGCGAGAGCAGGTGTGACGGAT <SEQ ID NO. 620 Rt-3R; DNA; Artificial>
ATCCGTCACACCTGCTCTCGCTGCGGCGGGGTGTGGCGCCAGGAGGCGGGCGGTGGTGTTGGCTCCCGTAT <SEQ ID NO. 621 Rt-4F; DNA; Artificial>
ATACGGGAGCCAACACCAAATACAGTGCCTAATAGGTATGAAAATTATAGTAATAGAGCAGGTGTGACGGAT <SEQ ID NO. 622 Rt-4R; DNA; Artificial>
ATCCGTCACACCTGCTCTATTACTATAATTTTCATACCTATTAGGCACTGTATTTGGTGTTGGCTCCCGTAT <SEQ ID NO. 623 Rt-5/16F; DNA; Artificial>
ATACGGGAGCCAACACCACACTACCGTCCCACCCCCTCCCAGCTCCTCCGGCCGAGAGCAGGTGTGACGGAT TABLE 8-continued DNA Ligand Sequence ID Nos.
Arthropod Aptamer Sequences 2011-Final <SEQ ID NO. 624 Rt-5/16R; DNA; Artificial>
ATCCGTCACACCTGCTCTCGGCCGGAGGAGCTGGGAGGGGGTGGGACGGTAGTGTGGTGTTGGCTCCCGTAT <SEQ ID NO. 625 Rt-6F; DNA; Artificial>
ATACGGGAGCCAACACCACTAGTTATTTCATAGGGGAAATTAACAAATTTTGACAGAGCAGGTGTGACGGAT <SEQ ID NO. 626 Rt-6R; DNA; Artificial>
ATCCGTCACACCTGCTCTGTCAAAATTTGTTAATTTCCCCTATGAAATAACTAGTGGTGTTGGCTCCCGTAT <SEQ ID NO. 627 Rt-7aF; DNA; Artificial>
ATACGGGAGCCAACACCACGGACAATCTGGTAGTAGTAAACAATATATAAGTATAGAGCAGGTGTGACGGAT <SEQ ID NO. 628 Rt-7aR; DNA; Artificial>
ATCCGTCACACCTGCTCTATACTTATATATTGTTTACTACTACCAGATTGTCCGTGGTGTTGGCTCCCGTAT <SEQ ID NO. 629 Rt-7bF; DNA; Artificial>
ATACGGGAGCCAACACCAGTACTCGCTGTGGCAAAAGCAGCATTTCGTCTATCTAGAGCAGGTGTGACGGAT <SEQ ID NO. 630 Rt-7bR; DNA; Artificial>
ATCCGTCACACCTGCTCTAGATAGACGAAATGCTGCTTTTGCCACAGCGAGTACTGGTGTTGGCTCCCGTAT <SEQ ID NO. 631 Rt-8F; DNA; Artificial>
ATACGGGAGCCAACACCAAAGCTCCCCCCCTCATCCCTGGCATCTCCGCTAACCAGAGCAGGTGTGACGGAT <SEQ ID NO. 632 Rt-8R; DNA; Artificial>
ATCCGTCACACCTGCTCTGGTTAGCGGAGATGCCAGGGATGAGGGGGGAGCTTTGGTGTTGGCTCCCGTAT <SEQ ID NO. 633 Rt-9F; DNA; Artificial>
ATACGGGAGCCAACACCAGTCCGTTATGACATGTCCGGACCCGTACGCGTGTCAAGAGCAGGTGTGACGGAT <SEQ ID NO. 634 Rt-9R; DNA; Artificial>
ATCCGTCACACCTGCTCTTGACACGCGTACGGGTCCGGACATGTCATAACGGACTGGTGTTGGCTCCCGTAT <SEQ ID NO. 635 Rt-10F; DNA; Artificial>
ATACGGGAGCCAACACCATTAACGTCGCAATAGCGCTCATCTAACGTCAAGGGCAGAGCAGGTGTGACGGAT <SEQ ID NO. 636 Rt-10R; DNA; Artificial>
ATCCGTCACACCTGCTCTGCCCTTGACGTTAGATGAGCGCTATTGCGACGTTAATGGTGTTGGCTCCCGTAT <SEQ ID NO. 637 Rt-11F; DNA; Artificial>
ATACGGGAGCCAACACCAAAGTGTCGTAATTTAAGATGCATACGCATGCCGTTAAGAGCAGGTGTGACGGAT <SEQ ID NO. 638 Rt-11R; DNA; Artificial>
ATCCGTCACACCTGCTCTTAACGGCATGCGTATGCATCTTAAATTACGACACTTTGGTGTTGGCTCCCGTAT <SEQ ID NO. 639 Rt-12F; DNA; Artificial>
ATACGGGAGCCAACACCAGTGTCTTATGAATGTAGATGAGCTCAGATCGGAATTAGAGCAGGTGTGACGGAT <SEQ ID NO. 640 Rt-12R; DNA; Artificial>
ATCCGTCACACCTGCTCTAATTCCGATCTGAGCTCATCTACATTCATAAGACACTGGTGTTGGCTCCCGTAT <SEQ ID NO. 641 Rt-13F; DNA; Artificial>
ATACGGGAGCCAACACCACACATCACATACCTTCAAGAGCGATGACGGCCCTTTATAGGCAGAGCAGGTGTGACGGAT <SEQ ID NO. 642 Rt-13R; DNA; Artificial>
ATCCGTCACACCTGCTCTGCCTATAAAGGGCCGTCATCGCTCTTGAAGGTATGTGATGTGTGGTGTTGGCTCCCGTAT <SEQ ID NO. 643 Rt-16F; DNA; Artificial>
ATACGGGAGCCAACACCACACTACCGTCCCACCCCCTCCCAGCTCCTCCGGCCGAGAGCAGGTGTGACGGAT <SEQ ID NO. 644 Rt-16R; DNA; Artificial>
ATCCGTCACACCTGCTCTCGGCCGGAGGAGCTGGGAGGGGGTGGGACGGTAGTGTGGTGTTGGCTCCCGTAT <SEQ ID NO. 645 Rt-17F; DNA; Artificial>
ATACGGGAGCCAACACCAGTCCGTTATGACATGTCCGGACCCGTACGCGTGTCAAGAGCAGGTGTGACGGAT <SEQ ID NO. 646 Rt-17R; DNA; Artificial>
ATCCGTCACACCTGCTCTTGACACGCGTACGGGTCCGGACATGTCATAACGGACTGGTGTTGGCTCCCGTAT <SEQ ID NO. 647 Rt-18F; DNA; Artificial>
ATACGGGAGCCAACACCAATGTGGTGGATAGCAAACCCCGACGATTGAGGATTAGAGCAGGTGTGACGGAT <SEQ ID NO. 648 Rt-18R; DNA; Artificial>
ATCCGTCACACCTGCTCTAATCCTCAATCGTCGGGGGTTTGCTATCCACCACATTGGTGTTGGCTCCCGTAT <SEQ ID NO. 649 Rt-19F; DNA; Artificial>
ATACGGGAGCCAACACCAGTTGAAGCTAGTACTGCGGAAGCATAGTCCATAAGTAGAGCAGGTGTGACGGAT TABLE 8-continued DNA Ligand Sequence ID Nos.
Arthropod Aptamer Sequences 2011-Final <SEQ ID NO. 650 Rt-19R; DNA; Artificial>
ATCCGTCACACCTGCTCTACTTATGGACTATGCTTCCGCAGTACTAGCTTCAACTGGTGTTGGCTCCCGTAT <SEQ ID NO. 651 Rt-20F; DNA; Artificial>
ATACGGGAGCCAACACCAGCGAAATGAAGGTATGTTTTTGAATAATAATGTGGCAGAGCAGGTGTGACGGAT <SEQ ID NO. 652 Rt-20R; DNA; Artificial>
ATCCGTCACACCTGCTCTGCCACATTATTATTCAAAAACATACCTTCATTTCGCTGGTGTTGGCTCCCGTAT <SEQ ID NO. 653 Rt-12F; DNA; Artificial>
ATACGGGAGCCAACACCAAAATAGATCAAAACCGCATGCTGGAGCAGTTTTAGCAAGAGCAGGTGTGACGGAT <SEQ ID NO. 654 Rt-21R; DNA; Artificial>
ATCCGTCACACCTGCTCTTGCTAAAACTGCTCCAGCATGCGGTTTTGATCTATTTTGGTGTTGGCTCCCGTAT <SEQ ID NO. 655 Rt-22F; DNA; Artificial>
ATACGGGAGCCAACACCAATAATTGCTCGTTGATACTTATATAAAGTACAGGCAAGAGCAGGTGTGACGGAT <SEQ ID NO. 656 Rt-22R; DNA; Artificial>
ATCCGTCACACCTGCTCTTGCCTGTACTTTATATAAGTATCAACGAGCAATTATTGGTGTTGGCTCCCGTAT <SEQ ID NO. 657 Rt-23F; DNA; Artificial>
ATACGGGAGCCAACACCATCCAATGAGGCCATGGACCGGTAAACTCGGACGCGCAGAGCAGGTGTGACGGAT <SEQ ID NO. 658 Rt-23R; DNA; Artificial>
ATCCGTCACACCTGCTCTGCGCGTCCGAGTTTACCGGTCCATGGCCTCATTGGATGGTGTTGGCTCCCGTAT <SEQ ID NO. 659 Rt-24F; DNA; Artificial>
ATACGGGAGCCAACACCAGTCCGTTATGACATGTCCGGACCCGTACGCGTGTCAAGAGCAGGTGTGACGGAT <SEQ ID NO. 660 Rt-24R; DNA; Artificial>
ATCCGTCACACCTGCTCTTGACACGCGTACGGGTCCGGACATGTCATAACGGACTGGTGTTGGCTCCCGTAT <SEQ ID NO. 661 Rt-25F; DNA; Artificial>
ATACGGGAGCCAACACCAAGACGATAAGAATAATATCGAAAATATATGTTTTCAGAGCAGGTGTGACGGAT <SEQ ID NO. 662 Rt-25R; DNA; Artificial>
ATCCGTCACACCTGCTCTGAAAACATATATTTTCGATATTATTCTTATCGTCTTGGTGTTGGCTCCCGTAT <SEQ ID NO. 663 E7A-1F; DNA; Artificial>
ATACGGGAGCCAACACCAGCCTCGCCTTCAGATGTTCACTGCTGTTTATTGCATAGAGCAGGTGTGACGGAT <SEQ ID NO. 664 E7A-1R; DNA; Artificial>
ATCCGTCACACCTGCTCTATGCAATAAACAGCAGTGAACATCTGAAGGCGAGGCTGGTGTTGGCTCCCGTAT <SEQ ID NO. 665 E7A-2/6/28/30bF; DNA; Artificial>
ATACGGGAGCCAACACCAATAGATGGATAAGGGGGAAACTGCCATTCGGTTAGTAGAGCAGGTGTGACGGAT <SEQ ID NO. 666 E7A-2/6/28/30bR; DNA; Artificial>
ATCCGTCACACCTGCTCTACTAACCGAATGGCAGTTTCCCCCTTATCCATCTATTGGTGTTGGCTCCCGTAT <SEQ ID NO. 667 E7A-3/10/16/19/21/22F; DNA; Artificial>
ATACGGGAGCCAACACCAGTCCGTTATGACATGTCCGGACCCGTACGCGTGTCAAGAGCAGGTGTGACGGAT <SEQ ID NO. 668 E7A-3/10/16/19/21/22R; DNA; Artificial>
ATCCGTCACACCTGCTCTTGACACGCGTACGGGTCCGGACATGTCATAACGGACTGGTGTTGGCTCCCGTAT <SEQ ID NO. 669 E7A-4F; DNA; Artificial>
ATACGGGAGCCAACACCAGGACTCGCGCAAATAATTTTTATACGCACCACTTCAGAGCAGGTGTGACGGAT <SEQ ID NO. 670 E7A-4R; DNA; Artificial>
ATCCGTCACACCTGCTCTGAAGTGGTGCGTATAAAAATTATTTGCGCGAGTCCTGGTGTTGGCTCCCGTAT <SEQ ID NO. 671 E7A-5F; DNA; Artificial>
ATACGGGAGCCAACACCAGTCCGTTATGACATGTCCGGACCCCGTACGCGTGTCAAGAGCAGGTGTGACGGAT <SEQ ID NO. 672 E7A-5R; DNA; Artificial>
ATCCGTCACACCTGCTCTTGACACGCGTACGGGGTCCGGACATGTCATAACGGACTGGTGTTGGCTCCCGTAT <SEQ ID NO. 673 E7A-7F; DNA; Artificial>
ATACGGGAGCCAACACCATAAAGCTCGTATTGCCACCCCCTGTTATTTAATACAGAGCAGGTGTGACGGAT <SEQ ID NO. 674 E7A-7R; DNA; Artificial>
ATCCGTCACACCTGCTCTGTATTAAATAACAGGGGGGTGGCAATACGAGCTTTATGGTGTTGGCTCCCGTAT <SEQ ID NO. 675 E7A-8F; DNA; Artificial>
ATACGGGAGCCAACACCATCACGGCAATGTCCCGATAATGTCTTGCTTCAGCGAGAGCAGGTGTGACGGAT TABLE 8-continued DNA Ligand Sequence ID Nos.
Arthropod Aptamer Sequences 2011-Final <SEQ ID NO. 676 E7A-8R; DNA; Artificial>
ATCCGTCACACCTGCTCTCGCTGAAGCAAGACATTATCGGGACATTGCCGTGATGGTGTTGGCTCCCGTAT <SEQ ID NO. 677 E7A-11F; DNA; Artificial>
ATACGGGAGCCAACACCAGCAGTACTAACCCCCCTTACCATATATATCACACGAGAGCAGGTGTGACGGAT <SEQ ID NO. 678 E7A-11R; DNA; Artificial>
ATCCGTCACACCTGCTCTCGTGTGATATATATGGTAAGGGGGGTTAGTACTGCTGGTGTTGGCTCCCGTAT <SEQ ID NO. 679 E7A-12/30a/32/34F; DNA; Artificial>
ATACGGGAGCCAACACCACCCTAAATTCCAGAGTGTACAAGAGAACGAACTACCAGAGCAGGTGTGACGGAT <SEQ ID NO. 680 E7A-12/30a/32/34F; DNA; Artificial>
ATCCGTCACACCTGCTCTGGTAGTTCGTTCTCTTGTACACTCTGGAATTTAGGGTGGTGTTGGCTCCCGTAT <SEQ ID NO. 681 E7A-13F; DNA; Artificial>
ATACGGGAGCCAACACCATAGCGACTTGGCAAAAAATTTACATCCATTACTCCAGAGCAGGTGTGACGGAT <SEQ ID NO. 682 E7A-13R; DNA; Artificial>
ATCCGTCACACCTGCTCTGGAGTAATGGATGTAAATTTTTTGCCAAGTCGCTATGGTGTTGGCTCCCGTAT <SEQ ID NO. 683 E7A-14F; DNA; Artificial>
ATACGGGAGCCAACACCACGTACACAAACCAAATACGCACCTTCCCACCCTCCAGAGCAGGTGTGACGGAT <SEQ ID NO. 684 E7A-14R; DNA; Artificial>
ATCCGTCACACCTGCTCTGGAGGGTGGGAAGGTGCGTATTTGGTTTGTGTACGTGGTGTTGGCTCCCGTAT <SEQ ID NO. 685 E7A-15F; DNA; Artificial>
ATACGGGAGCCAACACCACATCTAGCACGAGACCCTATCCCAGAGCAGGTGTGACGGAT <SEQ ID NO. 686 E7A-15R; DNA; Artificial>
ATCCGTCACACCTGCTCTGGGATAGGGTCTCGTGCTAGATGTGGTGTTGGCTCCCGTAT <SEQ ID NO. 687 E7A-17F; DNA; Artificial>
ATACGGGAGCCAACACCAAATCGTCAACAGCCCTGCGCCACTTATCTTTTTGCCAGAGCAGGTGTGACGGAT <SEQ ID NO. 688 E7A-17R; DNA; Artificial>
ATCCGTCACACCTGCTCTGGCAAAAAGATAAGTGGCGCAGGGCTGTTGACGATTTGGTGTTGGCTCCCGTAT <SEQ ID NO. 689 E7A-18F; DNA; Artificial>
ATACGGGAGCCAACACCAACAGATGGATAAGGGGGAAACTGCCCATTCGGTTAGTAGAGCAGGTGTGACGGAT <SEQ ID NO. 690 E7A-18R; DNA; Artificial>
ATCCGTCACACCTGCTCTACTAACCGAATGGGCAGTTTCCCCCTTATCCATCTGTTGGTGTTGGCTCCCGTAT <SEQ ID NO. 691 E7A-20F; DNA; Artificial>
ATACGGGAGCCAACACCACGCAGTTATAACGGCAGGCCCCATATCGTTTAACCAGAGCAGGTGTGACGGAT <SEQ ID NO. 692 E7A-20R; DNA; Artificial>
ATCCGTCACACCTGCTCTGGTTAAACGATATGGGGCCTGCCGTTATAACTGCGTGGTGTTGGCTCCCGTAT <SEQ ID NO. 693 E7A-23F; DNA; Artificial>
ATACGGGAGCCAACACCATGTCAGGACCTCCATCGCCCGGGCCCGCCGCCGCTGAGAGCAGGTGTGAC <SEQ ID NO. 694 E7A-23R; DNA; Artificial>
GTCACACCTGCTCTCAGCGGCGGCGGGCCCGGGCGATGGAGGTCCTGACATGGTGTTGGCTCCCGTAT <SEQ ID NO. 695 E7A-25F; DNA; Artificial>
ATACGGGAGCCAACACCATAACAAATAACCACCCTCAATGCTAGATAGTGGCAGAGCAGGTGTGACGGAT <SEQ ID NO. 696 E7A-25R; DNA; Artificial>
ATCCGTCACACCTGCTCTGCCACTATCTAGCATTGAGGGTGGTTATTTGTTATGGTGTTGGCTCCCGTAT <SEQ ID NO. 697 E7A-29F; DNA; Artificial>
ATACGGCAGCCAACACCACACACATAGCGCTTTGTATTCAGCCGGATGTGATGTAGAGCAGGTGTGACGGAT <SEQ ID NO. 698 E7A-29F; DNA; Artificial>
ATCCGTCACACCTGCTCTACATCACATCCGGCTGAATACAAAGCGCTATGTGTGGTGTTGGCTGCCGTAA <SEQ ID NO. 699 E7A-33F; DNA; Artificial>
ATACGGGAGCCAACACCACACACAGAGCGCCATGGACTCAGTCAGATGTGATGTAGAGCAGGTGTGACGGAT <SEQ ID NO. 700 E7A-33R; DNA; Artificial>
ATCCGTCACACCTGCTCTACATCACATCTGACTGAGTCCATGGCGCTCTGTGTGTGGTGTTGGCTCCCGTAT <SEQ ID NO. 701 E7A-35F; DNA; Artificial>
ATACGGGAGCCAACGCCACAGGCGTGACATCACCCGTACCCTACCTTAGTGCCAGAGCAGGTGTGACGGAT TABLE 8-continued DNA Ligand Sequence ID Nos.
Arthropod Aptamer Sequences 2011-Final <SEQ ID NO. 702 E7A-35R; DNA; Artificial>
ATCCGTCACACCTGCTCTGGCACTAAGGTAGGGTACGGGTGATGTCACGCCTGTGGCGTTGGCTCCCGTAT <SEQ ID NO. 703 E7B-1aF; DNA; Artificial>
ATACGGGAGCCAACACCATAATTCAAGAGGATTCCTCAAAATATGAAGCTTCCAGAGCAGGTGTGACGGAT <SEQ ID NO. 704 E7B-1aR; DNA; Artificial>
ATCCGTCACACCTGCTCTGGAAGCTTCATATTTTGAGGAATCCTCTTGAATTATGGTGTTGGCTCCCGTAT <SEQ ID NO. 705 E7B-1bF; DNA; Artificial>
ATACGGGAGCCAACACCAGTCCGTTATGACATGTCCGGACCCGTACGCGTGTCAAAGAGCAGGTGTGACGGAT <SEQ ID NO. 706 E7B-1bR; DNA; Artificial>
ATCCGTCACACCTGCTCTTTGACACGCGTACGGGTCCGGACATGTCATAACGGACTGGTGTTGGCTCCCGTAT <SEQ ID NO. 707 E7B-3F; DNA; Artificial>
ATACGGGAGCCAACACCATATCTTATCATAATGTGATGCTAAGAAGGATCCTTTAGAGCAGGTGTGACGGAT <SEQ ID NO. 708 E7B-3R; DNA; Artificial>
ATCCGTCACACCTGCTCTAAAGGATCCTTCTTAGCATCACATTATGATAAGATATGGTGTTGGCTCCCGTAT <SEQ ID NO. 709 E7B-4F; DNA; Artificial>
ATACGGGAGCCAACACCAGATTGATGTAAGTAGCCCTCAAATGATTTAAAGTTTAGAGCAGGTGTGACGGAT <SEQ ID NO. 710 E7B-4R; DNA; Artificial>
ATCCGTCACACCTGCTCTAAACTTTAAATCATTTGAGGGCTACTTACATCAATCTGGTGTTGGCTCCCGTAT <SEQ ID NO. 711 E7B-5F; DNA; Artificial>
ATACGGGAGCCAACACCACACTAATTTATCGCATGCATCGCCCGCTGATGCCCAAGAGCAGGTGTGACGGAT <SEQ ID NO. 712 E7B-5R; DNA; Artificial>
ATCCGTCACACCTGCTCTTGGGCATCAGCGGGCGATGCATGCGATAAATTAGTGTGGTGTTGGCTCCCGTAT <SEQ ID NO. 713 E7B-6F; DNA; Artificial>
ATACGGGAGCCAACACCACAGAAGTTATTTTGAGAACGCGACCCAAATAGGTTAAGAGCAGGTGTGACGGAT <SEQ ID NO. 714 E7B-6R; DNA; Artificial>
ATCCGTCACACCTGCTCTTAACCTATTTGGGTCGCGTTCTCAAAATAACTTCTGTGGTGTTGGCTCCCGTAT <SEQ ID NO. 715 E7B-7F; DNA; Artificial>
ATACGGGAGCCAACACCATTAATGTAGAACACCACTCTTATTGACAAGCCTATTAGAGCAGGTGTGACGGAT <SEQ ID NO. 716 E7B-7R; DNA; Artificial>
ATCCGTCACACCTGCTCTAATAGGCTTGTCAATAAGAGTGGTGTTCTACATTAATGGTGTTGGCTCCCGTAT <SEQ ID NO. 717 E7B-8a/10/16-19/23-25F; DNA; Artificial>
ATACGGGAGCCAACACCAGTCCGTTATGACATGTCCGGACCCGTACGCGTGTCAAGAGCAGGTGTGACGGAT <SEQ ID NO. 718 E7B-8a/10/16-19/23-25R; DNA; Artificial>
ATCCGTCACACCTGCTCTTGACACGCGTACGGGTCCGGACATGTCATAACGGACTGGTGTTGGCTCCCGTAT <SEQ ID NO. 719 E7B-8bF; DNA; Artificial>
ATACGGGAGCCAACACCACAGTTTGTAGTGTAACAATGCTAGATAATAATGAAAAGAGCAGGTGTGACGGAT <SEQ ID NO. 720 E7B-8bR; DNA; Artificial>
ATCCGTCACACCTGCTCTTTTTCATTATTATCTAGCATTGTTACACTACAAACTGTGGTGTTGGCTCCCGTAT <SEQ ID NO. 721 E7B-11F; DNA; Artificial>
ATACGGGAGCCAACACCAAGCAAATCACCAGAAATCTTTTAACAATCTATTGACAGAGCAGGTGTGACGGAT <SEQ ID NO. 722 E7B-11R; DNA; Artificial>
ATCCGTCACACCTGCTCTGTCAATAGATTGTTAAAAGATTTCTGGTGATTTGCTTGGTGTTGGCTCCCGTAT <SEQ ID NO. 723 E7B-12F; DNA; Artificial>
ATACGGGAGCCAACACCACACAGGAACTAGAAGAAAGTATCTTTTTTCGATTTAAGAGCAGGTGTGACGGAT <SEQ ID NO. 724 E7B-12R; DNA; Artificial>
ATCCGTCACACCTGCTCTTAAATCGAAAAAAGATACTTTCTTCTAGTTCCTGTGTGGTGTTGGCTCCCGTAT <SEQ ID NO. 725 E7B-13/15F; DNA; Artificial>
ATACGGGAGCCAACACCACATCTAGCACGAGACCCTATCCCAGAGCAGGTGTGACGGAT <SEQ ID NO. 726 E7B-13/15R; DNA; Artificial>
ATCCGTCACACCTGCTCTGGGATAGGGTCTCGTGCTAGATGGTGTTGGCTCCCGTAT <SEQ ID NO. 727 E7B-14F; DNA; Artificial>
ATACGGGAGCCAGCACCATTCCGTTATGACGTGTCCGGACCCGTTCGCGCGTCAAGAGCAGGTGTGACGGAT TABLE 8-continued DNA Ligand Sequence ID Nos.
Arthropod Aptamer Sequences 2011-Final <SEQ ID NO. 728 E7B-14R; DNA; Artificial>
ATCCGTCACACCTGCTCTTGACGCGCGAACGGGTCCGGACACGTCATAACGGAATGGTGCTGGCTCCCGTAA <SEQ ID NO. 729 E7B-20/21F; DNA; Artificial>
ATACGGGAGCCAACACCATCACGGCAATGTCCCGATAATGTCTTGCTTCAGCGAGAGCAGGTGTGACGGAT <SEQ ID NO. 730 E7B-20/21R; DNA; Artificial>
ATCCGTCACACCTGCTCTCGCTGAAGCAAGACATTATCGGGACATTGCCGTGATGGTGTTGGCTCCCGTAT <SEQ ID NO. 731 E7B-22F; DNA; Artificial>
ATACGGGAGCCAACACCAGTCCGTTATGACATTGTCAAGAGCAGGTGTGACGGAT <SEQ ID NO. 732 E7B-22R; DNA; Artificial>
ATCCGTCACACCTGCTCTTGACAATGTCATAACGGACTGGTGTTGGCTCCCGTAT <SEQ ID NO. 733 E7B-26F; DNA; Artificial>
ATACGGGAGCCAACACCACATACTCAGACGATTACCCAGCGCATGCTTGTAACAGAGCAGGTGTGACGGAT <SEQ ID NO. 734 E7B-26R; DNA; Artificial>
ATCCGTCACACCTGCTCTGTTACAAGCATGCGCTGGGTAATCGTCTGAGTATGTGGTGTTGGCTCCCGTAT <SEQ ID NO. 735 E7B-27F; DNA; Artificial>
ATACGGGAGCCAACACCACTCTCTAGCCCACGGCGGGGTTTTCTCGCAAGTCCAGAGCAGGTGTGACGGAT <SEQ ID NO. 736 E7B-27R; DNA; Artificial>
ATCCGTCACACCTGCTCTGGACTTGCGAGAAAACCCCGCCGTGGGCTAGAGAGTGGTGTTGGCTCCCGTAT <SEQ ID NO. 737 E7B-30F; DNA; Artificial>
ATACGGGAGCCAACACCAATTGCGCCCTAAGGCTACCCACATTACCCATGTGTAGAGCAGGTGTGACGGAT <SEQ ID NO. 738 E7B-30R; DNA; Artificial>
ATCCGTCACACCTGCTCTACACATGGGTAATGTGGGTAGCCTTAGGGCGCAATTGGTGTTGGCTCCCGTAT <SEQ ID NO. 739 E7B-31F; DNA; Artificial>
ATACGGGAGCCAACACCAGCTGCTGCTTCAACGAAATCCCAGGCACCCTGACAAGAGCAGGTGTGACGGAT <SEQ ID NO. 740 E7B-31R; DNA; Artificial>
ATCCGTCACACCTGCTCTTGTCAGGGTGCCTGGGATTTCGTTGAAGCAGCAGCTGGTGTTGGCTCCCGTAT <SEQ ID NO. 741 E7B-33F; DNA; Artificial>
ATACGGGAGCCAACACCAGTACCTGATACCGGGGTACATAAACACCAACATCTAGAGCAGGTGTGACGGAT <SEQ ID NO. 742 E7B-33R; DNA; Artificial>
ATCCGTCACACCTGCTCTAGATGTTGGTGTTTATGTACCCCGGTATCAGGTACTGGTGTTGGCTCCCGTAT <SEQ ID NO. 743 E7B-34F; DNA; Artificial>
ATACGGGAGCCAACACCAGATACCGTGAATATACTAATTTCGCAATAGTTAATAGAGCAGGTGTGACGGAT <SEQ ID NO. 744 E7B-34R; DNA; Artificial>
ATCCGTCACACCTGCTCTATTAACTATTGCGAAATTAGTATATTCACGGTATCTGGTGTTGGCTCCCGTAT <SEQ ID NO. 745 IbAr 10200 - 2-6/8-23/25/26/28/30/31/33/34F; DNA; Artificial>
ATACGGGAGCCAACACCAGTCCGTTATGACATGTCCGGACCCGTACGCGTGTCAAGAGCAGGTGTGACGGAT <SEQ ID NO. 746 IbAr 10200 - 2-6/8-23/25/26/28/30/31/33/34R; DNA; Artificial>
ATCCGTCACACCTGCTCTTGACACGCGTACGGGTCCGGACATGTCATAACGGACTGGTGTTGGCTCCCGTAT <SEQ ID NO. 747 Drosdov - 4-7/10-12/14/18/20-24F; DNA; Artificial>
ATACGGGAGCCAACACCAGTCCGTTATGACATGTCCGGACCCGTACGCGTGTCAAGAGCAGGTGTGACGGAT <SEQ ID NO. 748 Drosdov - 4-7/10-12/14/18/20-24R; DNA; Artificial>
ATCCGTCACACCTGCTCTTGACACGCGTACGGGTCCGGACATGTCATAACGGACTGGTGTTGGCTCCCGTAT <SEQ ID NO. 749 Drosdov - 13F; DNA; Artificial>
ATACGGGAGCCAACACCAGTCCGTTTGACATGTCCGGACCCGTACGCGTGTCAAGAGCAGGTGTGACGGAT <SEQ ID NO. 750 Drosdov - 13R; DNA; Artificial>
ATCCGTCACACCTGCTCTTGACACGCGTACGGGTCCGGACATGTCAAACGGACTGGTGTTGGCTCCCGTAT <SEQ ID NO. 751 Drosdov - 16F; DNA; Artificial>
ATACGGGAGCCAACACCATCACGGCAATGTCCCGATAATGTCTTGCTTCAGCGAGAGCAGGTGTGACGGAT <SEQ ID NO. 752 Drosdov - 16RF; DNA; Artificial>
ATCCGTCACACCTGCTCTCGCTGAAGCAAGACATTATCGGGACATTGCCGTGATGGTGTTGGCTCCCGTAT <SEQ ID NO. 753 Drosdov - 17F; DNA; Artificial>
ATACGGGAGCCAACACCAGTCCGTTATGACATGTCCGGACCCGTACAAGAGCAGGTGTGACGGAT TABLE 8-continued DNA Ligand Sequence ID Nos.
Arthropod Aptamer Sequences 2011-Final <SEQ ID NO. 754 Drosdov - 17R; DNA; Artificial>
ATCCGTCACACCTGCTCTTGTACGGGTCCGGACATGTCATAACGGACTGGTGTTGGCTCCCGTAT <SEQ ID NO. 755 Drosdov - 19F; DNA; Artificial>
ATACGGGAGCCAACACCAAGTCCAAGCCAAACAAGAGCATAACACCCAAATCTGGAGAGCAGGTGTGACGGAT <SEQ ID NO. 756 Drosdov - 19R; DNA; Artificial>
ATCCGTCACACCTGCTCTCCAGATTTGGTGTTATGCTCTTGTTTGGCTTGGACTTGGTGTTGGCTCCCGTAT <SEQ ID NO. 757 TBEV-1F; DNA; Artificial>
ATACGGGAGCCAACACCACTCGGCACCGCCCTTCCGTATCGGCGAGTAACGTACAGAGCAGGTGTGACGGAT <SEQ ID NO. 758 TBEV-1R; DNA; Artificial>
ATCCGTCACACCTGCTCTGTACGTTACTCGCCGATACGGAAGGGCGGTGCCGAGTGGTGTTGGCTCCCGTAT <SEQ ID NO. 759 TBEV-2F; DNA; Artificial>
ATACGGGAGCCAACACCACCGCAGGAGTCCATCAGGGGTTGGCAGTCAGCGCTCAGAGCAGGTGTGACGGAT <SEQ ID NO. 760 TBEV-2R; DNA; Artificial>
ATCCGTCACACCTGCTCTGAGCGCTGACTGCCAACCCCTGATGGACTCCTGCGGTGGTGTTGGCTCCCGTAT <SEQ ID NO. 761 TBEV-3F; DNA; Artificial>
ATACGGGAGCCAACACCACACGAACGGAGTGCACCGGGGAAGATACTCCAACGCAGAGCAGGTGTGACGGAT <SEQ ID NO. 762 TBEV-3R; DNA; Artificial>
ATCCGTCACACCTGCTCTGCGTTGGAGTATCTTCCCCGGTGCACTCCGTTCGTGTGGTGTTGGCTCCCGTAT <SEQ ID NO. 763 TBEV-4F; DNA; Artificial>
ATACGGGAGCCAACACCAGCCAATTATACAGGTAGGTCAAAAAAGTTTAGGGGAAGAGCAGGTGTGACGGAT <SEQ ID NO. 764 TBEV-4R; DNA; Artificial>
ATCCGTCACACCTGCTCTTCCCCTAAACTTTTTTGACCTACCTGTATAATTGGCTGGTGTTGGCTCCCGTAT <SEQ ID NO. 765 TBEV-5F; DNA; Artificial>
ATACGGGAGCCAACACCACCATGCCCCTTTAAGTGAATAGACTAGTGGCCGTTGAGAGCAGGTGTGACGGAT <SEQ ID NO. 766 TBEV-5R; DNA; Artificial>
ATCCGTCACACCTGCTCTCAACGGCCACTAGTCTATTCACTTAAAGGGGCATGGTGGTGTTGGCTCCCGTAT <SEQ ID NO. 767 TBEV-6F; DNA; Artificial>
ATACGGGAGCCAACACCAGAGACGTCTTAGCCTCGCGATCCCGTCCGTTGGCCCAGAGCAGGTGTGACGGAT <SEQ ID NO. 768 TBEV-6R; DNA; Artificial>
ATCCGTCACACCTGCTCTGGGCCAACGGACGGGATCGCGAGGCTAAGACGTCTCTGGTGTTGGCTCCCGTAT <SEQ ID NO. 769 TBEV-7F; DNA; Artificial>
ATACGGGAGCCAACACCATCCTCCCGCGACGTCTGGAGAACAGCCTCTACTTTAAGAGCAGGTGTGACGGAT <SEQ ID NO. 770 TBEV-7R; DNA; Artificial>
ATCCGTCACACCTGCTCTTAAAGTAGAGGCTGTTCTCCAGACGTCGCGGGAGGATGGTGTTGGCTCCCGTAT <SEQ ID NO. 771 TBEV-8F; DNA; Artificial>
ATACGGGAGCCAACACCACACACAGAGCGCCATGGACTCAGTCAGATGTGATGTAGAGCAGGTGTGACGGAT <SEQ ID NO. 772 TBEV-8R; DNA; Artificial>
ATCCGTCACACCTGCTCTACATCACATCTGACTGAGTCCATGGCGCTCTGTGTGTGGTGTTGGCTCCCGTAT <SEQ ID NO. 773 TBEV-10F; DNA; Artificial>
ATACGGGAGCCAACACCATTGACTTGGCCGTCTCTGACCCCTAGCACCCCTCGCAGAGCAGGTGTGACGGAT <SEQ ID NO. 774 TBEV-10R; DNA; Artificial>
ATCCGTCACACCTGCTCTGCGAGGGGTGCTAGGGGTCAGAGACGGCCAAGTCAATGGTGTTGGCTCCCGTAT

I claim:

1. A DNA ligand sequence consisting of a nucleic acid sequence SEQ ID NO. 746.

2. A composition comprising the DNA ligand sequence of claim 1.

* * * * *